US009505812B2

(12) United States Patent
Doolan et al.

(10) Patent No.: US 9,505,812 B2

(45) Date of Patent: Nov. 29, 2016

(54) ***PLASMODIUM FALCIPARUM* ANTIGENS**

(71) Applicants: Denise Doolan, Camp Hill (AU); Angela Trieu, Enogera (AU); Phillip L. Felgner, Rancho Santa Fe, CA (US)

(72) Inventors: Denise Doolan, Camp Hill (AU); Angela Trieu, Enogera (AU); Phillip L. Felgner, Rancho Santa Fe, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 98 days.

(21) Appl. No.: 14/027,536

(22) Filed: Sep. 16, 2013

(65) Prior Publication Data

US 2015/0079126 A1 Mar. 19, 2015
US 2016/0083438 A9 Mar. 24, 2016

Related U.S. Application Data

(62) Division of application No. 13/426,768, filed on Mar. 22, 2012, now abandoned.

(60) Provisional application No. 61/467,517, filed on Mar. 25, 2011.

(51) Int. Cl.

| | |
|---|---|
| ***A61K 39/00*** | (2006.01) |
| ***A61K 39/015*** | (2006.01) |
| ***C07K 14/44*** | (2006.01) |
| ***C07K 14/445*** | (2006.01) |
| *A61K 48/00* | (2006.01) |

(52) U.S. Cl.

CPC .......... *C07K 14/445* (2013.01); *A61K 39/015* (2013.01); *A61K 48/00* (2013.01); *A61K 2039/53* (2013.01)

(58) Field of Classification Search

None

See application file for complete search history.

(56) References Cited

FOREIGN PATENT DOCUMENTS

WO WO 2004053086 A2 * 6/2004 .......... C07K 14/445

OTHER PUBLICATIONS

Hall et al. 2002 (Sequence of *Plasmodium falciparum* chromosomes 1, 3-9 and 13; Nature 419(3): 527-531).*

* cited by examiner

*Primary Examiner* — Gary Nickol

*Assistant Examiner* — Mary Lyons

(74) *Attorney, Agent, or Firm* — Albert M. Churilla; Ning Yang; Diane P. Tso

(57) ABSTRACT

The invention relates to antigens, associated with sterile immunity, and methods of their use, in an immunogenic formulation to confer an immune response against *Plasmodium falciparum*. The inventive antigens were identified by their association with sterile immunity against malaria.

7 Claims, 4 Drawing Sheets

*PLASMODIUM FALCIPARUM* ANTIGENS

This application is a Divisional application which claims the benefit of U.S. application Ser. No. 13/426,768, filed Mar. 22, 2012, which claims the benefit of U.S. Provisional Application No. 61/467,517, filed Mar. 25, 2011, which are incorporated herein by reference.

BACKGROUND OF INVENTION

1. Field of Invention

The inventive subject matter relates to DNA sequences and polypeptides from *Plasmodium falciparum* for use as an anti-malaria vaccine component and methods of inducing an immune response to these antigens.

2. Background Art

Malaria is caused by the vector borne organism *Plasmodium* spp. The parasite has a complex lifecycle requiring stage specific expression of proteins. These proteins can be expressed at different stages or be specific to stages. Malaria is an extremely important disease, with over 3 billion people living in malaria endemic areas. Over 1 million deaths are attributable to malaria per year. The emergence of drug resistant strains has compounded the problem of treating the disease. Unfortunately, no FDA-approved vaccine exists.

The entire genomic sequence of *P. falciparum* has been sequenced (Bowman et al., Nature, 400: 532-538 (1999), Gardner, et al., Nature, 419: 498-511 (2002)). The rodent malaria parasite, *P. yoelii* has also been sequenced (Carlton et al., Nature, 419: 512-519 (2002)). Despite this, however, the development of efficacious anti-malaria vaccines has been severely hampered by the paucity of promising antigens. Sequencing of the *Plasmodium falciparum* and *Plasmodium yoelii* genomes yielding identification over 5,200 genes in the genome. However, despite the large number of potential gene targets, use of the data set alone will not likely result in new vaccine constructs. Consequently, only 0.2% of the *P. falciparum* proteome is undergoing clinical testing. Moreover, these vaccine candidate antigens have failed to induce significant protection in volunteers. Nevertheless, immunization of mice and humans with radiation-attenuated sporozoites results in a high-grade immunity (>90%), suggesting that development of effective anti-malaria vaccines are possible. This protective immunity appears to target multiple sporozoite and liver stage antigens.

SUMMARY OF THE INVENTION

The invention relates to a vaccine composition and method of immunizing against *Plasmodium falciparum*. The inventive composition comprises *P. falciparum* liver-stage proteins associated with sterile protection against infectious *P. falciparum*. In one embodiment, the proteins can be incorporated into an immunogenic composition, singly or in multiple combinations, as subunit antigens. In another embodiment, for maximal immunogenicity, all identified proteins are included in a single immunogenic composition. Alternatively, multiple combinations of the proteins are administered in an immunization regimen through more than one immunogenic composition, each combination containing a specific combination of said immunogenic proteins. In one embodiment, the immunogenic composition comprises one of the identified proteins that has been isolated and purified. In another embodiment, the immunogenic composition comprises two or more, and up to all 19, of the identified proteins that have been purified and isolated.

In another embodiment, DNA encoding one or more of these proteins can be incorporated into vectors suitable for in vivo expression in a mammalian host. The expressed and purified proteins can then be administered, in one or multiple doses, to a mammal, such as humans. In this embodiment, DNA encoding one or more of the sterile-immunity associated proteins can be inserted into suitable expression systems. Suitable expression systems include, but are not limited to, adenoviral based systems, such as in Bruder, et al (patent application publication number US 20080248060, published Oct. 9, 2008) or a DNA plasmid system. In this embodiment, other vector systems include the DNA encoding *P. falciparum* is administered as an insert of the suitable expression system and expressed in vivo. In this embodiment, an immunogenic composition can comprise DNA encoding one or more, or all, of the sterile-immune associated proteins. The proteins can be expressed by a single vector encoding one or more of the proteins or by multiple expression systems suitable for expression of DNA in a mammal.

DETAILED DESCRIPTION OF PREFERRED EMBODIMENTS

Figure 1:
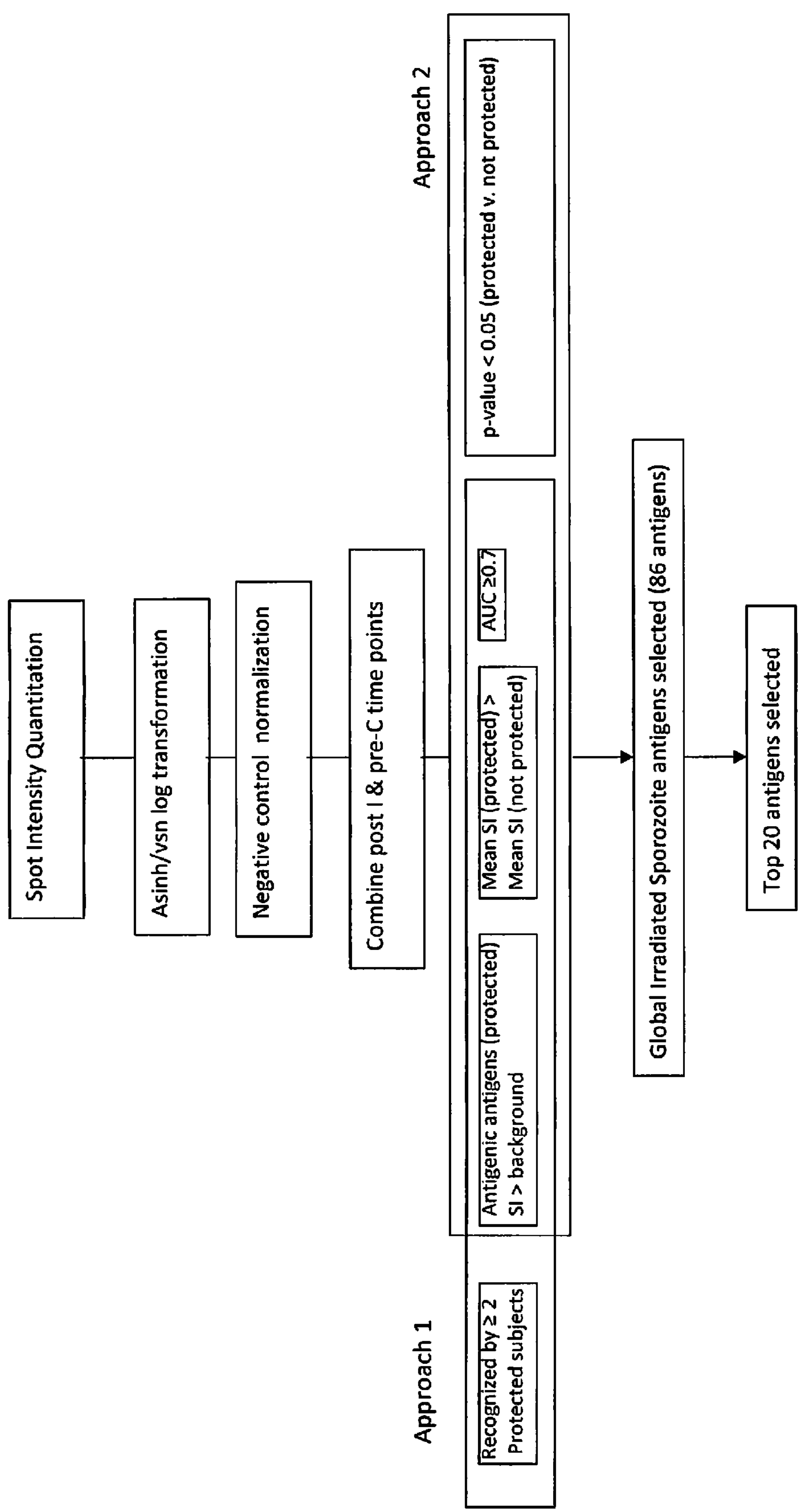
FIG. 1. Summary of selection criteria and AUC profile. (A) Analyses were conducted to identify antigens that are associated with sporozoite-induced protection. After spot quantification, the signal intensity was asinh/vsn log transformed to control variance, scaled by the negative control, post-immunization (post-I) and pre-challenge (pre-C) time points combined, and then analyzed according to defined statistical (Bayes-regularized t-tests, area under the receiver operating characteristics curve (AUC) analysis) and biological criteria. A total of 86 fragments (78 *P. falciparum* proteins) were identified by either approach through the global irradiated sporozoite list. Sterile immunity-associated proteins were in common to both approaches. (B) AUC values of all antigens for the not protected and protected cohorts were determined by R statistical environment software (available through: www.r-project.org). Antigen rank is plotted relative to their AUC value. An AUC value approaching 1.0 suggests a very strong association of an antigen to protection induced by irradiated sporozoite immunization; an AUC value of 0.5 indicates pure chance. An AUC value of 0.7 was chosen as a threshold for positivity.

As used, herein, "sterile immunity" refers to immunity, whereby the causative agent of the targeted disease causing organism is eliminated or inhibited from causing disease.

As used herein, the term "polypeptide" refers to a polymer of amino acids and does not refer to a specific length of the product. Proteins are included within the definition of polypeptides. As used herein, the proteins may be prepared for inclusion of an effective amount of one or more polypeptides described herein into an immunogenic composition by a number of means. For example, they may be included by first expressing the appropriate gene fragments by molecular methods, expression from plasmids or other expression systems such as viral systems and then isolated.

As used herein, "immunogenic fragments" of proteins refers to regions of proteins at least 8 amino acids in length, with the amino acid sequence derived from said protein, the fragment being capable of inducing an immune response or that is recognized by immune cells.

As used herein, "derivatives" of a protein is where a protein has more than 80% amino acid sequence identity to the sequences described herein. In this context, the term "identity" refers to two or more sequences or subsequences that are the same or have a specified percentage of amino acid residues that are the same, when aligned for maximum correspondence. Where sequences differ in conservative substitutions, i.e., substitution of residues with identical properties, the percent sequence identity may be adjusted upwards to correct for the conservative nature of the substitution.

As used herein, an aspect of the invention relates to nucleotide sequences that encode all or a substantial portion of the amino acid sequence encoding identified proteins or substantial portions, thereof. A "substantial portion" of a protein comprises enough of the amino acid sequence to afford putative identification of the protein the sequence encodes (Altschul, et al., J. Mol. Biol. 215: 403-410 (1993)). Furthermore, in general, this is approximately nine or more contiguous amino acids can lead to identification of the protein as homologous to a known protein. "Orthologous" nucleotide sequences are sequences encoding for proteins of the same function but in different species.

"Antigen" is a chemical moiety containing at least one epitope capable of stimulating or reacting with immune products, such as antibody or T-cells. An "immunogenic composition" refers to a chemical, compound or formulation that, once administered, will elicit an immune response; A "vaccine" is an immunogenic composition used to induce protective immunity; A "DNA expression system" is a molecular system containing plasmid or closed loop DNA containing elements for expressing an inserted DNA sequence as polypeptide; A "viral expression system" is any viral based system, including viral-like particles or viral replicons, containing elements for expressing an inserted DNA sequence as a polypeptide.

Example 1

Identification of Sterilely-Immune Associated Proteins

This example illustrates the identification of proteins associated with sterile immune against malaria. In this example, volunteers, experimentally immunized with radiation attenuated *P. falciparum* sporozoites (Irrspz), were clinically divergent after challenge with infectious *P. falciparum* sporozoites; six individuals were sterilely-protected and were classified as sporozoite-immune (IrrSpz protected) and five individuals developed blood stage parasitemia and were classified as sporozoite-exposed but non-immune (IrrSpz not protected).

Subjects were experimentally immunized with radiation-attenuated *P. falciparum*, (Pf(3D7)), sporozoites and challenged with *P. falciparum*-infected Anopheline mosquitoes, as described previously (Hoffman, et al., J. Infect. Dis. 185:1155-1164 (2002); Egan, et al., Am. J. Trop. Med. Hyg. 49:166-173 (1993)). Subjects were monitored daily, post-challenge, by thin blood smears to determine if they developed blood stage malaria. A complete absence of blood stage parasitemia during the 28 day follow up was considered sterile protection.

Six sporozoite-immunized volunteers were protected against sporozoite challenge and five were not protected (i.e. developed clinical malaria). One individual is represented in both groups since he was not protected in the initial challenge but was after a second series of immunizations. Plasma was collected from each individual before immunization (pre-immunization), post third immunization, at the completion of the immunization series ($5^{th}$, $6^{th}$, or $7^{th}$ immunization), immediately prior to challenge (pre-challenge) and following challenge (post-challenge). An infectivity control group (n=3) was simultaneously infected with the same *P. falciparum*-infected mosquitoes used for challenge to demonstrate parasite infectivity; plasma was collected from these individuals at corresponding time points before (pre-challenge) and after (post-challenge) challenge. An additional group (n=5) were mock immunized by the bite of non-infected mosquitoes and plasma was collected at the time points corresponding to pre-immunization, post-third immunization and post last immunization time points of the IrrSpz immunized subjects. Plasma collected from volunteers with no known history of malaria exposure (n=10) was also evaluated.

To identify antigens associated with IrrSpz-induced protection, plasma collected from protected, not protected, infectivity, mock immunized and naïve individuals at different stages of the immunization process (or corresponding time points for the non-immunized individuals) were probed on *P. falciparum* microarrays against 2,320 fragments, representing 1,200 *P. falciparum* proteins. Antibody recognition of each fragment was then assessed.

There were distinct antibody profiles for each immunization group, with variability in responses between individuals within all groups. Overall, a markedly different pattern in antibody recognition was apparent between the protected and not protected groups, consistent with previous data (Doolan, et al, Proteomics 8:4680-4694). There was no difference in antibody reactivity at pre-challenge and post-challenge time points for protected individuals who did not develop blood stage parasitemia or clinical disease ($P<0.6$) and no change in the number of antigens recognized (340 pre-challenge vs. 380 post-challenge).

Putative proteins, and protein and DNA sequences, were derived from the *P. falciparum* genomic sequence database (www.plasmodb.org) and selected based on stage-specific transcription or protein expression, subcellular localization, secondary protein structure, and documented immunogenicity in humans or animal models; this list included all putative *P. falciparum* proteins with evidence of expression at some point during the parasite life cycle by MudPIT (multidimensional protein identification technology) (Florens, et al., Nature 419:520-526 (2002)), www.plasmoDB.org) at the time of antigen selection (n=1049).

Selected genes were amplified by polymerase chain reaction (PCR) amplification of *P. falciparum* genomic DNA (3D7 strain) using custom PCR primers that included homologous cloning sites to the pXT7 plasmid (Davies, et al., Proc. Natl. Acad. Sci. (USA) 102:547-552 (2005)). Due to restrictions in producing long PCR products, proteins with exons longer than 3000 bp were divided into multiple overlapping sections, with 50 nucleotide overlaps. PCR reactions were carried out in a 50 μl reaction volume containing 1-10 ng of *P. falciparum* genomic DNA (gDNA) (3D7 strain), 0.04 U/μl proofreading Taq polymerase (Triplemaster™, Eppendorf, Hauppauge, N.Y.), and 0.4 mM each dNTPs, with the following cycling conditions: 95° C. for 3 min; 35 cycles of 95° C. for 15 s, 40° C. for 30 s and 50° C. for 60 s/kb; and a final extension of 50° C. for 10 min. For some proteins that proved difficult to amplify, 50 ng of gDNA was used. Products were visualized by agarose gel electrophoresis, and quantified by fluorometry (Picogreen™, Molecular Probes®, Invitrogen, Carlsbad, Calif.).

Plasmids were created from the PCR amplified fragments using in vitro recombination cloning and the pXT7 cloning vector, which encodes an N-terminal 10× Histidine (H is) and C-terminal Haemagglutinin (HA) tag (3.2 kb, KanR). Briefly, 1 ng of Bam HI, digested, linearized pXT7 template and custom primers 5'-CTACCCATACGATGTTCCGGATTAC and 5'-CTCGAGCATATGCTTGTCGTCGTCG were used to generate a linear acceptor vector containing the target gene by PCR (50 μl reaction) with 0.02 U/μl Taq polymerase, 0.1 mg/ml gelatine (Porcine), and 0.2 mM each dNTPs. The following cycling conditions were used: 95° C. for 5 min; 30 cycles of 95° C. for 0.5 min, 50° C. for 0.5 min and 72° C. for 3.5 min; and a final extension of 72° C. for 10 min. After purification (Qiagen, Valencia, Calif.), PCR products were visualized by gel electrophoresis, and quantified by fluorometry (Picogreen™, Molecular Probes®, Invitrogen, Carlsbad, Calif.).

Open reading frames (ORFs) were cloned into the linearized pXT7 plasmid by a recombination reaction as previously described (Davies, et al., Proc. Natl. Acad. Sci. (USA) 102:547-552 (2005). Briefly, a 20 μl mixture of linear vector and PCR-generated ORF fragment at a 1:1 molar ratio between vector and insert was transformed into DH5α competent cells without further purification and incubated for 1 h at 37° C., before dilution into an overnight culture of 3 ml LB broth containing Kanamycin 50 μg/ml. Plasmids were isolated and purified using the QIAprep™ spin miniprep, (Qiagen, Valencia, Calif.) without further selection. A subset of these plasmids was sequence confirmed.

Protein expression and detection was conducted using *E. coli* in vitro cell-free transcription and translation reactions (rapid translation system (RTS) 100 *E. coli* HY kits, Roche). Reactions were carried out in 25 μl volumes with a 5-hour incubation at 30° C., according to manufacturer's instructions. For quality control purposes, relative protein expression efficiency for approximately 31% of all ORFs was assessed by immunodot blots by spotting 0.3 μl of the RTS reaction on nitrocellulose (NC) and air drying before blocking in 5% nonfat milk powder in TBS containing 0.05% polysorbate 20. Dot blots were stained with mouse anti-polyHIS mAb (clone HIS-1; Sigma) and rat anti-HA mAb (clone 3F10) (F. Hoffmann-La Roche Ltd, Basel, Switzerland) and detected with alkaline phosphatase-conjugated goat anti-mouse IgG (H+L) or goat anti-rat IgG (H+L) secondary antibodies respectively or with human hyperimmune plasma (diluted 1:1000 in blocking buffer with 10% *E. coli* lysate) followed by alkaline phosphatase-conjugated goat anti-human IgG secondary antibody (H+L). Blots were visualized with nitroblue tetrazolium (NBT) developer.

Microchips were prepared by mixing 15 μl of RTS reaction with 10 μl of 0.125% polysorbate 20/PBS, and then 15 μl volumes were transferred to 384 well plates. Plates were centrifuged (1600×g, 5 min) to pellet any precipitates and proteins in the supernatant were immediately printed without further purification onto 3-pad NC-coated FAST™ glass slides (Schleicher & Schuell, Bioscience, Inc., Keene, N.H.) using an OmniGrid 100 microarray printer (Genomic Solutions, Ann Arbour, Mich.). Arrays were allowed to dry and stored away from light at room temperature in a desiccator.

RTS reactions carried out in the absence of DNA plasmids were printed on each array as negative or non-differentially recognized control spots. Purified human total IgG and Epstein-Barr nuclear antigen 1 (EBNA1) protein were also printed in serially diluted concentrations on each array, as probing and plasma controls respectively.

Since high titers of anti-*E. coli* antibodies present in the human plasma could mask protein-specific reactivity in the arrays, plasma were pre-absorbed against *E. coli* lysate in protein array blocking buffer (Schleicher & Schuell) (1:100 dilution) for 30 minutes at room temperature (Davis, et al., Proc. Natl. Acad. Sci. (USA) 102:547-552 (2005).

Slides were rehydrated and blocked in blocking buffer for 30 min at room temperature. Then 500 μl plasma diluted 1:100 in blocking buffer was added to each pad and slides were incubated overnight at 4° C. with a gentle constant speed on a platform rocker (Ratek™, InVitro Technologies). Serum antibodies were detected with biotin-conjugated goat anti-human IgG secondary antibody (1:1000 dilution, 1 h at room temperature with gentle constant speed, Fc fragment, (Jackson ImmunoResearch Laboratories, Inc, West Grove, Pa.) and visualized with a streptavidin P-3-conjugated antibody (1:200 dilution, 1 h at room temperature with gentle constant speed. Air dried slides were scanned on an Axon GenePix™ 4300A array scanner (Molecular Devices, CA) and fluorescence intensities quantified using the Axon GenePix Pro 7™ software (Molecular Devices, Sunnyvale, Calif.). Using the above software, all signal intensities were corrected for spot-specific background, where the background value for a spot was calculated from a region surrounding the spot.

To validate the *P. falciparum* protein microarrays, antibody reactivity to three well characterized malaria vaccine candidates, CSP, AMA1 and merozoite surface protein 2 (MSP2), were expressed via the RTS system or using traditional methods and were printed on the same protein microarray chip. There was a high degree of correlation between reactivity to the proteins produced by the two methods, (CSP (r=0.77; P<0.001), AMA1 (r=0.78; P<0.001), MSP2 (r=0.96; P<0.001)). To examine the reproducibility of the array probing, the reactivity against all HA spots from two independent chips was assessed and was highly correlated (r=0.92, P<0.001). Additionally, a smaller microarray chip was fabricated with a subset of 49 *P. falciparum* proteins and probed with the same plasma used to probe the larger 2320 fragment *P. falciparum* protein microarray. There was a strong correlation between plasma reactivity on the two microarrays (r=0.91, P<0.001).

In order to analyze low and high signal intensities (differential recognition) using standard statistical methods, the heteroskedastic nature of microarray platforms (Durbin, et al., Bioinformatics 18 Suppl. 1:S105-110 (2002); Ideker, et al., J. Comput. Biol 7:805-817 (2000) and inherent variance-mean dependence in the data (Sundaresh, et al., Bioinformatics 22:1760-1766 (2006); Sundaresh, et al., Bioinformatics 23:1508-518 (2007)) needed to be considered and stabilized. Raw signal intensities were therefore variant log transformed by using either asinh (Excel 2007, Microsoft; (Sundaresh, et al., Bioinformatics 22:1760-1766 (2006)) or variance stabilizing normalization (vsn) (Bioconductor software (www.bioconductor.org) (Huber, et al., Bioinformatics 18suppl. 1:S96-104 (2002)) transformation, to reduce the variance and experimental effects in the raw signal between differentially recognized antigens.

Before ranking and selection of antigens, data for each plasma sample was scaled by multiplication to a normalization ratio (average SI of all negative controls for that individual/average SI of all negative controls for all individuals) to apply the same baseline for all plasma. The post-immunization and pre-challenge time points for each individual in each group were combined for sample size purposes, since data showed no significant differences between those time points, and data was biologically and statistically analyzed. Area under receiver operating characteristic curves (ROC) (AUC) and Bayesian regularized t-tests (R statistical environment software, www.rproject.org) were used to identify differentially recognized antigens between the protected and not protected groups (Baldi and Long, Bioinformatics 17:509-519 (2001)) (FIG. 1). Please note that the statistical testing (both AUC and p-values) have not under gone multiple testing correction, rather these statistics were used as a method to compare the two groups and rank the data accordingly. The identification of antigens of interest was made on the combination of the rankings in addition to other relevant criteria i.e. recognition in different groups.

The criterion for positive immunoreactivity to a given protein for both transformation methods was determined as an average signal intensity two standard deviation above the negative control (all individuals). Data were visually presented as a heatmap where colors represent the SI range for that antigen. Red represents high SI (reactivity), black represents intermediate reactivity and green represents low reactivity. Gene ontology (GO) annotation analysis was performed using the GOstats and org.Pf.plasmo.db R packages. The significance of annotation enrichment was assessed using Fisher's exact test.

A marked change in seroreactivity was noted at pre-challenge vs. post-challenge time points for the not protected individuals where there was a significant increase in overall signal intensity (SI) (P<2e-91) and number of antigens recognized (292 pre-challenge vs. 739 post-challenge), consistent with exposure to blood stage antigens upon development of patent parasitemia.

The profile for the infectivity control individuals also showed a significant increase in SI pre-challenge vs. post-challenge (P<2e-30) to a subset of antigens (289 prechallenge vs. 546 post-challenge) and 89% (546) of the antigens recognized post-challenge were also recognized by the not protected group post-challenge, and therefore appear to be expressed by the blood stage parasite. Minimal reactivity to *P. falciparum* antigens was noted with plasma from malaria nave individuals or mock immunized individuals, consistent with a lack of exposure to *P. falciparum.*

To identify *P. falciparum* antigens putatively correlated with protection against sporozoite challenge, normalization and variance correction were performed using either the vsn and asinh methods. Since there were no significant changes in SI or number of antigens recognized at post-3$^{rd}$ immunization or post-last immunization (prechallenge) time points for both protected and not protected groups [P<0.25 (not protected), P<0.2 (protected)], data from these biologically similar time points were combined for subsequent analyses. CyberT™ (Institute for Genomics and Bioinformatics, University of California, Irvine, Calif.) (a Bayesian regularized t-test) p-values and a receiver operating characteristic (ROC) curve of the mean SI were used to measure the power of an antigen to discriminate between protected and not protected cohorts, thus identifying antigens putatively associated with sporozoite-induced protection. The selection criteria are depicted in FIG. 1. An area under the ROC curve (AUC) value of 1.0 is a perfect prediction, 0.5 is a random chance, and <0.5 is a prediction in the wrong direction.

For both vsn and asinh approaches, antigens were selected according to the Following criteria: (i) antigenic (protected); i.e. average SI greater than two standard deviations (SD) above negative control; (ii) recognized by at least two protected individuals; (iii) average SI greater in the protected group than not protected group; (iv) an AUC value equal to or greater than 0.7; and (v) CyberT™ p-value <0.05 (protected vs. not protected).

Combining the antigens identified by either approach revealed a total of 86 fragments representing 77 proteins, termed "global IrrSpz" list. Five proteins (PF14_0051, PFI0240c, PF10_0183, PF10_0211, MAL13P1.107) have two immunoreactive fragments on this list and two proteins (PF11_0395, MAL7P1.146) have three fragments, since open reading frames (ORFs)>3000 bp were cloned as overlapping segments. When ranked by AUC values, five antigens on this list (6%) have an AUC value greater than 0.9 (1.5e-3<P>3.8e-3), and 31 antigens (36%) have an AUC greater than 0.8 (1.5e-3<P>4.43e-2).

The global IrrSpz list included three current vaccine candidates: AMA1 (PF11_0344), CSP(PFC0210c), and SSP2/TRAP(PF13_0201). Interestingly, these were highly antigenic in protected individuals, with 92% (AMA1), 100% (CSP) and 100% (SSP2/TRAP) recognition within this cohort, but were also recognized to a similar extent by not protected individuals (92%, 100%, 100%, respectively). The other 75 proteins on this list have not been previously characterized.

Figure 2:
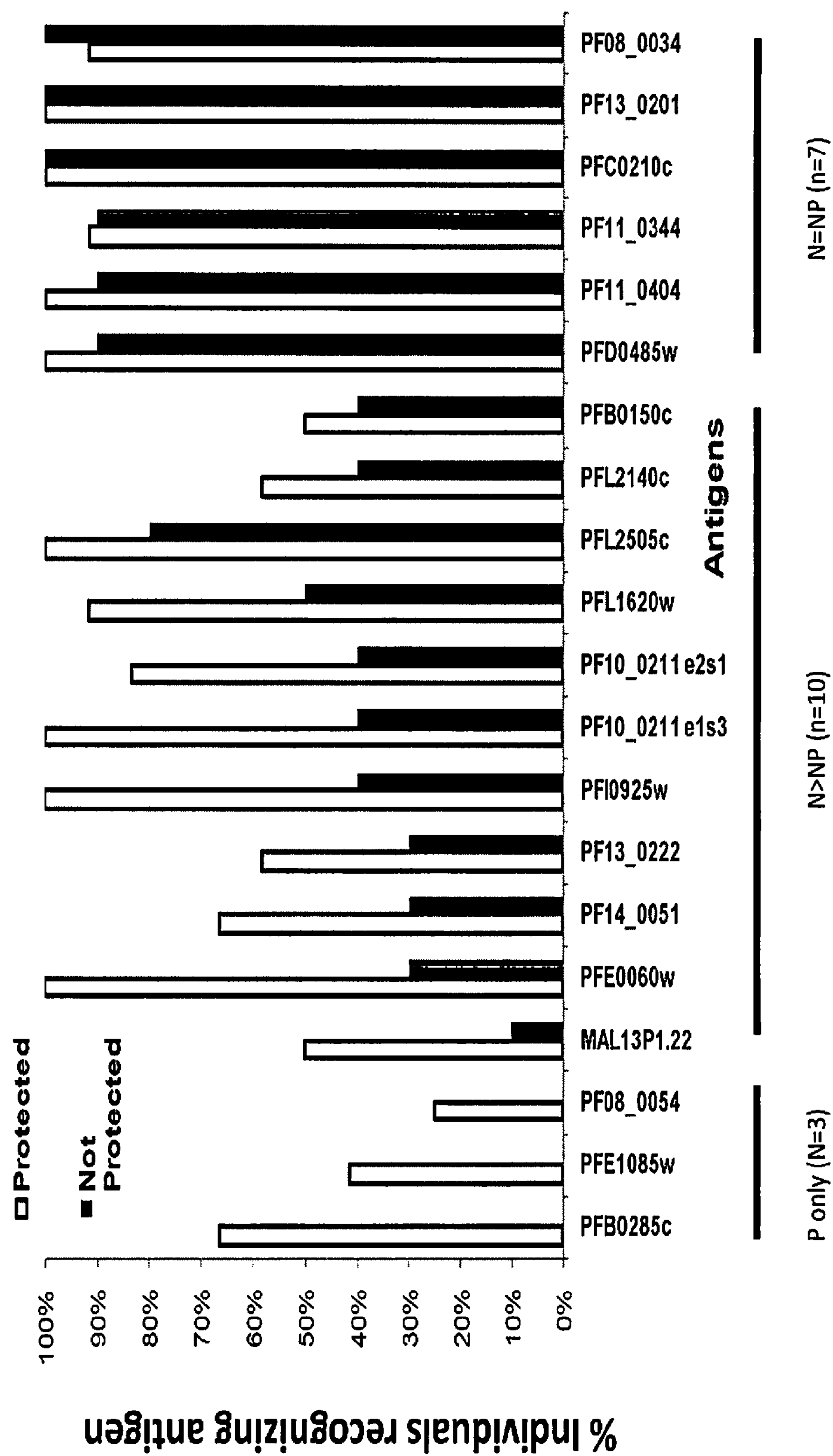
FIG. 2. Magnitude and frequency of recognition of the proteins in Table 1 associated with irradiated sporozoite induced protection. For the antigens (ranked by AUC), the cumulative signal intensity representing the sum of signal intensities for each antigen by all subjects from protected or not protected groups are presented. ***P<0.0055.
Figure 3:
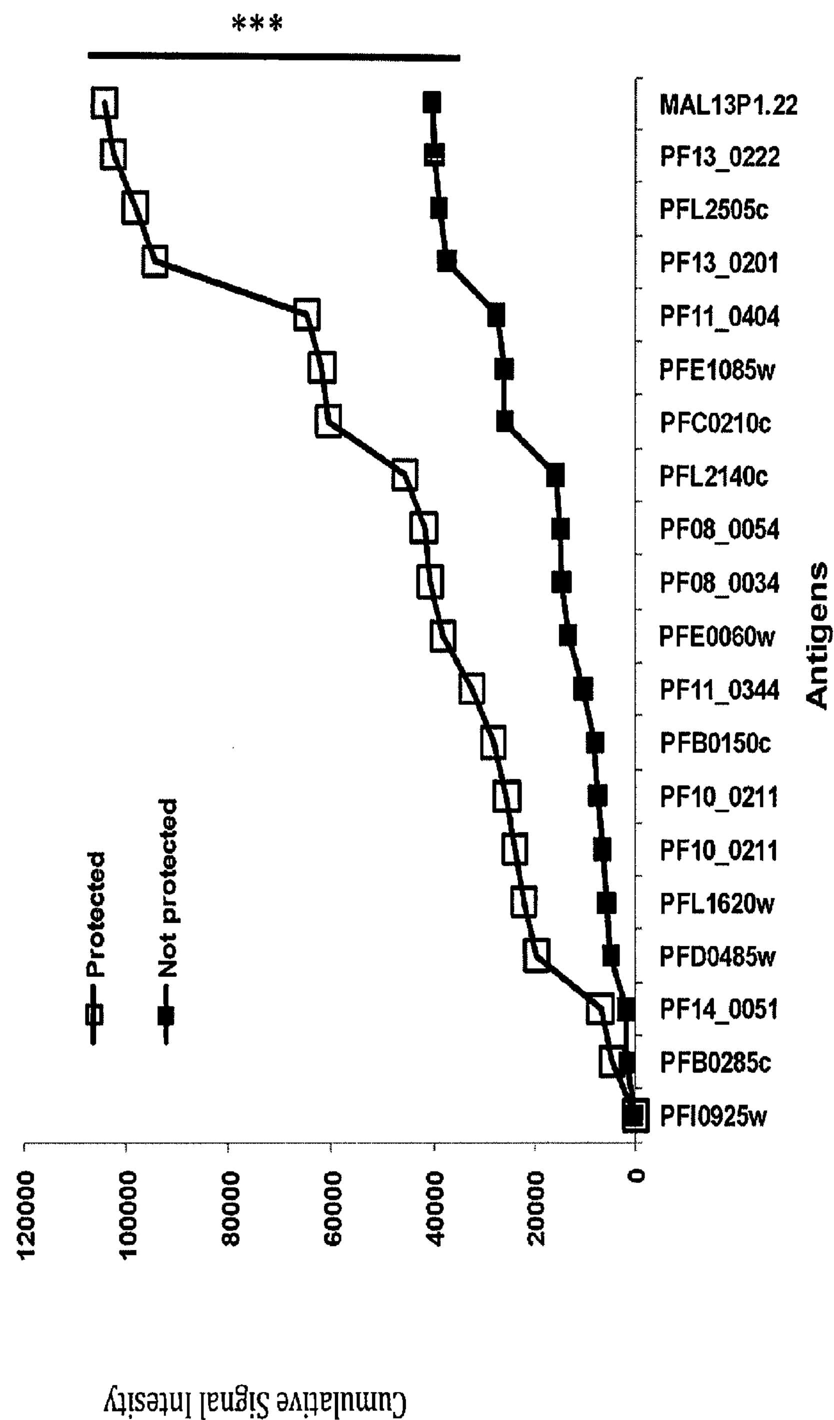
FIG. 3. Magnitude and frequency of recognition of the proteins in Table 1 associated with irradiated sporozoite induced protection. Frequency of recognition of proteins by protected (P) and not protected (NP) individuals. # represents current clinical candidates: AMA1 (PF11_0344); CSP (PFC0210c); SSP2/TRAP (PF13_0201).

A subset of 20 fragments representing 19 proteins was common to both vsn and asinh approaches. These are shown in Table 1. Three of these antigens (i.e., PFB0285c, PFE1085w, PF08_0054) were not recognized by not protected individuals and 10 of the antigens had a higher frequency of recognition in the protected cohort as compared with the not protected cohort. Seven antigens (including CSP, SSP2/TRAP, and AMA1) were recognized at a similar frequency by the two cohorts but the protected individuals had a significantly higher magnitude of response (0.0034<P>0.0077, 2-4 fold higher average SI) (FIG. 2).

TABLE 1

Characteristics of antigens associated with sporozoite-induced protection.

| Gene ID | Product Description | Details | AUC | P value (Protected v not Protected) | Average signal intensity | | Fold enrich (Protected v not Protected) | Frequency of recognition | |
|---|---|---|---|---|---|---|---|---|---|
| | | | | | Protected | Not Protected | | Protected | Not Protected |
| PFI0925w | gamma-glutamylcysteine synthetase | exon 1 | 0.917 | 1.67E−03 | 3324 | 1293 | 3 | 100% | 40% |
| PFB0285c | consened Plasmodium protein, unknown function | exon 1 | 0.917 | 2.77E−03 | 1341 | 337 | 4 | 67% | 0% |
| PF14_0051 ¶ | DNA mismatch repair protein, putative | exon 4 | 0.888 | 1.5E−03 | 2784 | 553 | 5 | 67% | 30% |
| PFD0485w | consened Plasmodium protein, unknown function | complete | 0.852 | 7.68E−03 | 12669 | 3205 | 4 | 100% | 90% |
| PFL1620w | asparaginelaspartate rich protein, putative | exon 1 | 0.833 | 1.06E−02 | 2471 | 807 | 3 | 92% | 50% |
| PF10_0211 § | consened Plasmodium membrane protein, unknown function | exon 1 | 0.833 | 4.43E−02 | 1752 | 863 | 2 | 100% | 40% |
| PF10_0211 § | consened Plasmodium membrane protein, unknown function | exon 2 | 0.833 | 4.43E−02 | 1752 | 853 | 2 | 83% | 40% |
| PFB0150c | protein kinase, putative | exon 2 | 0.824 | 2.37E−02 | 2528 | 620 | 4 | 50% | 40% |
| PF11_0344 | AMA1 | complete | 0.824 | 2.88E−02 | 4455 | 2248 | 2 | 92% | 90% |
| PFE0060w | PESP2 erythrocyte surface protein | exon 2 | 0.815 | 9.87E−03 | 5625 | 3330 | 2 | 100% | 30% |
| PF08_0034 | histone acetyltransferase GCN5, putative | exon 1 | 0.815 | 3.36E−02 | 2480 | 1293 | 2 | 92% | 100% |
| PF08_0054 | heat shock 70 kDa protein | complete | 0.806 | 1.52E−02 | 1214 | 221 | 5 | 25% | 0% |
| PFL2140c | ADP-ribosylation factor GTPase-activating protein | exon 1 | 0.806 | 2.16E−02 | 3738 | 965 | 4 | 58% | 40% |
| PFC0210c | CSP | complete | 0.800 | 1.72E−02 | 15118 | 10066 | 2 | 100% | 100% |
| PFE1085w | DEAD-box subfamily ATP-dependent helicase, putative | exon 1 | 0.796 | 1.03E−02 | 1201 | 203 | 6 | 42% | 0% |
| PF11_0404 | transcription factor with AP2 domain(s), putative | exon 2 | 0.787 | 3.42E−02 | 2907 | 1542 | 2 | 100% | 90% |
| PF13_0201 | SSP2/TRAP | complete | 0.769 | 3.11E−02 | 29578 | 9618 | 3 | 100% | 100% |
| PFL2505c | rhopay neck protein 3, putative | exon 8 | 0.759 | 1.57E−02 | 4011 | 1531 | 3 | 100% | 80% |
| PF13_0222 | phosphatase, putative | exon 1 | 0.750 | 4.98E−02 | 4243 | 960 | 4 | 58% | 30% |
| MAL13P1.22 | DNA figase 1 | exon 2 | 0.713 | 3.91E−02 | 1739 | 466 | 4 | 50% | 10% |

| Gene ID | Total # exons | bp | aa | Mw (kDa) | pl | # TM domains | # PEXEL/ motif | Exported protein | Signal Peptide | Presence in genomic/ proteomic datasets | Functional categories (plasmoDB) |
|---|---|---|---|---|---|---|---|---|---|---|---|
| PFI0925w | 1 | 3192 | 1063 | 124.46 | 5.1 | 0 | 0 | no | no | yes | Protein Synthesis |
| PFB0285c | 1 | 4311 | 1436 | 164.85 | 10.04 | 0 | 0 | no | no | yes | Hypothetical |
| PF14_0051 ¶ | 4 | 4548 | 1515 | 179.83 | 8.9 | 0 | 1 | no | yes | yes | Cell Cycle (DNA processing) |
| PFD0485w | 1 | 1728 | 575 | 68.53 | 9.42 | 0 | 0 | no | no | yes | Hypothetical |
| PFL1620w | 3 | 16320 | 5439 | 646.34 | 6.38 | 0 | 1 | no | no | yes | Protein Synthesis |
| PF10_0211 § | 5 | 20805 | 6934 | 830.20 | 9.51 | 5 | 4 | no | no | yes | Hypothetical |
| PF10_0211 § | 5 | 20805 | 6934 | 830.20 | 9.51 | 5 | 4 | no | no | yes | Protein Synthesis |
| PFB0150c | 1 | 7458 | 2485 | 293.77 | 7.21 | 0 | 0 | no | no | yes | Hypothetical |
| PF11_0344 | 1 | 1869 | 622 | 72.04 | 5.23 | 1 | 0 | no | yes | yes | Cell Surface (Apical organeller |
| PFE0060w | 2 | 1227 | 408 | 48.72 | 7.19 | 3 | 1 | yes | yes | no | Hypothetical |
| PF08_0034 | 4 | 4398 | 1485 | 170.92 | 6.65 | 0 | 0 | no | no | yes | Metabolism |
| PF08_0054 | 1 | 2034 | 677 | 73.92 | 5.33 | 0 | 0 | no | no | yes | Cell Cycle (DNA processing) |
| PFL2140c | 1 | 999 | 332 | 37.29 | 5.42 | 0 | 0 | no | no | yes | Hypothetical |
| PFC0210c | 1 | 1194 | 397 | 42.65 | 5.18 | 1 | 2 | no | yes | yes | Virulence |
| PFE1085w | 1 | 2526 | 841 | 97.34 | 7.96 | 0 | 3 | no | no | yes | Cell Cycle (DNA processing) |
| PF11_0404 | 3 | 7962 | 2653 | 309.45 | 6.12 | 0 | 0 | no | no | yes | Transcription |
| PF13_0201 | 1 | 1725 | 574 | 64.74 | 4.7 | 0 | 1 | no | yes | yes | Hypothetical |
| PFL2505c | 8 | 6648 | 2215 | 263.16 | 9.62 | 3 | 0 | no | yes | yes | Hypothetical |
| PF13_0222 | 1 | 1728 | 575 | 61.56 | 5.08 | 0 | 0 | no | no | no | Protein Synthesis |
| MAL13P1.22 | 2 | 2739 | 912 | 104.51 | 7.66 | 0 | 1 | no | yes | yes | Cell Cycle (DNA processing) |

The 10 antigens on the global list with the highest AUC values (0.86-0.93) also had very low p values (protected vs. not protected; 0.0015-0.033). Unexpectedly, all of these antigens had an average SI below 3000 (protected), suggesting that high antibody recognition and reactivity (i.e., sero-dominance) to a single antigen does not correlate with sporozoite-induced protection. Indeed, the average SI for 75 of the 86 antigens was below 5000, and 80 of the 86 were below 10000.

Figure 4:
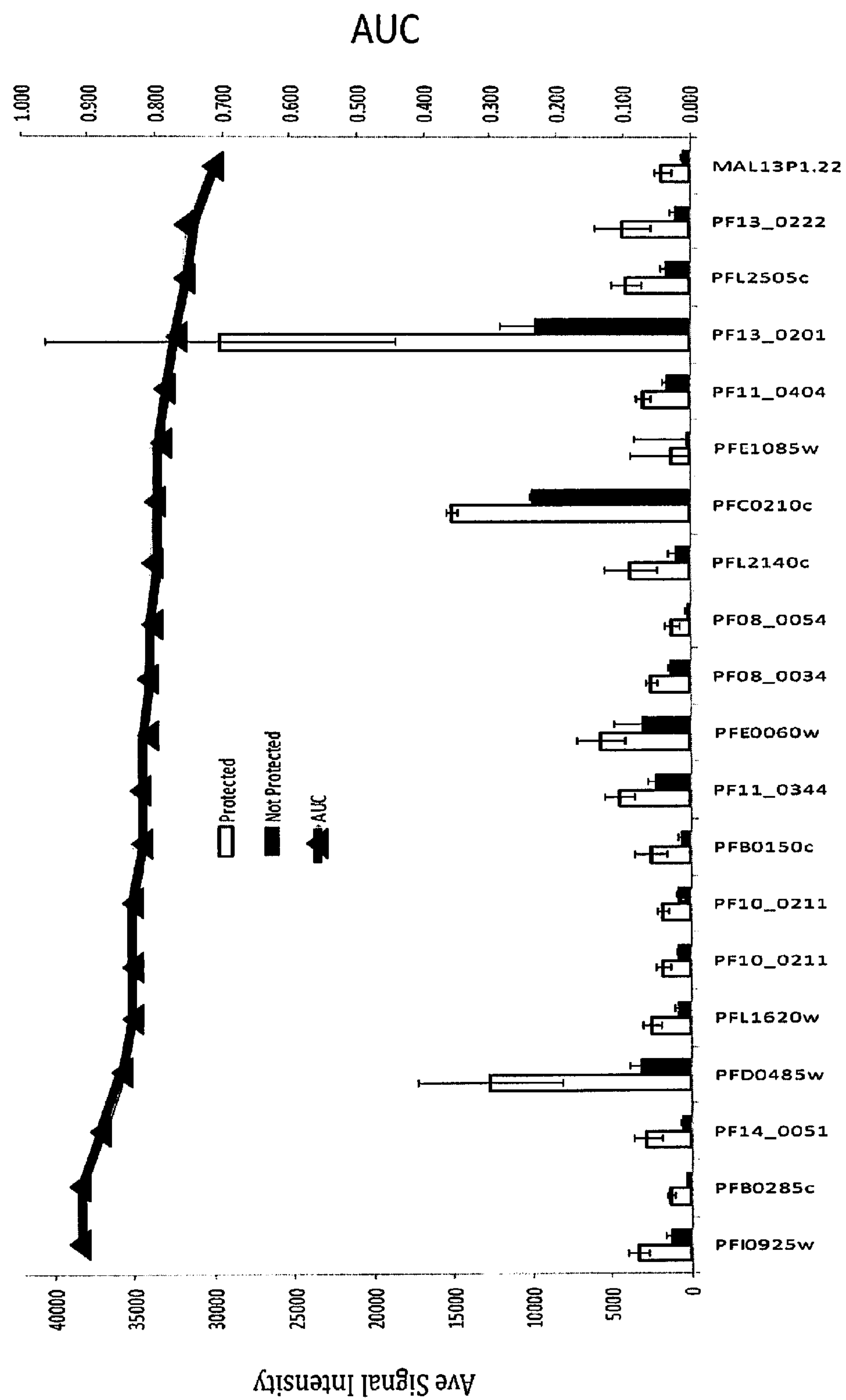
FIG. 4. Magnitude and frequency of recognition of the proteins in Table 1 associated with irradiated sporozoite induced protection. Average signal intensities of the antigens for each clinical group (protected, white bar; not protected, black bar) are presented as histograms, with antigen IDs listed on the x-axis. The average signal intensity (±s.e.m) for each antigen is shown. Antigens are ordered by decreasing AUC value.

As shown in FIG. 2, protected individuals had a significantly greater cumulative antibody response to the antigens of Table 1, as compared to not protected individuals (P<0.0055). FIG. 4 shows the average signal intensities of the 20 antigens in Table 1 for each clinical group. This remarkable difference in cumulative response between the protected and non-protected individuals, suggests that sterile immunity is associated with a panel of antigens, not with individual antigens.

The majority of the global IrrSpz list (93%; 72/77 proteins) and genes in Table 1 (89%, 17/19 proteins) were detected via independent mass spectrometry (MS/MS) analysis of sporozoites (Florens, et al., Nature 419:520-526 (2002); Hall, et al., Science 307:82-86 (2005); Lasonder, et al., PLoS Pathog. 4:e1000195 (2008); Kappe, et al., Proc.

Natl. Acad. Sci. (USA) 98:9895-9900 (2001)) or liver stage and/or sporozoite gene expression data (Kappe, et al., Proc. Natl. Acad. Sci. (USA) 98:9895-9900 (2001); Le Roch, et al., Science 301:1503-1508 (2003); Rosinski-Chupin, et al., BMC Genomics 8:466 (2007); Siau, et al., PLoS Pathog. 4:e1000121 (2008); Tarun, et al., Proc. Natl. Acad. Sci. (USA) 105:305-310 (2008)), PlasmoDB™), validating the expression of the genes during the pre-erythrocytic stage of the parasite life cycle.

Example 2

Characterization of Antigens Associated with Protection

This example illustrates the characterization of the proteins associated with protection. To identify specific genomic or proteomic features of antigens putatively associated with IrrSpz-induced protection, selected characteristics of the global IrrSpz list and the proteins listed in Table 1 were compared to the *Plasmodium falciparum* genome and to the known blood stage antigens (BSA) and sporozoite/liver stage antigens (SLA). The antigens from the global IrrSpz list and genes listed in Table 1 average respectively 3 and 2.5 fold larger for their transcription length, protein length and molecular weight as compared to the *Plasmodium falciparum* genome, BSA or SLA (Table 2); this is consistent with the fact that large proteins potentially present a greater number of B cell epitopes for antibody recognition. There was no difference in average isoelectric points (pI) or the number of exons compared to the *P. falciparum* genome, although the BSA and SLA had a lower average pI value than the other groups (Table 2).

TABLE 2

Comparison of genomic and proteomic features from antigens associated with protection[1]

| | Top 20 list (n = 20) | Global list (n = 86) | Known sporozoite/liver stage antigens (n = 7) | Known blood stage antigens (n = 17) | Pf genome (n = 5479) |
|---|---|---|---|---|---|
| Ave number of Exons | 2.3 | 3 | 1.6 | 1.9 | 2.5 |
| Ave Transcription Length (bp) | 5711 | 6909 | 2245 | 2274 | 2270 |
| Ave protein length (aa) | 1902 | 2302 | 747 | 760 | 755 |
| Ave pI value | 7.1 | 7.8 | 5.3 | 5.3 | 8 |
| Ave Mw (kDa) | 224 | 272 | 85 | 87 | 89 |
| Number with TM domains | 30% | 34% | 71% | 41% | 31% |
| Number with Signal peptide | 35% | 24% | 100% | 65% | 19% |
| Number with PEXEL motif | 45% | 53% | 71% | 23% | 27% |

[1]Characteristics of the global irradiated sporozoite list and top 20 list (i.e., antigens in Table 1) are compared to known vaccine candidates and the *P. falciparum* genome (PlasmoDB ™). Attributes such as average (Ave) number of exons, gene (bp) and protein (aa) size, isoelectric point (pI), presence of features that are recognized by antibodies (transmembrane domains, signal peptide, (PEXEL motif), were compared.

An enrichment of *Plasmodium* export element (PEXEL) motifs was noted in a global IrrSpz list (2-fold, Table 2) compared to whole genome and known BSA. The global list of revealed 86 fragments representing 77 proteins.

PEXEL motifs are found in five of seven known SLA, consistent with a function in the transport of liver stage parasite proteins to hepatocytes. Although signal peptides have been identified in all known SLA and 11 of 17 known BSA, consistent with a role for secretion in inducing antibody responses, antigens containing a signal peptide were not enriched in the proteins in Table 1 (35%, 7/20, p-value=0.08) or global list (24%, 21/68, p-value=0.31). These data are consistent with the concept that IrrSpz protection is mediated by T cells rather than antibodies. Also consistent with this is the observation that only 30% (p-value=0.64) and 34% (p-value=0.9) of genes in Table 1 or Global IrrSpz list antigens, respectively, had defined transmembrane domains, which are associated with exposure of surfaces for antibody recognition (Table 2).

Identified proteins were assigned functional categories based on annotation information available from PlasmoDB (PlasmoDB: a functional genomic database for malaria parasites. Nucleic Acids Res. 2008 Oct. 31. Aurrecoechea C, et al). Fifty-six percent of the global and 40% of the 20 sterile immunity-associated proteins were hypothetical proteins, with the remainder assigned to multiple functional categories. Interestingly, the functional categories for the proteins in Table 1 showed a notable concentration of genes/proteins involved in or regulating DNA processing/cell cycle (20%) and protein synthesis (20%); cellular communication, transport facilitation and protein fate were not represented in this subset. Gene ontology analysis also indicates an overrepresentation of biological processes involving DNA, invasion and metabolic processes, DNA related activity and perhaps a localization of these proteins for invasion purposes.

Example 3

Immunogenic Composition and Method of Use for Immunizing Against Malaria Using Identified Proteins This example illustrates a method of inducing an immune response against malaria. In a preferred embodiment, one or more of the identified proteins listed in Table 1, associated with sterile immunity, can be incorporated in an immunogenic composition, such as a vaccine. In one example, all of the proteins listed in Table 1 can be incorporated into an immunogenic composition.

In this embodiment, the immunogenic composition can be a subunit immunogenic composition or vaccine, composed of one or more of the isolated proteins, or immunogenic fragments or derivatives of the proteins, selected from the list of proteins in Table 1 that afforded sterile protection against malaria. Alternatively, an immunogenic composition or vaccine can be composed of nucleic acid, encoding one or more of the proteins of Table 1, or immunogenic fragments or derivatives of the proteins, inserted into one or more expression systems suitable for expression in mammals, such as humans. Table 3 lists the proteins from Table 1 and their associated sequence identification numbers.

TABLE 3

Summary of Sequence Numbers

| Protein Designation | Sequence ID No. (DNA) | SEQ ID. No. (Polypeptide) |
|---|---|---|
| PFI0925w | 1 | 2 |
| PFB0285c | 3 | 4 |
| PF14_0051 | 5 | 6 |
| PFD0485w | 7 | 8 |
| PFL1620w | 9 | 10 |
| PF10_0211 | 11 | 12 |
| PFB0150c | 13 | 14 |
| PF11_0344 | 15 | 16 |
| PFE0060w | 17 | 18 |
| PF08_0034 | 19 | 20 |
| PF08_0054 | 21 | 22 |
| PFL2140c | 23 | 24 |
| PFC0210c | 25 | 26 |
| PFE1085w | 27 | 28 |
| PF11_0404 | 29 | 30 |
| PF13_0201 | 31 | 32 |
| PFL2505c | 33 | 34 |
| PF13_0222 | 35 | 36 |
| MAL13P1.22 | 37 | 38 |

It is contemplated that the antigen(s) can be expressed either as a component of a DNA vaccine or other platform system. An example of a contemplated expression system includes, but is not limited to, viral systems, including replicating and nonreplicating vectors. Examples of contemplated viral vectors include adenovirus, alphavirus, poxvirus, cytopmegalovirus, canine distemper virus and yellow fever virus. The antigen(s) could be incorporated as an insert of a DNA or other vaccine expression system, either as a single antigen or multiple antigen expression systems from a single or multiple promoters.

The contemplated invention includes a method for inducing an immune response in mammals, including humans. In this example, antigen(s), either as polypeptide or incorporated into a nucleic acid expression system, such as a DNA or viral system, are administered in one or more doses. The method also contemplates inducing an immune response utilizing a prime-boost immunization regimen. In this embodiment, one or more priming immunization doses would be administered followed by one or more boosting immunizations.

The priming and boosting immunization comprises a composition containing a malaria polypeptide, wherein the polypeptide contains one or more of the polypeptide sequences of Table 3, or immunogenic derivatives, thereof. Alternatively, the immunogenic composition can comprise an expression system capable of expressing the polypeptides in mammals. In this embodiment, nucleic acid molecules, listed in Table 3 or encoding the polypeptides, or derivatives thereof, of Table 3 can be inserted into a DNA plasmid or a viral expression vectors. Examples of viral expression vector systems include: alphavirus (and alphavirus replicons), adenovirus, poxvirus, adeno-associated virus, cytomegalovirus, canine distemper virus, yellow fever virus and retrovirus.

The contemplated methods also include immunization regimens wherein the priming immunization comprises malarial peptides expressed from a DNA plasmid expression vector or an adenovirus, while the boosting immunization includes malaria peptides expressed from either: adenovirus, adenovirus that is heterologous to the priming adenovirus, poxvirus or one or more malaria polypeptides. The expressed malaria polypeptide and encoding nucleic acid can be any of a number of malarial polypeptides and nucleic acid sequences Table 3, or immunogenic derivatives of the polypeptides, thereof.

All references, including publications, patent applications and patents, cited are herein incorporated by reference.

Having described the invention, one of skill in the art will appreciate in the appended claims that many modifications and variations of the present invention are possible in light of the above teachings. It is therefore, to be understood that, within the scope of the appended claims, the invention may be practiced otherwise than as specifically described.

What is claimed is:

1. An immunogenic composition comprising a nucleic acid sequence expressed by a suitable expression system, wherein said nucleic acid sequence expresses an isolated protein expressed by *Plasmodium falciparum* sporozoites encoded by the locus PFD0485, wherein the isolated protein has the amino acid sequence of SEQ ID No. 8 and wherein said isolated protein is expressed from a nucleotide sequence inserted into a suitable expression vector capable of protein expression in a mammal, wherein the nucleotide sequence comprises the nucleotide sequence of SEQ ID No. 7, wherein said suitable expression vector is a DNA plasmid or replicating or nonreplicating viral vector.

2. The immunogenic composition of claim 1, wherein the composition also comprises a nucleic acid sequence expressed by a suitable expression system, wherein said nucleic acid sequence expresses isolated proteins expressed by *Plasmodium falciparum* sporozoites encoded by one or more of the loci selected from the group consisting of PFI0925w, PFB02S5c, PF14_0051, PFL1620w, PF10_0211, PFB0150c, PF11_0344, PFE0060w, PF08_0034, PF08_0054, PF2140c, PFC0210c, PFE1085w, PF11_0404, PF13_0201, PFL2505c, PF13_0222, and MAL13P1.22, wherein the isolated proteins have the amino acid sequences selected from the group consisting of, with the amino acid sequences of SEQ ID No. 2, SEQ ID No. 4, SEQ ID No. 6, SEQ ID No. 10, SEQ ID No. 12, SEQ ID No. 14, SEQ ID No. 16, SEQ ID No. 18, SEQ ID No. 20, SEQ ID No. 22, SEQ ID No. 24, SEQ ID No. 26, SEQ ID No. 28, SEQ ID No. 30, SEQ ID No. 32, SEQ ID No. 34, SEQ ID No. 36, and SEQ ID No. 38, wherein the one or more isolated proteins are encoded by one or more the nucleic acid sequences of SEQ ID No. 1, SEQ ID No. 3, SEQ ID No. 5, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID 25, SEQ ID No. 27, SEQ ID No. 29, SEQ ID No. 31, SEQ ID No. 33, SEQ ID No. 35, and SEQ ID No. 37 and inserted into and expressed from a suitable expression system, wherein said suitable expression vector is a DNA plasmid or replicating or nonreplicating viral vector.

3. The immunogenic composition of claim 1, wherein said viral vector is selected from the group consisting of DNA plasmid, alphavirus replicon, adenovirus, poxvirus, adeno-associated virus, cytomegalovirus, canine distemper virus, yellow fever virus and retrovirus.

4. The immunogenic composition of claim 3, wherein the alphavirus replicon preparation is selected from the group consisting of RNA replicons, DNA replicons and alphavirus replicon particles.

5. The immunogenic composition of claim 4, wherein the alphavirus is selected from the group consisting of Venezuelan Equine Encephalitis Virus, Semliki Forest Virus and Sindbis Virus.

6. The immunogenic composition of claim 1, wherein said viral vector is selected from the group consisting of DNA plasmid alphavirus replicon, adenovirus, poxvirus, adeno-associated virus, cytomegalovirus, canine distemper virus, yellow fever virus and retrovirus.

7. The immunogenic composition of claim 6, wherein the poxvirus is selected from the group consisting of cowpox, canarypox, vaccinia, modified vaccinia Ankara, or fowlpox.

* * * * *

SEQUENCE LISTING

```
<160> NUMBER OF SEQ ID NOS: 38

<210> SEQ ID NO 1
<211> LENGTH: 3192
<212> TYPE: DNA
<213> ORGANISM: Plasmodium falciparum

<400> SEQUENCE: 1

atgggttttc taaaaatcgg aacgccatta agctgggatg atgtacaaga tgtgaaatct      60

ttaattagat tatatggtat attacagttt gtacatgtat ataaattaaa taaagaccgt     120

tatgatgaaa atataatgtt tggtgatgaa attgaatata taataataag aaatgatgaa     180

agcttaaaag aatcgtctgc cttattatgt gcttctgatt taatagatga aatgatgaat     240

ttagaaagtg ttattgactg tcaatatggt tcacattgga ctccagaata ttcttctttt     300

actatagaag gtactccatc agtaccattt aaattagata ttaattcttc atgttttgtt     360

gaagattgta tgagaattag aagaagtaaa ttaaataatg ttcttagtgc cgttcaagga     420

gctagagcta ttacacttcc ttgttttcct aatgttcttt taaataatag tgttcttatg     480

gctagaagaa ttactggcca tgaaagtaca aaaaagaaat ttgattcaaa aggaaaagtc     540
```

```
gaatttatag aaaatgcgaa aattaaagaa aaggttcata attcaaataa taatatacac    600
aaaataatta ataataaaaa caatgaatct aaaattgtta ataatgcatt tgatcaaaat    660
aaaatctctt ctattgaaat ggtatcctat gagatggatg aaaataaatc taccaatttt    720
gttaattcag atacagtatt tgcaaaaaat gacgaagaag gagaagtaga agaagaagac    780
gaaaatgaaa acgaacaaca acaacaacag caacaatacc aatcgaattt acaacaacaa    840
aatgtacaac caaaacaacg tcaacaaatg atacaatatg tctatgatga tgaaatagaa    900
aataaaaata aagaaaagga taatacacca agaagctgta atgattacaa taatgttaat    960
gatagttcaa atacacaaga tatatttatt agttcattaa aaaaaacaga ttcacttttc   1020
gaatgtgaag tttttaaacc tgaacaaaca aataaatata gtaaaagtgc acttattaca   1080
gatatgacta taagtcctca tgccagatat gttaccttaa cacaaaatat aagaaaacga   1140
agaggaacca aaattgtatc ctttaatcct atatataaag atattaatac cgaaaaaatg   1200
gatcactgga aatgtcact tgattgtaat gataaaagac tttttaaaaa agttaagaag    1260
aaactcacat tagatgaaca cctaatatgg aataaatcta tgacaaacaa aaagattata   1320
gatagaaaaa ataacaatcc aagagatgag gtactaaaca cgtctaattt tacattagct   1380
atgacaaata aagaagaaaa taataatgaa aatagcctta tggatagggt tttgaaaaat   1440
agtttatttg cgaatatgga tgatgaaggt gattatattt atgtttataa tagagaattt   1500
atacaagaat attcagaaaa atgtaaaaat ccaattaaaa attatgtata tttagatgct   1560
atgtttttg gtatgagtat gtgttgtcaa caattaacca tgtcttttcc aactgttgat    1620
gatgcaaaat atgtgtatga tcaactagcc gttattgcac cacttttcct tgctcttact   1680
gcatgtactc cctatttagg tgggtttcta actgaaacag atacaagatg gagagtaata   1740
tctaacagtg ttgattgtag aacggaagaa gaattatcat atatatgtaa accaagatat   1800
tcaggaatat ccttatatat atccaatgag ttacctttaa aaagaaatta ctatttttat   1860
aacgatgtag atgtaatact tgacaaaaat gtgtatgaca aattgaaaaa ggaaaacgtg   1920
gatgaatatt tagctagaca tatagcatct ttatttgtaa gagatccaat tgttgttttt   1980
gaaggttcct atagtgaacg tgacattgct acaattcaga agaaaataat ggaattgtca   2040
aacgatgaag ataaaattaa aggtatggta gaagggtcat catcaaatag tttgtcatca   2100
aaagttttgt tagacaatga ggataggaat aaaaatgata gtagtataaa agaaatgaat   2160
aaatctaatg ataataacca taataataat tgccatattg aatataataa taaaaaagat   2220
ataaatatga ataagatata tttaagtgat aattttgaat ttatagaaga ttatgaagaa   2280
aaggttttat catctcatca acattttgaa aattttcaaa gtactaattg gaatagtgta   2340
cgttttaagc cacctccaat tcttgataat cattttaaag gacctagttc aattggatgg   2400
agagttgaat ttagaactcc tgatattcaa attaccgatt ttgagaattc ttgtgttgtt   2460
acattagtta tgttattatc taaatttata ttaaaagaaa gattaaattt atatattcct   2520
atgacattgt tagaagaaaa tttatttaga gcatccaaaa gagaagcttt aacaaaagaa   2580
aaattttatt tccgtaaaga tctaagttat gataccttga ataatgaatt tgaggaaaaa   2640
agtatatatg atatattttt taatgaaacc aatggattgt ttttcttatg ttacaaatat   2700
gtggacgaac tatttaaaga aggattatta aatcaatcag ccaaaaaataa aatagatgaa  2760
tatattgaat tcgttaaaca aagatgtagt ggaaaaatat gtacaggtgc tatgtattta   2820
agaaatttta tattaaatca tccagcttat gaaaaaaatt cttatatcaa tagtaaaatt   2880
aattatgata tatgtaaatt aatagctgat attggaaagg gattaatcat accacaagaa   2940
```

```
ttattaggtg tttttgtcga tccatataaa gaaaggataa aaagtgatat aaggcaaatt   3000

aatgaaagcc aatacctgaa gtccttggca tataaatata tttcaggaga ggattatacg   3060

caatacttgc tacttaatga agtacttaag gatgaccagg attattgtac atgtaccaga   3120

cgtacaattt atgaggaatc tatggataat acagtggagt ttgcaaaaaa aatgtacgaa   3180

ctgagtgcat aa                                                       3192


<210> SEQ ID NO 2
<211> LENGTH: 1063
<212> TYPE: PRT
<213> ORGANISM: Plasmodium falciparum

<400> SEQUENCE: 2

Met Gly Phe Leu Lys Ile Gly Thr Pro Leu Ser Trp Asp Asp Val Gln
1               5                   10                  15

Asp Val Lys Ser Leu Ile Arg Leu Tyr Gly Ile Leu Gln Phe Val His
            20                  25                  30

Val Tyr Lys Leu Asn Lys Asp Arg Tyr Asp Glu Asn Ile Met Phe Gly
        35                  40                  45

Asp Glu Ile Glu Tyr Ile Ile Ile Arg Asn Asp Glu Ser Leu Lys Glu
    50                  55                  60

Ser Ser Ala Leu Leu Cys Ala Ser Asp Leu Ile Asp Glu Met Met Asn
65                  70                  75                  80

Leu Glu Ser Val Ile Asp Cys Gln Tyr Gly Ser His Trp Thr Pro Glu
                85                  90                  95

Tyr Ser Ser Phe Thr Ile Glu Gly Thr Pro Ser Val Pro Phe Lys Leu
            100                 105                 110

Asp Ile Asn Ser Ser Cys Phe Val Glu Asp Cys Met Arg Ile Arg Arg
        115                 120                 125

Ser Lys Leu Asn Asn Val Leu Ser Ala Val Gln Gly Ala Arg Ala Ile
    130                 135                 140

Thr Leu Pro Cys Phe Pro Asn Val Leu Leu Asn Asn Ser Val Leu Met
145                 150                 155                 160

Ala Arg Arg Ile Thr Gly His Glu Ser Thr Lys Lys Lys Phe Asp Ser
                165                 170                 175

Lys Gly Lys Val Glu Phe Ile Glu Asn Ala Lys Ile Lys Glu Lys Val
            180                 185                 190

His Asn Ser Asn Asn Asn Ile His Lys Ile Ile Asn Asn Lys Asn Asn
        195                 200                 205

Glu Ser Lys Ile Val Asn Asn Ala Phe Asp Gln Asn Lys Ile Ser Ser
    210                 215                 220

Ile Glu Met Val Ser Tyr Glu Met Asp Glu Asn Lys Ser Thr Asn Phe
225                 230                 235                 240

Val Asn Ser Asp Thr Val Phe Ala Lys Asn Asp Glu Glu Gly Glu Val
                245                 250                 255

Glu Glu Glu Asp Glu Asn Glu Asn Glu Gln Gln Gln Gln Gln Gln Gln
            260                 265                 270

Tyr Gln Ser Asn Leu Gln Gln Gln Asn Val Gln Pro Lys Gln Arg Gln
        275                 280                 285

Gln Met Ile Gln Tyr Val Tyr Asp Asp Glu Ile Glu Asn Lys Asn Lys
    290                 295                 300

Glu Lys Asp Asn Thr Pro Arg Ser Cys Asn Asp Tyr Asn Asn Val Asn
305                 310                 315                 320
```

-continued

```
Asp Ser Ser Asn Thr Gln Asp Ile Phe Ile Ser Ser Leu Lys Lys Thr
                325                 330                 335

Asp Ser Leu Phe Glu Cys Glu Val Phe Lys Pro Glu Gln Thr Asn Lys
            340                 345                 350

Tyr Ser Lys Ser Ala Leu Ile Thr Asp Met Thr Ile Ser Pro His Ala
        355                 360                 365

Arg Tyr Val Thr Leu Thr Gln Asn Ile Arg Lys Arg Arg Gly Thr Lys
    370                 375                 380

Ile Val Ser Phe Asn Pro Ile Tyr Lys Asp Ile Asn Thr Glu Lys Met
385                 390                 395                 400

Asp His Trp Lys Met Ser Leu Asp Cys Asn Asp Lys Arg Leu Phe Lys
                405                 410                 415

Lys Val Lys Lys Lys Leu Thr Leu Asp Glu His Leu Ile Trp Asn Lys
            420                 425                 430

Ser Met Thr Asn Lys Lys Ile Ile Asp Arg Lys Asn Asn Asn Pro Arg
        435                 440                 445

Asp Glu Val Leu Asn Thr Ser Asn Phe Thr Leu Ala Met Thr Asn Lys
    450                 455                 460

Glu Glu Asn Asn Asn Glu Asn Ser Leu Met Asp Arg Val Leu Lys Asn
465                 470                 475                 480

Ser Leu Phe Ala Asn Met Asp Asp Glu Gly Asp Tyr Ile Tyr Val Tyr
                485                 490                 495

Asn Arg Glu Phe Ile Gln Glu Tyr Ser Glu Lys Cys Lys Asn Pro Ile
            500                 505                 510

Lys Asn Tyr Val Tyr Leu Asp Ala Met Phe Phe Gly Met Ser Met Cys
        515                 520                 525

Cys Gln Gln Leu Thr Met Ser Phe Pro Thr Val Asp Asp Ala Lys Tyr
    530                 535                 540

Val Tyr Asp Gln Leu Ala Val Ile Ala Pro Leu Phe Leu Ala Leu Thr
545                 550                 555                 560

Ala Cys Thr Pro Tyr Leu Gly Gly Phe Leu Thr Glu Thr Asp Thr Arg
                565                 570                 575

Trp Arg Val Ile Ser Asn Ser Val Asp Cys Arg Thr Glu Glu Glu Leu
            580                 585                 590

Ser Tyr Ile Cys Lys Pro Arg Tyr Ser Gly Ile Ser Leu Tyr Ile Ser
        595                 600                 605

Asn Glu Leu Pro Leu Lys Arg Asn Tyr Tyr Phe Tyr Asn Asp Val Asp
    610                 615                 620

Val Ile Leu Asp Lys Asn Val Tyr Asp Lys Leu Lys Lys Glu Asn Val
625                 630                 635                 640

Asp Glu Tyr Leu Ala Arg His Ile Ala Ser Leu Phe Val Arg Asp Pro
                645                 650                 655

Ile Val Val Phe Glu Gly Ser Tyr Ser Glu Arg Asp Ile Ala Thr Ile
            660                 665                 670

Gln Lys Lys Ile Met Glu Leu Ser Asn Asp Glu Asp Lys Ile Lys Gly
        675                 680                 685

Met Val Glu Gly Ser Ser Ser Asn Ser Leu Ser Ser Lys Val Leu Leu
    690                 695                 700

Asp Asn Glu Asp Arg Asn Lys Asn Asp Ser Ser Ile Lys Glu Met Asn
705                 710                 715                 720

Lys Ser Asn Asp Asn Asn His Asn Asn Asn Cys His Ile Glu Tyr Asn
                725                 730                 735

Asn Lys Lys Asp Ile Asn Met Asn Lys Ile Tyr Leu Ser Asp Asn Phe
```

```
            740                 745                 750

Glu Phe Ile Glu Asp Tyr Glu Glu Lys Val Leu Ser Ser His Gln His
        755                 760                 765

Phe Glu Asn Phe Gln Ser Thr Asn Trp Asn Ser Val Arg Phe Lys Pro
    770                 775                 780

Pro Pro Ile Leu Asp Asn His Phe Lys Gly Pro Ser Ser Ile Gly Trp
785                 790                 795                 800

Arg Val Glu Phe Arg Thr Pro Asp Ile Gln Ile Thr Asp Phe Glu Asn
                805                 810                 815

Ser Cys Val Val Thr Leu Val Met Leu Leu Ser Lys Phe Ile Leu Lys
            820                 825                 830

Glu Arg Leu Asn Leu Tyr Ile Pro Met Thr Leu Leu Glu Glu Asn Leu
        835                 840                 845

Phe Arg Ala Ser Lys Arg Glu Ala Leu Thr Lys Glu Lys Phe Tyr Phe
    850                 855                 860

Arg Lys Asp Leu Ser Tyr Asp Thr Leu Asn Asn Glu Phe Glu Glu Lys
865                 870                 875                 880

Ser Ile Tyr Asp Ile Phe Phe Asn Glu Thr Asn Gly Leu Phe Phe Leu
                885                 890                 895

Cys Tyr Lys Tyr Val Asp Glu Leu Phe Lys Glu Gly Leu Leu Asn Gln
            900                 905                 910

Ser Ala Lys Asn Lys Ile Asp Glu Tyr Ile Glu Phe Val Lys Gln Arg
        915                 920                 925

Cys Ser Gly Lys Ile Cys Thr Gly Ala Met Tyr Leu Arg Asn Phe Ile
    930                 935                 940

Leu Asn His Pro Ala Tyr Glu Lys Asn Ser Tyr Ile Asn Ser Lys Ile
945                 950                 955                 960

Asn Tyr Asp Ile Cys Lys Leu Ile Ala Asp Ile Gly Lys Gly Leu Ile
                965                 970                 975

Ile Pro Gln Glu Leu Leu Gly Val Phe Val Asp Pro Tyr Lys Glu Arg
            980                 985                 990

Ile Lys Ser Asp Ile Arg Gln Ile  Asn Glu Ser Gln Tyr  Leu Lys Ser
        995                 1000                1005

Leu Ala  Tyr Lys Tyr Ile Ser  Gly Glu Asp Tyr Thr  Gln Tyr Leu
    1010                1015                1020

Leu Leu  Asn Glu Val Leu Lys  Asp Asp Gln Asp Tyr  Cys Thr Cys
    1025                1030                1035

Thr Arg  Arg Thr Ile Tyr Glu  Glu Ser Met Asp Asn  Thr Val Glu
    1040                1045                1050

Phe Ala  Lys Lys Met Tyr Glu  Leu Ser Ala
    1055                1060


<210> SEQ ID NO 3
<211> LENGTH: 4311
<212> TYPE: DNA
<213> ORGANISM: Plasmodium falciparum

<400> SEQUENCE: 3

atgcagcaag atggtaatat acaagtaaaa atattaaaag atgtaaatcc ttattattat      60

aaaaaagaaa atccatacga caatttagaa tataataaat atgttatgaa tgtgaatgat     120

gttgagggaa cgaatattat tgatgataaa aaaaaggatt taggtaaatc aaaatatgat     180

atttttacga cagattcttt gtcaactact acagatgaag tatcttatag ttatcaaatc     240

gaaaataaaa atgaagaaaa agaatatttg agatattatg ataaacaggg aggtataata     300
```

```
cgacaagata ataataataa tgaaaataat aataataata tttgtaataa tgaccataat    360
aataataaca tttgtaataa tgaaaatatg ttaacaacaa aaaaaaatga taatacaata    420
ataaatagta atattaaata tttaaacaat aataatatat ttaataccaa catggtacca    480
caaaaaaatc acacacaaat atttaacccc tatgataaaa gtatgaggaa tattcaattg    540
tataataaag cagtaagctt tttaaaaaat gatggggaca taaattcaaa aaaaaatacc    600
catgataatt taatgttcct aaaaaatata cgaagtaaaa gtaataataa tcttattgta    660
aataggaaaa taacaaatca tgtgacaaat aatgtgataa gtggtatgac aaataaagtg    720
ataggtggta tggcaagtgg tatgacaaat aatgtgacaa gtagtataac aaataatatg    780
acaagtagta tgacaaataa tatggcaagt ggtatgacaa gtagtatgac aaataatatg    840
gcaagtggta tgacaagtag tataacaaat aatatgacaa gtagtatgac aaataatatg    900
gcaagtggta tgacaagtag tataacaaat aatatgacaa gtagtatgac aaataatatg    960
gcaagtagta tgacaagtag tatgacaaat aatatgacaa gtagtatgac aaataatatg   1020
acaagtagca tgacaaataa tatgcttaat aatatgaata gggttgtaac gaataatatt   1080
attactaata tgaacagatc agtttcggga agtaaaagta ttaacatgag caatctgtta   1140
atcataaata agatggatta tggtaatgac atttaccata acaacaacaa caataataat   1200
aatagtagta gtggtagcaa tattgtcagt ggtaaatatt ttgtgaattc tcaaaatagt   1260
agcaaaaata atttctttac aaaagtagga gaaagcacaa tacgatcacc aacaaacatt   1320
ttagatattt ataaacaggg aaatatgtat atgcacatcc caaaaaatgc agatttaatg   1380
aacaatgttt cttcatatag tatagcacat gaaaattata ttaaaaggga caacacaaat   1440
gtgactcatg tgttaaataa taaccacctt gtaaatataa ataatgtggt aaacaacaac   1500
aatttgaata ataacaacaa tttgaataat aacaacaatt tgaatagtaa caacaatttg   1560
aatagtaaca acaatttgaa taacaacaat aatttaatta ataacaataa tttaattaac   1620
aataattatg taagaaataa ccaagctgta aataacgctc atacattaaa tgctcatttt   1680
aacaaaagcg ataatgtgga taacatgaga aaccatattc caaacaatga caataaaaat   1740
attgtaaata tgttaaattt aaaaaaatatg aaaagtatta atgatttgtc agttttaata   1800
aataaaaata aacctattca tcatgtaata aatgggacag aggttcaaca aaaaagatcc   1860
ttgagtaatg ttcaaaaatt aaaaacgttg aacacttttc caaatgccaa gggaaggttt   1920
agtttgatca ataaaatggc tagcatgccg aatatgagca cgacgagtag tatgaacatg   1980
tcagggttaa acacaagctc gtctgaagga ttaaccaaca taattaatat gaataacata   2040
aacagtgtga ataatataaa cagtgtgaat aatataaaca gtgtgaataa tataaacagt   2100
gtgaataatt taaacagtgt gaataatata aacagtgtga ataatataaa cagtgtgaat   2160
aatataaaca gtgtgaataa cataaacagt gtgaataata taaacagtgt gaataatata   2220
aacagtgtga ataatttaaa cagtgtgaat aatataaaca gtgtgaataa tataaacaat   2280
ataaattata taaacaatat aaattatgta aatatgaaca agggtttgaa ccctataaat   2340
aatgtaagca atataagcag cctaaaattg ttaaacaata ataatgatat aaaaaagaaa   2400
tttaatacat atggaaaaag tgaggcgtcc gaaaatttaa gtaagaatgt caaatacata   2460
aaatatattc aagaaaatat taaatatttg aataatctgg atgataataa aaggaagtat   2520
tctctcacaa gtataaatga tgtgggatgt ataaaaaaaa aaaaaaatat gaatgattta   2580
tttttaggaa agcatgataa tatgttacgt acagatgaaa taccaaagat aaatttagga   2640
```

aaaaatatat tgaataataa taaaataata aattataatg ataatgataa aagtaatata 2700
ataaataatg ttataaataa gaacatttct acagatttgg tgaatgatag agagggtgat 2760
atgaataaaa tgaatattca taatagagag aaggatgaaa ataattatat aaatattggg 2820
gataataaaa taaagaaaaa tcaaattgat gttgttaata ataaggtaat gaaattggat 2880
aatatggagg atgaagaagc tatgaataaa ttatcattaa tatctttata tccaaacaat 2940
aatcacatta ttaataatgt gaataatgtg aataatgtga ataatgtgaa taatgtaaat 3000
aatgtgaata atgtaaataa tgtgaataat gtaaataatg tgaataatgt gaattatatg 3060
aataatatga ataatgtgaa taatgtgaat aatatgaata atgtgaataa tatgaataat 3120
gtgaataatg tgaatagtgt gaataatata aaaggaataa ataacatgaa caataataat 3180
aataatataa acatgaatcg aagttataaa atgaacatga aaaaagtgtc caaaaaagat 3240
aatggtcaaa atgtggtatc ggaaaaacga tttagcgaag aaaaatataa ttttcttaaa 3300
aatttaatac gaaataataa gaatatggta aaattaaaat atctgaataa atttttagga 3360
aaaagaagtg gaccatcaat aaaaaacaat atgaacgata tgatggttaa gatgaataat 3420
aacatgaagg atattatgca tataaaggat gcaactaata taaacaaaat taataataag 3480
ttggtaaatt taaatacgaa taattgtatt tcttataata gttgtaacaa aatgaattat 3540
atacataaat gtaaaaagaa aagagtttta tgtttagata cgaaacatgg gaaaaatgaa 3600
ataaaacaaa atgagaaatt aatttataca aattacgaaa taaaaatgtt tttgttaaat 3660
acgattaaag caataggtat agtttttaag aaatggaaat ttaaaaattt cggattatat 3720
ttttggtatc atattaaatg tatagaaaat gaaagagatt taaattttta tattaaaata 3780
tttaattttt tgtttgaaat cataacaggg aaaaatatat attaccaaat aaatgacatt 3840
cataacattg ttgcattatt taaagaattt aaaatatatg attgtaagca tgttcttaaa 3900
aaaagtatta aagttttaaa taaatatgca aaaaaaaatt caaaggaatt ctcacttttt 3960
gaaaataatc aacatgtagt attagacatc aataaacata tgttatttaa tgatgatgaa 4020
aaaaaattaa caacttgtaa tataaaacaa aatgaacaag aacaaattaa aaccaaagtt 4080
ctttatgatc atgataatat aaatgtagac acgaaacaaa attatcaaaa aataataaca 4140
aataaaaata atcatccaaa ggataatttt tattcatatc tatatgattc cttacaagga 4200
aaaaatcata tctttcaaca accaggcgta caaaatatgc atatatataa tatgtttgca 4260
caatttaatg aattaaattt taatgatatg tttaactttt caataaccta a 4311

<210> SEQ ID NO 4
<211> LENGTH: 1436
<212> TYPE: PRT
<213> ORGANISM: Plasmodium falciparum

<400> SEQUENCE: 4

Met Gln Gln Asp Gly Asn Ile Gln Val Lys Ile Leu Lys Asp Val Asn
1 5 10 15

Pro Tyr Tyr Tyr Lys Lys Glu Asn Pro Tyr Asp Asn Leu Glu Tyr Asn
20 25 30

Lys Tyr Val Met Asn Val Asn Asp Val Glu Gly Thr Asn Ile Ile Asp
35 40 45

Asp Lys Lys Lys Asp Leu Gly Lys Ser Lys Tyr Asp Ile Phe Thr Thr
50 55 60

Asp Ser Leu Ser Thr Thr Thr Asp Glu Val Ser Tyr Ser Tyr Gln Ile
65 70 75 80

```
Glu Asn Lys Asn Glu Glu Lys Glu Tyr Leu Arg Tyr Tyr Asp Lys Gln
                85                  90                  95

Gly Gly Ile Ile Arg Gln Asp Asn Asn Asn Asn Glu Asn Asn Asn Asn
            100                 105                 110

Asn Ile Cys Asn Asn Asp His Asn Asn Asn Asn Ile Cys Asn Asn Glu
        115                 120                 125

Asn Met Leu Thr Thr Lys Lys Asn Asp Asn Thr Ile Ile Asn Ser Asn
    130                 135                 140

Ile Lys Tyr Leu Asn Asn Asn Asn Ile Phe Asn Thr Asn Met Val Pro
145                 150                 155                 160

Gln Lys Asn His Thr Gln Ile Phe Asn Pro Tyr Asp Lys Ser Met Arg
                165                 170                 175

Asn Ile Gln Leu Tyr Asn Lys Ala Val Ser Phe Leu Lys Asn Asp Gly
            180                 185                 190

Asp Ile Asn Ser Lys Lys Asn Thr His Asp Asn Leu Met Phe Leu Lys
        195                 200                 205

Asn Ile Arg Ser Lys Ser Asn Asn Asn Leu Ile Val Asn Arg Lys Ile
    210                 215                 220

Thr Asn His Val Thr Asn Asn Val Ile Ser Gly Met Thr Asn Lys Val
225                 230                 235                 240

Ile Gly Gly Met Ala Ser Gly Met Thr Asn Asn Val Thr Ser Ser Ile
                245                 250                 255

Thr Asn Asn Met Thr Ser Ser Met Thr Asn Asn Met Ala Ser Gly Met
            260                 265                 270

Thr Ser Ser Met Thr Asn Asn Met Ala Ser Gly Met Thr Ser Ser Ile
        275                 280                 285

Thr Asn Asn Met Thr Ser Ser Met Thr Asn Asn Met Ala Ser Gly Met
    290                 295                 300

Thr Ser Ser Ile Thr Asn Asn Met Thr Ser Ser Met Thr Asn Asn Met
305                 310                 315                 320

Ala Ser Ser Met Thr Ser Ser Met Thr Asn Asn Met Thr Ser Ser Met
                325                 330                 335

Thr Asn Asn Met Thr Ser Ser Met Thr Asn Asn Met Leu Asn Asn Met
            340                 345                 350

Asn Arg Val Val Thr Asn Asn Ile Ile Thr Asn Met Asn Arg Ser Val
        355                 360                 365

Ser Gly Ser Lys Ser Ile Asn Met Ser Asn Leu Leu Ile Ile Asn Lys
    370                 375                 380

Met Asp Tyr Gly Asn Asp Ile Tyr His Asn Asn Asn Asn Asn Asn Asn
385                 390                 395                 400

Asn Ser Ser Ser Gly Ser Asn Ile Val Ser Gly Lys Tyr Phe Val Asn
                405                 410                 415

Ser Gln Asn Ser Ser Lys Asn Asn Phe Phe Thr Lys Val Gly Glu Ser
            420                 425                 430

Thr Ile Arg Ser Pro Thr Asn Ile Leu Asp Ile Tyr Lys Gln Gly Asn
        435                 440                 445

Met Tyr Met His Ile Pro Lys Asn Ala Asp Leu Met Asn Asn Val Ser
    450                 455                 460

Ser Tyr Ser Ile Ala His Glu Asn Tyr Ile Lys Arg Asp Asn Thr Asn
465                 470                 475                 480

Val Thr His Val Leu Asn Asn Asn His Leu Val Asn Ile Asn Asn Val
                485                 490                 495

Val Asn Asn Asn Asn Leu Asn Asn Asn Asn Asn Leu Asn Asn Asn Asn
```

```
            500                 505                 510

Asn Leu Asn Ser Asn Asn Asn Leu Asn Ser Asn Asn Asn Leu Asn Asn
        515                 520                 525

Asn Asn Asn Leu Ile Asn Asn Asn Asn Leu Ile Asn Asn Asn Tyr Val
    530                 535                 540

Arg Asn Asn Gln Ala Val Asn Asn Ala His Thr Leu Asn Ala His Phe
545                 550                 555                 560

Asn Lys Ser Asp Asn Val Asp Asn Met Arg Asn His Ile Pro Asn Asn
                565                 570                 575

Asp Asn Lys Asn Ile Val Asn Met Leu Asn Leu Lys Asn Met Lys Ser
            580                 585                 590

Ile Asn Asp Leu Ser Val Leu Ile Asn Lys Asn Lys Pro Ile His His
        595                 600                 605

Val Ile Asn Gly Thr Glu Val Gln Gln Lys Arg Ser Leu Ser Asn Val
    610                 615                 620

Gln Lys Leu Lys Thr Leu Asn Thr Phe Pro Asn Ala Lys Gly Arg Phe
625                 630                 635                 640

Ser Leu Ile Asn Lys Met Ala Ser Met Pro Asn Met Ser Thr Thr Ser
                645                 650                 655

Ser Met Asn Met Ser Gly Leu Asn Thr Ser Ser Ser Glu Gly Leu Thr
            660                 665                 670

Asn Ile Ile Asn Met Asn Asn Ile Asn Ser Val Asn Asn Ile Asn Ser
        675                 680                 685

Val Asn Asn Ile Asn Ser Val Asn Asn Ile Asn Ser Val Asn Asn Leu
    690                 695                 700

Asn Ser Val Asn Asn Ile Asn Ser Val Asn Asn Ile Asn Ser Val Asn
705                 710                 715                 720

Asn Ile Asn Ser Val Asn Asn Ile Asn Ser Val Asn Asn Ile Asn Ser
                725                 730                 735

Val Asn Asn Ile Asn Ser Val Asn Asn Leu Asn Ser Val Asn Asn Ile
            740                 745                 750

Asn Ser Val Asn Asn Ile Asn Asn Ile Asn Tyr Ile Asn Asn Ile Asn
        755                 760                 765

Tyr Val Asn Met Asn Lys Gly Leu Asn Pro Ile Asn Asn Val Ser Asn
    770                 775                 780

Ile Ser Ser Leu Lys Leu Leu Asn Asn Asn Asn Asp Ile Lys Lys Lys
785                 790                 795                 800

Phe Asn Thr Tyr Gly Lys Ser Glu Ala Ser Glu Asn Leu Ser Lys Asn
                805                 810                 815

Val Lys Tyr Ile Lys Tyr Ile Gln Glu Asn Ile Lys Tyr Leu Asn Asn
            820                 825                 830

Leu Asp Asp Asn Lys Arg Lys Tyr Ser Leu Thr Ser Ile Asn Asp Val
        835                 840                 845

Gly Cys Ile Lys Lys Lys Lys Asn Met Asn Asp Leu Phe Leu Gly Lys
    850                 855                 860

His Asp Asn Met Leu Arg Thr Asp Glu Ile Pro Lys Ile Asn Leu Gly
865                 870                 875                 880

Lys Asn Ile Leu Asn Asn Asn Lys Ile Ile Asn Tyr Asn Asp Asn Asp
                885                 890                 895

Lys Ser Asn Ile Ile Asn Asn Val Ile Asn Lys Asn Ile Ser Thr Asp
            900                 905                 910

Leu Val Asn Asp Arg Glu Gly Asp Met Asn Lys Met Asn Ile His Asn
        915                 920                 925
```

```
Arg Glu Lys Asp Glu Asn Asn Tyr Ile Asn Ile Gly Asp Asn Lys Ile
    930                 935                 940

Lys Lys Asn Gln Ile Asp Val Val Asn Asn Lys Val Met Lys Leu Asp
945                 950                 955                 960

Asn Met Glu Asp Glu Glu Ala Met Asn Lys Leu Ser Leu Ile Ser Leu
                965                 970                 975

Tyr Pro Asn Asn Asn His Ile Ile Asn Asn Val Asn Asn Val Asn Asn
            980                 985                 990

Val Asn Asn Val Asn Asn Val Asn  Asn Val Asn Asn Val  Asn Asn Val
        995                 1000                1005

Asn Asn  Val Asn Asn Val Asn  Asn Val Asn Tyr Met  Asn Asn Met
    1010                 1015                 1020

Asn Asn  Val Asn Asn Val Asn  Asn Met Asn Asn Val  Asn Asn Met
    1025                 1030                 1035

Asn Asn  Val Asn Asn Val Asn  Ser Val Asn Asn Ile  Lys Gly Ile
    1040                 1045                 1050

Asn Asn  Met Asn Asn Asn Asn  Asn Asn Ile Asn Met  Asn Arg Ser
    1055                 1060                 1065

Tyr Lys  Met Asn Met Lys Lys  Val Ser Lys Lys Asp  Asn Gly Gln
    1070                 1075                 1080

Asn Val  Val Ser Glu Lys Arg  Phe Ser Glu Glu Lys  Tyr Asn Phe
    1085                 1090                 1095

Leu Lys  Asn Leu Ile Arg Asn  Asn Lys Asn Met Val  Lys Leu Lys
    1100                 1105                 1110

Tyr Leu  Asn Lys Phe Leu Gly  Lys Arg Ser Gly Pro  Ser Ile Lys
    1115                 1120                 1125

Asn Asn  Met Asn Asp Met Met  Val Lys Met Asn Asn  Asn Met Lys
    1130                 1135                 1140

Asp Ile  Met His Ile Lys Asp  Ala Thr Asn Ile Asn  Lys Ile Asn
    1145                 1150                 1155

Asn Lys  Leu Val Asn Leu Asn  Thr Asn Asn Cys Ile  Ser Tyr Asn
    1160                 1165                 1170

Ser Cys  Asn Lys Met Asn Tyr  Ile His Lys Cys Lys  Lys Lys Arg
    1175                 1180                 1185

Val Leu  Cys Leu Asp Thr Lys  His Gly Lys Asn Glu  Ile Lys Gln
    1190                 1195                 1200

Asn Glu  Lys Leu Ile Tyr Thr  Asn Tyr Glu Ile Lys  Met Phe Leu
    1205                 1210                 1215

Leu Asn  Thr Ile Lys Ala Ile  Gly Ile Val Phe Lys  Lys Trp Lys
    1220                 1225                 1230

Phe Lys  Asn Phe Gly Leu Tyr  Phe Trp Tyr His Ile  Lys Cys Ile
    1235                 1240                 1245

Glu Asn  Glu Arg Asp Leu Asn  Phe Tyr Ile Lys Ile  Phe Asn Phe
    1250                 1255                 1260

Leu Phe  Glu Ile Ile Thr Gly  Lys Asn Ile Tyr Tyr  Gln Ile Asn
    1265                 1270                 1275

Asp Ile  His Asn Ile Val Ala  Leu Phe Lys Glu Phe  Lys Ile Tyr
    1280                 1285                 1290

Asp Cys  Lys His Val Leu Lys  Lys Ser Ile Lys Val  Leu Asn Lys
    1295                 1300                 1305

Tyr Ala  Lys Lys Asn Ser Lys  Glu Phe Ser Leu Phe  Glu Asn Asn
    1310                 1315                 1320
```

```
Gln His  Val Val Leu Asp Ile  Asn Lys His Met Leu  Phe Asn Asp
    1325                 1330                 1335

Asp Glu  Lys Lys Leu Thr Thr  Cys Asn Ile Lys Gln  Asn Glu Gln
    1340                 1345                 1350

Glu Gln  Ile Lys Thr Lys Val  Leu Tyr Asp His Asp  Asn Ile Asn
    1355                 1360                 1365

Val Asp  Thr Lys Gln Asn Tyr  Gln Lys Ile Ile Thr  Asn Lys Asn
    1370                 1375                 1380

Asn His  Pro Lys Asp Asn Phe  Tyr Ser Tyr Leu Tyr  Asp Ser Leu
    1385                 1390                 1395

Gln Gly  Lys Asn His Ile Phe  Gln Gln Pro Gly Val  Gln Asn Met
    1400                 1405                 1410

His Ile  Tyr Asn Met Phe Ala  Gln Phe Asn Glu Leu  Asn Phe Asn
    1415                 1420                 1425

Asp Met  Phe Asn Phe Ser Ile  Thr
    1430                 1435
```

<210> SEQ ID NO 5
<211> LENGTH: 4548
<212> TYPE: DNA
<213> ORGANISM: Plasmodium falciparum

<400> SEQUENCE: 5

```
atgtttttta tgtggttata taaatataag gtgtacatat atgtcatatt ttttgtactt     60

gttgaaaata cgatgagtat gaaaaagaat ttgatgttca catgttttaa taaaaaaaag    120

tttatatatg taaagaagaa tgtattattt ttgaataata aatatataag taatttggta    180

tataccaagg aagatgatat atataaaatt aatgagataa gtaatgttat aggaagaaat    240

agaaagaaaa agaatataat aataaataat gatgaggata atgataatat tgatagtaag    300

aataatgaac tgggtgataa tataatatca tcgaatagat atatgaataa tgtatttttt    360

acaaataata aaaatacatc actggaagtt agaaataata ataatgaaga tggtggtgat    420

gataacaaca acaataataa taataataat aataatatat tagatgtgtc atataatcat    480

gataaatata atttgtgtga taacgaatta caattatata aaaataaatg taaaattcca    540

ctttattgga ttaaaaaatt agataactta aaaaatatga atgctataaa ttgtatagaa    600

tatttgaaag atgataattt gttatatttt gataattata agaacaaagg attattaaaa    660

tttctaaatg atgaaaagag gaaatataat aattgtataa ttttgtcaag ggtaggtgat    720

ttttatgaaa catatggcct ggattctata ttcctcattg aatttttaaa cataaaaaaa    780

atgaataata gattatcatg tggttttatc aaaagcagta taaataaagc tttaaatata    840

ttaactaaca ataatttaaa tgtatgtata tatgaagaaa taaatgaaaa gtctttaaaa    900

atgaaaaaga gatatttatc gcaaattgta acacctgaat ttcctatata tttaaataat    960

atacaatact ataataagga tgaagatata ctacaaaatg gtaacaacaa taataataat   1020

agtaataata tgaatagtta taataacatg gataaatgtt tagataatgg aaatatgaat   1080

gcactatcct tttttagttc ttatgatcta gatgattatt ttgttataaa agaaattgtt   1140

tgtatatata tagaaagcaa aaatattttt tcattaagta aaattaattt aagcttaaaa   1200

actatatcta tatatgataa tataacattt gatgttttaa atgtatattt gaaaaatacg   1260

aattttttga aggtatatat acatcaacat attaatacat catttaccaa aaaaatcaca   1320

gagttattca aaatagaaaa ttattatttg tttaataatt tcaagtcaag tttttatttt   1380

catatgttta tattagacaa gctaaaaaaa caaatacacg taaaggggtt attcagattg   1440
```

```
ataaagaata aaaatgtttt caaaattaaa tcagctgatt gtaagaagga agagaaaaaa   1500

attgattcga atattagtga ttatatgaat tatgaggaga ataataaaat tagcaataga   1560

catataaata atgtaaataa taatattgaa gataatcaaa atgtagaaat aaataaaaat   1620

gtggaagata ataatattga gaaaattaaa aataaaaaca ttatagataa taattttgaa   1680

tattcttttt catcttattg tacacccttta aatatattta cgagttataa tatgggtata   1740

tataaacaaa ataatcatta tgaaaataaa agtaattttt tattttataa tattatagat   1800

ataaataata ataattcaaa tagtataaat atatcagaat cattagagtt ttttaaaaat   1860

atttttcttt tttatccacc ttttgaagtt acaaaacata taagatatat aaatgaatat   1920

attaaaaaga atgtgaaaga tttaatcata ccgaatgtaa aaccatttaa gaataatatt   1980

attatatctc ttttatcaaa tttaaaagcc gatcatcaca ttttaaaaaa aatattagta   2040

aatatagatg ctgtactaaa ttgtattaga aattatgatt tctcactttt agtatcaata   2100

tttaatgtat taaatcatca aaattctttt aaattaaata ttataaaatt ttatgaactt   2160

ttaatgaata ttcaaaaaat tatgaaagac aatttggatt taggtttatt ttctaaattc   2220

tcttatcagt cagatattca agcttttaat gattttgtta tatatcatga aaacgatgta   2280

cacaatataa ttaatgaaaa acttataact gaagaaaata aagaattaga aaaatccaga   2340

acagatttat tgaatacaat tatatcaaat tattcagaat gtgataaaac aaaaaatgca   2400

tataaagata ttaatttatt aaacaaaata ataaaaattg ataatgctaa tgatataata   2460

ggtatacgta aaaatataca aaaaaaaaaa aacaaaaatg aacaaatttc agattttttt   2520

catccattaa acaaaaaatc agatgttatg aaaaatttat atgtaactca agatgtacaa   2580

aataagatta aaacttattt attctcaatt tataaaaaaa aaaaaaaaat aaatgaaatt   2640

attcacaata taaatataca attgtcttcc tcagtgcaca tactttcatt tgtatctaac   2700

ttcttgcaga taattcaggc tctatacaac cataccatta acagtctcaa gaaaggatgg   2760

tccctaccaa tatgtaaaca cctacatttg tcatatgaaa atatgagctt caacaatatc   2820

gacgataagt tagcttatat acaaaaaaaa gtgtacgatg acaaagacga aataaaagag   2880

tacacattaa caaagaatgt aaataaaaat gatccttcga attattttat aaatgatcaa   2940

aagaatagca atgaatttgt aaaattatct ccatgtgatg aaaagaaaat tttagaaaac   3000

atagacaaag attcagcaga agaaataaaa aaaatgtata aagaaaaaaa ttacgttaac   3060

gattcaataa catatataat aggagccaaa ccttataata taataaaaca taatttaatt   3120

aaatatgatt ttttttaaa aaagaaaaat tttattttat tgactggaaa aaatatgagt   3180

ggaaaaacta cattgtcttt tacaattttg agtatattat ttttgtccaa tttgggtatg   3240

tatgcaccgt gtgatgaaaa cagcattata ggaaagtttc gagaatttta tagtttgaaa   3300

aatgtaaact atcaagagca aattgaaaat atgtccttat ttagggaaca agcttattat   3360

atcaattcag ttatagaaga aataaaagaa aattattctg ttgataaaag accaacaaga   3420

gaaaaggaaa tttttattgt cctcgatgaa ccatgtatag caaccacacc tgttgataat   3480

gcaattatta taagcgcagt ttcagattac ctgaaaaatt attgtggaat tataattaca   3540

cataactacg atttattaaa caaaatatgc cagagcgaaa acatcgtttt taaaagaatt   3600

agtaaagata ttaactacct gaaagaacaa gataataaaa tagttggtaa attagaagac   3660

ggtatttgta aaaacagtga agccttagaa acatgtagat atacaaatat agacccacat   3720

gttttaaatt tattaaatgt atatgaaaaa aaatataaat ttattcataa tttaagtaat   3780
```

```
acactatata ccaaattttt agaatatatt caatatagaa aagatgggaa gtgtctcaat   3840

gactttttg atcaatatat aaatgatata ataaaacaaa agagtgataa acatgaaata   3900

caatataata cacctagtaa tatggaaaat aattataata gttatagttc aaatgatcaa   3960

aagaattata tatcagaaaa tcacaagtat gattataatt atgatatcga ttacataaaa   4020

gataaagaat taaaaaatat aataaattct aataataata tacaagaatt tttaaacaat   4080

tatgataaga caaggataca taatgataat ccaactaatc ataaaccaga tcaatatgat   4140

aactcattag tttatgatga taaactaaat gttataatta aaaaaattga agaagcatca   4200

aataagaagg ttataaaaat aggaatgaat gaagaagtac ctatttatta taaaaataaa   4260

agtattgtat atattttatg tattttttca aaagatgaaa atgatccata tttttatata   4320

ggtataagtg ataatatttc agaaaggata aaatgtcata caagaaatct attaaataat   4380

aaaaatcttt taaaaaatcc aaagaaaaat aatctattaa attataaata tgattggact   4440

aaattctata ttttactttt tcatgttgat aataaaatgg ttgcatccaa atatgaaaag   4500

gacctttcga atttgttgaa gaataattat aacatattat ctaaataa                4548
```

```
<210> SEQ ID NO 6
<211> LENGTH: 1515
<212> TYPE: PRT
<213> ORGANISM: Plasmodium falciparum

<400> SEQUENCE: 6

Met Phe Phe Met Trp Leu Tyr Lys Tyr Lys Val Tyr Ile Tyr Val Ile
1               5                   10                  15

Phe Phe Val Leu Val Glu Asn Thr Met Ser Met Lys Lys Asn Leu Met
            20                  25                  30

Phe Thr Cys Phe Asn Lys Lys Lys Phe Ile Tyr Val Lys Lys Asn Val
        35                  40                  45

Leu Phe Leu Asn Asn Lys Tyr Ile Ser Asn Leu Val Tyr Thr Lys Glu
    50                  55                  60

Asp Asp Ile Tyr Lys Ile Asn Glu Ile Ser Asn Val Ile Gly Arg Asn
65                  70                  75                  80

Arg Lys Lys Lys Asn Ile Ile Ile Asn Asn Asp Glu Asp Asn Asp Asn
                85                  90                  95

Ile Asp Ser Lys Asn Asn Glu Leu Gly Asp Asn Ile Ile Ser Ser Asn
            100                 105                 110

Arg Tyr Met Asn Asn Val Phe Phe Thr Asn Asn Lys Asn Thr Ser Leu
        115                 120                 125

Glu Val Arg Asn Asn Asn Asn Glu Asp Gly Gly Asp Asp Asn Asn Asn
    130                 135                 140

Asn Asn Asn Asn Asn Asn Asn Asn Ile Leu Asp Val Ser Tyr Asn His
145                 150                 155                 160

Asp Lys Tyr Asn Leu Cys Asp Asn Glu Leu Gln Leu Tyr Lys Asn Lys
                165                 170                 175

Cys Lys Ile Pro Leu Tyr Trp Ile Lys Lys Leu Asp Asn Leu Lys Asn
            180                 185                 190

Met Asn Ala Ile Asn Cys Ile Glu Tyr Leu Lys Asp Asp Asn Leu Leu
        195                 200                 205

Tyr Phe Asp Asn Tyr Lys Asn Lys Gly Leu Leu Lys Phe Leu Asn Asp
    210                 215                 220

Glu Lys Arg Lys Tyr Asn Asn Cys Ile Ile Leu Ser Arg Val Gly Asp
225                 230                 235                 240
```

-continued

```
Phe Tyr Glu Thr Tyr Gly Leu Asp Ser Ile Phe Leu Ile Glu Phe Leu
                245                 250                 255

Asn Ile Lys Lys Met Asn Asn Arg Leu Ser Cys Gly Phe Ile Lys Ser
            260                 265                 270

Ser Ile Asn Lys Ala Leu Asn Ile Leu Thr Asn Asn Asn Leu Asn Val
        275                 280                 285

Cys Ile Tyr Glu Glu Ile Asn Glu Lys Ser Leu Lys Met Lys Lys Arg
    290                 295                 300

Tyr Leu Ser Gln Ile Val Thr Pro Glu Phe Pro Ile Tyr Leu Asn Asn
305                 310                 315                 320

Ile Gln Tyr Tyr Asn Lys Asp Glu Asp Ile Leu Gln Asn Gly Asn Asn
                325                 330                 335

Asn Asn Asn Asn Ser Asn Asn Met Asn Ser Tyr Asn Asn Met Asp Lys
            340                 345                 350

Cys Leu Asp Asn Gly Asn Met Asn Ala Leu Ser Phe Phe Ser Ser Tyr
        355                 360                 365

Asp Leu Asp Asp Tyr Phe Val Ile Lys Glu Ile Val Cys Ile Tyr Ile
    370                 375                 380

Glu Ser Lys Asn Ile Phe Ser Leu Ser Lys Ile Asn Leu Ser Leu Lys
385                 390                 395                 400

Thr Ile Ser Ile Tyr Asp Asn Ile Thr Phe Asp Val Leu Asn Val Tyr
                405                 410                 415

Leu Lys Asn Thr Asn Phe Leu Lys Val Tyr Ile His Gln His Ile Asn
            420                 425                 430

Thr Ser Phe Thr Lys Lys Ile Thr Glu Leu Phe Lys Ile Glu Asn Tyr
        435                 440                 445

Tyr Leu Phe Asn Asn Phe Lys Ser Ser Phe Tyr Phe His Met Phe Ile
    450                 455                 460

Leu Asp Lys Leu Lys Lys Gln Ile His Val Lys Gly Leu Phe Arg Leu
465                 470                 475                 480

Ile Lys Asn Lys Asn Val Phe Lys Ile Lys Ser Ala Asp Cys Lys Lys
                485                 490                 495

Glu Glu Lys Lys Ile Asp Ser Asn Ile Ser Asp Tyr Met Asn Tyr Glu
            500                 505                 510

Glu Asn Asn Lys Ile Ser Asn Arg His Ile Asn Asn Val Asn Asn Asn
        515                 520                 525

Ile Glu Asp Asn Gln Asn Val Glu Ile Asn Lys Asn Val Glu Asp Asn
    530                 535                 540

Asn Ile Glu Lys Ile Lys Asn Lys Asn Ile Ile Asp Asn Asn Phe Glu
545                 550                 555                 560

Tyr Ser Phe Ser Ser Tyr Cys Thr Pro Leu Asn Ile Phe Thr Ser Tyr
                565                 570                 575

Asn Met Gly Ile Tyr Lys Gln Asn Asn His Tyr Glu Asn Lys Ser Asn
            580                 585                 590

Phe Leu Phe Tyr Asn Ile Ile Asp Ile Asn Asn Asn Asn Ser Asn Ser
        595                 600                 605

Ile Asn Ile Ser Glu Ser Leu Glu Phe Phe Lys Asn Ile Phe Leu Phe
    610                 615                 620

Tyr Pro Pro Phe Glu Val Thr Lys His Ile Arg Tyr Ile Asn Glu Tyr
625                 630                 635                 640

Ile Lys Lys Asn Val Lys Asp Leu Ile Ile Pro Asn Val Lys Pro Phe
                645                 650                 655

Lys Asn Asn Ile Ile Ile Ser Leu Leu Ser Asn Leu Lys Ala Asp His
```

```
            660                 665                 670

His Ile Leu Lys Lys Ile Leu Val Asn Ile Asp Ala Val Leu Asn Cys
        675                 680                 685

Ile Arg Asn Tyr Asp Phe Ser Leu Leu Val Ser Ile Phe Asn Val Leu
    690                 695                 700

Asn His Gln Asn Ser Phe Lys Leu Asn Ile Ile Lys Phe Tyr Glu Leu
705                 710                 715                 720

Leu Met Asn Ile Gln Lys Ile Met Lys Asp Asn Leu Asp Leu Gly Leu
                725                 730                 735

Phe Ser Lys Phe Ser Tyr Gln Ser Asp Ile Gln Ala Phe Asn Asp Phe
            740                 745                 750

Val Ile Tyr His Glu Asn Asp Val His Asn Ile Ile Asn Glu Lys Leu
        755                 760                 765

Ile Thr Glu Glu Asn Lys Glu Leu Glu Lys Ser Arg Thr Asp Leu Leu
    770                 775                 780

Asn Thr Ile Ile Ser Asn Tyr Ser Glu Cys Asp Lys Thr Lys Asn Ala
785                 790                 795                 800

Tyr Lys Asp Ile Asn Leu Leu Asn Lys Ile Ile Lys Ile Asp Asn Ala
                805                 810                 815

Asn Asp Ile Ile Gly Ile Arg Lys Asn Ile Gln Lys Lys Lys Asn Lys
            820                 825                 830

Asn Glu Gln Ile Ser Asp Phe Phe His Pro Leu Asn Lys Lys Ser Asp
        835                 840                 845

Val Met Lys Asn Leu Tyr Val Thr Gln Asp Val Gln Asn Lys Ile Lys
    850                 855                 860

Thr Tyr Leu Phe Ser Ile Tyr Lys Lys Lys Lys Lys Ile Asn Glu Ile
865                 870                 875                 880

Ile His Asn Ile Asn Ile Gln Leu Ser Ser Ser Val His Ile Leu Ser
                885                 890                 895

Phe Val Ser Asn Phe Leu Gln Ile Ile Gln Ala Leu Tyr Asn His Thr
            900                 905                 910

Ile Asn Ser Leu Lys Lys Gly Trp Ser Leu Pro Ile Cys Lys His Leu
        915                 920                 925

His Leu Ser Tyr Glu Asn Met Ser Phe Asn Asn Ile Asp Asp Lys Leu
    930                 935                 940

Ala Tyr Ile Gln Lys Lys Val Tyr Asp Asp Lys Asp Glu Ile Lys Glu
945                 950                 955                 960

Tyr Thr Leu Thr Lys Asn Val Asn Lys Asn Asp Pro Ser Asn Tyr Phe
                965                 970                 975

Ile Asn Asp Gln Lys Asn Ser Asn Glu Phe Val Lys Leu Ser Pro Cys
            980                 985                 990

Asp Glu Lys Lys Ile Leu Glu Asn  Ile Asp Lys Asp Ser  Ala Glu Glu
        995                 1000                1005

Ile Lys  Lys Met Tyr Lys Glu  Lys Asn Tyr Val Asn  Asp Ser Ile
    1010                1015                1020

Thr Tyr  Ile Ile Gly Ala Lys  Pro Tyr Asn Ile Ile  Lys His Asn
    1025                1030                1035

Leu Ile  Lys Tyr Asp Phe Phe  Leu Lys Lys Lys Asn  Phe Ile Leu
    1040                1045                1050

Leu Thr  Gly Lys Asn Met Ser  Gly Lys Thr Thr Leu  Ser Phe Thr
    1055                1060                1065

Ile Leu  Ser Ile Leu Phe Leu  Ser Asn Leu Gly Met  Tyr Ala Pro
    1070                1075                1080
```

```
Cys Asp  Glu Asn Ser Ile Ile  Gly Lys Phe Arg Glu  Phe Tyr Ser
    1085                 1090                 1095

Leu Lys  Asn Val Asn Tyr Gln  Glu Gln Ile Glu Asn  Met Ser Leu
    1100                 1105                 1110

Phe Arg  Glu Gln Ala Tyr Tyr  Ile Asn Ser Val Ile  Glu Glu Ile
    1115                 1120                 1125

Lys Glu  Asn Tyr Ser Val Asp  Lys Arg Pro Thr Arg  Glu Lys Glu
    1130                 1135                 1140

Ile Phe  Ile Val Leu Asp Glu  Pro Cys Ile Ala Thr  Thr Pro Val
    1145                 1150                 1155

Asp Asn  Ala Ile Ile Ile Ser  Ala Val Ser Asp Tyr  Leu Lys Asn
    1160                 1165                 1170

Tyr Cys  Gly Ile Ile Ile Thr  His Asn Tyr Asp Leu  Leu Asn Lys
    1175                 1180                 1185

Ile Cys  Gln Ser Glu Asn Ile  Val Phe Lys Arg Ile  Ser Lys Asp
    1190                 1195                 1200

Ile Asn  Tyr Leu Lys Glu Gln  Asp Asn Lys Ile Val  Gly Lys Leu
    1205                 1210                 1215

Glu Asp  Gly Ile Cys Lys Asn  Ser Glu Ala Leu Glu  Thr Cys Arg
    1220                 1225                 1230

Tyr Thr  Asn Ile Asp Pro His  Val Leu Asn Leu Leu  Asn Val Tyr
    1235                 1240                 1245

Glu Lys  Lys Tyr Lys Phe Ile  His Asn Leu Ser Asn  Thr Leu Tyr
    1250                 1255                 1260

Thr Lys  Phe Leu Glu Tyr Ile  Gln Tyr Arg Lys Asp  Gly Lys Cys
    1265                 1270                 1275

Leu Asn  Asp Phe Phe Asp Gln  Tyr Ile Asn Asp Ile  Ile Lys Gln
    1280                 1285                 1290

Lys Ser  Asp Lys His Glu Ile  Gln Tyr Asn Thr Pro  Ser Asn Met
    1295                 1300                 1305

Glu Asn  Asn Tyr Asn Ser Tyr  Ser Ser Asn Asp Gln  Lys Asn Tyr
    1310                 1315                 1320

Ile Ser  Glu Asn His Lys Tyr  Asp Tyr Asn Tyr Asp  Ile Asp Tyr
    1325                 1330                 1335

Ile Lys  Asp Lys Glu Leu Lys  Asn Ile Ile Asn Ser  Asn Asn Asn
    1340                 1345                 1350

Ile Gln  Glu Phe Leu Asn Asn  Tyr Asp Lys Thr Arg  Ile His Asn
    1355                 1360                 1365

Asp Asn  Pro Thr Asn His Lys  Pro Asp Gln Tyr Asp  Asn Ser Leu
    1370                 1375                 1380

Val Tyr  Asp Asp Lys Leu Asn  Val Ile Ile Lys Lys  Ile Glu Glu
    1385                 1390                 1395

Ala Ser  Asn Lys Lys Val Ile  Lys Ile Gly Met Asn  Glu Glu Val
    1400                 1405                 1410

Pro Ile  Tyr Tyr Lys Asn Lys  Ser Ile Val Tyr Ile  Leu Cys Ile
    1415                 1420                 1425

Phe Ser  Lys Asp Glu Asn Asp  Pro Tyr Phe Tyr Ile  Gly Ile Ser
    1430                 1435                 1440

Asp Asn  Ile Ser Glu Arg Ile  Lys Cys His Thr Arg  Asn Leu Leu
    1445                 1450                 1455

Asn Asn  Lys Asn Leu Leu Lys  Asn Pro Lys Lys Asn  Asn Leu Leu
    1460                 1465                 1470
```

-continued

```
Asn Tyr  Lys Tyr Asp Trp Thr  Lys Phe Tyr Ile Leu  Leu Phe His
    1475                 1480                 1485

Val Asp  Asn Lys Met Val Ala  Ser Lys Tyr Glu Lys  Asp Leu Ser
    1490                 1495                 1500

Asn Leu  Leu Lys Asn Asn Tyr  Asn Ile Leu Ser Lys
    1505                 1510                 1515


<210> SEQ ID NO 7
<211> LENGTH: 1728
<212> TYPE: DNA
<213> ORGANISM: Plasmodium falciparum

<400> SEQUENCE: 7

atgagcgaag atataaaatt tgtagaacgc aacaacaata ataatattaa taacagcata     60

ccgaacaata ttataaatag tgtatccatt gcgacggata attcaaagtt gaacatatcg    120

ccaaaggttg ataatgtatg tgatgtgaaa aatatttata atataaaaaa agaagatgtt    180

ataattgaag agtatatgga tattaataaa agtagtacaa taaatctaga tcataataaa    240

caagttaata tatatattga aaatagcgat cttaataaaa aaatatatac atgtcataca    300

tgtaatatac aaatatataa ttattccttc tttcgttatc attttaaatc cgaatggcat    360

aaatataatt tgaaaagaaa attattaaat ctacattcag taaatgaata tgtttttaat    420

gaaaaattaa aaaatttaaa aaaaaatgaa gatcaagaaa atcaaaagaa agacaaaaga    480

gaaaatcaag ggagccattt aagtcataaa aaacgtaacg aaagtaataa aaaaaaaaag    540

gaaaaaaata tcacgaattt taataatatt aataatgatc ataatgcaat caatcaaaat    600

aattataata ataataatca tgtgaccaaa tcgaataatc ataccaatga acataacaat    660

cattcaaatg tttcatccac atcaaataat aacaatataa aatacgctac aaaagaaaat    720

gtacttttaa caaaaaatgc taaatatgac aatccagctg tctgtttttt tgataatcgt    780

atttttaatt ccatagaaga aaatataaaa catatgaatg atacttatac attttatatt    840

cctgatttaa aatacgtaac caatgtgaaa aaaatcctat taacaattgg aaagaaaata    900

tatgaagaaa atatatgtat ctattgtttt aaatatgcga aatgtgttaa atctttacaa    960

gcacatatga tttgtaaaag ccatacgaag ttacatacca attttatggt ctatatccaa   1020

aaatattatg acttctcaaa aacttatgtt gatttattaa ataaatatat taataataaa   1080

caagataaaa aattactcct ctatatgtta aatcacgaac aaaataaaga gaaacaatta   1140

caaattcatg ataataaaaa tcaaaatcat cataatgaca accatttgga aaataacaat   1200

gttcttacga aaaagaaact ttctaatgat acagacaata attctgagga ctatcctaat   1260

gatagttata tattaaaaaa agaaaagaac caagatacat ctttatcaaa ctcttatgat   1320

aatcatgata ataccagtga tgataatagt agcgacgatt ataaaataaa agaaacagat   1380

ctaaataaaa atattgacta taataaaatt tatcaagtat tagaagaatt tggatacatc   1440

aaacctgaat taaatgaata taacaattta attctaccag atggttcaga agccatcaat   1500

agaaaacttg cttacatatt taaacaaaaa ctacccttgg aaaataaaac aagcttttct   1560

tccaaatata atcaaatcga tgttttaaaa aataaaaaag acaaacactt acaacaacgc   1620

aaatataaat attatattga tattatgaag aaatataatt taaatctaaa tttgaagaca   1680

aacaatttga acaagtttta caaaagtgat tctatcttct tcctctaa                1728


<210> SEQ ID NO 8
<211> LENGTH: 575
<212> TYPE: PRT
```

```
<213> ORGANISM: Plasmodium falciparum

<400> SEQUENCE: 8

Met Ser Glu Asp Ile Lys Phe Val Glu Arg Asn Asn Asn Asn Asn Ile
1               5                   10                  15

Asn Asn Ser Ile Pro Asn Asn Ile Ile Asn Ser Val Ser Ile Ala Thr
            20                  25                  30

Asp Asn Ser Lys Leu Asn Ile Ser Pro Lys Val Asp Asn Val Cys Asp
        35                  40                  45

Val Lys Asn Ile Tyr Asn Ile Lys Lys Glu Asp Val Ile Ile Glu Glu
    50                  55                  60

Tyr Met Asp Ile Asn Lys Ser Ser Thr Ile Asn Leu Asp His Asn Lys
65                  70                  75                  80

Gln Val Asn Ile Tyr Ile Glu Asn Ser Asp Leu Asn Lys Lys Ile Tyr
                85                  90                  95

Thr Cys His Thr Cys Asn Ile Gln Ile Tyr Asn Tyr Ser Phe Phe Arg
            100                 105                 110

Tyr His Phe Lys Ser Glu Trp His Lys Tyr Asn Leu Lys Arg Lys Leu
        115                 120                 125

Leu Asn Leu His Ser Val Asn Glu Tyr Val Phe Asn Glu Lys Leu Lys
    130                 135                 140

Asn Leu Lys Lys Asn Glu Asp Gln Glu Asn Gln Lys Lys Asp Lys Arg
145                 150                 155                 160

Glu Asn Gln Gly Ser His Leu Ser His Lys Lys Arg Asn Glu Ser Asn
                165                 170                 175

Lys Lys Lys Lys Glu Lys Asn Ile Thr Asn Phe Asn Asn Ile Asn Asn
            180                 185                 190

Asp His Asn Ala Ile Asn Gln Asn Asn Tyr Asn Asn Asn Asn His Val
        195                 200                 205

Thr Lys Ser Asn Asn His Thr Asn Glu His Asn Asn His Ser Asn Val
    210                 215                 220

Ser Ser Thr Ser Asn Asn Asn Asn Ile Lys Tyr Ala Thr Lys Glu Asn
225                 230                 235                 240

Val Leu Leu Thr Lys Asn Ala Lys Tyr Asp Asn Pro Ala Val Cys Phe
                245                 250                 255

Phe Asp Asn Arg Ile Phe Asn Ser Ile Glu Glu Asn Ile Lys His Met
            260                 265                 270

Asn Asp Thr Tyr Thr Phe Tyr Ile Pro Asp Leu Lys Tyr Val Thr Asn
        275                 280                 285

Val Lys Lys Ile Leu Leu Thr Ile Gly Lys Lys Ile Tyr Glu Glu Asn
    290                 295                 300

Ile Cys Ile Tyr Cys Phe Lys Tyr Ala Lys Cys Val Lys Ser Leu Gln
305                 310                 315                 320

Ala His Met Ile Cys Lys Ser His Thr Lys Leu His Thr Asn Phe Met
                325                 330                 335

Val Tyr Ile Gln Lys Tyr Tyr Asp Phe Ser Lys Thr Tyr Val Asp Leu
            340                 345                 350

Leu Asn Lys Tyr Ile Asn Asn Lys Gln Asp Lys Lys Leu Leu Leu Tyr
        355                 360                 365

Met Leu Asn His Glu Gln Asn Lys Glu Lys Gln Leu Gln Ile His Asp
    370                 375                 380

Asn Lys Asn Gln Asn His His Asn Asp Asn His Leu Glu Asn Asn Asn
385                 390                 395                 400
```

```
Val Leu Thr Lys Lys Lys Leu Ser Asn Asp Thr Asp Asn Asn Ser Glu
                405                 410                 415

Asp Tyr Pro Asn Asp Ser Tyr Ile Leu Lys Lys Glu Lys Asn Gln Asp
            420                 425                 430

Thr Ser Leu Ser Asn Ser Tyr Asp Asn His Asp Asn Thr Ser Asp Asp
        435                 440                 445

Asn Ser Ser Asp Asp Tyr Lys Ile Lys Glu Thr Asp Leu Asn Lys Asn
    450                 455                 460

Ile Asp Tyr Asn Lys Ile Tyr Gln Val Leu Glu Glu Phe Gly Tyr Ile
465                 470                 475                 480

Lys Pro Glu Leu Asn Glu Tyr Asn Asn Leu Ile Leu Pro Asp Gly Ser
                485                 490                 495

Glu Ala Ile Asn Arg Lys Leu Ala Tyr Ile Phe Lys Gln Lys Leu Pro
            500                 505                 510

Leu Glu Asn Lys Thr Ser Phe Ser Ser Lys Tyr Asn Gln Ile Asp Val
        515                 520                 525

Leu Lys Asn Lys Lys Asp Lys His Leu Gln Gln Arg Lys Tyr Lys Tyr
    530                 535                 540

Tyr Ile Asp Ile Met Lys Lys Tyr Asn Leu Asn Leu Asn Leu Lys Thr
545                 550                 555                 560

Asn Asn Leu Asn Lys Phe Tyr Lys Ser Asp Ser Ile Phe Phe Leu
                565                 570                 575
```

<210> SEQ ID NO 9
<211> LENGTH: 16320
<212> TYPE: DNA
<213> ORGANISM: Plasmodium falciparum

<400> SEQUENCE: 9

```
atggaaccta aagaaactga taatgtaata aaagatgagg acaatgtgaa aaaggaagaa      60

cctatattat ctattgaaaa atatttatta aaagagtttg gtgatgggaa aacgaataag     120

aaggatgtta tgagaaaatt gagaaagagg atatataatc ataaaaattc agaagagata     180

tacaaaaaat taaaagagat tcatgggaat agtggtatat gtacacgtca atggaaggaa     240

ggtagttttg cttttaagtg ttataattgt gaaggggatc caacgtgtgc tatatgtgca     300

aaatgttttt ttgcatcaaa tcataagaat catatatata ggttaacaca tacaagtggt     360

ggttgttgtg attgtggaga tacttcatgg aatattaatg gttcatgttt tgatcataga     420

ggaattaatg aagattgttt gattaacaat tctatattaa atattgatat aaagaatcgt     480

gtaagagaag atttggaatg tttgatagga acattattta gggatatagt attaaaagat     540

ggatattttt tatctttagt aagtgctgat tatatagagc atgcatttga tttttttaaa     600

gatttaggta ttacaagtta tttatttcgg caagttatct gtgaagtatt tacaggtgca     660

aaaatagatt ttttagtaaa ttttcattat tgtttttatg taggtgtaca gaaagcttta     720

tattcttttt atttatcttt atttgttcat ccatatttta aacaaaggtt tgcttttaag     780

ttagctaaac attataaatt ggttgttcgt gttgctgatg atcgaattta taatgataat     840

catttgaatg gtttaagtgt tcaggtatta actgttcccg aaatagcata tactttagtt     900

ataaataatt tcttgaatga tttattaaaa ttaatagaaa atttatgtgt atttaataat     960

gtaacaaatt gtgttatgca taaaaatttc ttacgatctg atatcgaaat tataattcgt    1020

atatgtgttg atttgaaata tttgctttat catcatgaag ttataaaaat tgtattattt    1080

aataaatatg tcattaaaaa aatattaaaa atattatctc ttttgcatag aatgaattca    1140
```

```
caagtacgat atacaaaatc gcatattata tatgaagatt tatctagttc ctattccata   1200
acgattgaaa attatttact tcgtgtattt gaacccttgg ctaatttttg taaaagagaa   1260
gctaatgcaa attttagaaa tttattttta ttgtatcaat taacaattag aggtatacat   1320
aaattggatt tgtttccatt taatcgaaaa aaaaaggagg cagaaaattc ttttatgaat   1380
cgcaaaaaat tgaaggaaaa aaaaattaca aaaaagagga atattaaaga ggataattca   1440
acggatgact tgacaggtga tagtgataat agtagtacta ataatgtttg tcgctgtgat   1500
actagtaatt atgataatac gatgtttgat cgtagttgta gtataccagg gttaaataat   1560
atgaatgatg acgttaataa atctggaggg gtatctttaa atgatgataa tataaataat   1620
gataataata atacaaataa taatacaaac aataatacaa acaataataa taataataca   1680
aataataata caaacaataa taataataat aaaaattgtg agggcaaggc caatgatcaa   1740
acgaataaga aaaaaaaatt caaacatctt agatctttac attctccatt agttcgattc   1800
tttatcatga ttttaaattt tgatgtcatt aaaaaatgcc tagatgacgt gtactggtat   1860
aaatatttat atttaagaag ggtttatgaa aaaaaaagga tatataaaaa tagaaaaaaa   1920
agtcctgcat ataataccaa tgatgataat aaaaatgaag tgtgtactaa aaatattcca   1980
tgtgatgata ataaaaatga aatgtgtact aaaaatattc catgtgatga taataaaaat   2040
gaagtgtgta ctaaaaatat tccatgtgat gataataaaa atgaagtgtg tactaaaaat   2100
attccatgtg atgataataa aaatgaaatg tgtactaaaa atattccatg tgatgataat   2160
aaaaatattc caagagatga taataaatca tataataaaa tgtacaataa taataaaatg   2220
aataaggagt taacatataa tgatgaatat ataataaatg aatttattag agatttttat   2280
tctatagaaa agcattcaga agaaataata aatcagcgaa aaatattaca agaaagatat   2340
gaaaacgatg gtaataatat gaagataaca ctttttcatt ttaaaaaatt ttttacaagt   2400
aatgatgaac ataagaatga acatttagga aaatatatag atgaacatat atatttagaa   2460
agtaattatt ttaaatggat tatgaataat aattctagtt ctaaattacg tgaatgtaat   2520
aataagtata gaattaaata tagagaaacc atacaagaaa agaatataaa aataaaatgt   2580
aaaaatatat atatagagaa aaaattaaaa aattcaaaat atgaatttaa tgaatttttg   2640
gatataaaat atgataaaga aaaacataat atatatttac atcctttata tatagattta   2700
tatatgagag atatatttga gtttttaaat ttatttgatt taaaattatt aaaaaaatatt  2760
ctttttataa atatacaaat cttaacattt atatatgaaa ttaaatatgg ttattgggta   2820
agaaatggtc cacaaatgat tttccaggtt ggtgaatatg ataattcttt attttttcaa   2880
aatgatttaa taggaataca atttgctata ataatgatga atgtcttacc tttatacgaa   2940
aatcaaaaag tttatttaga ttcacatgtg atcaatctat ttcatcaaat atggaatatt   3000
aaggttcaat acgatgaacc acttaaaaaa ttaccatggt caaaaaatga atacaacgat   3060
gtgcaaaatg attatataca taaagctgat gatgaaatat gtataaatga aaaggtatat   3120
gatgaggata ctaataaata tatagataca tccccaaatt tttcatataa tcataatatt   3180
cagaatcact atatggtaga agaacattct gaggataaaa aaccgtatta tatgaataaa   3240
ataaaatata taaaaaaaaa tgatgaattt tttgaagaac atatgaaaat gtatgagagc   3300
atgcttatat ataatagatc caaaaaatca aatgataata ataccttacc tgttaataat   3360
aaaatgggaa attcaaaagg aaaaaatttg gatcacgatg atggtgatca tgtcaaattg   3420
ctttttggaa ttgacgacaa aaatgtaagc aataataata acacaaataa tataaatagt   3480
ataaatagta taaataatat aaataatata aatgtgtgta ataataacaa tacatatgtt   3540
```

```
tataataagg tggaatttaa atctatatgt gatcttttgt gtaaatattc atgcaaacaa   3600
ttaaaagacc aagaaaatga atcaaaccca ctgttaagag aaaccgaagg gaggttaacc   3660
tcggataata taaatttcaa caaattagat aataataatg ataatataca aagtgatttg   3720
ttagataatg ataaaaggta ttataataaa ggatctgtaa ggaaagaatc aatatataat   3780
gaagatagaa tatgtgaaaa atataaaaag agcaaactag aatggaatga atatttagaa   3840
gaatttatga atatagaaat aagaaatcca tttattatat tatatcaatt aatatttaag   3900
aattttcgta tgaatttaaa tataagaaaa ataaatgata tgtatgtaga aatcgaaata   3960
catcatataa agatggcata taaaatattt agtgatatat atacaaataa atctactgta   4020
gattctagga aaattggtca tatattttat tttcaatttt tttatgatat aattatacgt   4080
atctttaatg aattatatta tttagaatat agtaatatac caagaaaaac atcttatgaa   4140
aaatatatag aaagaggtaa atatcatgtt aagaaaatat taatacaatt attagcatca   4200
aaagatttc aatattttca actcgaaaat gtatttccta agcaatttag acaccatcca   4260
agtttttatg aacttgttaa taaatatgga tataaaacac atatgcctag aagtaatgtt   4320
aatttgataa agttaaataa gaattcgtgg tatctctatg atgccttttg gcccctttca   4380
gcattcaaag attttcaaac agctaatgaa aaatgtataa aagaagaaaa ttcttcctat   4440
ataggatgtt caagggaaga agacaaagaa tatttaaatt tttcatttcg caaagtacaa   4500
aatttattat tctatacatt taaaaatagt tgtctcgttt ctatactttt aattgtgttt   4560
attattaatg acgaatttca gaggaaaatc gaaaaaaaaa aaaaagaaga attagaaaag   4620
gaagaaatga aaaagcatat gaaagcggat gtaacgggag aagacgactc gttgcttaat   4680
caaaaaggtg gtacaacgaa taataatacg tgtgatgtag gagttgtcat taatgaggaa   4740
gcaaaccgat ccagtggaat gtcacaaaat gttgtgactt atgagagtgg tataaatatg   4800
aataatgatg atgtattagg agaagaaagg aataataacg atgatattaa ttatatggat   4860
gataatgatg atgataatga tgataatgat gatgataatg atgataatga tgatgataat   4920
gatgatgata ataatgatga taataatgat aatgacaata atgatgatga caataatgat   4980
gatgacaata atgatgatga caataatgat gatgacaata atgatgatga caataatgat   5040
gatgacaata atgatgatga caataatgat gatgacaata atgatgatga caataatgat   5100
gatgacaatg atgataatga tgaagattcc aatcttcatg gtagttcttc taatatgcta   5160
aatattataa acagcggtga taataattca gtaactaatt ctagtaatat aaatacagca   5220
cgaaataata atagtacata tataattgta gatcagaatg gagataatga aaccttattt   5280
gcagagatat taataaatcg taatcctaat aattctataa atatggaaat tgtaaatgta   5340
acggataata atgttggtga tgaaaataat aatagaaatt atcgtcattt aaatgctgat   5400
ggattatctg aattaatcag aagtcttata agtgaaaata atattattaa taatgtaata   5460
gatgaatctt ttttacaaaa taataatgta ggaggtgata attctattaa taatgatgac   5520
ataagaaata gaggtggatc aatatttgat gataatatat cttttgataa taattcatca   5580
agtgatgaat tgaatttaat ggattctaca aattcaaata atgtcagaat caatttatac   5640
ggtagaacaa atggattgta cgatttaaat tttattttgg atagtaatga aattatgggt   5700
aaccttaata cacataatgt gaataataca atagatatat tgatcaaaat tataaaaatt   5760
ttgagtgtcg ccatgggttc agcgcatccc tttattgagc taaatagttt ttattatttt   5820
aacgcggtga atttttatgg cacagataat gatgatgaca gtgaaaaaaa tgaggaaatt   5880
```

-continued

```
ggtaacgaag aaaatgacaa aaaatatatt gataaaaaat atattgataa aaaatatatt   5940

gataataatg aagaaattga aaaaaaacac cattgtgatc aaaataaaat ttatgatgat   6000

gttgataggc tatcctccgt atcatcaaat tcttatgata tattaatgaa tcatttggaa   6060

gaatcatgta tgtatacaag ttattcagat gaaacatatg agaagaatgg taatgtttat   6120

aatatgaggg agggatttaa tgtggaaaac ctttcttatg ataaagatat attaaatgaa   6180

aaaaaagaca tagtagaaat agaaaatgag aaagagaaat atataaaaat aaatgatcat   6240

actgtgagta gaaattatgg ttgtgtttcc ttattaaaag atgaacctaa attttcatca   6300

accgatggaa ataataataa tattattaat cgttgtaata ataataatta ttattatgat   6360

aatatgaaac atgttgatga gaaaggtggt gaaggtgaag gtgaagattc agaagaatgt   6420

caaataaaag aaagttacaa gaaaatgtct gaatgtaata ataaggaaaa tataattttt   6480

gattccatta atgtattaag aaaaaacaat ataaagagat taaaaaatta tatgtgtaaa   6540

aataaaaatt gttatatata ttatgatgat aataataata aaaagaagaa gaataaaaag   6600

aatgttgaaa atcaagaaaa agaattttac gtgttaaata aaatatttgt acataatttt   6660

ataaattgta ttaataatat aaatgtgaat gaagataagt gctttcaaaa agtgagatct   6720

accattttaa atagattaaa agagatgtat tctggaaatt atgattgtaa aaataataat   6780

agtaataatg aatttataga attagcaaaa aaaaaacaag aagatttatt aaaaagtatg   6840

aaagaacaac aatccaaatt tagtcatttt ttagaagagg aatattcatc tgaagaaaat   6900

gattcgctac caaatggagg aactgaagat tttgaagatg tcgattttgt ggatgatgct   6960

agtagttatt tagatagtaa tagtaataat aatagtgatg gtcatgaaga tgataataaa   7020

aatcgttgta ctgatgtaaa aacaaataaa caagaagaag aattctctat atctaatgtt   7080

aatgaaaaaa aaaaaaaaaa atatatgaaa ggaataacaa tttgtgaata tgaaaaaata   7140

aaagaaaaaa attgtatatg tgttttatgt aaagaaggga tgtctaaaaa taatttatta   7200

gcatatatat gtttttcatc acatactaat ttattaaaaa aaattataaa aaaaaataaa   7260

ttttcatttc cttgtaaaca cccatctata tatacgtgtg gtcattttat acatacaaaa   7320

tgtttacata atacaaggat attaaaatat agaaaattgt tcagtgtaaa aaatgaacca   7380

actctttatg aattcacatg tcctttatgt cgttcaatag ctaatagttt tgtggtgtat   7440

ataccaaaga ggtatatatc ggagaatgat aaatatagaa tttatgattg taatgaggag   7500

gaatttttct tggataactc aaataaaaat ttatccgaac ttttgaaaat ttcgaaatat   7560

tcagaagaga ggaattatgg aattaaaagg aagaaggaaa gagaagaaaa aaaaaaaagt   7620

aaaatgataa tgatgagagg aatggaaagc gataatataa acgaaatggt aagcgataat   7680

ataaacgaaa tggcaagcga taatataaac gaaatggtaa gcgataatat aaacgaaatg   7740

acaagcgata atataaacaa aatggcaaac caaatgaatt atgaacaaaa tacagatggt   7800

attataataa aatcaagtga taatataaac gaaatgacaa gcgataatat aaacaaaatg   7860

gcaaaccaaa tgaattatga acaaaataca gatggtatta taataaaatc aagtgatata   7920

ccaaataatg ttcaggtaga catatttata aataataata tatcacaaat ttatgagtgt   7980

gctgagcaaa acatagaatt attaaaagac ataaagaatg gagaatctac aaatatgtgc   8040

aacaaagcag ataatttgtt tgctatacaa aatgataaca attatcctta tagaaataaa   8100

gaaagtgaag aaatatgtga aggagaagat tttttattaa taaataaaaa gaatatttct   8160

tgtaattatt tgaataacta tgtaacaaac gatacattaa gaaatgacaa tgtaatgata   8220

cataaggata tcttattaga tgattatttt ttacaagatg ataataaatt ttctacatgt   8280
```

```
tctataacat tgaatgatta tctaatagct cgatatttta atataacaaa ttgtgattat   8340
attaaaaatg ataaatgtaa gagtaggaag gatatttgtt ttaatgataa taataataat   8400
tacaataatg atgatgataa tgatgatgat aatgatgata ataatgatga tgataataat   8460
aatgatggtg acaataatta cgatacgggg gaagaaagct tatccaccct gtcgtcttgc   8520
tcatcagaaa atgtatcatc cgataatcat atggatgata gtgatatagc tgaagaattt   8580
tattttaaat atacacatga taagaataaa aatataaaaa tggcgaacaa aaaaaataag   8640
aaaaggaact taaaggaaaa tcataaagaa gatttccata tgaataatag taatactcat   8700
aatgtgagtt catataattt tttcgatgaa aataagaaga atacaatttt taatttaaat   8760
ttctgtaatc ttataaaaaa ggatagttta ttaaatgata tgttagcata tgaatgttat   8820
gaaaaaaata aaaaaataat attaagaaat atttatttaa atgaaaataa tatgtatgat   8880
gaattatttg aaaaaaagaa aaatgataat aatgtgggta cacataatat tatatattca   8940
caagaaaata atgatgacct tttaaataat aaagatgata taaatattat atataaaaat   9000
agcaatatgg aaaaacaaaa aagaataaga aggagaaaaa aaggaagagg taccgaaata   9060
tatttttata aaaatacatc taattatgta aataaagatt atacatttac atatagaaat   9120
tcgaattttt attatcgtac gaaaaatggt tttttatctt actatgttag tttaccatta   9180
tcatttatta aagaaataca atattttatg ataaaaaata aattatataa ttacccagga   9240
aataatagat ataataaatt ttatttaacg acggaggtag ataaggaaga aatcaaaaaa   9300
gaagaaatgg agatgaatat cgatatgaaa atcgacccgt ctatgttttg taattttgaa   9360
gacaaaataa aaacgaagga agaatataat actgtattat attatgaaat gaataatgat   9420
attataacat atgtaaaatc taattttaat tatgaaagca taaatgccga tgaggcggtt   9480
aaaaagtatg aggtatgtga tttttataca gatggtactt ttgatagtgc tggtgaaaaa   9540
ttatgtagtg aagaaaagca agatcattta ataacgagac ataaaaataa agagtgttca   9600
catgaaaatg aaagtgagca gaaggaaaaa agattaaaag taggacatga gcatgaaatg   9660
gtggatggta taagtaatat gggcgtggct aataataatg ataatatata tggtgataat   9720
atatatggtg ataatatata tggtgataat atatatggtg ataatgataa tatatatggt   9780
gataatatat atgataataa taataatagt tgtgtagggg gtgaagattt tatttgtgat   9840
aacaaatcag atgatattaa ttttgaattt ataaaagatt taaataaaat aaattatgaa   9900
gaaaataaaa aagaaaaaaa agaaatgtta gaaatagaaa aattaaataa agagaatata   9960
aatggtgata aaaaagatat atataaattt aaatatccat gtaatataga agaaataaaa  10020
gatcataata tatcgatgaa aacaagttta tctatggatg tatatgaagg tattgtaagt  10080
acaaataaaa atatatatga aatatacaat gaattaaaaa ggaaacaata tttttattcc  10140
gtgtgcgata taaaatcatt aagacaatca attatattat tagatggtat atcggaaata  10200
tcatggagaa tatttcatca agaacataca acattttcat ctatattaca ccattcggaa  10260
aattataaaa gattaattga tttcgattat aatacaaaaa tagatgataa cgatgaagat  10320
attgatataa aaggtattgg tgttaacgat ttattaaaaa tatatcgtag attagaaata  10380
tatcctgatt ttatatttaa taataataac gtgggtttta ttaatagaca tgatttaaaa  10440
tttataacta aaaaagatct ccttttaatg aatagaaaag attatgagag aaataaaaag  10500
gaaaggaaaa aaaaaaatac taatttgtat ccaacaaatt cacaaactaa taataatgaa  10560
aatgatgata acaataataa taacaataat aacaataata acaataataa caataataat  10620
```

-continued

```
aataacaata ataataataa taatgatagt cgtggggatg ttaataaacc taagaataat  10680
aattccttta ataataatag tgagacaaaa gaaggtaata aaaagaaaaa gaagaatcat  10740
agtgatgtat taaacataaa atactggaga aatattaata cggctgttga tttttttaaa  10800
atatattgga ttttatataa tgagatatta ataaatattt tttataaaaa tataaattat  10860
atatcttgta ataatatgat agaaatttta gtacgtaatt tatttttata caaatatgaa  10920
ttaaatattt taaaagaaga aaatatgtgt aatcttttta atattcaaac atggaaaaat  10980
atgtataaaa tatgtttctt ttatgtctat ccttatcgat ttacctttaa taaatataaa  11040
aaatttttca ataaaattaa aaaaattcac tttttaaata atttatcctt tattccatta  11100
tcagtagatg tattaaaatt atttatgaat ttttttttaa atcaatattt atatactcct  11160
tcattaatta agcattttat ttcaatatca ttaatcataa tatcttttca aattatgaat  11220
gaaatattta taaaagaaat atcaaagaca tatgtaagat ttatttttaa gacaatacaa  11280
aattataaca aaatcaagaa atatattact cgtatatcta aatatatgta ttttcaaaaa  11340
atatatacaa attatattat cagccattat gaatatgtag actatattga gagggccaat  11400
acatttattc aaaccgaaga aacaaaaaaa ataagacata atgaaagttc gatttatcat  11460
aatattgaaa tggtaggaca taaacaaaat gaacagaaaa ggcattcttt aaattcttac  11520
gacagatttc acatttttct ttttgaaaaa tatgtaaaaa attctatacc aggaggtgaa  11580
aatataactt taaaatatgt gaatggtcga tataaattat atgacaatga gcaagaggta  11640
gtacgtatga gtgatcttga acattttgaa aagataaaaa atgtttattc gaaaaaagca  11700
acggatattt taaaaaagaa gaatgaaaaa atgaaaaatg ataaagagga aactggtaat  11760
gaacaagcaa ataattgtaa taaaacatta gatggtaata aaacattaga tggtaataaa  11820
atattagatg gtaataaaac attagatggt aataaaatat tagatggtaa taaaatatta  11880
gatgataata aattattaga tgataataaa ttattagatg gtaataaaac attagatggt  11940
aataaaatat tagatgataa taaaatatta gatagtaata ataataataa taataataat  12000
aataataatg gcgaaaacaa aagttggaac ttccagaatg tatcatctta caacgattta  12060
ataaaatccg tgcttgataa aaaaaatttc ttttttatta tagatattgt taacttattt  12120
aaaaatatac aaacattgtc gtatttattt gatgaagaaa caataaggta cgtacacatg  12180
attattatga atagtaaaat attatcatat gatttaaaag aaatagaaag aaaaaaaaac  12240
ttgcaaaaaa agatttatcc aaattttact tcttatatta caaaacagaa gaaggcaaat  12300
aaattaaaat gttataatta tgatttatta catattgaaa agaaatggat attatatctt  12360
atatataaaa ccatattaaa atattatgat atgcttatat ttaagaagaa agttcaaaaa  12420
cttatgcttt tgatgtgtga aattaatgat gaatatataa aatatatata ttttaatggt  12480
tatattccta taaatatata tttaagtaca aacttaataa aatacaatga attctttaca  12540
aattattatt cttatatata taacaaaaat gttaatgata aatggggtga tttccatgtc  12600
ttatatttcc aaaatgaaga aaataatata aaaaaagaaa acaaaaaaaa ttattattat  12660
tattattatt attattatta tacacttttt aaaaacaaac atgttttaaa aagagattat  12720
aatcatattg taagtaataa tatacaaccc attaataaaa tgaatgaacc cataacatct  12780
aatgaatgta cctctccaaa tatgtcttat catatagaat caaatgaaat atttaaaaat  12840
gaagatgatc ataatcttaa tatatataat gaacatatta tgtataattc gcacaaagat  12900
acaaatttgt tatcttcctc taaccatatg caacacgtac aaaaaaatac cctcaccatg  12960
aatcttgatc attccaataa tctaataata aatgataacc ataaaagaga taaagaacat  13020
```

```
aatataaata cgaaacattg gaataagaac ataataaata gtaattattt taatgtatat  13080
aataatgatt ctagcccaaa ggagcaaatc catttagagg aaggtggggg tggtttaata  13140
gatgttgatg atgataaaaa ggataatgtt attaatagtg ataatcattt taaggaaacg  13200
acatataatc atatagcata tcataaggac caagaattat ccacagaatt aaatttattt  13260
aaatataaat tatataatat atccagtgaa gaaattagta atttatattt aatggaagat  13320
tgtaataatg aaaaaggatt tttttcatgt gttcataaaa atgaagattt tgaatataag  13380
aatattaaca ttttaaatat attaaaatat caatttgaac tagttccata tattaatcat  13440
ttatattatc tttataatat ctatccatta ttatttaaat tgaaagagat aaaaaatatt  13500
catgatatga aagaaaaaca aattaattta tgtacagacc aatttttatt atccttagta  13560
gataaagata tttatgattg ttatgatgat gtaaattttt ctgatgctag tttttatagt  13620
gatcaaacta ttcatgtttc tgaaaaagaa tgtgaacata aaaatcataa tagtaataaa  13680
tatgattgta ataattatca tcctttttaat gtatctcatt tatcttatcc atataaagat  13740
caaaatggtg acgaagaaga tacattgcaa attaattctt cattaaatat tcttgaaaat  13800
gttgtcgatc ttgatgaact cataaaagat ttgaaaaaaa caaaaaaagag caaaaaaaaa  13860
actagtaaaa ataaatatgc tgataaattt tttgtctcat tttttaatac agcattgaaa  13920
agagacgaag ataaaggaaa aacaaattat gtacattata gaaaattacg aaatgctaaa  13980
aataatataa aattaaaaaa tttattctta tcacaccaac aaaatgatac tatttatgat  14040
aatataaatg gtaatatttg tgataattta tacggtaatg tcaataccta tcaaaactca  14100
gcttctctta tatttgtaga tccacataat ttaacaaata taaatatttc caacgaatta  14160
aataataata tcaatataaa ttgttcgaaa aataaaaaaa aaaaaaaacc atcatcaaat  14220
gatcaaaata atactgaaaa tgaagacatg caaaatagct catctgataa tccatatgat  14280
gattcaaatt ttatatctta tcatgaaagt atagattcta caagtagtac agataaatat  14340
cataaaagaa aaatgacccc tatggaaagt atgtttttaa aatatacatt aaatacatca  14400
gaagatgcat tatccaataa atataatgta actagcaaaa ataaaaataa aaaagaatat  14460
ttaagttttc ttaaatataa agatgcaaac aaaattcaac gttatcatat gttattaaga  14520
aaaaatggtc ttggaagatt gttttttat aatttaagaa aaatgtataa ttatgtatat  14580
aatctatatg atttcatacc tctttatctt atacaaaata tattaataca ttattatgat  14640
atatatcaac atgtaaacca atattattat catgatgata aagaatatcc cactttttt  14700
acacaacaaa atgaagatga tgaatatgaa tataccaagt tttctaaaaa tttctttaat  14760
actaataaat ggaaaaaaat gtattcgaaa tatgaagaca aactaaataa cgaaacatat  14820
ccggaaccac caaaaaaata tatttcaaat aaacagcgac ataaagaaaa tattctaata  14880
taccaaaatt tgcaaaatga tcatatgaat aatcattata atattgctaa taatgatata  14940
gaaaataaaa atcaaaccaa ttcatcatac ctttttaatg ttcaccatca aaattgccct  15000
tctctatcat caaacaatct tgtaaatatt aatagtactt taatcaatga ccaccatttt  15060
gtacaaacaa ataatgatca tatgaacatc atacaacata tggagaacat tccagaaatg  15120
tcggaatgta atttaaaaac tgaccaaaat aataacatct ttaattttcc acaagataaa  15180
ataaatcctg atacaatgaa gaaaaatgaa aaaatggaat tctcggtaaa taaaaaaata  15240
aaaacaaacc ataacacaac tggatataat aaaagaaata atgataggta taattattct  15300
agtactccta attttttgg aaaagatgaa tatgataaca catcatatga ggattatata  15360
```

```
aaaaaaaaaa aaaaaaactt ctcttcaaca agtagaagaa aacgaaataa taatataaat  15420

atgaaagaat tttttgcaaa tggacgttat gataaattat taagtataaa gaaaatattt  15480

atgatattct ataattattt gaggaagtgt cattttatcg ataaaaaaaa ttcttgtaag  15540

aatttatata aatcattttt aaaaaaatat ttaaaatcag ctaatgtata tttacaattt  15600

atagcttata ttatattctc catatatgat tataattcat tagcaaaaaa atatttagat  15660

tatatacact tatatagtga tattagtaaa tataatatat tccttcatat attaaatatc  15720

gacgaagact atgataaaat atatatatat caaacattac aattaatata tcatccatat  15780

ttttatctaa tgtataaatt atataaatat ctaaaaatag atgcctcccc agtattatta  15840

catgattttt atgaaaactg ggaagaattt acaaaatccc catctttatt tcaacctagc  15900

aaaaattatt tcacattaat taaaaaacat ttcaaaagaa aatgtgtaag ttgtaataag  15960

tctccaaaaa aaatacttat ctgtctctat tgtggttcaa ctgtttgtct gcatgaaggt  16020

gaccatgtgt ccggaccctt atcacaaact ataagtaaat gtgtgtacca tacgaccatc  16080

tgtggaggag agcaatgttt atacttatgt ttaaatacat catcggtgtt gtttacgagt  16140

gaaaaccgat tcgattttat gagtggacct tatgtcgaca aaaatggaga tgtggactat  16200

caattaaaga gaggaaaaaa tttatacctt tcttcttata agttgaacaa actttttgac  16260

gttataatta attcagcagt tgatgttgaa atatataagc atacgttgaa atcggaataa  16320
```

<210> SEQ ID NO 10
<211> LENGTH: 5439
<212> TYPE: PRT
<213> ORGANISM: Plasmodium falciparum

<400> SEQUENCE: 10

```
Met Glu Pro Lys Glu Thr Asp Asn Val Ile Lys Asp Glu Asp Asn Val
1               5                   10                  15

Lys Lys Glu Glu Pro Ile Leu Ser Ile Glu Lys Tyr Leu Leu Lys Glu
            20                  25                  30

Phe Gly Asp Gly Lys Thr Asn Lys Lys Asp Val Met Arg Lys Leu Arg
        35                  40                  45

Lys Arg Ile Tyr Asn His Lys Asn Ser Glu Glu Ile Tyr Lys Lys Leu
    50                  55                  60

Lys Glu Ile His Gly Asn Ser Gly Ile Cys Thr Arg Gln Trp Lys Glu
65                  70                  75                  80

Gly Ser Phe Ala Phe Lys Cys Tyr Asn Cys Glu Gly Asp Pro Thr Cys
                85                  90                  95

Ala Ile Cys Ala Lys Cys Phe Phe Ala Ser Asn His Lys Asn His Ile
            100                 105                 110

Tyr Arg Leu Thr His Thr Ser Gly Gly Cys Cys Asp Cys Gly Asp Thr
        115                 120                 125

Ser Trp Asn Ile Asn Gly Ser Cys Phe Asp His Arg Gly Ile Asn Glu
    130                 135                 140

Asp Cys Leu Ile Asn Asn Ser Ile Leu Asn Ile Asp Ile Lys Asn Arg
145                 150                 155                 160

Val Arg Glu Asp Leu Glu Cys Leu Ile Gly Thr Leu Phe Arg Asp Ile
                165                 170                 175

Val Leu Lys Asp Gly Tyr Phe Leu Ser Leu Val Ser Ala Asp Tyr Ile
            180                 185                 190

Glu His Ala Phe Asp Phe Phe Lys Asp Leu Gly Ile Thr Ser Tyr Leu
        195                 200                 205
```

```
Phe Arg Gln Val Ile Cys Glu Val Phe Thr Gly Ala Lys Ile Asp Phe
    210                 215                 220

Leu Val Asn Phe His Tyr Cys Phe Tyr Val Gly Val Gln Lys Ala Leu
225                 230                 235                 240

Tyr Ser Phe Tyr Leu Ser Leu Phe Val His Pro Tyr Phe Lys Gln Arg
                245                 250                 255

Phe Ala Phe Lys Leu Ala Lys His Tyr Lys Leu Val Val Arg Val Ala
            260                 265                 270

Asp Asp Arg Ile Tyr Asn Asp Asn His Leu Asn Gly Leu Ser Val Gln
        275                 280                 285

Val Leu Thr Val Pro Glu Ile Ala Tyr Thr Leu Val Ile Asn Asn Phe
    290                 295                 300

Leu Asn Asp Leu Leu Lys Leu Ile Glu Asn Leu Cys Val Phe Asn Asn
305                 310                 315                 320

Val Thr Asn Cys Val Met His Lys Asn Phe Leu Arg Ser Asp Ile Glu
                325                 330                 335

Ile Ile Ile Arg Ile Cys Val Asp Leu Lys Tyr Leu Leu Tyr His His
            340                 345                 350

Glu Val Ile Lys Ile Val Leu Phe Asn Lys Tyr Val Ile Lys Lys Ile
        355                 360                 365

Leu Lys Ile Leu Ser Leu Leu His Arg Met Asn Ser Gln Val Arg Tyr
    370                 375                 380

Thr Lys Ser His Ile Ile Tyr Glu Asp Leu Ser Ser Ser Tyr Ser Ile
385                 390                 395                 400

Thr Ile Glu Asn Tyr Leu Leu Arg Val Phe Glu Pro Leu Ala Asn Phe
                405                 410                 415

Cys Lys Arg Glu Ala Asn Ala Asn Phe Arg Asn Leu Phe Leu Leu Tyr
            420                 425                 430

Gln Leu Thr Ile Arg Gly Ile His Lys Leu Asp Leu Phe Pro Phe Asn
        435                 440                 445

Arg Lys Lys Lys Glu Ala Glu Asn Ser Phe Met Asn Arg Lys Lys Leu
    450                 455                 460

Lys Glu Lys Lys Ile Thr Lys Lys Arg Asn Ile Lys Glu Asp Asn Ser
465                 470                 475                 480

Thr Asp Asp Leu Thr Gly Asp Ser Asp Asn Ser Ser Thr Asn Asn Val
                485                 490                 495

Cys Arg Cys Asp Thr Ser Asn Tyr Asp Asn Thr Met Phe Asp Arg Ser
            500                 505                 510

Cys Ser Ile Pro Gly Leu Asn Asn Met Asn Asp Asp Val Asn Lys Ser
        515                 520                 525

Gly Gly Val Ser Leu Asn Asp Asp Asn Ile Asn Asn Asp Asn Asn Asn
    530                 535                 540

Thr Asn Asn Asn Thr Asn Asn Asn Thr Asn Asn Asn Asn Asn Asn Thr
545                 550                 555                 560

Asn Asn Asn Thr Asn Asn Asn Asn Asn Asn Lys Asn Cys Glu Gly Lys
                565                 570                 575

Ala Asn Asp Gln Thr Asn Lys Lys Lys Lys Phe Lys His Leu Arg Ser
            580                 585                 590

Leu His Ser Pro Leu Val Arg Phe Phe Ile Met Ile Leu Asn Phe Asp
        595                 600                 605

Val Ile Lys Lys Cys Leu Asp Asp Val Tyr Trp Tyr Lys Tyr Leu Tyr
    610                 615                 620

Leu Arg Arg Val Tyr Glu Lys Lys Arg Ile Tyr Lys Asn Arg Lys Lys
```

```
625                 630                 635                 640

Ser Pro Ala Tyr Asn Thr Asn Asp Asp Asn Lys Asn Glu Val Cys Thr
                645                 650                 655

Lys Asn Ile Pro Cys Asp Asp Asn Lys Asn Glu Met Cys Thr Lys Asn
            660                 665                 670

Ile Pro Cys Asp Asp Asn Lys Asn Glu Val Cys Thr Lys Asn Ile Pro
        675                 680                 685

Cys Asp Asp Asn Lys Asn Glu Val Cys Thr Lys Asn Ile Pro Cys Asp
    690                 695                 700

Asp Asn Lys Asn Glu Met Cys Thr Lys Asn Ile Pro Cys Asp Asp Asn
705                 710                 715                 720

Lys Asn Ile Pro Arg Asp Asp Asn Lys Ser Tyr Asn Lys Met Tyr Asn
                725                 730                 735

Asn Asn Lys Met Asn Lys Glu Leu Thr Tyr Asn Asp Glu Tyr Ile Ile
            740                 745                 750

Asn Glu Phe Ile Arg Asp Phe Tyr Ser Ile Glu Lys His Ser Glu Glu
        755                 760                 765

Ile Ile Asn Gln Arg Lys Ile Leu Gln Glu Arg Tyr Glu Asn Asp Gly
    770                 775                 780

Asn Asn Met Lys Ile Thr Leu Phe His Phe Lys Lys Phe Phe Thr Ser
785                 790                 795                 800

Asn Asp Glu His Lys Asn Glu His Leu Gly Lys Tyr Ile Asp Glu His
                805                 810                 815

Ile Tyr Leu Glu Ser Asn Tyr Phe Lys Trp Ile Met Asn Asn Asn Ser
            820                 825                 830

Ser Ser Lys Leu Arg Glu Cys Asn Asn Lys Tyr Arg Ile Lys Tyr Arg
        835                 840                 845

Glu Thr Ile Gln Glu Lys Asn Ile Lys Ile Lys Cys Lys Asn Ile Tyr
    850                 855                 860

Ile Glu Lys Lys Leu Lys Asn Ser Lys Tyr Glu Phe Asn Glu Phe Leu
865                 870                 875                 880

Asp Ile Lys Tyr Asp Lys Glu Lys His Asn Ile Tyr Leu His Pro Leu
                885                 890                 895

Tyr Ile Asp Leu Tyr Met Arg Asp Ile Phe Glu Phe Leu Asn Leu Phe
            900                 905                 910

Asp Leu Lys Leu Leu Lys Asn Ile Leu Phe Ile Asn Ile Gln Ile Leu
        915                 920                 925

Thr Phe Ile Tyr Glu Ile Lys Tyr Gly Tyr Trp Val Arg Asn Gly Pro
    930                 935                 940

Gln Met Ile Phe Gln Val Gly Glu Tyr Asp Asn Ser Leu Phe Phe Gln
945                 950                 955                 960

Asn Asp Leu Ile Gly Ile Gln Phe Ala Ile Ile Met Met Asn Val Leu
                965                 970                 975

Pro Leu Tyr Glu Asn Gln Lys Val Tyr Leu Asp Ser His Val Ile Asn
            980                 985                 990

Leu Phe His Gln Ile Trp Asn Ile  Lys Val Gln Tyr Asp  Glu Pro Leu
        995                 1000                1005

Lys Lys  Leu Pro Trp Ser Lys  Asn Glu Tyr Asn Asp  Val Gln Asn
    1010                1015                1020

Asp Tyr  Ile His Lys Ala Asp  Asp Glu Ile Cys Ile  Asn Glu Lys
    1025                1030                1035

Val Tyr  Asp Glu Asp Thr Asn  Lys Tyr Ile Asp Thr  Ser Pro Asn
    1040                1045                1050
```

```
Phe Ser  Tyr Asn His Asn Ile  Gln Asn His Tyr Met  Val Glu Glu
    1055                 1060                 1065

His Ser  Glu Asp Lys Lys Pro  Tyr Tyr Met Asn Lys  Ile Lys Tyr
    1070                 1075                 1080

Ile Lys  Lys Asn Asp Glu Phe  Phe Glu Glu His Met  Lys Met Tyr
    1085                 1090                 1095

Glu Ser  Met Leu Ile Tyr Asn  Arg Ser Lys Lys Ser  Asn Asp Asn
    1100                 1105                 1110

Asn Thr  Leu Pro Val Asn Asn  Lys Met Gly Asn Ser  Lys Gly Lys
    1115                 1120                 1125

Asn Leu  Asp His Asp Asp Gly  Asp His Val Lys Leu  Leu Phe Gly
    1130                 1135                 1140

Ile Asp  Asp Lys Asn Val Ser  Asn Asn Asn Asn Thr  Asn Asn Ile
    1145                 1150                 1155

Asn Ser  Ile Asn Ser Ile Asn  Asn Ile Asn Asn Ile  Asn Val Cys
    1160                 1165                 1170

Asn Asn  Asn Asn Thr Tyr Val  Tyr Asn Lys Val Glu  Phe Lys Ser
    1175                 1180                 1185

Ile Cys  Asp Leu Leu Cys Lys  Tyr Ser Cys Lys Gln  Leu Lys Asp
    1190                 1195                 1200

Gln Glu  Asn Glu Ser Asn Pro  Leu Leu Arg Glu Thr  Glu Gly Arg
    1205                 1210                 1215

Leu Thr  Ser Asp Asn Ile Asn  Phe Asn Lys Leu Asp  Asn Asn Asn
    1220                 1225                 1230

Asp Asn  Ile Gln Ser Asp Leu  Leu Asp Asn Asp Lys  Arg Tyr Tyr
    1235                 1240                 1245

Asn Lys  Gly Ser Val Arg Lys  Glu Ser Ile Tyr Asn  Glu Asp Arg
    1250                 1255                 1260

Ile Cys  Glu Lys Tyr Lys Lys  Ser Lys Leu Glu Trp  Asn Glu Tyr
    1265                 1270                 1275

Leu Glu  Glu Phe Met Asn Ile  Glu Ile Arg Asn Pro  Phe Ile Ile
    1280                 1285                 1290

Leu Tyr  Gln Leu Ile Phe Lys  Asn Phe Arg Met Asn  Leu Asn Ile
    1295                 1300                 1305

Arg Lys  Ile Asn Asp Met Tyr  Val Glu Ile Glu Ile  His His Ile
    1310                 1315                 1320

Lys Met  Ala Tyr Lys Ile Phe  Ser Asp Ile Tyr Thr  Asn Lys Ser
    1325                 1330                 1335

Thr Val  Asp Ser Arg Lys Ile  Gly His Ile Phe Tyr  Phe Gln Phe
    1340                 1345                 1350

Phe Tyr  Asp Ile Ile Ile Arg  Ile Phe Asn Glu Leu  Tyr Tyr Leu
    1355                 1360                 1365

Glu Tyr  Ser Asn Ile Pro Arg  Lys Thr Ser Tyr Glu  Lys Tyr Ile
    1370                 1375                 1380

Glu Arg  Gly Lys Tyr His Val  Lys Lys Ile Leu Ile  Gln Leu Leu
    1385                 1390                 1395

Ala Ser  Lys Asp Phe Gln Tyr  Phe Gln Leu Glu Asn  Val Phe Pro
    1400                 1405                 1410

Lys Gln  Phe Arg His His Pro  Ser Phe Tyr Glu Leu  Val Asn Lys
    1415                 1420                 1425

Tyr Gly  Tyr Lys Thr His Met  Pro Arg Ser Asn Val  Asn Leu Ile
    1430                 1435                 1440
```

```
Lys Leu Asn Lys Asn Ser Trp Tyr Leu Tyr Asp Ala Phe Trp Pro
    1445                1450                1455

Leu Ser Ala Phe Lys Asp Phe Gln Thr Ala Asn Glu Lys Cys Ile
    1460                1465                1470

Lys Glu Glu Asn Ser Ser Tyr Ile Gly Cys Ser Arg Glu Glu Asp
    1475                1480                1485

Lys Glu Tyr Leu Asn Phe Ser Phe Arg Lys Val Gln Asn Leu Leu
    1490                1495                1500

Phe Tyr Thr Phe Lys Asn Ser Cys Leu Val Ser Ile Leu Leu Ile
    1505                1510                1515

Val Phe Ile Ile Asn Asp Glu Phe Gln Arg Lys Ile Glu Lys Lys
    1520                1525                1530

Lys Lys Glu Glu Leu Glu Lys Glu Glu Met Lys Lys His Met Lys
    1535                1540                1545

Ala Asp Val Thr Gly Glu Asp Asp Ser Leu Leu Asn Gln Lys Gly
    1550                1555                1560

Gly Thr Thr Asn Asn Asn Thr Cys Asp Val Gly Val Val Ile Asn
    1565                1570                1575

Glu Glu Ala Asn Arg Ser Ser Gly Met Ser Gln Asn Val Val Thr
    1580                1585                1590

Tyr Glu Ser Gly Ile Asn Met Asn Asn Asp Asp Val Leu Gly Glu
    1595                1600                1605

Glu Arg Asn Asn Asn Asp Asp Ile Asn Tyr Met Asp Asp Asn Asp
    1610                1615                1620

Asp Asp Asn Asp Asp Asn Asp Asp Asp Asn Asp Asp Asn Asp Asp
    1625                1630                1635

Asp Asn Asp Asp Asp Asn Asn Asp Asp Asn Asn Asp Asn Asp Asn
    1640                1645                1650

Asn Asp Asp Asp Asn Asn Asp Asp Asp Asn Asn Asp Asp Asp Asn
    1655                1660                1665

Asn Asp Asp Asp Asn Asn Asp Asp Asp Asn Asn Asp Asp Asp Asn
    1670                1675                1680

Asn Asp Asp Asp Asn Asn Asp Asp Asp Asn Asn Asp Asp Asp Asn
    1685                1690                1695

Asn Asp Asp Asp Asn Asp Asp Asn Asp Glu Asp Ser Asn Leu His
    1700                1705                1710

Gly Ser Ser Ser Asn Met Leu Asn Ile Ile Asn Ser Gly Asp Asn
    1715                1720                1725

Asn Ser Val Thr Asn Ser Ser Asn Ile Asn Thr Ala Arg Asn Asn
    1730                1735                1740

Asn Ser Thr Tyr Ile Ile Val Asp Gln Asn Gly Asp Asn Glu Thr
    1745                1750                1755

Leu Phe Ala Glu Ile Leu Ile Asn Arg Asn Pro Asn Asn Ser Ile
    1760                1765                1770

Asn Met Glu Ile Val Asn Val Thr Asp Asn Asn Val Gly Asp Glu
    1775                1780                1785

Asn Asn Asn Arg Asn Tyr Arg His Leu Asn Ala Asp Gly Leu Ser
    1790                1795                1800

Glu Leu Ile Arg Ser Leu Ile Ser Glu Asn Asn Ile Ile Asn Asn
    1805                1810                1815

Val Ile Asp Glu Ser Phe Leu Gln Asn Asn Asn Val Gly Gly Asp
    1820                1825                1830

Asn Ser Ile Asn Asn Asp Asp Ile Arg Asn Arg Gly Gly Ser Ile
```

```
    1835                1840                1845

Phe Asp  Asp Asn Ile Ser Phe  Asp Asn Asn Ser Ser  Ser Asp Glu
    1850                1855                1860

Leu Asn  Leu Met Asp Ser Thr  Asn Ser Asn Asn Val  Arg Ile Asn
    1865                1870                1875

Leu Tyr  Gly Arg Thr Asn Gly  Leu Tyr Asp Leu Asn  Phe Ile Leu
    1880                1885                1890

Asp Ser  Asn Glu Ile Met Gly  Asn Leu Asn Thr His  Asn Val Asn
    1895                1900                1905

Asn Thr  Ile Asp Ile Leu Ile  Lys Ile Ile Lys Ile  Leu Ser Val
    1910                1915                1920

Ala Met  Gly Ser Ala His Pro  Phe Ile Glu Leu Asn  Ser Phe Tyr
    1925                1930                1935

Tyr Phe  Asn Ala Val Asn Phe  Tyr Gly Thr Asp Asn  Asp Asp Asp
    1940                1945                1950

Ser Glu  Lys Asn Glu Glu Ile  Gly Asn Glu Glu Asn  Asp Lys Lys
    1955                1960                1965

Tyr Ile  Asp Lys Lys Tyr Ile  Asp Lys Lys Tyr Ile  Asp Asn Asn
    1970                1975                1980

Glu Glu  Ile Glu Lys Lys His  His Cys Asp Gln Asn  Lys Ile Tyr
    1985                1990                1995

Asp Asp  Val Asp Arg Leu Ser  Ser Val Ser Ser Asn  Ser Tyr Asp
    2000                2005                2010

Ile Leu  Met Asn His Leu Glu  Glu Ser Cys Met Tyr  Thr Ser Tyr
    2015                2020                2025

Ser Asp  Glu Thr Tyr Glu Lys  Asn Gly Asn Val Tyr  Asn Met Arg
    2030                2035                2040

Glu Gly  Phe Asn Val Glu Asn  Leu Ser Tyr Asp Lys  Asp Ile Leu
    2045                2050                2055

Asn Glu  Lys Lys Asp Ile Val  Glu Ile Glu Asn Glu  Lys Glu Lys
    2060                2065                2070

Tyr Ile  Lys Ile Asn Asp His  Thr Val Ser Arg Asn  Tyr Gly Cys
    2075                2080                2085

Val Ser  Leu Leu Lys Asp Glu  Pro Lys Phe Ser Ser  Thr Asp Gly
    2090                2095                2100

Asn Asn  Asn Asn Ile Ile Asn  Arg Cys Asn Asn Asn  Asn Tyr Tyr
    2105                2110                2115

Tyr Asp  Asn Met Lys His Val  Asp Glu Lys Gly Gly  Glu Gly Glu
    2120                2125                2130

Gly Glu  Asp Ser Glu Glu Cys  Gln Ile Lys Glu Ser  Tyr Lys Lys
    2135                2140                2145

Met Ser  Glu Cys Asn Asn Lys  Glu Asn Ile Ile Phe  Asp Ser Ile
    2150                2155                2160

Asn Val  Leu Arg Lys Asn Asn  Ile Lys Arg Leu Lys  Asn Tyr Met
    2165                2170                2175

Cys Lys  Asn Lys Asn Cys Tyr  Ile Tyr Tyr Asp Asp  Asn Asn Asn
    2180                2185                2190

Lys Lys  Lys Lys Asn Lys Lys  Asn Val Glu Asn Gln  Glu Lys Glu
    2195                2200                2205

Phe Tyr  Val Leu Asn Lys Ile  Phe Val His Asn Phe  Ile Asn Cys
    2210                2215                2220

Ile Asn  Asn Ile Asn Val Asn  Glu Asp Lys Cys Phe  Gln Lys Val
    2225                2230                2235
```

```
Arg Ser  Thr Ile Leu Asn Arg  Leu Lys Glu Met Tyr  Ser Gly Asn
    2240                 2245                 2250

Tyr Asp  Cys Lys Asn Asn Asn  Ser Asn Asn Glu Phe  Ile Glu Leu
    2255                 2260                 2265

Ala Lys  Lys Lys Gln Glu Asp  Leu Leu Lys Ser Met  Lys Glu Gln
    2270                 2275                 2280

Gln Ser  Lys Phe Ser His Phe  Leu Glu Glu Glu Tyr  Ser Ser Glu
    2285                 2290                 2295

Glu Asn  Asp Ser Leu Pro Asn  Gly Gly Thr Glu Asp  Phe Glu Asp
    2300                 2305                 2310

Val Asp  Phe Val Asp Asp Ala  Ser Ser Tyr Leu Asp  Ser Asn Ser
    2315                 2320                 2325

Asn Asn  Asn Ser Asp Gly His  Glu Asp Asp Asn Lys  Asn Arg Cys
    2330                 2335                 2340

Thr Asp  Val Lys Thr Asn Lys  Gln Glu Glu Glu Phe  Ser Ile Ser
    2345                 2350                 2355

Asn Val  Asn Glu Lys Lys Lys  Lys Lys Tyr Met Lys  Gly Ile Thr
    2360                 2365                 2370

Ile Cys  Glu Tyr Glu Lys Ile  Lys Glu Lys Asn Cys  Ile Cys Val
    2375                 2380                 2385

Leu Cys  Lys Glu Gly Met Ser  Lys Asn Asn Leu Leu  Ala Tyr Ile
    2390                 2395                 2400

Cys Phe  Ser Ser His Thr Asn  Leu Leu Lys Lys Ile  Ile Lys Lys
    2405                 2410                 2415

Asn Lys  Phe Ser Phe Pro Cys  Lys His Pro Ser Ile  Tyr Thr Cys
    2420                 2425                 2430

Gly His  Phe Ile His Thr Lys  Cys Leu His Asn Thr  Arg Ile Leu
    2435                 2440                 2445

Lys Tyr  Arg Lys Leu Phe Ser  Val Lys Asn Glu Pro  Thr Leu Tyr
    2450                 2455                 2460

Glu Phe  Thr Cys Pro Leu Cys  Arg Ser Ile Ala Asn  Ser Phe Val
    2465                 2470                 2475

Val Tyr  Ile Pro Lys Arg Tyr  Ile Ser Glu Asn Asp  Lys Tyr Arg
    2480                 2485                 2490

Ile Tyr  Asp Cys Asn Glu Glu  Glu Phe Phe Leu Asp  Asn Ser Asn
    2495                 2500                 2505

Lys Asn  Leu Ser Glu Leu Leu  Lys Ile Ser Lys Tyr  Ser Glu Glu
    2510                 2515                 2520

Arg Asn  Tyr Gly Ile Lys Arg  Lys Lys Glu Arg Glu  Glu Lys Lys
    2525                 2530                 2535

Lys Ser  Lys Met Ile Met Met  Arg Gly Met Glu Ser  Asp Asn Ile
    2540                 2545                 2550

Asn Glu  Met Val Ser Asp Asn  Ile Asn Glu Met Ala  Ser Asp Asn
    2555                 2560                 2565

Ile Asn  Glu Met Val Ser Asp  Asn Ile Asn Glu Met  Thr Ser Asp
    2570                 2575                 2580

Asn Ile  Asn Lys Met Ala Asn  Gln Met Asn Tyr Glu  Gln Asn Thr
    2585                 2590                 2595

Asp Gly  Ile Ile Ile Lys Ser  Ser Asp Asn Ile Asn  Glu Met Thr
    2600                 2605                 2610

Ser Asp  Asn Ile Asn Lys Met  Ala Asn Gln Met Asn  Tyr Glu Gln
    2615                 2620                 2625
```

-continued

```
Asn Thr  Asp Gly Ile Ile Ile  Lys Ser Ser Asp Ile  Pro Asn Asn
    2630                 2635                 2640

Val Gln  Val Asp Ile Phe Ile  Asn Asn Asn Ile Ser  Gln Ile Tyr
    2645                 2650                 2655

Glu Cys  Ala Glu Gln Asn Ile  Glu Leu Leu Lys Asp  Ile Lys Asn
    2660                 2665                 2670

Gly Glu  Ser Thr Asn Met Cys  Asn Lys Ala Asp Asn  Leu Phe Ala
    2675                 2680                 2685

Ile Gln  Asn Asp Asn Asn Tyr  Pro Tyr Arg Asn Lys  Glu Ser Glu
    2690                 2695                 2700

Glu Ile  Cys Glu Gly Glu Asp  Phe Leu Leu Ile Asn  Lys Lys Asn
    2705                 2710                 2715

Ile Ser  Cys Asn Tyr Leu Asn  Asn Tyr Val Thr Asn  Asp Thr Leu
    2720                 2725                 2730

Arg Asn  Asp Asn Val Met Ile  His Lys Asp Ile Leu  Leu Asp Asp
    2735                 2740                 2745

Tyr Phe  Leu Gln Asp Asp Asn  Lys Phe Ser Thr Cys  Ser Ile Thr
    2750                 2755                 2760

Leu Asn  Asp Tyr Leu Ile Ala  Arg Tyr Phe Asn Ile  Thr Asn Cys
    2765                 2770                 2775

Asp Tyr  Ile Lys Asn Asp Lys  Cys Lys Ser Arg Lys  Asp Ile Cys
    2780                 2785                 2790

Phe Asn  Asp Asn Asn Asn Asn  Tyr Asn Asn Asp Asp  Asp Asn Asp
    2795                 2800                 2805

Asp Asp  Asn Asp Asp Asn Asn  Asp Asp Asp Asn Asn  Asn Asp Gly
    2810                 2815                 2820

Asp Asn  Asn Tyr Asp Thr Gly  Glu Glu Ser Leu Ser  Thr Leu Ser
    2825                 2830                 2835

Ser Cys  Ser Ser Glu Asn Val  Ser Ser Asp Asn His  Met Asp Asp
    2840                 2845                 2850

Ser Asp  Ile Ala Glu Glu Phe  Tyr Phe Lys Tyr Thr  His Asp Lys
    2855                 2860                 2865

Asn Lys  Asn Ile Lys Met Ala  Asn Lys Lys Asn Lys  Lys Arg Asn
    2870                 2875                 2880

Leu Lys  Glu Asn His Lys Glu  Asp Phe His Met Asn  Asn Ser Asn
    2885                 2890                 2895

Thr His  Asn Val Ser Ser Tyr  Asn Phe Phe Asp Glu  Asn Lys Lys
    2900                 2905                 2910

Asn Thr  Ile Phe Asn Leu Asn  Phe Cys Asn Leu Ile  Lys Lys Asp
    2915                 2920                 2925

Ser Leu  Leu Asn Asp Met Leu  Ala Tyr Glu Cys Tyr  Glu Lys Asn
    2930                 2935                 2940

Lys Lys  Ile Ile Leu Arg Asn  Ile Tyr Leu Asn Glu  Asn Asn Met
    2945                 2950                 2955

Tyr Asp  Glu Leu Phe Glu Lys  Lys Lys Asn Asp Asn  Asn Val Gly
    2960                 2965                 2970

Thr His  Asn Ile Ile Tyr Ser  Gln Glu Asn Asn Asp  Asp Leu Leu
    2975                 2980                 2985

Asn Asn  Lys Asp Asp Ile Asn  Ile Ile Tyr Lys Asn  Ser Asn Met
    2990                 2995                 3000

Glu Lys  Gln Lys Arg Ile Arg  Arg Arg Lys Lys Gly  Arg Gly Thr
    3005                 3010                 3015

Glu Ile  Tyr Phe Tyr Lys Asn  Thr Ser Asn Tyr Val  Asn Lys Asp
```

```
    3020                3025                3030

Tyr Thr  Phe Thr Tyr Arg Asn  Ser Asn Phe Tyr Tyr  Arg Thr Lys
    3035                3040                3045

Asn Gly  Phe Leu Ser Tyr Tyr  Val Ser Leu Pro Leu  Ser Phe Ile
    3050                3055                3060

Lys Glu  Ile Gln Tyr Phe Met  Ile Lys Asn Lys Leu  Tyr Asn Tyr
    3065                3070                3075

Pro Gly  Asn Asn Arg Tyr Asn  Lys Phe Tyr Leu Thr  Thr Glu Val
    3080                3085                3090

Asp Lys  Glu Glu Ile Lys Lys  Glu Glu Met Glu Met  Asn Ile Asp
    3095                3100                3105

Met Lys  Ile Asp Pro Ser Met  Phe Cys Asn Phe Glu  Asp Lys Ile
    3110                3115                3120

Lys Thr  Lys Glu Glu Tyr Asn  Thr Val Leu Tyr Tyr  Glu Met Asn
    3125                3130                3135

Asn Asp  Ile Ile Thr Tyr Val  Lys Ser Asn Phe Asn  Tyr Glu Ser
    3140                3145                3150

Ile Asn  Ala Asp Glu Ala Val  Lys Lys Tyr Glu Val  Cys Asp Phe
    3155                3160                3165

Tyr Thr  Asp Gly Thr Phe Asp  Ser Ala Gly Glu Lys  Leu Cys Ser
    3170                3175                3180

Glu Glu  Lys Gln Asp His Leu  Ile Thr Arg His Lys  Ile Lys Glu
    3185                3190                3195

Cys Ser  His Glu Asn Glu Ser  Glu Gln Lys Glu Lys  Arg Leu Lys
    3200                3205                3210

Val Gly  His Glu His Glu Met  Val Asp Gly Ile Ser  Asn Met Gly
    3215                3220                3225

Val Ala  Asn Asn Asn Asp Asn  Ile Tyr Gly Asp Asn  Ile Tyr Gly
    3230                3235                3240

Asp Asn  Ile Tyr Gly Asp Asn  Ile Tyr Gly Asp Asn  Asp Asn Ile
    3245                3250                3255

Tyr Gly  Asp Asn Ile Tyr Asp  Asn Asn Asn Asn Ser  Cys Val Gly
    3260                3265                3270

Gly Glu  Asp Phe Ile Cys Asp  Asn Lys Ser Asp Asp  Ile Asn Phe
    3275                3280                3285

Glu Phe  Ile Lys Asp Leu Asn  Lys Ile Asn Tyr Glu  Glu Asn Lys
    3290                3295                3300

Lys Glu  Lys Lys Glu Met Leu  Glu Ile Glu Lys Leu  Asn Lys Glu
    3305                3310                3315

Asn Ile  Asn Gly Asp Lys Lys  Asp Ile Tyr Lys Phe  Lys Tyr Pro
    3320                3325                3330

Cys Asn  Ile Glu Glu Ile Lys  Asp His Asn Ile Ser  Met Lys Thr
    3335                3340                3345

Ser Leu  Ser Met Asp Val Tyr  Glu Gly Ile Val Ser  Thr Asn Lys
    3350                3355                3360

Asn Ile  Tyr Glu Ile Tyr Asn  Glu Leu Lys Arg Lys  Gln Tyr Phe
    3365                3370                3375

Tyr Ser  Val Cys Asp Ile Lys  Ser Leu Arg Gln Ser  Ile Ile Leu
    3380                3385                3390

Leu Asp  Gly Ile Ser Glu Ile  Ser Trp Arg Ile Phe  His Gln Glu
    3395                3400                3405

His Thr  Thr Phe Ser Ser Ile  Leu His His Ser Glu  Asn Tyr Lys
    3410                3415                3420
```

```
Arg Leu  Ile Asp Phe Asp Tyr  Asn Thr Lys Ile Asp  Asp Asn Asp
    3425                 3430                 3435

Glu Asp  Ile Asp Ile Lys Gly  Ile Gly Val Asn Asp  Leu Leu Lys
    3440                 3445                 3450

Ile Tyr  Arg Arg Leu Glu Ile  Tyr Pro Asp Phe Ile  Phe Asn Asn
    3455                 3460                 3465

Asn Asn  Val Gly Phe Ile Asn  Arg His Asp Leu Lys  Phe Ile Thr
    3470                 3475                 3480

Lys Lys  Asp Leu Leu Leu Met  Asn Arg Lys Asp Tyr  Glu Arg Asn
    3485                 3490                 3495

Lys Lys  Glu Arg Lys Lys Lys  Asn Thr Asn Leu Tyr  Pro Thr Asn
    3500                 3505                 3510

Ser Gln  Thr Asn Asn Asn Glu  Asn Asp Asp Asn Asn  Asn Asn Asn
    3515                 3520                 3525

Asn Asn  Asn Asn Asn Asn Asn  Asn Asn Asn Asn Asn  Asn Asn Asn
    3530                 3535                 3540

Asn Asn  Asn Asn Asn Asp Ser  Arg Gly Asp Val Asn  Lys Pro Lys
    3545                 3550                 3555

Asn Asn  Asn Ser Phe Asn Asn  Asn Ser Glu Thr Lys  Glu Gly Asn
    3560                 3565                 3570

Lys Lys  Lys Lys Lys Asn His  Ser Asp Val Leu Asn  Ile Lys Tyr
    3575                 3580                 3585

Trp Arg  Asn Ile Asn Thr Ala  Val Asp Phe Phe Lys  Ile Tyr Trp
    3590                 3595                 3600

Ile Leu  Tyr Asn Glu Ile Leu  Ile Asn Ile Phe Tyr  Lys Asn Ile
    3605                 3610                 3615

Asn Tyr  Ile Ser Cys Asn Asn  Met Ile Glu Ile Leu  Val Arg Asn
    3620                 3625                 3630

Leu Phe  Leu Tyr Lys Tyr Glu  Leu Asn Ile Leu Lys  Glu Glu Asn
    3635                 3640                 3645

Met Cys  Asn Leu Phe Asn Ile  Gln Thr Trp Lys Asn  Met Tyr Lys
    3650                 3655                 3660

Ile Cys  Phe Phe Tyr Val Tyr  Pro Tyr Arg Phe Thr  Phe Asn Lys
    3665                 3670                 3675

Tyr Lys  Lys Phe Phe Asn Lys  Ile Lys Lys Ile His  Phe Leu Asn
    3680                 3685                 3690

Asn Leu  Ser Phe Ile Pro Leu  Ser Val Asp Val Leu  Lys Leu Phe
    3695                 3700                 3705

Met Asn  Phe Phe Leu Asn Gln  Tyr Leu Tyr Thr Pro  Ser Leu Ile
    3710                 3715                 3720

Lys His  Phe Ile Ser Ile Ser  Leu Ile Ile Ile Ser  Phe Gln Ile
    3725                 3730                 3735

Met Asn  Glu Ile Phe Ile Lys  Glu Ile Ser Lys Thr  Tyr Val Arg
    3740                 3745                 3750

Phe Ile  Phe Lys Thr Ile Gln  Asn Tyr Asn Lys Ile  Lys Lys Tyr
    3755                 3760                 3765

Ile Thr  Arg Ile Ser Lys Tyr  Met Tyr Phe Gln Lys  Ile Tyr Thr
    3770                 3775                 3780

Asn Tyr  Ile Ile Ser His Tyr  Glu Tyr Val Asp Tyr  Ile Glu Arg
    3785                 3790                 3795

Ala Asn  Thr Phe Ile Gln Thr  Glu Glu Thr Lys Lys  Ile Arg His
    3800                 3805                 3810
```

```
Asn Glu  Ser Ser Ile Tyr His  Asn Ile Glu Met Val  Gly His Lys
    3815                 3820                 3825

Gln Asn  Glu Gln Lys Arg His  Ser Leu Asn Ser Tyr  Asp Arg Phe
    3830                 3835                 3840

His Ile  Phe Leu Phe Glu Lys  Tyr Val Lys Asn Ser  Ile Pro Gly
    3845                 3850                 3855

Gly Glu  Asn Ile Thr Leu Lys  Tyr Val Asn Gly Arg  Tyr Lys Leu
    3860                 3865                 3870

Tyr Asp  Asn Glu Gln Glu Val  Val Arg Met Ser Asp  Leu Glu His
    3875                 3880                 3885

Phe Glu  Lys Ile Lys Asn Val  Tyr Ser Lys Lys Ala  Thr Asp Ile
    3890                 3895                 3900

Leu Lys  Lys Lys Asn Glu Lys  Met Lys Asn Asp Lys  Glu Glu Thr
    3905                 3910                 3915

Gly Asn  Glu Gln Ala Asn Asn  Cys Asn Lys Thr Leu  Asp Gly Asn
    3920                 3925                 3930

Lys Thr  Leu Asp Gly Asn Lys  Ile Leu Asp Gly Asn  Lys Thr Leu
    3935                 3940                 3945

Asp Gly  Asn Lys Ile Leu Asp  Gly Asn Lys Ile Leu  Asp Asp Asn
    3950                 3955                 3960

Lys Leu  Leu Asp Asp Asn Lys  Leu Leu Asp Gly Asn  Lys Thr Leu
    3965                 3970                 3975

Asp Gly  Asn Lys Ile Leu Asp  Asp Asn Lys Ile Leu  Asp Ser Asn
    3980                 3985                 3990

Asn Asn  Asn Asn Asn Asn Asn  Asn Asn Asn Gly Glu  Asn Lys Ser
    3995                 4000                 4005

Trp Asn  Phe Gln Asn Val Ser  Ser Tyr Asn Asp Leu  Ile Lys Ser
    4010                 4015                 4020

Val Leu  Asp Lys Lys Asn Phe  Phe Phe Ile Ile Asp  Ile Val Asn
    4025                 4030                 4035

Leu Phe  Lys Asn Ile Gln Thr  Leu Ser Tyr Leu Phe  Asp Glu Glu
    4040                 4045                 4050

Thr Ile  Arg Tyr Val His Met  Ile Ile Met Asn Ser  Lys Ile Leu
    4055                 4060                 4065

Ser Tyr  Asp Leu Lys Glu Ile  Glu Arg Lys Lys Asn  Leu Gln Lys
    4070                 4075                 4080

Lys Ile  Tyr Pro Asn Phe Thr  Ser Tyr Ile Thr Lys  Gln Lys Lys
    4085                 4090                 4095

Ala Asn  Lys Leu Lys Cys Tyr  Asn Tyr Asp Leu Leu  His Ile Glu
    4100                 4105                 4110

Lys Lys  Trp Ile Leu Tyr Leu  Ile Tyr Lys Thr Ile  Leu Lys Tyr
    4115                 4120                 4125

Tyr Asp  Met Leu Ile Phe Lys  Lys Lys Val Gln Lys  Leu Met Leu
    4130                 4135                 4140

Leu Met  Cys Glu Ile Asn Asp  Glu Tyr Ile Lys Tyr  Ile Tyr Phe
    4145                 4150                 4155

Asn Gly  Tyr Ile Pro Ile Asn  Ile Tyr Leu Ser Thr  Asn Leu Ile
    4160                 4165                 4170

Lys Tyr  Asn Glu Phe Phe Thr  Asn Tyr Tyr Ser Tyr  Ile Tyr Asn
    4175                 4180                 4185

Lys Asn  Val Asn Asp Lys Trp  Gly Asp Phe His Val  Leu Tyr Phe
    4190                 4195                 4200

Gln Asn  Glu Glu Asn Asn Ile  Lys Lys Glu Asn Lys  Lys Asn Tyr
```

```
    4205                4210                4215

Tyr Tyr  Tyr Tyr Tyr Tyr Tyr  Tyr Tyr Thr Leu Phe  Lys Asn Lys
    4220                4225                4230

His Val  Leu Lys Arg Asp Tyr  Asn His Ile Val Ser  Asn Asn Ile
    4235                4240                4245

Gln Pro  Ile Asn Lys Met Asn  Glu Pro Ile Thr Ser  Asn Glu Cys
    4250                4255                4260

Thr Ser  Pro Asn Met Ser Tyr  His Ile Glu Ser Asn  Glu Ile Phe
    4265                4270                4275

Lys Asn  Glu Asp Asp His Asn  Leu Asn Ile Tyr Asn  Glu His Ile
    4280                4285                4290

Met Tyr  Asn Ser His Lys Asp  Thr Asn Leu Leu Ser  Ser Ser Asn
    4295                4300                4305

His Met  Gln His Val Gln Lys  Asn Thr Leu Thr Met  Asn Leu Asp
    4310                4315                4320

His Ser  Asn Asn Leu Ile Ile  Asn Asp Asn His Lys  Arg Asp Lys
    4325                4330                4335

Glu His  Asn Ile Asn Thr Lys  His Trp Asn Lys Asn  Ile Ile Asn
    4340                4345                4350

Ser Asn  Tyr Phe Asn Val Tyr  Asn Asn Asp Ser Ser  Pro Lys Glu
    4355                4360                4365

Gln Ile  His Leu Glu Glu Gly  Gly Gly Gly Leu Ile  Asp Val Asp
    4370                4375                4380

Asp Asp  Lys Lys Asp Asn Val  Ile Asn Ser Asp Asn  His Phe Lys
    4385                4390                4395

Glu Thr  Thr Tyr Asn His Ile  Ala Tyr His Lys Asp  Gln Glu Leu
    4400                4405                4410

Ser Thr  Glu Leu Asn Leu Phe  Lys Tyr Lys Leu Tyr  Asn Ile Ser
    4415                4420                4425

Ser Glu  Glu Ile Ser Asn Leu  Tyr Leu Met Glu Asp  Cys Asn Asn
    4430                4435                4440

Glu Lys  Gly Phe Phe Ser Cys  Val His Lys Asn Glu  Asp Phe Glu
    4445                4450                4455

Tyr Lys  Asn Ile Asn Ile Leu  Asn Ile Leu Lys Tyr  Gln Phe Glu
    4460                4465                4470

Leu Val  Pro Tyr Ile Asn His  Leu Tyr Tyr Leu Tyr  Asn Ile Tyr
    4475                4480                4485

Pro Leu  Leu Phe Lys Leu Lys  Glu Ile Lys Asn Ile  His Asp Met
    4490                4495                4500

Lys Glu  Lys Gln Ile Asn Leu  Cys Thr Asp Gln Phe  Leu Leu Ser
    4505                4510                4515

Leu Val  Asp Lys Asp Ile Tyr  Asp Cys Tyr Asp Asp  Val Asn Phe
    4520                4525                4530

Ser Asp  Ala Ser Phe Tyr Ser  Asp Gln Thr Ile His  Val Ser Glu
    4535                4540                4545

Lys Glu  Cys Glu His Lys Asn  His Asn Ser Asn Lys  Tyr Asp Cys
    4550                4555                4560

Asn Asn  Tyr His Pro Phe Asn  Val Ser His Leu Ser  Tyr Pro Tyr
    4565                4570                4575

Lys Asp  Gln Asn Gly Asp Glu  Glu Asp Thr Leu Gln  Ile Asn Ser
    4580                4585                4590

Ser Leu  Asn Ile Leu Glu Asn  Val Val Asp Leu Asp  Glu Leu Ile
    4595                4600                4605
```

```
Lys Asp  Leu Lys Lys Thr Lys  Lys Ser Lys Lys Lys  Thr Ser Lys
    4610                 4615                 4620

Asn Lys  Tyr Ala Asp Lys Phe  Phe Val Ser Phe Phe  Asn Thr Ala
    4625                 4630                 4635

Leu Lys  Arg Asp Glu Asp Lys  Gly Lys Thr Asn Tyr  Val His Tyr
    4640                 4645                 4650

Arg Lys  Leu Arg Asn Ala Lys  Asn Asn Ile Lys Leu  Lys Asn Leu
    4655                 4660                 4665

Phe Leu  Ser His Gln Gln Asn  Asp Thr Ile Tyr Asp  Asn Ile Asn
    4670                 4675                 4680

Gly Asn  Ile Cys Asp Asn Leu  Tyr Gly Asn Val Asn  Thr Tyr Gln
    4685                 4690                 4695

Asn Ser  Ala Ser Leu Ile Phe  Val Asp Pro His Asn  Leu Thr Asn
    4700                 4705                 4710

Ile Asn  Ile Ser Asn Glu Leu  Asn Asn Asn Ile Asn  Ile Asn Cys
    4715                 4720                 4725

Ser Lys  Asn Lys Lys Lys Lys  Lys Pro Ser Ser Asn  Asp Gln Asn
    4730                 4735                 4740

Asn Thr  Glu Asn Glu Asp Met  Gln Asn Ser Ser Ser  Asp Asn Pro
    4745                 4750                 4755

Tyr Asp  Asp Ser Asn Phe Ile  Ser Tyr His Glu Ser  Ile Asp Ser
    4760                 4765                 4770

Thr Ser  Ser Thr Asp Lys Tyr  His Lys Arg Lys Met  Thr Pro Met
    4775                 4780                 4785

Glu Ser  Met Phe Leu Lys Tyr  Thr Leu Asn Thr Ser  Glu Asp Ala
    4790                 4795                 4800

Leu Ser  Asn Lys Tyr Asn Val  Thr Ser Lys Asn Lys  Asn Lys Lys
    4805                 4810                 4815

Glu Tyr  Leu Ser Phe Leu Lys  Tyr Lys Asp Ala Asn  Lys Ile Gln
    4820                 4825                 4830

Arg Tyr  His Met Leu Leu Arg  Lys Asn Gly Leu Gly  Arg Leu Phe
    4835                 4840                 4845

Phe Tyr  Asn Leu Arg Lys Met  Tyr Asn Tyr Val Tyr  Asn Leu Tyr
    4850                 4855                 4860

Asp Phe  Ile Pro Leu Tyr Leu  Ile Gln Asn Ile Leu  Ile His Tyr
    4865                 4870                 4875

Tyr Asp  Ile Tyr Gln His Val  Asn Gln Tyr Tyr Tyr  His Asp Asp
    4880                 4885                 4890

Lys Glu  Tyr Pro Thr Phe Phe  Thr Gln Gln Asn Glu  Asp Asp Glu
    4895                 4900                 4905

Tyr Glu  Tyr Thr Lys Phe Ser  Lys Asn Phe Phe Asn  Thr Asn Lys
    4910                 4915                 4920

Trp Lys  Lys Met Tyr Ser Lys  Tyr Glu Asp Lys Leu  Asn Asn Glu
    4925                 4930                 4935

Thr Tyr  Pro Glu Pro Pro Lys  Lys Tyr Ile Ser Asn  Lys Gln Arg
    4940                 4945                 4950

His Lys  Glu Asn Ile Leu Ile  Tyr Gln Asn Leu Gln  Asn Asp His
    4955                 4960                 4965

Met Asn  Asn His Tyr Asn Ile  Ala Asn Asn Asp Ile  Glu Asn Lys
    4970                 4975                 4980

Asn Gln  Thr Asn Ser Ser Tyr  Leu Phe Asn Val His  His Gln Asn
    4985                 4990                 4995
```

```
Cys Pro  Ser Leu Ser Ser Asn  Asn Leu Val Asn Ile  Asn Ser Thr
    5000                 5005                 5010

Leu Ile  Asn Asp His His Phe  Val Gln Thr Asn Asn  Asp His Met
    5015                 5020                 5025

Asn Ile  Ile Gln His Met Glu  Asn Ile Pro Glu Met  Ser Glu Cys
    5030                 5035                 5040

Asn Leu  Lys Thr Asp Gln Asn  Asn Asn Ile Phe Asn  Phe Pro Gln
    5045                 5050                 5055

Asp Lys  Ile Asn Pro Asp Thr  Met Lys Lys Asn Glu  Lys Met Glu
    5060                 5065                 5070

Phe Ser  Val Asn Lys Lys Ile  Lys Thr Asn His Asn  Thr Thr Gly
    5075                 5080                 5085

Tyr Asn  Lys Arg Asn Asn Asp  Arg Tyr Asn Tyr Ser  Ser Thr Pro
    5090                 5095                 5100

Asn Phe  Phe Gly Lys Asp Glu  Tyr Asp Asn Thr Ser  Tyr Glu Asp
    5105                 5110                 5115

Tyr Ile  Lys Lys Lys Lys Lys  Asn Phe Ser Ser Thr  Ser Arg Arg
    5120                 5125                 5130

Lys Arg  Asn Asn Asn Ile Asn  Met Lys Glu Phe Phe  Ala Asn Gly
    5135                 5140                 5145

Arg Tyr  Asp Lys Leu Leu Ser  Ile Lys Lys Ile Phe  Met Ile Phe
    5150                 5155                 5160

Tyr Asn  Tyr Leu Arg Lys Cys  His Phe Ile Asp Lys  Lys Asn Ser
    5165                 5170                 5175

Cys Lys  Asn Leu Tyr Lys Ser  Phe Leu Lys Lys Tyr  Leu Lys Ser
    5180                 5185                 5190

Ala Asn  Val Tyr Leu Gln Phe  Ile Ala Tyr Ile Ile  Phe Ser Ile
    5195                 5200                 5205

Tyr Asp  Tyr Asn Ser Leu Ala  Lys Lys Tyr Leu Asp  Tyr Ile His
    5210                 5215                 5220

Leu Tyr  Ser Asp Ile Ser Lys  Tyr Asn Ile Phe Leu  His Ile Leu
    5225                 5230                 5235

Asn Ile  Asp Glu Asp Tyr Asp  Lys Ile Tyr Ile Tyr  Gln Thr Leu
    5240                 5245                 5250

Gln Leu  Ile Tyr His Pro Tyr  Phe Tyr Leu Met Tyr  Lys Leu Tyr
    5255                 5260                 5265

Lys Tyr  Leu Lys Ile Asp Ala  Ser Pro Val Leu Leu  His Asp Phe
    5270                 5275                 5280

Tyr Glu  Asn Trp Glu Glu Phe  Thr Lys Ser Pro Ser  Leu Phe Gln
    5285                 5290                 5295

Pro Ser  Lys Asn Tyr Phe Thr  Leu Ile Lys Lys His  Phe Lys Arg
    5300                 5305                 5310

Lys Cys  Val Ser Cys Asn Lys  Ser Pro Lys Lys Ile  Leu Ile Cys
    5315                 5320                 5325

Leu Tyr  Cys Gly Ser Thr Val  Cys Leu His Glu Gly  Asp His Val
    5330                 5335                 5340

Ser Gly  Pro Leu Ser Gln Thr  Ile Ser Lys Cys Val  Tyr His Thr
    5345                 5350                 5355

Thr Ile  Cys Gly Gly Glu Gln  Cys Leu Tyr Leu Cys  Leu Asn Thr
    5360                 5365                 5370

Ser Ser  Val Leu Phe Thr Ser  Glu Asn Arg Phe Asp  Phe Met Ser
    5375                 5380                 5385

Gly Pro  Tyr Val Asp Lys Asn  Gly Asp Val Asp Tyr  Gln Leu Lys
```

```
    5390                5395                5400

Arg Gly  Lys Asn Leu Tyr Leu  Ser Ser Tyr Lys Leu  Asn Lys Leu
    5405                5410                5415

Phe Asp  Val Ile Ile Asn Ser  Ala Val Asp Val Glu  Ile Tyr Lys
    5420                5425                5430

His Thr  Leu Lys Ser Glu
    5435


<210> SEQ ID NO 11
<211> LENGTH: 20805
<212> TYPE: DNA
<213> ORGANISM: Plasmodium falciparum

<400> SEQUENCE: 11

atgataaagg cattatacaa aagtattgta aattttttat tgtcatcctt ttttgaaaac     60

attgaagaaa aacaattaca aacatcatta atacgaggaa aagttcattt gcaaaatgta    120

aaaataaaaa aattttttttg tgattttata tatttacctt atactatcaa atatggttat    180

attcgttcct tggacttaca aataccactc ttgtatttgt ttcaaaaagc ttctttaaaa    240

gtaagcgacg ttgtaatagt tttgaaggaa aaacatttca gcgaatataa catagaagaa    300

gaaataaatg gaataaaagg agggaaaaag aataatttaa aacttgaaga ttataattat    360

aatagtaatg atgtgaatca gaaaattaat aaaggcttaa attatttatt ttatgaatta    420

tataataata tgtctattga tattgaaaat gtagaaatta tattagaaag ttctgaaaag    480

actactaatg ttattggatt gtttgtaaaa aaaataagta gtgttaaaac tcataattgt    540

acaaataaaa taataaaaga tttttctttt gtggatgcta ttttttatat gaatgatgaa    600

aaagcgaaat atgcaattaa taaaattata aaaaaagaag aaaagaaaaa gaaaaataaa    660

agaaatatta atgaagaaga tatatataat aaaattaaat atatttgtaa taatttacat    720

aaaaaaaaat atataatttc agaaatacca tccattgttt taagtacaag tatgtatgtt    780

agtaatagta ctgattatta ttatcataat tcaaaatttc tttttaaaaa aaatagctat    840

tttaatatta catgtacaca ttgtgataaa tatctttttc aatgtaaaga agtgaaaaaa    900

gataaatcga tatttcaaaa tatattcata aagaaagaaa aaattcaaca aagaaataaa    960

cagctctata gtgaaattaa ttgtaaatgt atgaaaaata ataaaaatat tttccagaaa   1020

gatcaaaata caaattgtac gtataattca gatcatgtac ctgagaactc tcttaagggt   1080

actaatgaaa tgaataaaaa tattccccct gatcttgaca gtataaatgt gggacacccc   1140

aagattgatg atgataatga aaaaaataac catgaaaata atagtcataa tgataatcat   1200

aataatagtc ataatgataa tcataataat agtcataatg ataatcataa taatagtcat   1260

aatgataatc ataatgataa tcataataat aatcataatg ataatcacaa tcttaaacat   1320

aaacgtaatt ataatcatcg taatggtggt gtcggacaaa ataatactgg tgataacaac   1380

cttttaaata atacatttaa taaacataac gaagaaagaa ccgtacaaga gaaagatgaa   1440

aaaaaaagtg aagattgcat tgattgtaat tgtaaaaaaa atattagtga agatcttgat   1500

aattgtttat attgtaggat taataataaa aatcaatcgt atattgaaaa atttcatatg   1560

ttagaagaaa atataaattt aaaagaaaat gaatatatga cctttgaatt gaatgtagat   1620

aaaatagatt taatattatc attcaaacaa ttctattata tcttagatat tgtaaattat   1680

tattttatat atagttgtct tgttaatggt ttgtgtatag aagaatggtt aaatatccca   1740

gaaattaatg atatattaat ttataaaaga gaattaataa aaaaaaagaa aaaagaaaaa   1800
```

```
tttgataaag attttataga taaatttgaa tatacacata gctttcaaat tatttcaaat   1860
ataaaaaaac atgtcgaaga atattcttta gacaataata aaaggaaaaa aagtataaga   1920
ggaacaggcg aagatttatc aacacttctg aatagtaatc ataacaatga atataattat   1980
aaaaatgaac ataatcgtca caatgaacat aatcatcaca atgaacatga taataataat   2040
aataaggtga caaaatcaca atccgcgtcg tctcatttgt caaacgtatc aacatggaat   2100
aaaccttttt ttgtatataa taaaaaaatt tcagtaaatt gttcatttaa cattttaatt   2160
aaaaaattaa atttttgttt atgtagtggg gataaaataa ataaaatcat acaaattaat   2220
acggatgatt ttaattttaa tgttaaatct tatattaatg ctgattttgc atattcctta   2280
ttgttaaaag atattagtgt tttctttata cataaagata aaaaatatcc tttgtttgaa   2340
ttatttaatg ttaatgaaca taataaaaaa gaagataaga aaaaagagaa tatgaaagta   2400
aataaaagaa aaagtaaaac ttatatattc aatacacact tatgtaatga tgcgatgact   2460
tcttttaaaa gcgtttcatc tataaaaaat gttccaggta atatgaataa tattacagat   2520
aatatgaaaa atgataatta taataatata tataagaata atgaaaaaaa tgtggaaaat   2580
ggaaagaaat gtagtaaata tgttgagtct agaaatttag tggaaataaa taatagacat   2640
aatgaatatt caaaagaaaa gaaaaatata acaaatataa agaatgacaa tattaataat   2700
aatgaaaata ataattatga taataatatt aataataaag aagaatatgc aatatcatta   2760
ttaacattta ctaaatatga aactacacaa gctaaaacat ttataaaatt taataaaaat   2820
attcttataa cattaagtgt taaagaaatt tataatattt taaatatgaa ctgtgattat   2880
aaaccagtcg atttagaaaa aaaattgaaa tcttataaaa ttttatttta ttattatctt   2940
ctaggaaaaa aatattgtaa agaattatat atggcatcag ataaaaattt tgaggatatg   3000
aatatacatt ttatgcataa tatttatttt aatataataa ttaataaaaa atataattta   3060
ttatttaaaa tgaaaaaggg acttgtaaat tctttcttct ttacaaaaat gtatttacat   3120
tgtgatttga agaaactaac tatgataaca gaccataatg atatgcaaca aaatatggat   3180
aacaaattag ttgatcaata tactgaacaa atgaaagaaa actcttcata tcagaatagt   3240
caaagttgta gtaatacaag tagtgtgggc tttacaaatg aggacccaac gaaaagaaga   3300
aataaagaaa aaaataatct aaatataaat ataaatttaa atttaagtac gaatgacgat   3360
gtaataatta ataaaaatga agaaaaagaa aatgaaaata aagaaagtaa taggacagag   3420
catataaaac gtgataattc tatacattcg aatgataatt gtagtatagg tactcatagt   3480
gagcttttta aaaattcgga atataattct atgattaata ataataataa taataactct   3540
tttataaata atgataatac aagtattgat aataaggtgt caatgcaatg tagaaagtat   3600
tatcaggagt ttttaaaaat gaataattta gaagatatta aacaattag aaaaatagaa   3660
aaaagggcaa accaaaataa cacaagcaat aataatacta taaataatat acacaatata   3720
aataatgtac acaatgtaaa taatatacac aatgtaaata atatacacaa tgtaaataat   3780
atacacaatg taaataatat acacaatgta aataatatac acaatgtaaa taatgtacac   3840
aatataaata ataattatta tgatcatatt tatagtcata acaatatcca tattaataat   3900
catgcgatta tccacaataa cagccattat aataataaaa aaacaaacat tattctgaac   3960
aacaacaaat atgatgaata taatgataaa cacagttttc atagcgaaaa tacaaattct   4020
tatagtaatt caaataagga tgattattta aatgaagatt taaatttata taaagatcat   4080
atgtatatac aaaattgtat aacggaaaaa gaagataata taattactac aatttatcag   4140
aaaagaacaa attttgaact ttctcttttt attcttaaaa ataaaaataa tgaaaagata   4200
```

```
caaaatatat tatctcataa aaataaaata aataagaaat atatattaaa accattaaaa   4260
atatatattg atgaaattac atataatttt aaaaattcga gtgataagaa aataaccttt   4320
tttcatacta ataattataa aaactatcta aattttacac ttgatgataa aattatattc   4380
aaacttattt tcttttatta tcattataaa gattatgttg atcatatttt tgaaaagttt   4440
gaaagcaaag atgaatccaa ctatttaaat ttaaatacaa tagatgtacg tagttataaa   4500
actttacaaa ttttattaga taatgctgtt cataataaga atgatcactg gttcaatgaa   4560
cagaaggatg ttcatgataa agatgagcag aataaaggaa caatatatta tgaacaaaat   4620
gaacatgata tcaaaattga tgataataat gaggaggaga ataacgacca cacagataat   4680
aataataaaa acaataataa taataataat aacaataata ataaaaacaa taataataat   4740
aacaataata ataaaaacaa tatggtggat ggtcaaatcg aatgtaatga aaatgttaca   4800
gaaaaagaga taccaagtaa tgtacccaat tcaaataact taacaaatga aagttcaaat   4860
gataatcata ataaaacaac tattgaacat aataataatt tttgtgaaga acagaacaaa   4920
aatgatttaa taaaaacatc ctttaatatt actcattgtg aagaagaaaa tgcaaataaa   4980
aataaataca cggaggaaga taaaaaggaa ataaaaggaa atgataaaaa aaatgttgaa   5040
atgtgtagaa aagatacatt agattatgta aaagaagata taaataaata taagatgtat   5100
attaatgaaa ataataataa aaaagaagaa gaatattcac ataataataa taatcatcat   5160
catcattacc atcataataa tatgttgaaa gatgatacat caaattataa ccatgtacaa   5220
tatttccatg gagaaaaaaa agaaataata tgttttataa ataaaagtaa aatacatttt   5280
aataattata aaaaaagtaa aagaatgata tcgatacatt tatcagatgt cctaatgtat   5340
ttatttagtg ataataatat tacaaacttt ttatttaatt taaaaaaaat taatatatta   5400
aattgtttat ctcatgaaga tagttataat agtttctttt catatataca acataaaaaa   5460
ttttctacac ataaaataag taaaaaagga tcaaaattaa gtgataaaag aaagagttca   5520
aatgttaatg gaatttattt ttataatagt gtttttaaat taattcaaaa cggtaccttt   5580
cttttaaaat attcatcaaa gaataatatt tcatgcttat cttccataca tctaaaccca   5640
aatcataatc attatataga aaataataat tcaaaagaaa aaaattattt tctaaacaac   5700
aataataata ataataataa aatggaaata gaagaaacta ctgaatttag atattttaat   5760
acaaataatt ttgaacaact aaataataca tcaggaaata aatctattga tggatccaac   5820
gtgaaaatta ataatagtct tgattttgtt cataaaaatt attataataa tttgaataat   5880
gactatttta attttaatgt acctcaggat tctaataaac gaaaggatgc cacaagttct   5940
ccaagtaatg ttagtaataa aagtggggaa atcaaaagta gtcacaagaa ggaacaaagg   6000
aaagataatc atatgaatga aaatattaga ggtagtcata gaagttatag tactcatcaa   6060
agttatagaa cccatcaaag ttataaacgt catgctaata atagtaatat acgatgtagt   6120
agcagcccaa gcgaaagaac acacatctcc aaaaaagatg aaataaaatt caataaagaa   6180
aacattatga cattgttaaa tgattgtaca aataatgaag gagaaaatca tcatgttaaa   6240
ataacgaaca aacaaatcaa aagaagtaaa agtaaagaac aatttgaaga tataataaat   6300
agtaatacaa aaaaaacaaa tgatatagaa catatttggg atgaacaaaa taatcaaaac   6360
aataaagaaa atgataatgt tgtaaataga gttgagaaaa aaagtattat tacggaaaat   6420
tatatacctt ataaaagttg tatagaacaa attgatgata ttgattataa taaagaatcg   6480
ttacaacatg aaaaaaacat agatggaaaa acaaatatta tatatcataa taataataat   6540
```

```
aataatgatc atataaatat gaatactact acttgtattc ctataaatga aaagaacttt   6600
gttatacaaa gaaataaaaa aatttctcat tactataatg caaaagaata taatgattca   6660
aataaaagga gaagaaataa ttatatatta actggagagg taaataatat aaaaggttat   6720
aataaagatg atatgcattc atcacatgtt aataatatga ataattcatt atgctcatca   6780
gcttatcata atatgaaata tgaaaaatat gtagatattg agaaatatag aaatgatgac   6840
gaattttatg aagctgaaga tgatgaagat gaagaaaatg atatagataa tcaagaagaa   6900
gaatatattg atatgaaaaa aaaagaaaat gaaaatatta gtagtattga atttcatatg   6960
attaatagtg aatttattgt agattattta tattttatat atttatttaa atggattaat   7020
aaattatata gaaaatatga aaaaattaaa caattgtcag attttgcata ttcaaataat   7080
aatagtacag atgatgaaga aagtaatata aatgtatcaa aatgtaatta tattcttttc   7140
ttacaaaata ataaaattta tgtaccaata tataattatt caatatcaca atataagtat   7200
tataatagtt taaagggaac ctcttatgta tccttattac ctgtattaga gttacatttc   7260
tcatgttcct acaaatctat gaacgaaaac gatgaaaatg taaagtcgat aaacgtgcga   7320
aatttgggaa gcgctcttgt cattccaagt attaacattt acaaacataa aaaaaacaag   7380
aaaagcaata tatgtgtaat aacgtttaat aggaaggata agaataatga aagtatcatt   7440
aacgatttaa gatttcaaat aaatatgaga agaaattata attatgaaat tatagaaaat   7500
gaagatgata atagtagtag ttgtaataat atggagattc catattatga acctaaatat   7560
acatcattaa atacatattg cacggttata tctaaagagc agatgtattc agaaaagaac   7620
aagaataaaa ataataatat taacaacaat aataatgata ataatataat tatgtatgat   7680
aataatatgt ataattatca tggttaccat actaaaacag gatcatatcc aaaaaagatt   7740
attagtttcc attgtgatcc tataatttta aatttttcaa aagatatatt aaaaaatgta   7800
cttatatttt ataatacatt ttgttatttt ataaataatt gtagtaaaaa cgatgataca   7860
ggtaatgata gtaatatgat tagagatatg ttatattatt tatacaacca aagtagtgat   7920
atattatttg aatattttct tgatgatata cgtttaaatt gttatgatgg taatattaat   7980
cgaaatgtac cattgatagt agttagtttg tttaatttaa aattcttttt acaaaaggat   8040
ataataagta tatataattt tttgaatttt tatttaaata tagatatata tgatagttat   8100
aaaatattat atgatacgtt attagaaaag atggaaatat atttaacttt tgaaaataat   8160
agaaataaat tgaatatatt aaatttaaca ttagaaacat cttatattaa tattttatat   8220
acaaataaaa gtaaaaatat attaataaat ttccttgagc caatattaaa taaaaatttt   8280
tattatttca gttcatcata ttataataat ttggatatta caaaaaataa aagaagaaaa   8340
cgaagtattt atcatcatca taatcataat tatcatcatg aatgttatga aaataatatt   8400
ttaattaaaa atacaaaagg aaaatcatta gttacacata taacatctaa aatatttaat   8460
tatacaggtt tatcaataaa tgtaagattt aaacaatcat tacgaaataa aatacaaaac   8520
aatagtttaa ataataagaa taaaaataaa tatttatttt atgaattaca aaataatgag   8580
catggggcat tattaaatga tgaaaatgga gaagtgtgtg aagtcgtagt tattataaaa   8640
atatttaatt atatatttga aataatagat atagaaagaa ataaaaatac atgtgatatt   8700
agatttttac ctataatata tgaattaaaa aaatttaatg aaaaaaaaaa aattactatt   8760
aaaaagtatg atataaatta tgatatatat aatgaatatt cattaaaaaa taaagtattt   8820
aaaacattta ttaaattata tatacaaaca aatattgatg aaaagggaat agtctcaata   8880
tatttctcat caaatctatt tattaataat tcaacaaata gtgattttgt tttattgttt   8940
```

```
caccctgtac tttattattt tatgttattt aatgaacagt ccacaaatag taacactaac   9000
aataatataa acaacaacaa taaaaatgag gataacatgg tcgataataa tgaaaataat   9060
gataaaaata atgataaaaa taatgataaa aataataatg aaaataagga ttgtgatagt   9120
gtccataata ttaataatgt ggaaagcgat tcaccagtaa atataaactt tttcaaaaat   9180
gataattata ataataatta ccataataat taccataata attaccataa taataatgac   9240
aaaggtgcaa atataactat tattaattcc aatgaaaggt attttttacc tcttatttct   9300
tttataccta ttattatttt atatgattat ttaaagaaaa aaaatgaaat cgaagaaaat   9360
aattaccctg acaagtatcc aatgaattct aagaattctt atgtaacacc tgtctcaatg   9420
gtatgtgatt taaaaggaag cttcagtgca gatataaaaa aaaataattt cataaaacga   9480
tttaattcgt taaattataa tatgaatatt cataatggtg aagaggaaga aatatctaag   9540
cagaatgaag ccaatgatat gttaaattat acccacgtgg ataatagtaa caacgaaaca   9600
tcttgcagaa ataataatga agataaaata ttaagttata agaaaagaat tacttatgat   9660
tattcttcga ttaattcttt aaaaaaattg tcatacaata acttaacacg tgctagctgt   9720
tatgttaact ccagaagtag cgaaatgaac ctttgtaata taatatcgaa taaaggagat   9780
aaaagaaatt ttatgaacaa tgaaaaaata atagaatctc ttaatttgaa tgctttaaga   9840
gaaattaata aaataagaac taatagaata ttaaaaagat tagaaaaata tgtaaatgaa   9900
aaaagtaata gtaagaatat gaaaaatatt aattatattt atattattaa aaaagaattt   9960
tatgatttct atattcataa aaatgaaaat aataataaat gttattttga aatgtttaat  10020
tttttaataa aaaatggagc caaaaaagtt ttaaataatt caagtataaa agaaattatc  10080
tgtagacatt cctttgattt tttaaaatat aatttatatg cacaaacatt aaaattaaaa  10140
actttaaaaa ttatatgtta tgataagtat agtagatatt taagggagaa gaaaaaggaa  10200
atggaagaag ctaaaacgta taataataat aataataaaa ataacatcaa caataataat  10260
aacaacaatg ataataacaa caataataat aacaacaaca ataataataa caataataat  10320
aataatatga agaaaaagca aattggtgat atatatatga aaaattataa agaagaaaaa  10380
aatgatataa aggaagaaca agaaaaacat gataatagta gtagtattgt ggtgttaaat  10440
aaatttcatg attattatga taaaagagat aagtattatt ttgaaaacaa ccacaggaat  10500
gaccattaca caagtgactt aaataatgat gataataata aatataatat ttatgataat  10560
aataaatata gtatttatga taataataaa tatcatattt atgataataa tgaaagtaac  10620
aataaaaagg atgattttta ttatagcata cctactaatc tcgatatttc acttaaatgt  10680
ataaatcgaa atgaaagaca catcaacagt cttctattta atcatagtaa gaggaaatct  10740
acattaagca acatactaat aaaacatgat atgattaaaa atagtgtatc taaacatatc  10800
ctgaataatg attatgcata tgaatatgat aaaaaggaag aaatagaata taactataat  10860
aataaggata attgtgaaaa aaatatatat gtgcttgatg taaaaaataa aaaacaaaat  10920
aataataata atatgaacga tgatgatgat gataataata atatgaacga tgatgatgat  10980
gataataata atatgaacga tgatgatgat gataataata atatgaacga tgatgataat  11040
aataatgata ataataatga taagaagaag catcatatta tccattataa taataataat  11100
attataaaaa agaaaagaag gaaatttata tttactgcaa agaaacaaag tagttatagt  11160
aatacaatta tatgtgaaca aaagaatata gatgtgaata aaatatattc gtttggtata  11220
tatattgatt atatatttga aatccataac tttatgcatg aagaaatgaa aattggttat  11280
```

-continued

```
tgtcagaaat attatataaa cagtatacct aaaaagatta aaagaattaa acgagaagag  11340
atatcaccta aatcaataaa atatttagat acgataccga aatatattaa attattttat  11400
gtattaaata atgataatta tatatttaat tttttttcta aaaaaattca attatataaa  11460
tatgctaata caccagataa aattcatcaa ataaaaatgt atatagaata tattaatgat  11520
gaaaataaaa atataatata taagaaaaga aaatataaat taaattcttt atttaaaaga  11580
aaatcaaaaa ataaaaggaa atataaatat ctagaatcaa aagattatga taaattatgt  11640
aaagaagtac ctaagttttt ttatcttaat attacatttc gaaagaaaac agatcattca  11700
aataatacat attataatga aaataatttt aaacatgtaa tagacagtaa tgttttgcaa  11760
ttattaattt atccatcttt ctttttcaa aataatctag ataacgattt aataattaaa  11820
tccaatggaa atttacaaaa aattaaaaaa aaatcaataa tgtttttgg tgatgttgat  11880
aatagtaaag ttatattaca aatagtatat aataatcaaa tattcctttc taaaaaaata  11940
aaaataaatc aagtatgttt aaataaaaaa atcatcttaa caagtaaaaa taaaaaagaa  12000
aatattttct tatctatgaa tattacatta aatggtaata tctataatac aaaaacaatt  12060
actattaata atagatatac aattattaat aataccaatc gaactttata tgtgcaagaa  12120
gttaataaag atttcaaaat tattaaaaaa aaggaaaaaa aatatatgac gtattcattt  12180
tctttagaaa atttacaaaa tcaaaataat cattcaaatg atgaaaatat ggaaaaatta  12240
tatataccta gtagtaatga tcttactaat ataaaacgta attataatca aaaagaaaaa  12300
aatgaaaaaa atgaaaaaaa agaaaaaaat gaaaatttaa acaaaattac aatcaataaa  12360
cgatcagatt taacgtatga gcacgaaaat gatgaaacaa aaattatgga tacttgtgaa  12420
atttctgata agaaatatac ggaaaaaggt atgacaaaaa tatgtgaatt taataaaaag  12480
catataaaat ataataaaca taaaaaatat aacgacaaga aatataatca aaaggaaaac  12540
aataataata ataataatac tacgagtagt aataatagta atagtaatag taatagtagt  12600
aacaacagac ctaatattat ttcaataaaa ccatatgaat ctttttatta tcatcctatt  12660
aacacaaata aatgcttcct aactttttct tatacaaata ttatggaatg taaaaatgat  12720
aagaattttt atagaagaag aggtagctat gaatttacac atacacaaaa tgaaatcaca  12780
aacttattca ataattattt aaaaaaaaaa attatgaaat ctcaaaatat atctataata  12840
aatgataaag aagaaaacat aaataataat gtacataaaa atcaagaatt ctataattta  12900
ttttatacta gtcctataga aatcgaaaag gtaggtaatt acaaaatttt tcacaagaca  12960
gtacataaaa ttgatgttac gtacaataat gaaaaagacg caaccgacga tcaacctaca  13020
tatgaggatg atattattca aaaggaaata aaacaacaag aaaaagaaat tgaagaagaa  13080
ataaaaagag aaatagaaga actagaagaa catcgtgaaa aggaaactat tattgtattt  13140
tcaaatttga aagattcata tgaaaaagaa atgcaaaaaa aaaaaaaaga tcgacataag  13200
aaaaataact ttcttaatat aaactctgat catattaatg ataagaacat tattaattct  13260
tataaaaatg aacaaaccac tgaaatgata tatatacaac acgactatac agataatata  13320
cctgctgacg atgagaaaaa aagttcgcat aatgaaacta tacttataga tgatttaaca  13380
ttatttaata aaaataataa acatagtatt aatgaaaggg aaaataaaga aaacatattt  13440
aatgaaacgg ttttgacagt cgataataat gatactgaac atataaaaag cgactatgta  13500
aatataaaag gcgattgtat aaatataaaa ggcgattgta taaatataaa aggcgattat  13560
gtaaatataa aagataattg ggtagatata aaagataatt gtgtaaatat aaaagataat  13620
tgtgtaaata taaaagataa ttgtgtaaat ataaaaggca attgtgtaaa tacaaaggag  13680
```

```
gattctcata ataattatca acagaatggt atgaatctaa gacatgattc gttttgtgaa  13740
aattatgtta tagattttaa tgatgatgat tcttgtattc attttaaaaa aaataaaaat  13800
gatataaata cagcagatga tataaatat aatacggtga ttatccctat taaaagtata  13860
aagcaactag aaggagaaga aaatgtgcat aatatagaaa ataaaaataa taacagcaat  13920
aataataata ataatctttt atgtgaattg aataaaacga gtgataataa agaacgaata  13980
aacacaaaac atatgttttt atataaagaa gaaagtatta ttacagaaat taatatagca  14040
ttaaatagta atacaaatat cgaaataaat atatctatag aaaataaccc agatactatt  14100
atatataata aaacaaacta ttatttaata ttttatcaaa gaaaaacaaa taaaaaaata  14160
gtaaatttgt tgaaaccttt tgataaagaa atattcggat ggactgatgt ttgtaaacct  14220
aaagttataa aatgcttttt aattattcaa aaaaatgatg tgtatgtatt ttcatgtaat  14280
ttaaatatag taaaagaaca taataatatt atattaaata ataatagaag aattattgtg  14340
ttaaccaaaa ttgaaaatgg gaaacgagtt ttttgtttag aagaaatgaa tatcgaatta  14400
ttagattgta atgaaaaata tgaacacaaa aaatctctag ctccattttt ttccgcaagt  14460
aaaggtttta atagatttag agaaaagaaa aaaaagaaaa tcaaaaagaa attacataaa  14520
ataagtttat ataatagttt aatcaaatca tcacaaatga gaaaggaaaa gaataaaagt  14580
aaaaataaaa aaaaaaataa aaaacaaaaa aaaaatcaaa tgaatcaaat gaatcaaacc  14640
aatcaaacca atcatatgtt acaaaaaaac aaacaaacta atgataacta tttagtaaaa  14700
tataaaaatg aaaaatttaa taagaaatta ccattactta gtaaaaaacg ttttaatatt  14760
gcatatttaa aaaaaaaaag aaaacaaatc aaaaaaaaaa aaaataataa atattttcat  14820
ttaagttcct ttttcctatt aaaaagtatg gattcatcaa tccataaaga tgttgaaaag  14880
gaaaggaaaa aacaaaaagg aaaaagccaa caggcagaaa aattattcaa ggtagaaaaa  14940
attgtacaca atgaatctta caatgaatcg tataatgaat cgtataatga atatcataat  15000
gaatatcaca atgaatatca caatgaatat cacaatgaat atcataacga aaataatggt  15060
aatataaatt caattaagta taataatatt attaaagaag aagaaaatgt gaaaaaataa  15120
aatgcaacaa gtaataataa tagtagtttt agtaaaaaaa atattaaatt aaataatgta  15180
tctataaaaa aagatgataa aaaaaaatct acatcaaaat ataaaagctt gaattctaaa  15240
aaacatatta ataaattttt taatgacaat tatacatttc gaaaaaaaaa gaaaagaaaa  15300
aaaagtaata aaaaaaattt atatgtgaat aaaaataatg aagagacaga aacaagtgat  15360
tattatatag aacataatga aaacaagaaa aatatcgaac tttcttctca tgataacaat  15420
tcttttgata atgagaaaag gaaaactagt ttaggcatga caaaatccaa aggatataac  15480
gatcttttta ctgttaagtt tagaaaaagt gtaaatgaaa atgataaaat tgatgaatat  15540
aaagaaaata gttttgaaga ctctagtaca tataatgatt catttttaag cagttcttca  15600
aataatgaga attatatttc taataataat aagaaacaca tgtttcttaa tagatattat  15660
gataataaag atgataagaa gaaatataga gaatataatt taatatataa taaagaaatg  15720
aaagctaaaa ataatttaaa aaaacctaag aagaaaatta aaagaaaact tagtgatttt  15780
atatttacaa aaattaaaaa aaatcaaaag aaatttaaag gacttagtag aatatatcca  15840
atgtttttaa aaagtaataa aagtgatgaa tttaatgttc ttataagaaa ttatttatcg  15900
gacaaagatg atagcactag tataaggaaa gaatataaaa ttataaatga taattatata  15960
aataataatg aaaataataa taatgaaaat atgaattatg atttaaaaac aaatacttat  16020
```

```
aataatattc ttcataataa taattataga ttagataaaa aaagtgtatt tgaagaaaat  16080
agaaaaatac ccataaaatt tataacaaat ttaaatgtaa tgttacgtgg aataaaaatt  16140
agtttatttg agcacacctg tgattatgtt atatcttttg aaatcaatga attattagtt  16200
acaaaggaat atatggaata tatagattat tataatgtag acataaaaat aaataatatt  16260
ttatgttatg ctgtatataa atatttaagt gcatgtgctg tattatatac aaataatgat  16320
agcaacataa aaaataatca cttacgtatg ttaatgaatg aattaaaaat taaaaggaat  16380
ttatttttac aaaaaaaaag aagaaatgaa aataaaaagg aatattctga tgttaatatt  16440
gacaaaaata atgacaatat taaaaataat gacaatatta aaaataatga ccatattaat  16500
gataatgacc atattaatga taatgaccat attaatgata aggaccatat taataataag  16560
gaccatatta ataataagga ccatattaat gataatgaaa aagaaatgta ctcatcaggt  16620
tcatccagaa caagttatac aaataaaaag aagggatata aatataaaaa caattataag  16680
aaaaaaaaaa aaaaaactga aaaaaatatt tatgataata aaaaagccaa aaaaaaaaaa  16740
aaagagaaag tagagaaaaa gaaaaagaac ctttttgtaa acaatgaatt tcttatatgt  16800
aattttcaat atgtaaggaa atgtgaaaca ttattttta aatatttctt attaagttta  16860
aaacctattg ttattaatgc agatattaat tctataacta tattgttcta tttttataaa  16920
acgttttata attttcatac caaaaaaaat gaacagggtc aaggagtcca aaatggattc  16980
aacacggata attatgaaaa ggtgcacatg agggaaataa atatgatgaa agaacaacaa  17040
caacaacaaa aaaaaaaaaa aaaagaagaa gaagaagaag aagaagaaga agaagaagaa  17100
gaagaagaaa aaaaaaaaaa aaacaaggaa aatgtattac aaaaaaaaaa aaccaaacaa  17160
gaaatggaga gacctttaaa agattattat tattattatt attcatctat gaatatatta  17220
aatgatccag ataataataa aagatgtgat atacaaaaaa accgtatgat cgaaaaaaat  17280
gatagctttt ttataaatgt agatgaaaat agaaaacaaa aaatacaaga tataactggt  17340
gatcatatta ttgataataa tattttaagt cgaatgaaaa atatggaatc atttattata  17400
catgaagaac aacaaaaaaa tgatttaact ttaacattac ataataatat atataatgta  17460
gaaggagaat attataatat aaaaaagagt aatatgaatt attataataa tataattaac  17520
aataaaaagt cttctgttca aataaaaaaa aaaacaactc ttatcgaaaa aaatgatatt  17580
aataataaat atgtatattt acaatatata agtatagata aaataaatat tttattaaat  17640
ttccaatcag aatataaaaa agaattaaca aatcatgtta atgatttatt ttataaagaa  17700
catataagtg cttataataa attaggagat atttctaatt gtaatatata tttaaaaagt  17760
ttatccaata tacatatctt tacaaattat aatttgttaa taaatttcct acaaaatttt  17820
tattataacc aaactatagt taacctatca aacttattaa tttcttttaa tattattgga  17880
agccctacat ctttaatagc gcatgttaaa aatgcattta atgaattctt ctatataatt  17940
aatgaagaca cactatccaa aaaaaacaga tatgatgatg acaaggacat taacgattac  18000
acaacaaaat acaacagaaa aaacaacaaa aaaaacaaca gaaaaaacaa caaaaaaaac  18060
aacagaaaaa acaacagaaa aaacaacaaa aataatgata ataacaatat taatagtatg  18120
tatggtagtc attataataa taattatatt tattataacg attattatta taataataat  18180
tacatgtatc gtcgtagtac tcttaattat cattattatg aacaaggtta tgataaatac  18240
aaattgaatc gtatatataa taataacccg aaattaagaa aaaataataa agaaagaaaa  18300
aataatatac aacaaattaa ttatacaacc aaaaaagaag acaaacataa tttcctaaat  18360
ttaatagatc aatccaggga aagctcattt ttagatgaga aagatgattc cttaaccaat  18420
```

```
gatgataaat atattatgca tctactaaat gattataatt cttcttatca aaataattta  18480
ttaagtgaag aagaatcttt tgttaaaagg aatttcagct ggaacttttt taaaaaacaa  18540
catacaaata ataataataa taattcggat gatgacaatt attttaatga ttcatataat  18600
aacataaaac atgaaagttc ggggaactta aattatatgt acacaaaaag tattaaaaat  18660
aaagatttac ataaactagt aattgatgat aataactctt ctatgaattc attccttttt  18720
aataataaaa aaaatgttat catattagat caagtttcta aaaaaaagaa aaagaaatta  18780
caatatatca aaaattttga agaaccacaa aagggacata tatatatgga tgatgacatg  18840
tatatagatg tagatgtaga tctaaattct tatgcggaag gaaaaaatac tacaaaagat  18900
acatccaaat atccaccaca ttttaaaata tcatatgatg aagaaaaaaa aaaaaggaaa  18960
aagaaaaggc tttcaaccgg tagtaataat aatagataca aaaatgatgc ggaaatatta  19020
gatatgaatc caaacaaaaa aaacaagaaa aaaaataaaa tgctaaaaaa taataataat  19080
aataataata ataataaaaa taaaaaaaat aaaagaaata ataaaagaag tggttgtact  19140
aaaatgttca gatttttttaa aaaaatagga ttaaatatta tttatatttt ttcaaaaact  19200
aagagaatat gtattggtat atatgtatta tttatacaat taatattatc cttattattt  19260
tctattacac taatattaca atctttaata aatttagtag aaaaggtaaa tataaataat  19320
gcagataatg tgtttttaat atttaataaa aaatatgaaa gaaaaaaagt agtggtattt  19380
aataatatag aggaatataa taaatttaat attaccaaat tattttatta ttatattagt  19440
atatatatga atatagtgaa tttcttatat tataatatgt tatataaaat gaagaagaaa  19500
aaaaaagatt tatcgggaga agataaaatt tttatgaaga aattaaaaat caatttaaaa  19560
aataaaagaa aattttcttt ctttattaat ttctttttaa atatatttaa tatcatcaat  19620
atattattat ttggacatat agttttctta cttttatgtt tattaacaat gaataatatt  19680
tttcaaaaaa tacttacagc atgtattaaa ttagtatatt accaaagaaa taaaaattat  19740
ctagattttc tcaataaaaa cagttttaat catatgaata ttataagtta tattaaaatt  19800
aatcaagtta taagtaaata tgtactatta aaagaaccct tcaaatattt cttatctcat  19860
caagatttct tggatattaa agcacctaaa aaaagaaatt attttgtata taccaaagag  19920
ctcttctttt atatacaaga aaataaaatt gtattcttat ttagaaaaaa cgatatgaaa  19980
aaaattgaca ttattataca tactataaat aatagtttcg caataaatag ttactataag  20040
aaaaagggta gtaagacagc caaaaaaagt agatccaaaa ataccccatc gaattatact  20100
cttaatatgg aacatgtgac aggagaagaa aataatagct ttacttcatc tttatataac  20160
aaaactaacg tatcgaatga tatatcagag gataaaaatg ttatatgttt tttaaatcaa  20220
gaattagctt taaccaaaag aaacgaaatt atacatataa ataataaaaa ctatgattat  20280
attatttcca taaaaataac aatcaaaaat aatatgaatg ttatggagaa tatttattat  20340
aaccccaaaa aattttttaa gtgcttgtca aaaatacaaa aaagcttcaa taatatttat  20400
ttacctttat gtaaaaataa taataatgaa accaaaaata ataaggaaaa acatttaaat  20460
aataaaggtg cagatatata taaagcagat ataaatgtaa aaaaaagaag aacttttttt  20520
tcagcaatta tttgtttctt taaaagcatt ttcatatttt tgtacttttg tctatgccca  20580
tggaaattgt taaagttaaa aaagaaaaaa tcaaatgaca ataaaaaaaa acaaatggac  20640
gaaaaagata aagaaaatgc agtccataaa aatatacaac taaaacataa aaataaaaag  20700
gaaaagacaa cacccaacag tattattttt aaattaaact ttgaagattt tcaatcaact  20760
```

```
ttaaatatat ttgaatgttt gtgtaggatt atgaataata attaa              20805


<210> SEQ ID NO 12
<211> LENGTH: 6934
<212> TYPE: PRT
<213> ORGANISM: Plasmodium falciparum

<400> SEQUENCE: 12

Met Ile Lys Ala Leu Tyr Lys Ser Ile Val Asn Phe Leu Leu Ser Ser
1               5                   10                  15

Phe Phe Glu Asn Ile Glu Glu Lys Gln Leu Gln Thr Ser Leu Ile Arg
            20                  25                  30

Gly Lys Val His Leu Gln Asn Val Lys Ile Lys Lys Phe Phe Cys Asp
        35                  40                  45

Phe Ile Tyr Leu Pro Tyr Thr Ile Lys Tyr Gly Tyr Ile Arg Ser Leu
    50                  55                  60

Asp Leu Gln Ile Pro Leu Leu Tyr Leu Phe Gln Lys Ala Ser Leu Lys
65                  70                  75                  80

Val Ser Asp Val Val Ile Val Leu Lys Glu Lys His Phe Ser Glu Tyr
                85                  90                  95

Asn Ile Glu Glu Glu Ile Asn Gly Ile Lys Gly Gly Lys Lys Asn Asn
            100                 105                 110

Leu Lys Leu Glu Asp Tyr Asn Tyr Asn Ser Asn Asp Val Asn Gln Lys
        115                 120                 125

Ile Asn Lys Gly Leu Asn Tyr Leu Phe Tyr Glu Leu Tyr Asn Asn Met
    130                 135                 140

Ser Ile Asp Ile Glu Asn Val Glu Ile Ile Leu Glu Ser Ser Glu Lys
145                 150                 155                 160

Thr Thr Asn Val Ile Gly Leu Phe Val Lys Lys Ile Ser Ser Val Lys
                165                 170                 175

Thr His Asn Cys Thr Asn Lys Ile Ile Lys Asp Phe Ser Phe Val Asp
            180                 185                 190

Ala Ile Phe Tyr Met Asn Asp Glu Lys Ala Lys Tyr Ala Ile Asn Lys
        195                 200                 205

Ile Ile Lys Lys Glu Glu Lys Lys Lys Lys Asn Lys Arg Asn Ile Asn
    210                 215                 220

Glu Glu Asp Ile Tyr Asn Lys Ile Lys Tyr Ile Cys Asn Asn Leu His
225                 230                 235                 240

Lys Lys Lys Tyr Ile Ile Ser Glu Ile Pro Ser Ile Val Leu Ser Thr
                245                 250                 255

Ser Met Tyr Val Ser Asn Ser Thr Asp Tyr Tyr Tyr His Asn Ser Lys
            260                 265                 270

Phe Leu Phe Lys Lys Asn Ser Tyr Phe Asn Ile Thr Cys Thr His Cys
        275                 280                 285

Asp Lys Tyr Leu Phe Gln Cys Lys Glu Val Lys Lys Asp Lys Ser Ile
    290                 295                 300

Phe Gln Asn Ile Phe Ile Lys Lys Glu Lys Ile Gln Gln Arg Asn Lys
305                 310                 315                 320

Gln Leu Tyr Ser Glu Ile Asn Cys Lys Cys Met Lys Asn Asn Lys Asn
                325                 330                 335

Ile Phe Gln Lys Asp Gln Asn Thr Asn Cys Thr Tyr Asn Ser Asp His
            340                 345                 350

Val Pro Glu Asn Ser Leu Lys Gly Thr Asn Glu Met Asn Lys Asn Ile
        355                 360                 365
```

-continued

```
Pro Pro Asp Leu Asp Ser Ile Asn Val Gly His Pro Lys Ile Asp Asp
    370                 375                 380

Asp Asn Glu Lys Asn Asn His Glu Asn Asn Ser His Asn Asp Asn His
385                 390                 395                 400

Asn Asn Ser His Asn Asp Asn His Asn Asn Ser His Asn Asp Asn His
                405                 410                 415

Asn Asn Ser His Asn Asp Asn His Asn Asp Asn His Asn Asn Asn His
            420                 425                 430

Asn Asp Asn His Asn Leu Lys His Lys Arg Asn Tyr Asn His Arg Asn
        435                 440                 445

Gly Gly Val Gly Gln Asn Asn Thr Gly Asp Asn Asn Leu Leu Asn Asn
    450                 455                 460

Thr Phe Asn Lys His Asn Glu Glu Arg Thr Val Gln Glu Lys Asp Glu
465                 470                 475                 480

Lys Lys Ser Glu Asp Cys Ile Asp Cys Asn Cys Lys Lys Asn Ile Ser
                485                 490                 495

Glu Asp Leu Asp Asn Cys Leu Tyr Cys Arg Ile Asn Asn Lys Asn Gln
            500                 505                 510

Ser Tyr Ile Glu Lys Phe His Met Leu Glu Glu Asn Ile Asn Leu Lys
        515                 520                 525

Glu Asn Glu Tyr Met Thr Phe Glu Leu Asn Val Asp Lys Ile Asp Leu
    530                 535                 540

Ile Leu Ser Phe Lys Gln Phe Tyr Tyr Ile Leu Asp Ile Val Asn Tyr
545                 550                 555                 560

Tyr Phe Ile Tyr Ser Cys Leu Val Asn Gly Leu Cys Ile Glu Glu Trp
                565                 570                 575

Leu Asn Ile Pro Glu Ile Asn Asp Ile Leu Ile Tyr Lys Arg Glu Leu
            580                 585                 590

Ile Lys Lys Lys Lys Lys Glu Lys Phe Asp Lys Asp Phe Ile Asp Lys
        595                 600                 605

Phe Glu Tyr Thr His Ser Phe Gln Ile Ile Ser Asn Ile Lys Lys His
    610                 615                 620

Val Glu Glu Tyr Ser Leu Asp Asn Asn Lys Arg Lys Lys Ser Ile Arg
625                 630                 635                 640

Gly Thr Gly Glu Asp Leu Ser Thr Leu Leu Asn Ser Asn His Asn Asn
                645                 650                 655

Glu Tyr Asn Tyr Lys Asn Glu His Asn Arg His Asn Glu His Asn His
            660                 665                 670

His Asn Glu His Asp Asn Asn Asn Asn Lys Val Thr Lys Ser Gln Ser
        675                 680                 685

Ala Ser Ser His Leu Ser Asn Val Ser Thr Trp Asn Lys Pro Phe Phe
    690                 695                 700

Val Tyr Asn Lys Lys Ile Ser Val Asn Cys Ser Phe Asn Ile Leu Ile
705                 710                 715                 720

Lys Lys Leu Asn Phe Cys Leu Cys Ser Gly Asp Lys Ile Asn Lys Ile
                725                 730                 735

Ile Gln Ile Asn Thr Asp Asp Phe Asn Phe Asn Val Lys Ser Tyr Ile
            740                 745                 750

Asn Ala Asp Phe Ala Tyr Ser Leu Leu Leu Lys Asp Ile Ser Val Phe
        755                 760                 765

Phe Ile His Lys Asp Lys Lys Tyr Pro Leu Phe Glu Leu Phe Asn Val
    770                 775                 780

Asn Glu His Asn Lys Lys Glu Asp Lys Lys Lys Glu Asn Met Lys Val
```

-continued

```
785                 790                 795                 800

Asn Lys Arg Lys Ser Lys Thr Tyr Ile Phe Asn Thr His Leu Cys Asn
                805                 810                 815

Asp Ala Met Thr Ser Phe Lys Ser Val Ser Ser Ile Lys Asn Val Pro
            820                 825                 830

Gly Asn Met Asn Asn Ile Thr Asp Asn Met Lys Asn Asp Asn Tyr Asn
        835                 840                 845

Asn Ile Tyr Lys Asn Asn Glu Lys Asn Val Glu Asn Gly Lys Lys Cys
    850                 855                 860

Ser Lys Tyr Val Glu Ser Arg Asn Leu Val Glu Ile Asn Asn Arg His
865                 870                 875                 880

Asn Glu Tyr Ser Lys Glu Lys Lys Asn Ile Thr Asn Ile Lys Asn Asp
                885                 890                 895

Asn Ile Asn Asn Asn Glu Asn Asn Asn Tyr Asp Asn Asn Ile Asn Asn
            900                 905                 910

Lys Glu Glu Tyr Ala Ile Ser Leu Leu Thr Phe Thr Lys Tyr Glu Thr
        915                 920                 925

Thr Gln Ala Lys Thr Phe Ile Lys Phe Asn Lys Asn Ile Leu Ile Thr
    930                 935                 940

Leu Ser Val Lys Glu Ile Tyr Asn Ile Leu Asn Met Asn Cys Asp Tyr
945                 950                 955                 960

Lys Pro Val Asp Leu Glu Lys Lys Leu Lys Ser Tyr Lys Ile Leu Phe
                965                 970                 975

Tyr Tyr Tyr Leu Leu Gly Lys Lys Tyr Cys Lys Glu Leu Tyr Met Ala
            980                 985                 990

Ser Asp Lys Asn Phe Glu Asp Met  Asn Ile His Phe Met  His Asn Ile
        995                 1000                1005

Tyr Phe  Asn Ile Ile Ile Asn  Lys Lys Tyr Asn Leu  Leu Phe Lys
    1010                1015                1020

Met Lys  Lys Gly Leu Val Asn  Ser Phe Phe Phe Thr  Lys Met Tyr
    1025                1030                1035

Leu His  Cys Asp Leu Lys Lys  Leu Thr Met Ile Thr  Asp His Asn
    1040                1045                1050

Asp Met  Gln Gln Asn Met Asp  Asn Lys Leu Val Asp  Gln Tyr Thr
    1055                1060                1065

Glu Gln  Met Lys Glu Asn Ser  Ser Tyr Gln Asn Ser  Gln Ser Cys
    1070                1075                1080

Ser Asn  Thr Ser Ser Val Gly  Phe Thr Asn Glu Asp  Pro Thr Lys
    1085                1090                1095

Arg Arg  Asn Lys Glu Lys Asn  Asn Leu Asn Ile Asn  Ile Asn Leu
    1100                1105                1110

Asn Leu  Ser Thr Asn Asp Asp  Val Ile Ile Asn Lys  Asn Glu Glu
    1115                1120                1125

Lys Glu  Asn Glu Asn Lys Glu  Ser Asn Arg Thr Glu  His Ile Lys
    1130                1135                1140

Arg Asp  Asn Ser Ile His Ser  Asn Asp Asn Cys Ser  Ile Gly Thr
    1145                1150                1155

His Ser  Glu Leu Phe Lys Asn  Ser Glu Tyr Asn Ser  Met Ile Asn
    1160                1165                1170

Asn Asn  Asn Asn Asn Asn Ser  Phe Ile Asn Asn Asp  Asn Thr Ser
    1175                1180                1185

Ile Asp  Asn Lys Val Ser Met  Gln Cys Arg Lys Tyr  Tyr Gln Glu
    1190                1195                1200
```

```
Phe Leu  Lys Met Asn Asn Leu  Glu Asp Ile Lys Thr  Ile Arg Lys
    1205                 1210                 1215

Ile Glu  Lys Arg Ala Asn Gln  Asn Asn Thr Ser Asn  Asn Asn Thr
    1220                 1225                 1230

Ile Asn  Asn Ile His Asn Ile  Asn Asn Val His Asn  Val Asn Asn
    1235                 1240                 1245

Ile His  Asn Val Asn Asn Ile  His Asn Val Asn Asn  Ile His Asn
    1250                 1255                 1260

Val Asn  Asn Ile His Asn Val  Asn Asn Ile His Asn  Val Asn Asn
    1265                 1270                 1275

Val His  Asn Ile Asn Asn Asn  Tyr Tyr Asp His Ile  Tyr Ser His
    1280                 1285                 1290

Asn Asn  Ile His Ile Asn Asn  His Ala Ile Ile His  Asn Asn Ser
    1295                 1300                 1305

His Tyr  Asn Asn Lys Lys Thr  Asn Ile Ile Leu Asn  Asn Asn Lys
    1310                 1315                 1320

Tyr Asp  Glu Tyr Asn Asp Lys  His Ser Phe His Ser  Glu Asn Thr
    1325                 1330                 1335

Asn Ser  Tyr Ser Asn Ser Asn  Lys Asp Asp Tyr Leu  Asn Glu Asp
    1340                 1345                 1350

Leu Asn  Leu Tyr Lys Asp His  Met Tyr Ile Gln Asn  Cys Ile Thr
    1355                 1360                 1365

Glu Lys  Glu Asp Asn Ile Ile  Thr Thr Ile Tyr Gln  Lys Arg Thr
    1370                 1375                 1380

Asn Phe  Glu Leu Ser Leu Phe  Ile Leu Lys Asn Lys  Asn Asn Glu
    1385                 1390                 1395

Lys Ile  Gln Asn Ile Leu Ser  His Lys Asn Lys Ile  Asn Lys Lys
    1400                 1405                 1410

Tyr Ile  Leu Lys Pro Leu Lys  Ile Tyr Ile Asp Glu  Ile Thr Tyr
    1415                 1420                 1425

Asn Phe  Lys Asn Ser Ser Asp  Lys Lys Ile Thr Phe  Phe His Thr
    1430                 1435                 1440

Asn Asn  Tyr Lys Asn Tyr Leu  Asn Phe Thr Leu Asp  Asp Lys Ile
    1445                 1450                 1455

Ile Phe  Lys Leu Ile Phe Phe  Tyr Tyr His Tyr Lys  Asp Tyr Val
    1460                 1465                 1470

Asp His  Ile Phe Glu Lys Phe  Glu Ser Lys Asp Glu  Ser Asn Tyr
    1475                 1480                 1485

Leu Asn  Leu Asn Thr Ile Asp  Val Arg Ser Tyr Lys  Thr Leu Gln
    1490                 1495                 1500

Ile Leu  Leu Asp Asn Ala Val  His Asn Lys Asn Asp  His Trp Phe
    1505                 1510                 1515

Asn Glu  Gln Lys Asp Val His  Asp Lys Asp Glu Gln  Asn Lys Gly
    1520                 1525                 1530

Thr Ile  Tyr Tyr Glu Gln Asn  Glu His Asp Ile Lys  Ile Asp Asp
    1535                 1540                 1545

Asn Asn  Glu Glu Glu Asn Asn  Asp His Thr Asp Asn  Asn Asn Lys
    1550                 1555                 1560

Asn Asn  Asn Asn Asn Asn Asn  Asn Asn Asn Asn Lys  Asn Asn Asn
    1565                 1570                 1575

Asn Asn  Asn Asn Asn Asn Lys  Asn Asn Met Val Asp  Gly Gln Ile
    1580                 1585                 1590
```

```
Glu Cys  Asn Glu Asn Val Thr  Glu Lys Glu Ile Pro  Ser Asn Val
    1595                 1600                 1605

Pro Asn  Ser Asn Asn Leu Thr  Asn Glu Ser Ser Asn  Asp Asn His
    1610                 1615                 1620

Asn Lys  Thr Thr Ile Glu His  Asn Asn Asn Phe Cys  Glu Glu Gln
    1625                 1630                 1635

Asn Lys  Asn Asp Leu Ile Lys  Thr Ser Phe Asn Ile  Thr His Cys
    1640                 1645                 1650

Glu Glu  Glu Asn Ala Asn Lys  Asn Lys Tyr Thr Glu  Glu Asp Lys
    1655                 1660                 1665

Lys Glu  Ile Lys Gly Asn Asp  Lys Lys Asn Val Glu  Met Cys Arg
    1670                 1675                 1680

Lys Asp  Thr Leu Asp Tyr Val  Lys Glu Asp Ile Asn  Lys Tyr Lys
    1685                 1690                 1695

Met Tyr  Ile Asn Glu Asn Asn  Asn Lys Lys Glu Glu  Glu Tyr Ser
    1700                 1705                 1710

His Asn  Asn Asn Asn His His  His His Tyr His His  Asn Asn Met
    1715                 1720                 1725

Leu Lys  Asp Asp Thr Ser Asn  Tyr Asn His Val Gln  Tyr Phe His
    1730                 1735                 1740

Gly Glu  Lys Lys Glu Ile Ile  Cys Phe Ile Asn Lys  Ser Lys Ile
    1745                 1750                 1755

His Phe  Asn Asn Tyr Lys Lys  Ser Lys Arg Met Ile  Ser Ile His
    1760                 1765                 1770

Leu Ser  Asp Val Leu Met Tyr  Leu Phe Ser Asp Asn  Asn Ile Thr
    1775                 1780                 1785

Asn Phe  Leu Phe Asn Leu Lys  Lys Ile Asn Ile Leu  Asn Cys Leu
    1790                 1795                 1800

Ser His  Glu Asp Ser Tyr Asn  Ser Phe Phe Ser Tyr  Ile Gln His
    1805                 1810                 1815

Lys Lys  Phe Ser Thr His Lys  Ile Ser Lys Lys Gly  Ser Lys Leu
    1820                 1825                 1830

Ser Asp  Lys Arg Lys Ser Ser  Asn Val Asn Gly Ile  Tyr Phe Tyr
    1835                 1840                 1845

Asn Ser  Val Phe Lys Leu Ile  Gln Asn Gly Thr Phe  Leu Leu Lys
    1850                 1855                 1860

Tyr Ser  Ser Lys Asn Asn Ile  Ser Cys Leu Ser Ser  Ile His Leu
    1865                 1870                 1875

Asn Pro  Asn His Asn His Tyr  Ile Glu Asn Asn Asn  Ser Lys Glu
    1880                 1885                 1890

Lys Asn  Tyr Phe Leu Asn Asn  Asn Asn Asn Asn Asn  Asn Lys Met
    1895                 1900                 1905

Glu Ile  Glu Glu Thr Thr Glu  Phe Arg Tyr Phe Asn  Thr Asn Asn
    1910                 1915                 1920

Phe Glu  Gln Leu Asn Asn Thr  Ser Gly Asn Lys Ser  Ile Asp Gly
    1925                 1930                 1935

Ser Asn  Val Lys Ile Asn Asn  Ser Leu Asp Phe Val  His Lys Asn
    1940                 1945                 1950

Tyr Tyr  Asn Asn Leu Asn Asn  Asp Tyr Phe Asn Phe  Asn Val Pro
    1955                 1960                 1965

Gln Asp  Ser Asn Lys Arg Lys  Asp Ala Thr Ser Ser  Pro Ser Asn
    1970                 1975                 1980

Val Ser  Asn Lys Ser Gly Glu  Ile Lys Ser Ser His  Lys Lys Glu
```

```
    1985                1990                1995

Gln Arg  Lys Asp Asn His Met  Asn Glu Asn Ile Arg  Gly Ser His
    2000                2005                2010

Arg Ser  Tyr Ser Thr His Gln  Ser Tyr Arg Thr His  Gln Ser Tyr
    2015                2020                2025

Lys Arg  His Ala Asn Asn Ser  Asn Ile Arg Cys Ser  Ser Ser Pro
    2030                2035                2040

Ser Glu  Arg Thr His Ile Ser  Lys Lys Asp Glu Ile  Lys Phe Asn
    2045                2050                2055

Lys Glu  Asn Ile Met Thr Leu  Leu Asn Asp Cys Thr  Asn Asn Glu
    2060                2065                2070

Gly Glu  Asn His His Val Lys  Ile Thr Asn Lys Gln  Ile Lys Arg
    2075                2080                2085

Ser Lys  Ser Lys Glu Gln Phe  Glu Asp Ile Ile Asn  Ser Asn Thr
    2090                2095                2100

Lys Lys  Thr Asn Asp Ile Glu  His Ile Trp Asp Glu  Gln Asn Asn
    2105                2110                2115

Gln Asn  Asn Lys Glu Asn Asp  Asn Val Val Asn Arg  Val Glu Lys
    2120                2125                2130

Lys Ser  Ile Ile Thr Glu Asn  Tyr Ile Pro Tyr Lys  Ser Cys Ile
    2135                2140                2145

Glu Gln  Ile Asp Asp Ile Asp  Tyr Asn Lys Glu Ser  Leu Gln His
    2150                2155                2160

Glu Lys  Asn Ile Asp Gly Lys  Thr Asn Ile Ile Tyr  His Asn Asn
    2165                2170                2175

Asn Asn  Asn Asn Asp His Ile  Asn Met Asn Thr Thr  Thr Cys Ile
    2180                2185                2190

Pro Ile  Asn Glu Lys Asn Phe  Val Ile Gln Arg Asn  Lys Lys Ile
    2195                2200                2205

Ser His  Tyr Tyr Asn Ala Lys  Glu Tyr Asn Asp Ser  Asn Lys Arg
    2210                2215                2220

Arg Arg  Asn Asn Tyr Ile Leu  Thr Gly Glu Val Asn  Asn Ile Lys
    2225                2230                2235

Gly Tyr  Asn Lys Asp Asp Met  His Ser Ser His Val  Asn Asn Met
    2240                2245                2250

Asn Asn  Ser Leu Cys Ser Ser  Ala Tyr His Asn Met  Lys Tyr Glu
    2255                2260                2265

Lys Tyr  Val Asp Ile Glu Lys  Tyr Arg Asn Asp Asp  Glu Phe Tyr
    2270                2275                2280

Glu Ala  Glu Asp Asp Glu Asp  Glu Glu Asn Asp Ile  Asp Asn Gln
    2285                2290                2295

Glu Glu  Glu Tyr Ile Asp Met  Lys Lys Lys Glu Asn  Glu Asn Ile
    2300                2305                2310

Ser Ser  Ile Glu Phe His Met  Ile Asn Ser Glu Phe  Ile Val Asp
    2315                2320                2325

Tyr Leu  Tyr Phe Ile Tyr Leu  Phe Lys Trp Ile Asn  Lys Leu Tyr
    2330                2335                2340

Arg Lys  Tyr Glu Lys Ile Lys  Gln Leu Ser Asp Phe  Ala Tyr Ser
    2345                2350                2355

Asn Asn  Asn Ser Thr Asp Asp  Glu Glu Ser Asn Ile  Asn Val Ser
    2360                2365                2370

Lys Cys  Asn Tyr Ile Leu Phe  Leu Gln Asn Asn Lys  Ile Tyr Val
    2375                2380                2385
```

```
Pro Ile Tyr Asn Tyr Ser Ile Ser Gln Tyr Lys Tyr Tyr Asn Ser
    2390                2395                2400

Leu Lys Gly Thr Ser Tyr Val Ser Leu Leu Pro Val Leu Glu Leu
    2405                2410                2415

His Phe Ser Cys Ser Tyr Lys Ser Met Asn Glu Asn Asp Glu Asn
    2420                2425                2430

Val Lys Ser Ile Asn Val Arg Asn Leu Gly Ser Ala Leu Val Ile
    2435                2440                2445

Pro Ser Ile Asn Ile Tyr Lys His Lys Lys Asn Lys Lys Ser Asn
    2450                2455                2460

Ile Cys Val Ile Thr Phe Asn Arg Lys Asp Lys Asn Asn Glu Ser
    2465                2470                2475

Ile Ile Asn Asp Leu Arg Phe Gln Ile Asn Met Arg Arg Asn Tyr
    2480                2485                2490

Asn Tyr Glu Ile Ile Glu Asn Glu Asp Asp Asn Ser Ser Ser Cys
    2495                2500                2505

Asn Asn Met Glu Ile Pro Tyr Tyr Glu Pro Lys Tyr Thr Ser Leu
    2510                2515                2520

Asn Thr Tyr Cys Thr Val Ile Ser Lys Glu Gln Met Tyr Ser Glu
    2525                2530                2535

Lys Asn Lys Asn Lys Asn Asn Asn Ile Asn Asn Asn Asn Asn Asp
    2540                2545                2550

Asn Asn Ile Ile Met Tyr Asp Asn Asn Met Tyr Asn Tyr His Gly
    2555                2560                2565

Tyr His Thr Lys Thr Gly Ser Tyr Pro Lys Lys Ile Ile Ser Phe
    2570                2575                2580

His Cys Asp Pro Ile Ile Leu Asn Phe Ser Lys Asp Ile Leu Lys
    2585                2590                2595

Asn Val Leu Ile Phe Tyr Asn Thr Phe Cys Tyr Phe Ile Asn Asn
    2600                2605                2610

Cys Ser Lys Asn Asp Asp Thr Gly Asn Asp Ser Asn Met Ile Arg
    2615                2620                2625

Asp Met Leu Tyr Tyr Leu Tyr Asn Gln Ser Ser Asp Ile Leu Phe
    2630                2635                2640

Glu Tyr Phe Leu Asp Asp Ile Arg Leu Asn Cys Tyr Asp Gly Asn
    2645                2650                2655

Ile Asn Arg Asn Val Pro Leu Ile Val Val Ser Leu Phe Asn Leu
    2660                2665                2670

Lys Phe Phe Leu Gln Lys Asp Ile Ile Ser Ile Tyr Asn Phe Leu
    2675                2680                2685

Asn Phe Tyr Leu Asn Ile Asp Ile Tyr Asp Ser Tyr Lys Ile Leu
    2690                2695                2700

Tyr Asp Thr Leu Leu Glu Lys Met Glu Ile Tyr Leu Thr Phe Glu
    2705                2710                2715

Asn Asn Arg Asn Lys Leu Asn Ile Leu Asn Leu Thr Leu Glu Thr
    2720                2725                2730

Ser Tyr Ile Asn Ile Leu Tyr Thr Asn Lys Ser Lys Asn Ile Leu
    2735                2740                2745

Ile Asn Phe Leu Glu Pro Ile Leu Asn Lys Asn Phe Tyr Tyr Phe
    2750                2755                2760

Ser Ser Ser Tyr Tyr Asn Asn Leu Asp Ile Thr Lys Asn Lys Arg
    2765                2770                2775
```

```
Arg Lys  Arg Ser Ile Tyr His  His His Asn His Asn  Tyr His His
    2780                 2785                 2790

Glu Cys  Tyr Glu Asn Asn Ile  Leu Ile Lys Asn Thr  Lys Gly Lys
    2795                 2800                 2805

Ser Leu  Val Thr His Ile Thr  Ser Lys Ile Phe Asn  Tyr Thr Gly
    2810                 2815                 2820

Leu Ser  Ile Asn Val Arg Phe  Lys Gln Ser Leu Arg  Asn Lys Ile
    2825                 2830                 2835

Gln Asn  Asn Ser Leu Asn Asn  Lys Asn Lys Asn Lys  Tyr Leu Phe
    2840                 2845                 2850

Tyr Glu  Leu Gln Asn Asn Glu  His Gly Ala Leu Leu  Asn Asp Glu
    2855                 2860                 2865

Asn Gly  Glu Val Cys Glu Val  Val Val Ile Ile Lys  Ile Phe Asn
    2870                 2875                 2880

Tyr Ile  Phe Glu Ile Ile Asp  Ile Glu Arg Asn Lys  Asn Thr Cys
    2885                 2890                 2895

Asp Ile  Arg Phe Leu Pro Ile  Ile Tyr Glu Leu Lys  Lys Phe Asn
    2900                 2905                 2910

Glu Lys  Lys Lys Ile Thr Ile  Lys Lys Tyr Asp Ile  Asn Tyr Asp
    2915                 2920                 2925

Ile Tyr  Asn Glu Tyr Ser Leu  Lys Asn Lys Val Phe  Lys Thr Phe
    2930                 2935                 2940

Ile Lys  Leu Tyr Ile Gln Thr  Asn Ile Asp Glu Lys  Gly Ile Val
    2945                 2950                 2955

Ser Ile  Tyr Phe Ser Ser Asn  Leu Phe Ile Asn Asn  Ser Thr Asn
    2960                 2965                 2970

Ser Asp  Phe Val Leu Leu Phe  His Pro Val Leu Tyr  Tyr Phe Met
    2975                 2980                 2985

Leu Phe  Asn Glu Gln Ser Thr  Asn Ser Asn Thr Asn  Asn Asn Ile
    2990                 2995                 3000

Asn Asn  Asn Asn Lys Asn Glu  Asp Asn Met Val Asp  Asn Asn Glu
    3005                 3010                 3015

Asn Asn  Asp Lys Asn Asn Asp  Lys Asn Asn Asp Lys  Asn Asn Asn
    3020                 3025                 3030

Glu Asn  Lys Asp Cys Asp Ser  Val His Asn Ile Asn  Asn Val Glu
    3035                 3040                 3045

Ser Asp  Ser Pro Val Asn Ile  Asn Phe Phe Lys Asn  Asp Asn Tyr
    3050                 3055                 3060

Asn Asn  Asn Tyr His Asn Asn  Tyr His Asn Asn Tyr  His Asn Asn
    3065                 3070                 3075

Asn Asp  Lys Gly Ala Asn Ile  Thr Ile Ile Asn Ser  Asn Glu Arg
    3080                 3085                 3090

Tyr Phe  Leu Pro Leu Ile Ser  Phe Ile Pro Ile Ile  Ile Leu Tyr
    3095                 3100                 3105

Asp Tyr  Leu Lys Lys Lys Asn  Glu Ile Glu Glu Asn  Asn Tyr Pro
    3110                 3115                 3120

Asp Lys  Tyr Pro Met Asn Ser  Lys Asn Ser Tyr Val  Thr Pro Val
    3125                 3130                 3135

Ser Met  Val Cys Asp Leu Lys  Gly Ser Phe Ser Ala  Asp Ile Lys
    3140                 3145                 3150

Lys Asn  Asn Phe Ile Lys Arg  Phe Asn Ser Leu Asn  Tyr Asn Met
    3155                 3160                 3165

Asn Ile  His Asn Gly Glu Glu  Glu Glu Ile Ser Lys  Gln Asn Glu
```

```
    3170                3175                3180

Ala Asn  Asp Met Leu Asn Tyr  Thr His Val Asp Asn  Ser Asn Asn
    3185                3190                3195

Glu Thr  Ser Cys Arg Asn Asn  Asn Glu Asp Lys Ile  Leu Ser Tyr
    3200                3205                3210

Lys Lys  Arg Ile Thr Tyr Asp  Tyr Ser Ser Ile Asn  Ser Leu Lys
    3215                3220                3225

Lys Leu  Ser Tyr Asn Asn Leu  Thr Arg Ala Ser Cys  Tyr Val Asn
    3230                3235                3240

Ser Arg  Ser Ser Glu Met Asn  Leu Cys Asn Ile Ile  Ser Asn Lys
    3245                3250                3255

Gly Asp  Lys Arg Asn Phe Met  Asn Asn Glu Lys Ile  Ile Glu Ser
    3260                3265                3270

Leu Asn  Leu Asn Ala Leu Arg  Glu Ile Asn Lys Ile  Arg Thr Asn
    3275                3280                3285

Arg Ile  Leu Lys Arg Leu Glu  Lys Tyr Val Asn Glu  Lys Ser Asn
    3290                3295                3300

Ser Lys  Asn Met Lys Asn Ile  Asn Tyr Ile Tyr Ile  Ile Lys Lys
    3305                3310                3315

Glu Phe  Tyr Asp Phe Tyr Ile  His Lys Asn Glu Asn  Asn Asn Lys
    3320                3325                3330

Cys Tyr  Phe Glu Met Phe Asn  Phe Leu Ile Lys Asn  Gly Ala Lys
    3335                3340                3345

Lys Val  Leu Asn Asn Ser Ser  Ile Lys Glu Ile Ile  Cys Arg His
    3350                3355                3360

Ser Phe  Asp Phe Leu Lys Tyr  Asn Leu Tyr Ala Gln  Thr Leu Lys
    3365                3370                3375

Leu Lys  Thr Leu Lys Ile Ile  Cys Tyr Asp Lys Tyr  Ser Arg Tyr
    3380                3385                3390

Leu Arg  Glu Lys Lys Lys Glu  Met Glu Glu Ala Lys  Thr Tyr Asn
    3395                3400                3405

Asn Asn  Asn Asn Lys Asn Asn  Ile Asn Asn Asn Asn  Asn Asn Asn
    3410                3415                3420

Asp Asn  Asn Asn Asn Asn Asn  Asn Asn Asn Asn Asn  Asn Asn Asn
    3425                3430                3435

Asn Asn  Asn Asn Met Lys Lys  Lys Gln Ile Gly Asp  Ile Tyr Met
    3440                3445                3450

Lys Asn  Tyr Lys Glu Glu Lys  Asn Asp Ile Lys Glu  Glu Gln Glu
    3455                3460                3465

Lys His  Asp Asn Ser Ser Ser  Ile Val Val Leu Asn  Lys Phe His
    3470                3475                3480

Asp Tyr  Tyr Asp Lys Arg Asp  Lys Tyr Tyr Phe Glu  Asn Asn His
    3485                3490                3495

Arg Asn  Asp His Tyr Thr Ser  Asp Leu Asn Asn Asp  Asp Asn Asn
    3500                3505                3510

Lys Tyr  Asn Ile Tyr Asp Asn  Asn Lys Tyr Ser Ile  Tyr Asp Asn
    3515                3520                3525

Asn Lys  Tyr His Ile Tyr Asp  Asn Asn Glu Ser Asn  Asn Lys Lys
    3530                3535                3540

Asp Asp  Phe Tyr Tyr Ser Ile  Pro Thr Asn Leu Asp  Ile Ser Leu
    3545                3550                3555

Lys Cys  Ile Asn Arg Asn Glu  Arg His Ile Asn Ser  Leu Leu Phe
    3560                3565                3570
```

```
Asn His Ser Lys Arg Lys Ser Thr Leu Ser Asn Ile Leu Ile Lys
    3575                3580                3585

His Asp Met Ile Lys Asn Ser Val Ser Lys His Ile Leu Asn Asn
    3590                3595                3600

Asp Tyr Ala Tyr Glu Tyr Asp Lys Lys Glu Glu Ile Glu Tyr Asn
    3605                3610                3615

Tyr Asn Asn Lys Asp Asn Cys Glu Lys Asn Ile Tyr Val Leu Asp
    3620                3625                3630

Val Lys Asn Lys Lys Gln Asn Asn Asn Asn Asn Met Asn Asp Asp
    3635                3640                3645

Asp Asp Asp Asn Asn Asn Met Asn Asp Asp Asp Asp Asp Asn Asn
    3650                3655                3660

Asn Met Asn Asp Asp Asp Asp Asp Asn Asn Asn Met Asn Asp Asp
    3665                3670                3675

Asp Asn Asn Asn Asp Asn Asn Asn Asp Lys Lys Lys His His Ile
    3680                3685                3690

Ile His Tyr Asn Asn Asn Asn Ile Ile Lys Lys Lys Arg Arg Lys
    3695                3700                3705

Phe Ile Phe Thr Ala Lys Lys Gln Ser Ser Tyr Ser Asn Thr Ile
    3710                3715                3720

Ile Cys Glu Gln Lys Asn Ile Asp Val Asn Lys Ile Tyr Ser Phe
    3725                3730                3735

Gly Ile Tyr Ile Asp Tyr Ile Phe Glu Ile His Asn Phe Met His
    3740                3745                3750

Glu Glu Met Lys Ile Gly Tyr Cys Gln Lys Tyr Tyr Ile Asn Ser
    3755                3760                3765

Ile Pro Lys Lys Ile Lys Arg Ile Lys Arg Glu Glu Ile Ser Pro
    3770                3775                3780

Lys Ser Ile Lys Tyr Leu Asp Thr Ile Pro Lys Tyr Ile Lys Leu
    3785                3790                3795

Phe Tyr Val Leu Asn Asn Asp Asn Tyr Ile Phe Asn Phe Phe Ser
    3800                3805                3810

Lys Lys Ile Gln Leu Tyr Lys Tyr Ala Asn Thr Pro Asp Lys Ile
    3815                3820                3825

His Gln Ile Lys Met Tyr Ile Glu Tyr Ile Asn Asp Glu Asn Lys
    3830                3835                3840

Asn Ile Ile Tyr Lys Lys Arg Lys Tyr Lys Leu Asn Ser Leu Phe
    3845                3850                3855

Lys Arg Lys Ser Lys Asn Lys Arg Lys Tyr Lys Tyr Leu Glu Ser
    3860                3865                3870

Lys Asp Tyr Asp Lys Leu Cys Lys Glu Val Pro Lys Phe Phe Tyr
    3875                3880                3885

Leu Asn Ile Thr Phe Arg Lys Lys Thr Asp His Ser Asn Asn Thr
    3890                3895                3900

Tyr Tyr Asn Glu Asn Asn Phe Lys His Val Ile Asp Ser Asn Val
    3905                3910                3915

Leu Gln Leu Leu Ile Tyr Pro Ser Phe Phe Phe Gln Asn Asn Leu
    3920                3925                3930

Asp Asn Asp Leu Ile Ile Lys Ser Asn Gly Asn Leu Gln Lys Ile
    3935                3940                3945

Lys Lys Lys Ser Ile Met Phe Phe Gly Asp Val Asp Asn Ser Lys
    3950                3955                3960
```

```
Val Ile  Leu Gln Ile Val Tyr  Asn Asn Gln Ile Phe  Leu Ser Lys
    3965                 3970                 3975

Lys Ile  Lys Ile Asn Gln Val  Cys Leu Asn Lys Lys  Ile Ile Leu
    3980                 3985                 3990

Thr Ser  Lys Asn Lys Lys Glu  Asn Ile Phe Leu Ser  Met Asn Ile
    3995                 4000                 4005

Thr Leu  Asn Gly Asn Ile Tyr  Asn Thr Lys Thr Ile  Thr Ile Asn
    4010                 4015                 4020

Asn Arg  Tyr Thr Ile Ile Asn  Asn Thr Asn Arg Thr  Leu Tyr Val
    4025                 4030                 4035

Gln Glu  Val Asn Lys Asp Phe  Lys Ile Ile Lys Lys  Lys Glu Lys
    4040                 4045                 4050

Lys Tyr  Met Thr Tyr Ser Phe  Ser Leu Glu Asn Leu  Gln Asn Gln
    4055                 4060                 4065

Asn Asn  His Ser Asn Asp Glu  Asn Met Glu Lys Leu  Tyr Ile Pro
    4070                 4075                 4080

Ser Ser  Asn Asp Leu Thr Asn  Ile Lys Arg Asn Tyr  Asn Gln Lys
    4085                 4090                 4095

Glu Lys  Asn Glu Lys Asn Glu  Lys Lys Glu Lys Asn  Glu Asn Leu
    4100                 4105                 4110

Asn Lys  Ile Thr Ile Asn Lys  Arg Ser Asp Leu Thr  Tyr Glu His
    4115                 4120                 4125

Glu Asn  Asp Glu Thr Lys Ile  Met Asp Thr Cys Glu  Ile Ser Asp
    4130                 4135                 4140

Lys Lys  Tyr Thr Glu Lys Gly  Met Thr Lys Ile Cys  Glu Phe Asn
    4145                 4150                 4155

Lys Lys  His Ile Lys Tyr Asn  Lys His Lys Lys Tyr  Asn Asp Lys
    4160                 4165                 4170

Lys Tyr  Asn Gln Lys Glu Asn  Asn Asn Asn Asn Asn  Asn Thr Thr
    4175                 4180                 4185

Ser Ser  Asn Asn Ser Asn Ser  Asn Ser Asn Ser Ser  Asn Asn Arg
    4190                 4195                 4200

Pro Asn  Ile Ile Ser Ile Lys  Pro Tyr Glu Ser Phe  Tyr Tyr His
    4205                 4210                 4215

Pro Ile  Asn Thr Asn Lys Cys  Phe Leu Thr Phe Ser  Tyr Thr Asn
    4220                 4225                 4230

Ile Met  Glu Cys Lys Asn Asp  Lys Asn Phe Tyr Arg  Arg Arg Gly
    4235                 4240                 4245

Ser Tyr  Glu Phe Thr His Thr  Gln Asn Glu Ile Thr  Asn Leu Phe
    4250                 4255                 4260

Asn Asn  Tyr Leu Lys Lys Lys  Ile Met Lys Ser Gln  Asn Ile Ser
    4265                 4270                 4275

Ile Ile  Asn Asp Lys Glu Glu  Asn Ile Asn Asn Asn  Val His Lys
    4280                 4285                 4290

Asn Gln  Glu Phe Tyr Asn Leu  Phe Tyr Thr Ser Pro  Ile Glu Ile
    4295                 4300                 4305

Glu Lys  Val Gly Asn Tyr Lys  Ile Phe His Lys Thr  Val His Lys
    4310                 4315                 4320

Ile Asp  Val Thr Tyr Asn Asn  Glu Lys Asp Ala Thr  Asp Asp Gln
    4325                 4330                 4335

Pro Thr  Tyr Glu Asp Asp Ile  Ile Gln Lys Glu Ile  Lys Gln Gln
    4340                 4345                 4350

Glu Lys  Glu Ile Glu Glu Glu  Ile Lys Arg Glu Ile  Glu Glu Leu
```

```
    4355                4360                4365

Glu Glu His Arg Glu Lys Glu Thr Ile Ile Val Phe Ser Asn Leu
    4370                4375                4380

Lys Asp Ser Tyr Glu Lys Glu Met Gln Lys Lys Lys Lys Asp Arg
    4385                4390                4395

His Lys Lys Asn Asn Phe Leu Asn Ile Asn Ser Asp His Ile Asn
    4400                4405                4410

Asp Lys Asn Ile Ile Asn Ser Tyr Lys Asn Glu Gln Thr Thr Glu
    4415                4420                4425

Met Ile Tyr Ile Gln His Asp Tyr Thr Asp Asn Ile Pro Ala Asp
    4430                4435                4440

Asp Glu Lys Lys Ser Ser His Asn Glu Thr Ile Leu Ile Asp Asp
    4445                4450                4455

Leu Thr Leu Phe Asn Lys Asn Asn Lys His Ser Ile Asn Glu Arg
    4460                4465                4470

Glu Asn Lys Glu Asn Ile Phe Asn Glu Thr Val Leu Thr Val Asp
    4475                4480                4485

Asn Asn Asp Thr Glu His Ile Lys Ser Asp Tyr Val Asn Ile Lys
    4490                4495                4500

Gly Asp Cys Ile Asn Ile Lys Gly Asp Cys Ile Asn Ile Lys Gly
    4505                4510                4515

Asp Tyr Val Asn Ile Lys Asp Asn Trp Val Asp Ile Lys Asp Asn
    4520                4525                4530

Cys Val Asn Ile Lys Asp Asn Cys Val Asn Ile Lys Asp Asn Cys
    4535                4540                4545

Val Asn Ile Lys Gly Asn Cys Val Asn Thr Lys Glu Asp Ser His
    4550                4555                4560

Asn Asn Tyr Gln Gln Asn Gly Met Asn Leu Arg His Asp Ser Phe
    4565                4570                4575

Cys Glu Asn Tyr Val Ile Asp Phe Asn Asp Asp Asp Ser Cys Ile
    4580                4585                4590

His Phe Lys Lys Asn Lys Asn Asp Ile Asn Thr Ala Asp Asp Ile
    4595                4600                4605

Asn Asn Asn Thr Val Ile Ile Pro Ile Lys Ser Ile Lys Gln Leu
    4610                4615                4620

Glu Gly Glu Glu Asn Val His Asn Ile Glu Asn Lys Asn Asn Asn
    4625                4630                4635

Ser Asn Asn Asn Asn Asn Asn Leu Leu Cys Glu Leu Asn Lys Thr
    4640                4645                4650

Ser Asp Asn Lys Glu Arg Ile Asn Thr Lys His Met Phe Leu Tyr
    4655                4660                4665

Lys Glu Glu Ser Ile Ile Thr Glu Ile Asn Ile Ala Leu Asn Ser
    4670                4675                4680

Asn Thr Asn Ile Glu Ile Asn Ile Ser Ile Glu Asn Asn Pro Asp
    4685                4690                4695

Thr Ile Ile Tyr Asn Lys Thr Asn Tyr Tyr Leu Ile Phe Tyr Gln
    4700                4705                4710

Arg Lys Thr Asn Lys Lys Ile Val Asn Leu Leu Lys Pro Phe Asp
    4715                4720                4725

Lys Glu Ile Phe Gly Trp Thr Asp Val Cys Lys Pro Lys Val Ile
    4730                4735                4740

Lys Cys Phe Leu Ile Ile Gln Lys Asn Asp Val Tyr Val Phe Ser
    4745                4750                4755
```

```
Cys Asn  Leu Asn Ile Val Lys  Glu His Asn Asn Ile  Ile Leu Asn
    4760                 4765                 4770

Asn Asn  Arg Arg Ile Ile Val  Leu Thr Lys Ile Glu  Asn Gly Lys
    4775                 4780                 4785

Arg Val  Phe Cys Leu Glu Glu  Met Asn Ile Glu Leu  Leu Asp Cys
    4790                 4795                 4800

Asn Glu  Lys Tyr Glu His Lys  Lys Ser Leu Ala Pro  Phe Phe Ser
    4805                 4810                 4815

Ala Ser  Lys Gly Phe Asn Arg  Phe Arg Glu Lys Lys  Lys Lys Lys
    4820                 4825                 4830

Ile Lys  Lys Lys Leu His Lys  Ile Ser Leu Tyr Asn  Ser Leu Ile
    4835                 4840                 4845

Lys Ser  Ser Gln Met Arg Lys  Glu Lys Asn Lys Ser  Lys Asn Lys
    4850                 4855                 4860

Lys Lys  Asn Lys Lys Gln Lys  Lys Asn Gln Met Asn  Gln Met Asn
    4865                 4870                 4875

Gln Thr  Asn Gln Thr Asn His  Met Leu Gln Lys Asn  Lys Gln Thr
    4880                 4885                 4890

Asn Asp  Asn Tyr Leu Val Lys  Tyr Lys Asn Glu Lys  Phe Asn Lys
    4895                 4900                 4905

Lys Leu  Pro Leu Leu Ser Lys  Lys Arg Phe Asn Ile  Ala Tyr Leu
    4910                 4915                 4920

Lys Lys  Lys Arg Lys Gln Ile  Lys Lys Lys Lys Asn  Asn Lys Tyr
    4925                 4930                 4935

Phe His  Leu Ser Ser Phe Phe  Leu Leu Lys Ser Met  Asp Ser Ser
    4940                 4945                 4950

Ile His  Lys Asp Val Glu Lys  Glu Arg Lys Lys Gln  Lys Gly Lys
    4955                 4960                 4965

Ser Gln  Gln Ala Glu Lys Leu  Phe Lys Val Glu Lys  Ile Val His
    4970                 4975                 4980

Asn Glu  Ser Tyr Asn Glu Ser  Tyr Asn Glu Ser Tyr  Asn Glu Tyr
    4985                 4990                 4995

His Asn  Glu Tyr His Asn Glu  Tyr His Asn Glu Tyr  His Asn Glu
    5000                 5005                 5010

Tyr His  Asn Glu Asn Asn Gly  Asn Ile Asn Ser Ile  Lys Tyr Asn
    5015                 5020                 5025

Asn Ile  Ile Lys Glu Glu Glu  Asn Val Lys Asn Lys  Asn Ala Thr
    5030                 5035                 5040

Ser Asn  Asn Asn Ser Ser Phe  Ser Lys Lys Asn Ile  Lys Leu Asn
    5045                 5050                 5055

Asn Val  Ser Ile Lys Lys Asp  Asp Lys Lys Lys Ser  Thr Ser Lys
    5060                 5065                 5070

Tyr Lys  Ser Leu Asn Ser Lys  Lys His Ile Asn Lys  Phe Phe Asn
    5075                 5080                 5085

Asp Asn  Tyr Thr Phe Arg Lys  Lys Lys Lys Arg Lys  Lys Ser Asn
    5090                 5095                 5100

Lys Lys  Asn Leu Tyr Val Asn  Lys Asn Asn Glu Glu  Thr Glu Thr
    5105                 5110                 5115

Ser Asp  Tyr Tyr Ile Glu His  Asn Glu Asn Lys Lys  Asn Ile Glu
    5120                 5125                 5130

Leu Ser  Ser His Asp Asn Asn  Ser Phe Asp Asn Glu  Lys Arg Lys
    5135                 5140                 5145
```

```
Thr Ser  Leu Gly Met Thr Lys  Ser Lys Gly Tyr Asn  Asp Leu Phe
    5150                 5155                 5160

Thr Val  Lys Phe Arg Lys Ser  Val Asn Glu Asn Asp  Lys Ile Asp
    5165                 5170                 5175

Glu Tyr  Lys Glu Asn Ser Phe  Glu Asp Ser Ser Thr  Tyr Asn Asp
    5180                 5185                 5190

Ser Phe  Leu Ser Ser Ser Ser  Asn Asn Glu Asn Tyr  Ile Ser Asn
    5195                 5200                 5205

Asn Asn  Lys Lys His Met Phe  Leu Asn Arg Tyr Tyr  Asp Asn Lys
    5210                 5215                 5220

Asp Asp  Lys Lys Lys Tyr Arg  Glu Tyr Asn Leu Ile  Tyr Asn Lys
    5225                 5230                 5235

Glu Met  Lys Ala Lys Asn Asn  Leu Lys Lys Pro Lys  Lys Lys Ile
    5240                 5245                 5250

Lys Arg  Lys Leu Ser Asp Phe  Ile Phe Thr Lys Ile  Lys Lys Asn
    5255                 5260                 5265

Gln Lys  Lys Phe Lys Gly Leu  Ser Arg Ile Tyr Pro  Met Phe Leu
    5270                 5275                 5280

Lys Ser  Asn Lys Ser Asp Glu  Phe Asn Val Leu Ile  Arg Asn Tyr
    5285                 5290                 5295

Leu Ser  Asp Lys Asp Asp Ser  Thr Ser Ile Arg Lys  Glu Tyr Lys
    5300                 5305                 5310

Ile Ile  Asn Asp Asn Tyr Ile  Asn Asn Asn Glu Asn  Asn Asn Asn
    5315                 5320                 5325

Glu Asn  Met Asn Tyr Asp Leu  Lys Thr Asn Thr Tyr  Asn Asn Ile
    5330                 5335                 5340

Leu His  Asn Asn Asn Tyr Arg  Leu Asp Lys Lys Ser  Val Phe Glu
    5345                 5350                 5355

Glu Asn  Arg Lys Ile Pro Ile  Lys Phe Ile Thr Asn  Leu Asn Val
    5360                 5365                 5370

Met Leu  Arg Gly Ile Lys Ile  Ser Leu Phe Glu His  Thr Cys Asp
    5375                 5380                 5385

Tyr Val  Ile Ser Phe Glu Ile  Asn Glu Leu Leu Val  Thr Lys Glu
    5390                 5395                 5400

Tyr Met  Glu Tyr Ile Asp Tyr  Tyr Asn Val Asp Ile  Lys Ile Asn
    5405                 5410                 5415

Asn Ile  Leu Cys Tyr Ala Val  Tyr Lys Tyr Leu Ser  Ala Cys Ala
    5420                 5425                 5430

Val Leu  Tyr Thr Asn Asn Asp  Ser Asn Ile Lys Asn  Asn His Leu
    5435                 5440                 5445

Arg Met  Leu Met Asn Glu Leu  Lys Ile Lys Arg Asn  Leu Phe Leu
    5450                 5455                 5460

Gln Lys  Lys Arg Arg Asn Glu  Asn Lys Lys Glu Tyr  Ser Asp Val
    5465                 5470                 5475

Asn Ile  Asp Lys Asn Asn Asp  Asn Ile Lys Asn Asn  Asp Asn Ile
    5480                 5485                 5490

Lys Asn  Asn Asp His Ile Asn  Asp Asn Asp His Ile  Asn Asp Asn
    5495                 5500                 5505

Asp His  Ile Asn Asp Lys Asp  His Ile Asn Asn Lys  Asp His Ile
    5510                 5515                 5520

Asn Asn  Lys Asp His Ile Asn  Asp Asn Glu Lys Glu  Met Tyr Ser
    5525                 5530                 5535

Ser Gly  Ser Ser Arg Thr Ser  Tyr Thr Asn Lys Lys  Lys Gly Tyr
```

```
    5540                5545                5550

Lys Tyr Lys Asn Asn Tyr Lys Lys Lys Lys Lys Lys Thr Glu Lys
    5555                5560                5565

Asn Ile Tyr Asp Asn Lys Lys Ala Lys Lys Lys Lys Lys Glu Lys
    5570                5575                5580

Val Glu Lys Lys Lys Lys Asn Leu Phe Val Asn Asn Glu Phe Leu
    5585                5590                5595

Ile Cys Asn Phe Gln Tyr Val Arg Lys Cys Glu Thr Leu Phe Phe
    5600                5605                5610

Lys Tyr Phe Leu Leu Ser Leu Lys Pro Ile Val Ile Asn Ala Asp
    5615                5620                5625

Ile Asn Ser Ile Thr Ile Leu Phe Tyr Phe Tyr Lys Thr Phe Tyr
    5630                5635                5640

Asn Phe His Thr Lys Lys Asn Glu Gln Gly Gln Gly Val Gln Asn
    5645                5650                5655

Gly Phe Asn Thr Asp Asn Tyr Glu Lys Val His Met Arg Glu Ile
    5660                5665                5670

Asn Met Met Lys Glu Gln Gln Gln Gln Gln Lys Lys Lys Lys Lys
    5675                5680                5685

Glu Glu Glu Glu Glu Glu Glu Glu Glu Glu Glu Glu Glu Glu Glu
    5690                5695                5700

Lys Lys Lys Lys Asn Lys Glu Asn Val Leu Gln Lys Lys Lys Thr
    5705                5710                5715

Lys Gln Glu Met Glu Arg Pro Leu Lys Asp Tyr Tyr Tyr Tyr Tyr
    5720                5725                5730

Tyr Ser Ser Met Asn Ile Leu Asn Asp Pro Asp Asn Asn Lys Arg
    5735                5740                5745

Cys Asp Ile Gln Lys Asn Arg Met Ile Glu Lys Asn Asp Ser Phe
    5750                5755                5760

Phe Ile Asn Val Asp Glu Asn Arg Lys Gln Lys Ile Gln Asp Ile
    5765                5770                5775

Thr Gly Asp His Ile Ile Asp Asn Asn Ile Leu Ser Arg Met Lys
    5780                5785                5790

Asn Met Glu Ser Phe Ile Ile His Glu Glu Gln Gln Lys Asn Asp
    5795                5800                5805

Leu Thr Leu Thr Leu His Asn Asn Ile Tyr Asn Val Glu Gly Glu
    5810                5815                5820

Tyr Tyr Asn Ile Lys Lys Ser Asn Met Asn Tyr Tyr Asn Asn Ile
    5825                5830                5835

Ile Asn Asn Lys Lys Ser Ser Val Gln Ile Lys Lys Lys Thr Thr
    5840                5845                5850

Leu Ile Glu Lys Asn Asp Ile Asn Asn Lys Tyr Val Tyr Leu Gln
    5855                5860                5865

Tyr Ile Ser Ile Asp Lys Ile Asn Ile Leu Leu Asn Phe Gln Ser
    5870                5875                5880

Glu Tyr Lys Lys Glu Leu Thr Asn His Val Asn Asp Leu Phe Tyr
    5885                5890                5895

Lys Glu His Ile Ser Ala Tyr Asn Lys Leu Gly Asp Ile Ser Asn
    5900                5905                5910

Cys Asn Ile Tyr Leu Lys Ser Leu Ser Asn Ile His Ile Phe Thr
    5915                5920                5925

Asn Tyr Asn Leu Leu Ile Asn Phe Leu Gln Asn Phe Tyr Tyr Asn
    5930                5935                5940
```

```
Gln Thr  Ile Val Asn Leu Ser  Asn Leu Leu Ile Ser  Phe Asn Ile
    5945                 5950                 5955

Ile Gly  Ser Pro Thr Ser Leu  Ile Ala His Val Lys  Asn Ala Phe
    5960                 5965                 5970

Asn Glu  Phe Phe Tyr Ile Ile  Asn Glu Asp Thr Leu  Ser Lys Lys
    5975                 5980                 5985

Asn Arg  Tyr Asp Asp Asp Lys  Asp Ile Asn Asp Tyr  Thr Thr Lys
    5990                 5995                 6000

Tyr Asn  Arg Lys Asn Asn Lys  Lys Asn Asn Arg Lys  Asn Asn Lys
    6005                 6010                 6015

Lys Asn  Asn Arg Lys Asn Asn  Arg Lys Asn Asn Lys  Asn Asn Asp
    6020                 6025                 6030

Asn Asn  Asn Ile Asn Ser Met  Tyr Gly Ser His Tyr  Asn Asn Asn
    6035                 6040                 6045

Tyr Ile  Tyr Tyr Asn Asp Tyr  Tyr Tyr Asn Asn Asn  Tyr Met Tyr
    6050                 6055                 6060

Arg Arg  Ser Thr Leu Asn Tyr  His Tyr Tyr Glu Gln  Gly Tyr Asp
    6065                 6070                 6075

Lys Tyr  Lys Leu Asn Arg Ile  Tyr Asn Asn Asn Pro  Lys Leu Arg
    6080                 6085                 6090

Lys Asn  Asn Lys Glu Arg Lys  Asn Asn Ile Gln Gln  Ile Asn Tyr
    6095                 6100                 6105

Thr Thr  Lys Lys Glu Asp Lys  His Asn Phe Leu Asn  Leu Ile Asp
    6110                 6115                 6120

Gln Ser  Arg Glu Ser Ser Phe  Leu Asp Glu Lys Asp  Asp Ser Leu
    6125                 6130                 6135

Thr Asn  Asp Asp Lys Tyr Ile  Met His Leu Leu Asn  Asp Tyr Asn
    6140                 6145                 6150

Ser Ser  Tyr Gln Asn Asn Leu  Leu Ser Glu Glu Glu  Ser Phe Val
    6155                 6160                 6165

Lys Arg  Asn Phe Ser Trp Asn  Phe Phe Lys Lys Gln  His Thr Asn
    6170                 6175                 6180

Asn Asn  Asn Asn Asn Ser Asp  Asp Asp Asn Tyr Phe  Asn Asp Ser
    6185                 6190                 6195

Tyr Asn  Asn Ile Lys His Glu  Ser Ser Gly Asn Leu  Asn Tyr Met
    6200                 6205                 6210

Tyr Thr  Lys Ser Ile Lys Asn  Lys Asp Leu His Lys  Leu Val Ile
    6215                 6220                 6225

Asp Asp  Asn Asn Ser Ser Met  Asn Ser Phe Leu Phe  Asn Asn Lys
    6230                 6235                 6240

Lys Asn  Val Ile Ile Leu Asp  Gln Val Ser Lys Lys  Lys Lys Lys
    6245                 6250                 6255

Lys Leu  Gln Tyr Ile Lys Asn  Phe Glu Glu Pro Gln  Lys Gly His
    6260                 6265                 6270

Ile Tyr  Met Asp Asp Asp Met  Tyr Ile Asp Val Asp  Val Asp Leu
    6275                 6280                 6285

Asn Ser  Tyr Ala Glu Gly Lys  Asn Thr Thr Lys Asp  Thr Ser Lys
    6290                 6295                 6300

Tyr Pro  Pro His Phe Lys Ile  Ser Tyr Asp Glu Glu  Lys Lys Lys
    6305                 6310                 6315

Arg Lys  Lys Lys Arg Leu Ser  Thr Gly Ser Asn Asn  Asn Arg Tyr
    6320                 6325                 6330
```

```
Lys Asn Asp Ala Glu Ile Leu Asp Met Asn Pro Asn Lys Lys Asn
    6335                6340                6345

Lys Lys Lys Asn Lys Met Leu Lys Asn Asn Asn Asn Asn Asn Asn
    6350                6355                6360

Asn Asn Lys Asn Lys Lys Asn Lys Arg Asn Asn Lys Arg Ser Gly
    6365                6370                6375

Cys Thr Lys Met Phe Arg Phe Phe Lys Lys Ile Gly Leu Asn Ile
    6380                6385                6390

Ile Tyr Ile Phe Ser Lys Thr Lys Arg Ile Cys Ile Gly Ile Tyr
    6395                6400                6405

Val Leu Phe Ile Gln Leu Ile Leu Ser Leu Leu Phe Ser Ile Thr
    6410                6415                6420

Leu Ile Leu Gln Ser Leu Ile Asn Leu Val Glu Lys Val Asn Ile
    6425                6430                6435

Asn Asn Ala Asp Asn Val Phe Leu Ile Phe Asn Lys Lys Tyr Glu
    6440                6445                6450

Arg Lys Lys Val Val Val Phe Asn Asn Ile Glu Glu Tyr Asn Lys
    6455                6460                6465

Phe Asn Ile Thr Lys Leu Phe Tyr Tyr Tyr Ile Ser Ile Tyr Met
    6470                6475                6480

Asn Ile Val Asn Phe Leu Tyr Tyr Asn Met Leu Tyr Lys Met Lys
    6485                6490                6495

Lys Lys Lys Lys Asp Leu Ser Gly Glu Asp Lys Ile Phe Met Lys
    6500                6505                6510

Lys Leu Lys Ile Asn Leu Lys Asn Lys Arg Lys Phe Ser Phe Phe
    6515                6520                6525

Ile Asn Phe Phe Leu Asn Ile Phe Asn Ile Ile Asn Ile Leu Leu
    6530                6535                6540

Phe Gly His Ile Val Phe Leu Leu Leu Cys Leu Leu Thr Met Asn
    6545                6550                6555

Asn Ile Phe Gln Lys Ile Leu Thr Ala Cys Ile Lys Leu Val Tyr
    6560                6565                6570

Tyr Gln Arg Asn Lys Asn Tyr Leu Asp Phe Leu Asn Lys Asn Ser
    6575                6580                6585

Phe Asn His Met Asn Ile Ile Ser Tyr Ile Lys Ile Asn Gln Val
    6590                6595                6600

Ile Ser Lys Tyr Val Leu Leu Lys Glu Pro Phe Lys Tyr Phe Leu
    6605                6610                6615

Ser His Gln Asp Phe Leu Asp Ile Lys Ala Pro Lys Lys Arg Asn
    6620                6625                6630

Tyr Phe Val Tyr Thr Lys Glu Leu Phe Phe Tyr Ile Gln Glu Asn
    6635                6640                6645

Lys Ile Val Phe Leu Phe Arg Lys Asn Asp Met Lys Lys Ile Asp
    6650                6655                6660

Ile Ile Ile His Thr Ile Asn Asn Ser Phe Ala Ile Asn Ser Tyr
    6665                6670                6675

Tyr Lys Lys Lys Gly Ser Lys Thr Ala Lys Lys Ser Arg Ser Lys
    6680                6685                6690

Asn Thr Pro Ser Asn Tyr Thr Leu Asn Met Glu His Val Thr Gly
    6695                6700                6705

Glu Glu Asn Asn Ser Phe Thr Ser Ser Leu Tyr Asn Lys Thr Asn
    6710                6715                6720

Val Ser Asn Asp Ile Ser Glu Asp Lys Asn Val Ile Cys Phe Leu
```

```
    6725                6730                6735

Asn Gln  Glu Leu Ala Leu Thr  Lys Arg Asn Glu Ile  Ile His Ile
    6740                6745                6750

Asn Asn  Lys Asn Tyr Asp Tyr  Ile Ile Ser Ile Lys  Ile Thr Ile
    6755                6760                6765

Lys Asn  Asn Met Asn Val Met  Glu Asn Ile Tyr Tyr  Asn Pro Lys
    6770                6775                6780

Lys Phe  Phe Lys Cys Leu Ser  Lys Ile Gln Lys Ser  Phe Asn Asn
    6785                6790                6795

Ile Tyr  Leu Pro Leu Cys Lys  Asn Asn Asn Asn Glu  Thr Lys Asn
    6800                6805                6810

Asn Lys  Glu Lys His Leu Asn  Asn Lys Gly Ala Asp  Ile Tyr Lys
    6815                6820                6825

Ala Asp  Ile Asn Val Lys Lys  Arg Arg Thr Phe Phe  Ser Ala Ile
    6830                6835                6840

Ile Cys  Phe Phe Lys Ser Ile  Phe Ile Phe Leu Tyr  Phe Cys Leu
    6845                6850                6855

Cys Pro  Trp Lys Leu Leu Lys  Leu Lys Lys Lys Lys  Ser Asn Asp
    6860                6865                6870

Asn Lys  Lys Lys Gln Met Asp  Glu Lys Asp Lys Glu  Asn Ala Val
    6875                6880                6885

His Lys  Asn Ile Gln Leu Lys  His Lys Asn Lys Lys  Glu Lys Thr
    6890                6895                6900

Thr Pro  Asn Ser Ile Ile Phe  Lys Leu Asn Phe Glu  Asp Phe Gln
    6905                6910                6915

Ser Thr  Leu Asn Ile Phe Glu  Cys Leu Cys Arg Ile  Met Asn Asn
    6920                6925                6930

Asn
```

<210> SEQ ID NO 13
<211> LENGTH: 7458
<212> TYPE: DNA
<213> ORGANISM: Plasmodium falciparum

<400> SEQUENCE: 13

```
atgttttcag tcgaattaga aaatcgatca ggttataaaa aaaggaaaaa aaagaaatgg     60

aataataaaa gtactggtca ggataaattt acgaacaaag atattatatc agaggaaaaa    120

gaagaaggac ttgatataga atgtggtcat aatattctgg gggatgtaca atatgatggt    180

acatataata taaatgaaca agttaagaaa aattcattgt tctattttaa atgtaaagag    240

gaaattaatt taaaagatgg aaatataata ttggatgata aaaatagaaa agtggatgat    300

ataaatataa caggggatga taaaaatata aaagtggatg ataaaaatat aaaagtggat    360

gataaaaata taacagggga ggataaaaat ataacagggg aggataaaaa tataacaggg    420

gatgataaaa atataatttt tgatgttgat gaaatattaa tccatcaaca taatacatca    480

aatagtaata tatatataaa ttgtaatgat aataataatg atattaggaa cagttcaaat    540

gtacagcatt attataatga taaaataaaa gaaaatataa ataaacaaaa taaaaagtat    600

gttttaataa atgattatat aaataataaa tatattttat caaaaaataa gacatgtaaa    660

ataaataaag gaaaaaaatt aattaaaaaa aaaaaagtaa ataatatttc taggaggagg    720

aatcatatat tatataaatg tcgtaataag ttatataatg gaaatgtttt ttctgacgat    780

attattaaaa gtgaagtgaa tgtatgtaat tcgttaactg tacttcataa gaattataat    840
```

```
attaatatgg ataattattt agatgataat atacatacaa ataatagcaa tatttatgat    900
attaattata caaatgaaaa tgttattaat tcaacatgtc gttattatcc cataggtaat    960
aataacacat taagtaaaga tgaagttaca aaatcaagtt caaaaattaa ttccctttct   1020
tattttgatg atattattaa tgtaaataaa aatgatatac ctattttaca tgataaagaa   1080
aatataaata taataagtaa caaggaaagc tgtcataagg atgaaaagga ggaagagaaa   1140
tatatcatgt ataattcaaa tttagtagaa gaaaaaaaac aaaaaaaaat gatttggaat   1200
tctcttaatg tattaccaat agatatacta cttaaaaatg gacatgatga aattaataaa   1260
gagatatgca aaaaaaaaaa aaaaagtttt tttagtcaga atgatataaa gtctaaaatg   1320
ttatacaata ataaaagtta ttcaaaaagt gaaaaagtat tatatacaaa taataaaaac   1380
agtaatacgt tcattcctat atttttctta aataaggtag gagacaagtt taaaaactct   1440
gagaatatat atgatatgta taataataaa aaaaatgtct atatacatga taagaagata   1500
tatactaata tgtattctaa taaattaaaa cagaaacatt attatagcac ttctaatata   1560
aatttattat ataataatat aggaaaggta ttagataatg gtctacattt atcgaataat   1620
atgtattgtc gtttaaattc aaatccacca tataagagta tctcgttaat taataacaat   1680
gttttttttt ataaaaagag gaaaagtaat agtaataata ataataataa taataatatt   1740
agtagtagta gtagtagtag tagtaaaaaa aatcacgtga tcattaataa aaaaatatca   1800
tcttataata ttcattataa agaaagaaag gattcgttta aagagaattt tttatttttc   1860
aaagagaaaa ttttaccatc aaaaaaagat acttgtgttt ttaatgaaag acaaaaagat   1920
ctttttgaaa aaagtaatga acatattaaa tgcgtttctt cttttaataa tacatcagat   1980
gatatttctt cacattcaag cgtaaataag aaagaacctt tttttgcttt aaaaaataat   2040
tccataaggc acataccaaa agaaaataat ataatatata catctgggaa atcttttaat   2100
catgtgcagg ataaggaaaa gactgttcta cttaaaaaaa agaaagaaat aaatgataag   2160
aatacattta gctcttgttt aataaaccat aatataacaa catatacatt acaaaatgga   2220
gtaaataaaa atttaaatat gttaggaata agagattcta tttataaaat agatgaaaag   2280
aacaatatgt tgaaagaatg ttataatgga aataatgata gtaataataa gaaaaaaaag   2340
aagaaaaaaa aattatcttt ttcatgtgat attataaatg ataatattac accttatgaa   2400
tcagataagg agaaaaacaa ttctaataat attaagagta tggatatatt taattatgta   2460
aaaagaaaaa gcaaccttta taataattta tcttcgaaca gggattctac tgtagatatg   2520
cataataaat ataatagtga agaatatata aatatacaga gaacaaataa aatatatgaa   2580
ttgagtaata aaagaattag aaattataaa ttgtatagta tggatgaaat atttaaggtg   2640
tctcttaagg aaaaaaaata tatagataat atttctaata atatggaaag agtaacatat   2700
aaaaatgaaa tgataaatga aaagataagt aagatggacg atatattata tccttgtgac   2760
aaaaataaat ctttaaacat gtcttgtcct gttataatag aaaataatat atcaagagaa   2820
gaaaatgaaa aaaattcaag tgttatatta aataaaaaaa agaatgagaa tatgtttaat   2880
tgtgttggaa ggttacattg tcacatgggc aaaatgaata atcaagataa tatatatgac   2940
caagggaata taaaaaaaaa tgaagaagaa ataaccaaac atgatgaata tatatcaagg   3000
gaagaaaaaa ataaatataa tagtaaatgt attagaaatt ttgatgacta taaatatgaa   3060
caagtgttga gttaccatac gttggatgaa gacaaaaaaa aaaatgatat gaacaattta   3120
atagatatga ataatgaggc gattattgaa acggtgaatg gtgttattaa taatattata   3180
ttggatagaa aagataataa cagtaggaag gatatggaga aagagatgga gaaggagatg   3240
```

```
gagaagaaga tggagaagga gatggagaag gtgatggaga aggagatgga gaaggtgatg   3300
gagaaggagg tggagaaaga attgaaaaat gagatgaaca ataggatgaa caataggatg   3360
aacaatgaga tgaaaaatga aataaacatt tataaaaaca atgagatata tgtagataat   3420
gataaagaac tagaaattgt aaatgaggag aagaaactta tttacccatt taattacgaa   3480
tctgatgtac ataaaaatat gaatatgtca attaatataa ataattgtaa agatgattat   3540
aataatatat taaaagaata tgtagataat tcatgtcttg ctcaaaagga agagaatata   3600
tttcgacctt tattcaattt aaataagaaa gataaagtat ggaaacgttt taatataaag   3660
aataatatta agacaataat acataatgaa gagatgaaaa gaatatatca aactattaat   3720
aaaaatgttt ttcctattta taattttaat cgatatgaaa attttttaat aaatcattta   3780
acatataatt ttccaaaaaa tgatttattt aaattatcat acaaagtaag tatgaataat   3840
ataaggaatt tgtatattgc taataaacat ataaataata attatgatta tatgaataaa   3900
ttatataatc aaaatatata tacattaaaa tatcaggtag ctaatataga taatgatcat   3960
catatatgta agaaaggggg agggttggat tatataaata tgaatatatc aaaagaatgt   4020
aaaaatagga aagacaaaac atatttaaat aaaatatttc attataagaa gaaaaaggat   4080
gcacgctttt ttataaatga cgaaattggt tctaatgatt atatgtatga tataaaaaaa   4140
aaatatagta acgatgaaaa taattataaa ttaaatgaaa agatgaacat atctatgtca   4200
aatgatgaag atatgattcc tacgttaaat agtgaacatg gaaataattt tccaagttgt   4260
caaccgaatt tattagaaaa aaaaagtact tatatagatt tgaacttata tgatagtaat   4320
tctatggacg attttacaga agaaaaatat aattttgtta ataatgaaaa tgatttattc   4380
aatactaaaa gatggaagtt taatttttcc aagggtaaaa atctgtttaa taataaattt   4440
tttaatgtat ctaatgagga tggtgtgttt tcttttttta aaaatatgaa tctttttagg   4500
gaacttaata aatcaaataa tagcttaaaa ctagagagtg ttaaaaaatag taataataat   4560
tgtagtaata ataagggtga tgataatatt ggaaatatgg agaatatgaa tacaacaaat   4620
gttacaattg cgagtgatga acatatatct acaaagggag atatacacga cgaatcattt   4680
tctagagacg ataatgattg tatccttta aaaattgaag gtagaagtaa aaaatatagt   4740
gatataacct tatataatga ggacaaaagt aatttggaga atgacaatga gactattaat   4800
gaatatgaaa atgtatgtag taacatagat gttaatgaat gggaagataa ggtaaatggt   4860
acatgtaata gtgttggtga taaagagact gaaaagaata atgaaaagaa taatgaaaag   4920
aataatgaaa agaataatga aaagaataat gaaaagaata atgaaaagaa taatgaaaag   4980
aataatgaaa agaataatga agaaaataat gaaggaaata atgaagaaaa taatgaagaa   5040
aataatgaag aaaataatga agaaaataat gatatagaaa agaatgatat aaaggataat   5100
aattcgggac aagtgaaaga aaatataatt gttatgaata atacaaacaa tatggatgtt   5160
gataatgatg ataataacaa taattacaat aatgttagta ctgatgaagg tatagatata   5220
attaaaaaca tcaaaagtga gatgaatgat tatatttata atgataatat tatgattaag   5280
ataaataata aaagtataga tcttatgaat ataaaaaatc aaaagaatga accttttta   5340
aattatacaa atgaaaagga tatacatatg aagagcaatt catcatataa tgtaaatgat   5400
aaaatgaatt tatttaataa taatgagaaa acagaaaaaa ataatactag tttaaacgat   5460
ttattatata aaagaaaaga agaattagat gatgaaaaaa tatctgaata taaggataca   5520
aatttaacaa acaatacctt tgaacatata gctaaaagga ttaatttaat tttgaatgat   5580
```

```
acaattgaat tttttcaaaa acatacatat cttcataatg gttatggtaa tgttcaggtg   5640
tgcaaaaaga acaagaggaa attagaaaaa aagaagttga aaaaatggtc ctgtatttat   5700
aaaattaata aaattgtacg taaaggggcc cacggggtgg tgttttctgc gtggagaagt   5760
gagaatgttg atttttttaa tcattcgttt tttgaaaact taaatttgga gaataaaaag   5820
aagggatata tcgatgaaac aaatgttaat gaaaattatg agtctgataa tgaatatgat   5880
agtgatgaag atgatactga aagtgataat gatgatgagc aaaataaaga gaatgaaaga   5940
ggtgatgaaa aggatggata tgaagaaatg aatgggggag ataagaatga agaaatgaat   6000
gggggagata agaatgaaga aatgaatgtg ggagataaaa atggaggaat aaatgaggaa   6060
cataaaaatg aaggaataaa tgaggaacat aaggatgaac taataaataa ggaacataaa   6120
aacgagcgaa taaatgagga acataaaaac gaacgaataa atgaggaaca taaaaatgaa   6180
ggaataaatg aggaacataa aaatgaagga ataaatgagg aacataaaaa cgaacgaata   6240
aatgaggaac ataaaaatga aggaataaat aaactgacct atcataatat gaataaaaat   6300
aatatttcaa atgaaaataa ttataatgat gacgattctt atgatgaaga taatttggta   6360
tccctgaaga taataaactt aaaatattta agtaaaaaga atagtttaaa aaacattttg   6420
agagaagtaa atttttaaa aatgtgtgaa catccaaatg tagtaaaata tttcgaatct   6480
tttttttggc ctccttgtta tttagttatt gtgtgtgaat atttatcagg aggaacatta   6540
tatgatttat ataaaaatta tggtagaata tcagaagatc ttttagtata tatcttagat   6600
gatgtattaa atggtttaaa ttatttacat aatgaatgta gttcaccact tatacataga   6660
gatataaaac caacaaatat cgttctttcc aaagatggta tagctaagat aattgatttt   6720
ggttcttgtg aagaattgaa aaatagtgat cagtctaaag aattagtggg tactatatat   6780
tatatatcac ctgaaatatt gatgagaact aattatgatt gttcatctga tatatggtca   6840
ttgggtatta caatatatga aattgtttta tgtaccttac catggaaaag aaatcaatca   6900
tttgaaaatt atataaaaac cataattaat tcatcaccaa aaattaacat aacagaagga   6960
tatagtaaac acttatgtta ttttgttgag aagtgtttac aaaagaaacc tgagaacaga   7020
ggaaatgtga aagatttatt aaatcataaa tttttgatta aaaagaggta tattaaaaag   7080
aaacctagtt ctatatatga aataagagat atattaaaaa tatataatgg taaaggtaaa   7140
acaaatatct tccgaaattt ttttaagaac cttttttttct tcaatgataa gaataaaaaa   7200
aaaaaaccaa ataaaatgat cagttccaaa tcctgtgatg cagaaatgtt ctttgaacag   7260
ttaaaaaggg aaaattttga ttttttttgaa attaaattaa aagatgatga aaatagtaga   7320
tccttgaata cgtttaatat aaatatatct aaagaaaagag acgacatatc atattcttct   7380
ttaaatttgg aaaaaatcaa agaacacagt ctcaatatgg tagcatctgt tgtcgggact   7440
gaacaatccc agaaatga                                                7458
```

<210> SEQ ID NO 14
<211> LENGTH: 2485
<212> TYPE: PRT
<213> ORGANISM: Plasmodium falciparum

<400> SEQUENCE: 14

```
Met Phe Ser Val Glu Leu Glu Asn Arg Ser Gly Tyr Lys Lys Arg Lys
1               5                   10                  15

Lys Lys Lys Trp Asn Asn Lys Ser Thr Gly Gln Asp Lys Phe Thr Asn
            20                  25                  30

Lys Asp Ile Ile Ser Glu Glu Lys Glu Glu Gly Leu Asp Ile Glu Cys
```

```
        35                  40                  45

Gly His Asn Ile Leu Gly Asp Val Gln Tyr Asp Gly Thr Tyr Asn Ile
    50                  55                  60

Asn Glu Gln Val Lys Lys Asn Ser Leu Phe Tyr Phe Lys Cys Lys Glu
65                  70                  75                  80

Glu Ile Asn Leu Lys Asp Gly Asn Ile Ile Leu Asp Asp Lys Asn Arg
                85                  90                  95

Lys Val Asp Asp Ile Asn Ile Thr Gly Asp Asp Lys Asn Ile Lys Val
            100                 105                 110

Asp Asp Lys Asn Ile Lys Val Asp Asp Lys Asn Ile Thr Gly Glu Asp
        115                 120                 125

Lys Asn Ile Thr Gly Glu Asp Lys Asn Ile Thr Gly Asp Asp Lys Asn
    130                 135                 140

Ile Ile Phe Asp Val Asp Glu Ile Leu Ile His Gln His Asn Thr Ser
145                 150                 155                 160

Asn Ser Asn Ile Tyr Ile Asn Cys Asn Asp Asn Asn Asn Asp Ile Arg
                165                 170                 175

Asn Ser Ser Asn Val Gln His Tyr Tyr Asn Asp Lys Ile Lys Glu Asn
            180                 185                 190

Ile Asn Lys Gln Asn Lys Lys Tyr Val Leu Ile Asn Asp Tyr Ile Asn
        195                 200                 205

Asn Lys Tyr Ile Leu Ser Lys Asn Lys Thr Cys Lys Ile Asn Lys Gly
    210                 215                 220

Lys Lys Leu Ile Lys Lys Lys Lys Val Asn Asn Ile Ser Arg Arg Arg
225                 230                 235                 240

Asn His Ile Leu Tyr Lys Cys Arg Asn Lys Leu Tyr Asn Gly Asn Val
                245                 250                 255

Phe Ser Asp Asp Ile Ile Lys Ser Glu Val Asn Val Cys Asn Ser Leu
            260                 265                 270

Thr Val Leu His Lys Asn Tyr Asn Ile Asn Met Asp Asn Tyr Leu Asp
        275                 280                 285

Asp Asn Ile His Thr Asn Asn Ser Asn Ile Tyr Asp Ile Asn Tyr Thr
    290                 295                 300

Asn Glu Asn Val Ile Asn Ser Thr Cys Arg Tyr Tyr Pro Ile Gly Asn
305                 310                 315                 320

Asn Asn Thr Leu Ser Lys Asp Glu Val Thr Lys Ser Ser Ser Lys Ile
                325                 330                 335

Asn Ser Leu Ser Tyr Phe Asp Asp Ile Ile Asn Val Asn Lys Asn Asp
            340                 345                 350

Ile Pro Ile Leu His Asp Lys Glu Asn Ile Asn Ile Ile Ser Asn Lys
        355                 360                 365

Glu Ser Cys His Lys Asp Glu Lys Glu Glu Glu Lys Tyr Ile Met Tyr
    370                 375                 380

Asn Ser Asn Leu Val Glu Glu Lys Lys Gln Lys Lys Met Ile Trp Asn
385                 390                 395                 400

Ser Leu Asn Val Leu Pro Ile Asp Ile Leu Leu Lys Asn Gly His Asp
                405                 410                 415

Glu Ile Asn Lys Glu Ile Cys Lys Lys Lys Lys Lys Ser Phe Phe Ser
            420                 425                 430

Gln Asn Asp Ile Lys Ser Lys Met Leu Tyr Asn Asn Lys Ser Tyr Ser
        435                 440                 445

Lys Ser Glu Lys Val Leu Tyr Thr Asn Asn Lys Asn Ser Asn Thr Phe
    450                 455                 460
```

```
Ile Pro Ile Phe Phe Leu Asn Lys Val Gly Asp Lys Phe Lys Asn Ser
465                 470                 475                 480

Glu Asn Ile Tyr Asp Met Tyr Asn Asn Lys Lys Asn Val Tyr Ile His
                485                 490                 495

Asp Lys Lys Ile Tyr Thr Asn Met Tyr Ser Asn Lys Leu Lys Gln Lys
            500                 505                 510

His Tyr Tyr Ser Thr Ser Asn Ile Asn Leu Leu Tyr Asn Asn Ile Gly
        515                 520                 525

Lys Val Leu Asp Asn Gly Leu His Leu Ser Asn Asn Met Tyr Cys Arg
    530                 535                 540

Leu Asn Ser Asn Pro Pro Tyr Lys Ser Ile Ser Leu Ile Asn Asn Asn
545                 550                 555                 560

Val Phe Phe Tyr Lys Lys Arg Lys Ser Asn Ser Asn Asn Asn Asn Asn
                565                 570                 575

Asn Asn Asn Ile Ser Ser Ser Ser Ser Ser Ser Ser Lys Lys Asn His
            580                 585                 590

Val Ile Ile Asn Lys Lys Ile Ser Ser Tyr Asn Ile His Tyr Lys Glu
        595                 600                 605

Arg Lys Asp Ser Phe Lys Glu Asn Phe Leu Phe Phe Lys Glu Lys Ile
    610                 615                 620

Leu Pro Ser Lys Lys Asp Thr Cys Val Phe Asn Glu Arg Gln Lys Asp
625                 630                 635                 640

Leu Phe Glu Lys Ser Asn Glu His Ile Lys Cys Val Ser Ser Phe Asn
                645                 650                 655

Asn Thr Ser Asp Asp Ile Ser Ser His Ser Ser Val Asn Lys Lys Glu
            660                 665                 670

Pro Phe Phe Ala Leu Lys Asn Asn Ser Ile Arg His Ile Pro Lys Glu
        675                 680                 685

Asn Asn Ile Ile Tyr Thr Ser Gly Lys Ser Phe Asn His Val Gln Asp
    690                 695                 700

Lys Glu Lys Thr Val Leu Leu Lys Lys Lys Lys Glu Ile Asn Asp Lys
705                 710                 715                 720

Asn Thr Phe Ser Ser Cys Leu Ile Asn His Asn Ile Thr Thr Tyr Thr
                725                 730                 735

Leu Gln Asn Gly Val Asn Lys Asn Leu Asn Met Leu Gly Ile Arg Asp
            740                 745                 750

Ser Ile Tyr Lys Ile Asp Glu Lys Asn Asn Met Leu Lys Glu Cys Tyr
        755                 760                 765

Asn Gly Asn Asn Asp Ser Asn Asn Lys Lys Lys Lys Lys Lys Lys Lys
    770                 775                 780

Leu Ser Phe Ser Cys Asp Ile Ile Asn Asp Asn Ile Thr Pro Tyr Glu
785                 790                 795                 800

Ser Asp Lys Glu Lys Asn Asn Ser Asn Asn Ile Lys Ser Met Asp Ile
                805                 810                 815

Phe Asn Tyr Val Lys Arg Lys Ser Asn Leu Tyr Asn Asn Leu Ser Ser
            820                 825                 830

Asn Arg Asp Ser Thr Val Asp Met His Asn Lys Tyr Asn Ser Glu Glu
        835                 840                 845

Tyr Ile Asn Ile Gln Arg Thr Asn Lys Ile Tyr Glu Leu Ser Asn Lys
    850                 855                 860

Arg Ile Arg Asn Tyr Lys Leu Tyr Ser Met Asp Glu Ile Phe Lys Val
865                 870                 875                 880
```

```
Ser Leu Lys Glu Lys Lys Tyr Ile Asp Asn Ile Ser Asn Asn Met Glu
                885                 890                 895

Arg Val Thr Tyr Lys Asn Glu Met Ile Asn Glu Lys Ile Ser Lys Met
            900                 905                 910

Asp Asp Ile Leu Tyr Pro Cys Asp Lys Asn Lys Ser Leu Asn Met Ser
        915                 920                 925

Cys Pro Val Ile Ile Glu Asn Asn Ile Ser Arg Glu Glu Asn Glu Lys
    930                 935                 940

Asn Ser Ser Val Ile Leu Asn Lys Lys Lys Asn Glu Asn Met Phe Asn
945                 950                 955                 960

Cys Val Gly Arg Leu His Cys His Met Gly Lys Met Asn Asn Gln Asp
                965                 970                 975

Asn Ile Tyr Asp Gln Gly Asn Ile Lys Lys Asn Glu Glu Glu Ile Thr
            980                 985                 990

Lys His Asp Glu Tyr Ile Ser Arg  Glu Glu Lys Asn Lys  Tyr Asn Ser
        995                 1000                1005

Lys Cys  Ile Arg Asn Phe Asp  Asp Tyr Lys Tyr Glu  Gln Val Leu
    1010                1015                1020

Ser Tyr  His Thr Leu Asp Glu  Asp Lys Lys Lys Asn  Asp Met Asn
    1025                1030                1035

Asn Leu  Ile Asp Met Asn Asn  Glu Ala Ile Ile Glu  Thr Val Asn
    1040                1045                1050

Gly Val  Ile Asn Asn Ile Ile  Leu Asp Arg Lys Asp  Asn Asn Ser
    1055                1060                1065

Arg Lys  Asp Met Glu Lys Glu  Met Glu Lys Glu Met  Glu Lys Lys
    1070                1075                1080

Met Glu  Lys Glu Met Glu Lys  Val Met Glu Lys Glu  Met Glu Lys
    1085                1090                1095

Val Met  Glu Lys Glu Val Glu  Lys Glu Leu Lys Asn  Glu Met Asn
    1100                1105                1110

Asn Arg  Met Asn Asn Arg Met  Asn Asn Glu Met Lys  Asn Glu Ile
    1115                1120                1125

Asn Ile  Tyr Lys Asn Asn Glu  Ile Tyr Val Asp Asn  Asp Lys Glu
    1130                1135                1140

Leu Glu  Ile Val Asn Glu Glu  Lys Lys Leu Ile Tyr  Pro Phe Asn
    1145                1150                1155

Tyr Glu  Ser Asp Val His Lys  Asn Met Asn Met Ser  Ile Asn Ile
    1160                1165                1170

Asn Asn  Cys Lys Asp Asp Tyr  Asn Asn Ile Leu Lys  Glu Tyr Val
    1175                1180                1185

Asp Asn  Ser Cys Leu Ala Gln  Lys Glu Glu Asn Ile  Phe Arg Pro
    1190                1195                1200

Leu Phe  Asn Leu Asn Lys Lys  Asp Lys Val Trp Lys  Arg Phe Asn
    1205                1210                1215

Ile Lys  Asn Asn Ile Lys Thr  Ile Ile His Asn Glu  Glu Met Lys
    1220                1225                1230

Arg Ile  Tyr Gln Thr Ile Asn  Lys Asn Val Phe Pro  Ile Tyr Asn
    1235                1240                1245

Phe Asn  Arg Tyr Glu Asn Phe  Leu Ile Asn His Leu  Thr Tyr Asn
    1250                1255                1260

Phe Pro  Lys Asn Asp Leu Phe  Lys Leu Ser Tyr Lys  Val Ser Met
    1265                1270                1275

Asn Asn  Ile Arg Asn Leu Tyr  Ile Ala Asn Lys His  Ile Asn Asn
```

```
    1280                1285                1290

Asn Tyr  Asp Tyr Met Asn Lys  Leu Tyr Asn Gln Asn  Ile Tyr Thr
    1295                1300                1305

Leu Lys  Tyr Gln Val Ala Asn  Ile Asp Asn Asp His  His Ile Cys
    1310                1315                1320

Lys Lys  Gly Gly Gly Leu Asp  Tyr Ile Asn Met Asn  Ile Ser Lys
    1325                1330                1335

Glu Cys  Lys Asn Arg Lys Asp  Lys Thr Tyr Leu Asn  Lys Ile Phe
    1340                1345                1350

His Tyr  Lys Lys Lys Lys Asp  Ala Arg Phe Phe Ile  Asn Asp Glu
    1355                1360                1365

Ile Gly  Ser Asn Asp Tyr Met  Tyr Asp Ile Lys Lys  Lys Tyr Ser
    1370                1375                1380

Asn Asp  Glu Asn Asn Tyr Lys  Leu Asn Glu Lys Met  Asn Ile Ser
    1385                1390                1395

Met Ser  Asn Asp Glu Asp Met  Ile Pro Thr Leu Asn  Ser Glu His
    1400                1405                1410

Gly Asn  Asn Phe Pro Ser Cys  Gln Pro Asn Leu Leu  Glu Lys Lys
    1415                1420                1425

Ser Thr  Tyr Ile Asp Leu Asn  Leu Tyr Asp Ser Asn  Ser Met Asp
    1430                1435                1440

Asp Phe  Thr Glu Glu Lys Tyr  Asn Phe Val Asn Asn  Glu Asn Asp
    1445                1450                1455

Leu Phe  Asn Thr Lys Arg Trp  Lys Phe Asn Phe Ser  Lys Gly Lys
    1460                1465                1470

Asn Leu  Phe Asn Asn Lys Phe  Phe Asn Val Ser Asn  Glu Asp Gly
    1475                1480                1485

Val Phe  Ser Phe Phe Lys Asn  Met Asn Leu Phe Arg  Glu Leu Asn
    1490                1495                1500

Lys Ser  Asn Asn Ser Leu Lys  Leu Glu Ser Val Lys  Asn Ser Asn
    1505                1510                1515

Asn Asn  Cys Ser Asn Asn Lys  Gly Asp Asp Asn Ile  Gly Asn Met
    1520                1525                1530

Glu Asn  Met Asn Thr Thr Asn  Val Thr Ile Ala Ser  Asp Glu His
    1535                1540                1545

Ile Ser  Thr Lys Gly Asp Ile  His Asp Glu Ser Phe  Ser Arg Asp
    1550                1555                1560

Asp Asn  Asp Cys Ile Leu Leu  Lys Ile Glu Gly Arg  Ser Lys Lys
    1565                1570                1575

Tyr Ser  Asp Ile Thr Leu Tyr  Asn Glu Asp Lys Ser  Asn Leu Glu
    1580                1585                1590

Asn Asp  Asn Glu Thr Ile Asn  Glu Tyr Glu Asn Val  Cys Ser Asn
    1595                1600                1605

Ile Asp  Val Asn Glu Trp Glu  Asp Lys Val Asn Gly  Thr Cys Asn
    1610                1615                1620

Ser Val  Gly Asp Lys Glu Thr  Glu Lys Asn Asn Glu  Lys Asn Asn
    1625                1630                1635

Glu Lys  Asn Asn Glu Lys Asn  Asn Glu Lys Asn Asn  Glu Lys Asn
    1640                1645                1650

Asn Glu  Lys Asn Asn Glu Lys  Asn Asn Glu Lys Asn  Asn Glu Glu
    1655                1660                1665

Asn Asn  Glu Gly Asn Asn Glu  Glu Asn Asn Glu Glu  Asn Asn Glu
    1670                1675                1680
```

```
Glu Asn Asn Glu Glu Asn Asn Asp Ile Glu Lys Asn Asp Ile Lys
    1685                1690                1695

Asp Asn Asn Ser Gly Gln Val Lys Glu Asn Ile Ile Val Met Asn
    1700                1705                1710

Asn Thr Asn Asn Met Asp Val Asp Asn Asp Asp Asn Asn Asn Asn
    1715                1720                1725

Tyr Asn Asn Val Ser Thr Asp Glu Gly Ile Asp Ile Ile Lys Asn
    1730                1735                1740

Ile Lys Ser Glu Met Asn Asp Tyr Ile Tyr Asn Asp Asn Ile Met
    1745                1750                1755

Ile Lys Ile Asn Asn Lys Ser Ile Asp Leu Met Asn Ile Lys Asn
    1760                1765                1770

Gln Lys Asn Glu Pro Phe Leu Asn Tyr Thr Asn Glu Lys Asp Ile
    1775                1780                1785

His Met Lys Ser Asn Ser Ser Tyr Asn Val Asn Asp Lys Met Asn
    1790                1795                1800

Leu Phe Asn Asn Asn Glu Lys Thr Glu Lys Asn Asn Thr Ser Leu
    1805                1810                1815

Asn Asp Leu Leu Tyr Lys Arg Lys Glu Glu Leu Asp Asp Glu Lys
    1820                1825                1830

Ile Ser Glu Tyr Lys Asp Thr Asn Leu Thr Asn Asn Thr Phe Glu
    1835                1840                1845

His Ile Ala Lys Arg Ile Asn Leu Ile Leu Asn Asp Thr Ile Glu
    1850                1855                1860

Phe Phe Gln Lys His Thr Tyr Leu His Asn Gly Tyr Gly Asn Val
    1865                1870                1875

Gln Val Cys Lys Lys Asn Lys Arg Lys Leu Glu Lys Lys Lys Leu
    1880                1885                1890

Lys Lys Trp Ser Cys Ile Tyr Lys Ile Asn Lys Ile Val Arg Lys
    1895                1900                1905

Gly Ala His Gly Val Val Phe Ser Ala Trp Arg Ser Glu Asn Val
    1910                1915                1920

Asp Phe Phe Asn His Ser Phe Phe Glu Asn Leu Asn Leu Glu Asn
    1925                1930                1935

Lys Lys Lys Gly Tyr Ile Asp Glu Thr Asn Val Asn Glu Asn Tyr
    1940                1945                1950

Glu Ser Asp Asn Glu Tyr Asp Ser Asp Glu Asp Asp Thr Glu Ser
    1955                1960                1965

Asp Asn Asp Asp Glu Gln Asn Lys Glu Asn Glu Arg Gly Asp Glu
    1970                1975                1980

Lys Asp Gly Tyr Glu Glu Met Asn Gly Gly Asp Lys Asn Glu Glu
    1985                1990                1995

Met Asn Gly Gly Asp Lys Asn Glu Glu Met Asn Val Gly Asp Lys
    2000                2005                2010

Asn Gly Gly Ile Asn Glu Glu His Lys Asn Glu Gly Ile Asn Glu
    2015                2020                2025

Glu His Lys Asp Glu Leu Ile Asn Lys Glu His Lys Asn Glu Arg
    2030                2035                2040

Ile Asn Glu Glu His Lys Asn Glu Arg Ile Asn Glu Glu His Lys
    2045                2050                2055

Asn Glu Gly Ile Asn Glu Glu His Lys Asn Glu Gly Ile Asn Glu
    2060                2065                2070
```

```
Glu His Lys Asn Glu Arg Ile Asn Glu Glu His Lys Asn Glu Gly
    2075                2080                2085

Ile Asn Lys Leu Thr Tyr His Asn Met Asn Lys Asn Asn Ile Ser
    2090                2095                2100

Asn Glu Asn Asn Tyr Asn Asp Asp Asp Ser Tyr Asp Glu Asp Asn
    2105                2110                2115

Leu Val Ser Leu Lys Ile Ile Asn Leu Lys Tyr Leu Ser Lys Lys
    2120                2125                2130

Asn Ser Leu Lys Asn Ile Leu Arg Glu Val Asn Phe Leu Lys Met
    2135                2140                2145

Cys Glu His Pro Asn Val Val Lys Tyr Phe Glu Ser Phe Phe Trp
    2150                2155                2160

Pro Pro Cys Tyr Leu Val Ile Val Cys Glu Tyr Leu Ser Gly Gly
    2165                2170                2175

Thr Leu Tyr Asp Leu Tyr Lys Asn Tyr Gly Arg Ile Ser Glu Asp
    2180                2185                2190

Leu Leu Val Tyr Ile Leu Asp Asp Val Leu Asn Gly Leu Asn Tyr
    2195                2200                2205

Leu His Asn Glu Cys Ser Ser Pro Leu Ile His Arg Asp Ile Lys
    2210                2215                2220

Pro Thr Asn Ile Val Leu Ser Lys Asp Gly Ile Ala Lys Ile Ile
    2225                2230                2235

Asp Phe Gly Ser Cys Glu Glu Leu Lys Asn Ser Asp Gln Ser Lys
    2240                2245                2250

Glu Leu Val Gly Thr Ile Tyr Tyr Ile Ser Pro Glu Ile Leu Met
    2255                2260                2265

Arg Thr Asn Tyr Asp Cys Ser Ser Asp Ile Trp Ser Leu Gly Ile
    2270                2275                2280

Thr Ile Tyr Glu Ile Val Leu Cys Thr Leu Pro Trp Lys Arg Asn
    2285                2290                2295

Gln Ser Phe Glu Asn Tyr Ile Lys Thr Ile Ile Asn Ser Ser Pro
    2300                2305                2310

Lys Ile Asn Ile Thr Glu Gly Tyr Ser Lys His Leu Cys Tyr Phe
    2315                2320                2325

Val Glu Lys Cys Leu Gln Lys Lys Pro Glu Asn Arg Gly Asn Val
    2330                2335                2340

Lys Asp Leu Leu Asn His Lys Phe Leu Ile Lys Lys Arg Tyr Ile
    2345                2350                2355

Lys Lys Lys Pro Ser Ser Ile Tyr Glu Ile Arg Asp Ile Leu Lys
    2360                2365                2370

Ile Tyr Asn Gly Lys Gly Lys Thr Asn Ile Phe Arg Asn Phe Phe
    2375                2380                2385

Lys Asn Leu Phe Phe Phe Asn Asp Lys Asn Lys Lys Lys Lys Pro
    2390                2395                2400

Asn Lys Met Ile Ser Ser Lys Ser Cys Asp Ala Glu Met Phe Phe
    2405                2410                2415

Glu Gln Leu Lys Arg Glu Asn Phe Asp Phe Phe Glu Ile Lys Leu
    2420                2425                2430

Lys Asp Asp Glu Asn Ser Arg Ser Leu Asn Thr Phe Asn Ile Asn
    2435                2440                2445

Ile Ser Lys Glu Arg Asp Asp Ile Ser Tyr Ser Ser Leu Asn Leu
    2450                2455                2460

Glu Lys Ile Lys Glu His Ser Leu Asn Met Val Ala Ser Val Val
```

```
    2465                2470                2475

Gly Thr  Glu Gln Ser Gln Lys
    2480                2485


<210> SEQ ID NO 15
<211> LENGTH: 1869
<212> TYPE: DNA
<213> ORGANISM: Plasmodium falciparum

<400> SEQUENCE: 15

atgagaaaat tatactgcgt attattattg agcgcctttg agtttacata tatgataaac     60

tttggaagag gacagaatta ttgggaacat ccatatcaaa atagtgatgt gtatcgtcca    120

atcaacgaac atagggaaca tccaaaagaa tacgaatatc cattacacca ggaacataca    180

taccaacaag aagattcagg agaagacgaa aatacattac aacacgcata tccaatagac    240

cacgaaggtg ccgaacccgc accacaagaa caaaatttat tttcaagcat tgaaatagta    300

gaaagaagta attatatggg taatccatgg acggaatata tggcaaaata tgatattgaa    360

gaagttcatg gttcaggtat aagagtagat ttaggagaag atgctgaagt agctggaact    420

caatatagac ttccatcagg gaaatgtcca gtatttggta aaggtataat tattgagaat    480

tcaaatacta ctttttttaac accggtagct acgggaaatc aatatttaaa agatggaggt    540

tttgcttttc ctccaacaga acctcttatg tcaccaatga cattagatga aatgagacat    600

ttttataaag ataataaata tgtaaaaaat ttagatgaat tgactttatg ttcaagacat    660

gcaggaaata tgattccaga taatgataaa aattcaaatt ataaatatcc agctgtttat    720

gatgacaaag ataaaaagtg tcatatatta tatattgcag ctcaagaaaa taatggtcct    780

agatattgta ataaagacga aagtaaaaga aacagcatgt tttgttttag accagcaaaa    840

gatatatcat ttcaaaacta tacatattta agtaagaatg tagttgataa ctgggaaaaa    900

gtttgcccta gaaagaattt acagaatgca aaattcggat tatgggtcga tggaaattgt    960

gaagatatac cacatgtaaa tgaatttcca gcaattgatc tttttgaatg taataaatta   1020

gtttttgaat tgagtgcttc ggatcaacct aaacaatatg aacaacattt aacagattat   1080

gaaaaaatta aagaaggttt caaaaataag aacgctagta tgatcaaaag tgcttttctt   1140

cccactggtg cttttaaagc agatagatat aaaagtcatg gtaagggtta taattgggga   1200

aattataaca cagaaacaca aaaatgtgaa atttttaatg tcaaaccaac atgtttaatt   1260

aacaattcat catacattgc tactactgct ttgtcccatc ccatcgaagt tgaaaacaat   1320

tttccatgtt cattatataa agatgaaata atgaaagaaa tcgaaagaga atcaaaacga   1380

attaaattaa atgataatga tgatgaaggg aataaaaaaa ttatagctcc aagaattttt   1440

atttcagatg ataaagacag tttaaaatgc ccatgtgacc ctgaaatggt aagtaatagt   1500

acatgtcgtt tctttgtatg taaatgtgta gaaagaaggg cagaagtaac atcaaataat   1560

gaagttgtag ttaaagaaga atataaagat gaatatgcag atattcctga acataaacca   1620

acttatgata aaatgaaaat tataattgca tcatcagctg ctgtcgctgt attagcaact   1680

attttaatgg tttatcttta taaaagaaaa ggaaatgctg aaaaatatga taaaatggat   1740

gaaccacaag attatgggaa atcaaattca agaaatgatg aaatgttaga tcctgaggca   1800

tctttttggg gggaagaaaa aagagcatca catacaacac cagttctgat ggaaaaacca   1860

tactattaa                                                           1869


<210> SEQ ID NO 16
```

<211> LENGTH: 622
<212> TYPE: PRT
<213> ORGANISM: Plasmodium falciparum

<400> SEQUENCE: 16

Met Arg Lys Leu Tyr Cys Val Leu Leu Leu Ser Ala Phe Glu Phe Thr
1 5 10 15

Tyr Met Ile Asn Phe Gly Arg Gly Gln Asn Tyr Trp Glu His Pro Tyr
20 25 30

Gln Asn Ser Asp Val Tyr Arg Pro Ile Asn Glu His Arg Glu His Pro
35 40 45

Lys Glu Tyr Glu Tyr Pro Leu His Gln Glu His Thr Tyr Gln Gln Glu
50 55 60

Asp Ser Gly Glu Asp Glu Asn Thr Leu Gln His Ala Tyr Pro Ile Asp
65 70 75 80

His Glu Gly Ala Glu Pro Ala Pro Gln Glu Gln Asn Leu Phe Ser Ser
85 90 95

Ile Glu Ile Val Glu Arg Ser Asn Tyr Met Gly Asn Pro Trp Thr Glu
100 105 110

Tyr Met Ala Lys Tyr Asp Ile Glu Glu Val His Gly Ser Gly Ile Arg
115 120 125

Val Asp Leu Gly Glu Asp Ala Glu Val Ala Gly Thr Gln Tyr Arg Leu
130 135 140

Pro Ser Gly Lys Cys Pro Val Phe Gly Lys Gly Ile Ile Ile Glu Asn
145 150 155 160

Ser Asn Thr Thr Phe Leu Thr Pro Val Ala Thr Gly Asn Gln Tyr Leu
165 170 175

Lys Asp Gly Gly Phe Ala Phe Pro Pro Thr Glu Pro Leu Met Ser Pro
180 185 190

Met Thr Leu Asp Glu Met Arg His Phe Tyr Lys Asp Asn Lys Tyr Val
195 200 205

Lys Asn Leu Asp Glu Leu Thr Leu Cys Ser Arg His Ala Gly Asn Met
210 215 220

Ile Pro Asp Asn Asp Lys Asn Ser Asn Tyr Lys Tyr Pro Ala Val Tyr
225 230 235 240

Asp Asp Lys Asp Lys Lys Cys His Ile Leu Tyr Ile Ala Ala Gln Glu
245 250 255

Asn Asn Gly Pro Arg Tyr Cys Asn Lys Asp Glu Ser Lys Arg Asn Ser
260 265 270

Met Phe Cys Phe Arg Pro Ala Lys Asp Ile Ser Phe Gln Asn Tyr Thr
275 280 285

Tyr Leu Ser Lys Asn Val Val Asp Asn Trp Glu Lys Val Cys Pro Arg
290 295 300

Lys Asn Leu Gln Asn Ala Lys Phe Gly Leu Trp Val Asp Gly Asn Cys
305 310 315 320

Glu Asp Ile Pro His Val Asn Glu Phe Pro Ala Ile Asp Leu Phe Glu
325 330 335

Cys Asn Lys Leu Val Phe Glu Leu Ser Ala Ser Asp Gln Pro Lys Gln
340 345 350

Tyr Glu Gln His Leu Thr Asp Tyr Glu Lys Ile Lys Glu Gly Phe Lys
355 360 365

Asn Lys Asn Ala Ser Met Ile Lys Ser Ala Phe Leu Pro Thr Gly Ala
370 375 380

Phe Lys Ala Asp Arg Tyr Lys Ser His Gly Lys Gly Tyr Asn Trp Gly

```
385                 390                 395                 400

Asn Tyr Asn Thr Glu Thr Gln Lys Cys Glu Ile Phe Asn Val Lys Pro
                405                 410                 415

Thr Cys Leu Ile Asn Asn Ser Ser Tyr Ile Ala Thr Thr Ala Leu Ser
            420                 425                 430

His Pro Ile Glu Val Glu Asn Asn Phe Pro Cys Ser Leu Tyr Lys Asp
        435                 440                 445

Glu Ile Met Lys Glu Ile Glu Arg Glu Ser Lys Arg Ile Lys Leu Asn
    450                 455                 460

Asp Asn Asp Asp Glu Gly Asn Lys Lys Ile Ile Ala Pro Arg Ile Phe
465                 470                 475                 480

Ile Ser Asp Asp Lys Asp Ser Leu Lys Cys Pro Cys Asp Pro Glu Met
                485                 490                 495

Val Ser Asn Ser Thr Cys Arg Phe Phe Val Cys Lys Cys Val Glu Arg
            500                 505                 510

Arg Ala Glu Val Thr Ser Asn Asn Glu Val Val Val Lys Glu Glu Tyr
        515                 520                 525

Lys Asp Glu Tyr Ala Asp Ile Pro Glu His Lys Pro Thr Tyr Asp Lys
    530                 535                 540

Met Lys Ile Ile Ile Ala Ser Ser Ala Ala Val Ala Val Leu Ala Thr
545                 550                 555                 560

Ile Leu Met Val Tyr Leu Tyr Lys Arg Lys Gly Asn Ala Glu Lys Tyr
                565                 570                 575

Asp Lys Met Asp Glu Pro Gln Asp Tyr Gly Lys Ser Asn Ser Arg Asn
            580                 585                 590

Asp Glu Met Leu Asp Pro Glu Ala Ser Phe Trp Gly Glu Glu Lys Arg
        595                 600                 605

Ala Ser His Thr Thr Pro Val Leu Met Glu Lys Pro Tyr Tyr
    610                 615                 620
```

<210> SEQ ID NO 17
<211> LENGTH: 1227
<212> TYPE: DNA
<213> ORGANISM: Plasmodium falciparum

<400> SEQUENCE: 17

```
atgttactct tttttgcaaa acttgtcgta tttacctttt tcttttggct tttaaaatat      60

gggaaaacga ggtcatatcc caaatctggc cataagggac atacgaaatt aaatcaacca     120

gtagttagaa cattagcaga ttttaatgac atgtttgcaa accaaaaaaa tacatttaat     180

tttctaaaac atataaatca ttataaaaat gaacaagata caaataatac acacacgcca     240

aatcatgatg aatattctca taatttgcca aaaaatcacg aagagtcaaa tgcaaatatg     300

aacaatcata attctttcaa tgacaaatct gttaataaaa aagaagcttt cgatcaattt     360

ttacaaacgt tattaaacaa ttatgaaata atgcataaag aagatgaaag taaagaatca     420

aatcaacata actataaaga aggtccctca tatgaagata aaaaaaatat gtacaaagaa     480

atattgaaag gatattataa tgtatttttt gaaaattatg caaacgacac agaatcaaat     540

gtacataata aacctgagga agttcataaa catgaggaaa ttcataaaca taggaaactt     600

cataaacatg aagaagttca taaacctgag gaatttcata aacctgagga atttcataaa     660

catgagaaag ttcataaaca tgaagaagtt cataaacctg aggaagttca taaacatgag     720

gaaaatcata aacatgagga aaatcataaa cctcaaatgg taggtcaagc acctccagaa     780

aaagagatac gccaagaatc aagaactcta atacttggtt catttcccca agcaggtgaa     840
```

```
atattaagag aggatttatg gaacaaagag gataacaaat ttagttacgc acttgaccct    900

aatgattatg catctataga agataaactt ttaggatcta tatttggata ctttaaaaaa    960

aatcatgaca atttggttaa acatttgtta caacaaatta atacttacaa acataaatat   1020

atggaactta aagaacaata tattaatgaa gttatgaaac ttaaaaaaat atataacaaa   1080

agcatcatgg tcatatttat agcatcttgt atttcaatat taggacctgt aatgttacac   1140

atgcatcaaa ataatccaga agaatttttt gcgaccatat taagtttttc tatatcatta   1200

ggtcttcata atttattact aacttaa                                       1227
```

```
<210> SEQ ID NO 18
<211> LENGTH: 408
<212> TYPE: PRT
<213> ORGANISM: Plasmodium falciparum

<400> SEQUENCE: 18

Met Leu Leu Phe Phe Ala Lys Leu Val Val Phe Thr Phe Phe Phe Trp
1               5                   10                  15

Leu Leu Lys Tyr Gly Lys Thr Arg Ser Tyr Pro Lys Ser Gly His Lys
            20                  25                  30

Gly His Thr Lys Leu Asn Gln Pro Val Val Arg Thr Leu Ala Asp Phe
        35                  40                  45

Asn Asp Met Phe Ala Asn Gln Lys Asn Thr Phe Asn Phe Leu Lys His
    50                  55                  60

Ile Asn His Tyr Lys Asn Glu Gln Asp Thr Asn Asn Thr His Thr Pro
65                  70                  75                  80

Asn His Asp Glu Tyr Ser His Asn Leu Pro Lys Asn His Glu Glu Ser
                85                  90                  95

Asn Ala Asn Met Asn Asn His Asn Ser Phe Asn Asp Lys Ser Val Asn
            100                 105                 110

Lys Lys Glu Ala Phe Asp Gln Phe Leu Gln Thr Leu Leu Asn Asn Tyr
        115                 120                 125

Glu Ile Met His Lys Glu Asp Glu Ser Lys Glu Ser Asn Gln His Asn
    130                 135                 140

Tyr Lys Glu Gly Pro Ser Tyr Glu Asp Lys Lys Asn Met Tyr Lys Glu
145                 150                 155                 160

Ile Leu Lys Gly Tyr Tyr Asn Val Phe Phe Glu Asn Tyr Ala Asn Asp
                165                 170                 175

Thr Glu Ser Asn Val His Asn Lys Pro Glu Glu Val His Lys His Glu
            180                 185                 190

Glu Ile His Lys His Arg Lys Leu His Lys His Glu Glu Val His Lys
        195                 200                 205

Pro Glu Glu Phe His Lys Pro Glu Glu Phe His Lys His Glu Lys Val
    210                 215                 220

His Lys His Glu Glu Val His Lys Pro Glu Glu Val His Lys His Glu
225                 230                 235                 240

Glu Asn His Lys His Glu Glu Asn His Lys Pro Gln Met Val Gly Gln
                245                 250                 255

Ala Pro Pro Glu Lys Glu Ile Arg Gln Glu Ser Arg Thr Leu Ile Leu
            260                 265                 270

Gly Ser Phe Pro Gln Ala Gly Glu Ile Leu Arg Glu Asp Leu Trp Asn
        275                 280                 285

Lys Glu Asp Asn Lys Phe Ser Tyr Ala Leu Asp Pro Asn Asp Tyr Ala
    290                 295                 300
```

```
Ser Ile Glu Asp Lys Leu Leu Gly Ser Ile Phe Gly Tyr Phe Lys Lys
305                 310                 315                 320

Asn His Asp Asn Leu Val Lys His Leu Leu Gln Gln Ile Asn Thr Tyr
                325                 330                 335

Lys His Lys Tyr Met Glu Leu Lys Glu Gln Tyr Ile Asn Glu Val Met
            340                 345                 350

Lys Leu Lys Lys Ile Tyr Asn Lys Ser Ile Met Val Ile Phe Ile Ala
        355                 360                 365

Ser Cys Ile Ser Ile Leu Gly Pro Val Met Leu His Met His Gln Asn
    370                 375                 380

Asn Pro Glu Glu Phe Phe Ala Thr Ile Leu Ser Phe Ser Ile Ser Leu
385                 390                 395                 400

Gly Leu His Asn Leu Leu Leu Thr
                405
```

<210> SEQ ID NO 19
<211> LENGTH: 4398
<212> TYPE: DNA
<213> ORGANISM: Plasmodium falciparum

<400> SEQUENCE: 19

```
atggattatt tgattaggaa taatgaatac tgtaatgttt tatatgatgg aaatgaatta     60

ttaaggaaaa gaaaaataaa ttttgacaat gagatttgtc cttataaaat gaattattgg    120

aataattaca acaataacat aaatattgat aatgataata tgaataatga aatagtaaat    180

gaagaatttg agaatactta taataatatt aataataata tgtattatct tcttggaaaa    240

gaggacatgg acgaacctag attgtgtaat aaaaaaagaa atgtttacaa tgaaaatttt    300

aagaataact tagaatatga tgagaatgta aataattatg ataatgataa cagtagtaat    360

atatcataca aatttattaa taatgagtgt gacaagatga aaaaatctgg agaaggtact    420

caggagaaca atgataatga aaataataat aatgatgaga gtaacaataa taataataat    480

aataataatg agagtaataa taataataat aataatgaga gtaacaataa taataataat    540

aataataata atgagagtaa caataataat aataataatg agagtaataa taataatcat    600

gggaataata ataatagtag taataataac aacaataata ataataataa caacaacaac    660

aacaataata ataataataa taataataat aataacaata ataataacaa caataataat    720

gataagaatg aagatgatga aaatactaca gggaaaggaa aaaaaacaga agtcaaaaaa    780

cgtgcaggga gaaaaagaaa tgattccaca atgtatgcca atagtaatac aatgttaaaa    840

aataattttt tacaaaataa taaaatgatt tataataata tggatcatat aaatgataca    900

aatgaacaag ataaattttt atatgaacaa agaaaaatga tgatgaataa taaaatggaa    960

aatatgggac ccaatatgaa tatgacaaat aaaaattatt ttcaaacagt aaataacatg   1020

aaaatgaatg tagaaaataa taaaaatctt ataggtataa atacaaataa tatgaataat   1080

tatcaaaata atataaatag tattaatact aatatgaata taccaaagaa caaaaattta   1140

cattcaaata aacaaatgat gtttatgaat aataatatga atatacatgg aaaaaccaat   1200

aaattaaatg atatggctag aatgaatagt ataaacttta atgaagaaaa taaaatgtct   1260

gttatgaatg acgacacaag aatggataat aaaatgaggg atataatgaa aagtggtgga   1320

atggaggtac atttaaaaaa tgaagaatcc ttatatatga ataaatatgta taatatgaat   1380

agtaataatc caaataatat acctagaatt agtacaatga atattgcaaa acctatgaat   1440

aattttaata atatgaatat gcctataaat aatatgaatg catataacaa tcacatgatt   1500
```

```
aattcgtata ataatatgat gatgacaaat aatatgaaca acataaataa tataaataat   1560
ataaatcata taaataataa taataatagt aataataata ataatagtaa taatagtaat   1620
aataatatta attttggtca gcatattcag ggggtacaat ttatgaatcc taatatgaat   1680
aacgacatga acagtaatat gaataatatt aataataatc aaatgttctt gaataataac   1740
cagaataatg cacatgttca tatggttaac aacatgaatt tgaatccctc tggaaataat   1800
tcatttttta ataattcaaa taaacatctg aatatgatga ccatgagttc aaaaaataaa   1860
aaaaacgcca tattaaaaaa tacagaaaat aatgaatttg aaaatataaa aagagtacat   1920
tcaaacagct ccaactataa taataataat aataataata gtgatagtaa taataaaaaa   1980
tcgattaaaa tgaatagcaa tgaaaacaat aatacaacaa caactattat aaaaaatata   2040
cgagttgaaa acataaagtt taatgaaagt gtcaatttaa aaaatattga tggcttagat   2100
ctaagtacta attttgttaa tggaaaatat atatccaaat taaataatga tgagaaaata   2160
tataatgtag tacattctat tgtgaaagat tctctcaaag attgtttagt tgatttttat   2220
aataatgcaa attatatttt taaagataaa ttagattttg tatgtaatag taatactcct   2280
acatgtaata atataaatga tttagaagac aacaaaaagg atgacgggca tgtggataaa   2340
caaaattatt cacttgaaaa gaaagataat gaagaacaca caaataataa ttctgatcct   2400
ataatggatg gtgttgagtt ggatgtaaaa aagatatctg aaaagaagga ggatcaaatt   2460
gaaaaggaca aaccaaaaaa tgataataca aaaaatgata atacaaagga agacaaaaat   2520
caaaatgatg ataataaaac taatacatca attccaaaaa ctcccaaaaa tgaagttaaa   2580
aatgttatta cctcttcctt attgtcaagt tttaatatat ttagtgcttt cagtaatagt   2640
aatacaccta attcgaaaaa aaataaatat gatgaagagg aagaaaaaga agaaaaagaa   2700
gaagaagaag aaaataataa atgtaatgat aaagatgatg aggataaaaa taagtctcct   2760
caaaatgaag ataataaaaa tattaccaat gataataatg ataataataa taataatgta   2820
gacaaagaaa acaatttaaa agaatctata gataacctag gaaatgttga tacagataat   2880
aatattaaga gagatgtact aaattataat aatatagaag aaaatgaaca aagcagagaa   2940
tatattttaa tagaaattac aaaaagtata tgctctataa tcaatctaca acaattaatg   3000
cctgttaata ctaggttagc taaccctaat cttatatatg atccaaatta tgaaaccata   3060
tattctaaat ggaaaacatt tttaagaaaa gagcaatcaa gtggaaattt aattagtaat   3120
tgtttttcac gagatttttt acatactatt ttgttatgta attatgtaac tataattgaa   3180
gatttaagaa aaacggccgt taagaaaaag ttgaaatatt ttttcttaca cttatgtttg   3240
gaatcgggca tatcgattaa cgttgcattg atgctgttta taaatgccac gaagcagagc   3300
gataagttac agtctctact accctccgaa acaggattag gatatttgca cagagatgcg   3360
ggtggagcaa aagaagagaa tatgggtatt ataacatttg aatgtataac gaacgatagg   3420
gaaccagatc atttaataaa attaataact ttgaaaaata ttttctcaag acagttacca   3480
aaaatgccta gagaatatat agtaaggctt gtatttgata gaaatcatta tacattttgt   3540
ttattaaaaa aaaatactgt tataggtgga gtatgtttca gaccatattt tgaacagaaa   3600
tttgcggaaa ttgcattttt agctgttacc tcaactgagc aggtaaaagg atatggtaca   3660
agattaatga atcatttgaa ggagcatgta aagaagtttg gtatagaata tttcttaacc   3720
tatgcagata actttgccat aggatatttt agaaaacaag gattttcaca aaaaatttcc   3780
atgccaaaag aaagatggtt tggatatatt aaagattatg atggtggtac attaatggaa   3840
```

```
tgttacattt tcccaaacat caattatttg agactttcgg aaatgttata tgagcaaaaa   3900

aaagcagtaa agaaagctat acattttata aaacctcaag ttatatataa gggtattaat   3960

tattttgctg ataataaagg ggctgcttta catccaagta ctattcctgg attattagaa   4020

gttggctgga aaaaggaaac gagggaaatt actaaaaagg ttcaacataa agaagttcaa   4080

ttgaaagatc aaattttagg tgttctggat tatttagaaa aacaacagtc tgcatggcca   4140

tttcttaagc cagttagtct ttcagaagct cctgattatt atgatattat aaaagaacca   4200

acagatattt tgaccatgag aagaaaggcc agacatggtg attataaaac gaaggaagat   4260

tttggtattg agcttaagag aatgtttgat aattgtcgtt tgtataatgc tccaacaact   4320

atttatttca aatatgcaaa tgaactacaa acacttatat ggcctaaata tgaagctata   4380

actgatacag caaaataa                                                 4398
```

```
<210> SEQ ID NO 20
<211> LENGTH: 1465
<212> TYPE: PRT
<213> ORGANISM: Plasmodium falciparum

<400> SEQUENCE: 20

Met Asp Tyr Leu Ile Arg Asn Asn Glu Tyr Cys Asn Val Leu Tyr Asp
1               5                   10                  15

Gly Asn Glu Leu Leu Arg Lys Arg Lys Ile Asn Phe Asp Asn Glu Ile
            20                  25                  30

Cys Pro Tyr Lys Met Asn Tyr Trp Asn Asn Tyr Asn Asn Asn Ile Asn
        35                  40                  45

Ile Asp Asn Asp Asn Met Asn Asn Glu Ile Val Asn Glu Glu Phe Glu
    50                  55                  60

Asn Thr Tyr Asn Asn Ile Asn Asn Asn Met Tyr Tyr Leu Leu Gly Lys
65                  70                  75                  80

Glu Asp Met Asp Glu Pro Arg Leu Cys Asn Lys Lys Arg Asn Val Tyr
                85                  90                  95

Asn Glu Asn Phe Lys Asn Asn Leu Glu Tyr Asp Glu Asn Val Asn Asn
            100                 105                 110

Tyr Asp Asn Asp Asn Ser Ser Asn Ile Ser Tyr Lys Phe Ile Asn Asn
        115                 120                 125

Glu Cys Asp Lys Met Lys Lys Ser Gly Glu Gly Thr Gln Glu Asn Asn
    130                 135                 140

Asp Asn Glu Asn Asn Asn Asn Asp Glu Ser Asn Asn Asn Asn Asn Asn
145                 150                 155                 160

Asn Asn Asn Glu Ser Asn Asn Asn Asn Asn Asn Asn Glu Ser Asn Asn
                165                 170                 175

Asn Asn Asn Asn Asn Asn Asn Asn Glu Ser Asn Asn Asn Asn Asn Asn
            180                 185                 190

Asn Glu Ser Asn Asn Asn Asn His Gly Asn Asn Asn Asn Ser Ser Asn
        195                 200                 205

Asn Asn Asn Asn Asn Asn Asn Asn Asn Asn Asn Asn Asn Asn Asn Asn
    210                 215                 220

Asn Asn Asn Asn Asn Asn Asn Asn Asn Asn Asn Asn Asn Asn Asn Asn
225                 230                 235                 240

Asp Lys Asn Glu Asp Asp Glu Asn Thr Thr Gly Lys Gly Lys Lys Thr
                245                 250                 255

Glu Val Lys Lys Arg Ala Gly Arg Lys Arg Asn Asp Ser Thr Met Tyr
            260                 265                 270
```

```
Ala Asn Ser Asn Thr Met Leu Lys Asn Asn Phe Leu Gln Asn Asn Lys
        275                 280                 285

Met Ile Tyr Asn Asn Met Asp His Ile Asn Asp Thr Asn Glu Gln Asp
    290                 295                 300

Lys Phe Leu Tyr Glu Gln Arg Lys Met Met Met Asn Asn Lys Met Glu
305                 310                 315                 320

Asn Met Gly Pro Asn Met Asn Met Thr Asn Lys Asn Tyr Phe Gln Thr
                325                 330                 335

Val Asn Asn Met Lys Met Asn Val Glu Asn Asn Lys Asn Leu Ile Gly
            340                 345                 350

Ile Asn Thr Asn Asn Met Asn Asn Tyr Gln Asn Asn Ile Asn Ser Ile
        355                 360                 365

Asn Thr Asn Met Asn Ile Pro Lys Asn Lys Asn Leu His Ser Asn Lys
    370                 375                 380

Gln Met Met Phe Met Asn Asn Asn Met Asn Ile His Gly Lys Thr Asn
385                 390                 395                 400

Lys Leu Asn Asp Met Ala Arg Met Asn Ser Ile Asn Phe Asn Glu Glu
                405                 410                 415

Asn Lys Met Ser Val Met Asn Asp Asp Thr Arg Met Asp Asn Lys Met
            420                 425                 430

Arg Asp Ile Met Lys Ser Gly Gly Met Glu Val His Leu Lys Asn Glu
        435                 440                 445

Glu Ser Leu Tyr Met Asn Asn Met Tyr Asn Met Asn Ser Asn Asn Pro
    450                 455                 460

Asn Asn Ile Pro Arg Ile Ser Thr Met Asn Ile Ala Lys Pro Met Asn
465                 470                 475                 480

Asn Phe Asn Asn Met Asn Met Pro Ile Asn Asn Met Asn Ala Tyr Asn
                485                 490                 495

Asn His Met Ile Asn Ser Tyr Asn Asn Met Met Met Thr Asn Asn Met
            500                 505                 510

Asn Asn Ile Asn Asn Ile Asn Asn Ile Asn His Ile Asn Asn Asn Asn
        515                 520                 525

Asn Ser Asn Asn Asn Asn Asn Ser Asn Asn Ser Asn Asn Asn Ile Asn
    530                 535                 540

Phe Gly Gln His Ile Gln Gly Val Gln Phe Met Asn Pro Asn Met Asn
545                 550                 555                 560

Asn Asp Met Asn Ser Asn Met Asn Asn Ile Asn Asn Asn Gln Met Phe
                565                 570                 575

Leu Asn Asn Asn Gln Asn Asn Ala His Val His Met Val Asn Asn Met
            580                 585                 590

Asn Leu Asn Pro Ser Gly Asn Asn Ser Phe Phe Asn Asn Ser Asn Lys
        595                 600                 605

His Leu Asn Met Met Thr Met Ser Ser Lys Asn Lys Lys Asn Ala Ile
    610                 615                 620

Leu Lys Asn Thr Glu Asn Asn Glu Phe Glu Asn Ile Lys Arg Val His
625                 630                 635                 640

Ser Asn Ser Ser Asn Tyr Asn Asn Asn Asn Asn Asn Asn Ser Asp Ser
                645                 650                 655

Asn Asn Lys Lys Ser Ile Lys Met Asn Ser Asn Glu Asn Asn Asn Thr
            660                 665                 670

Thr Thr Thr Ile Ile Lys Asn Ile Arg Val Glu Asn Ile Lys Phe Asn
        675                 680                 685

Glu Ser Val Asn Leu Lys Asn Ile Asp Gly Leu Asp Leu Ser Thr Asn
```

```
    690                 695                 700

Phe Val Asn Gly Lys Tyr Ile Ser Lys Leu Asn Asn Asp Glu Lys Ile
705                 710                 715                 720

Tyr Asn Val Val His Ser Ile Val Lys Asp Ser Leu Lys Asp Cys Leu
                725                 730                 735

Val Asp Phe Tyr Asn Asn Ala Asn Tyr Ile Phe Lys Asp Lys Leu Asp
            740                 745                 750

Phe Val Cys Asn Ser Asn Thr Pro Thr Cys Asn Asn Ile Asn Asp Leu
        755                 760                 765

Glu Asp Asn Lys Lys Asp Asp Gly His Val Asp Lys Gln Asn Tyr Ser
    770                 775                 780

Leu Glu Lys Lys Asp Asn Glu Glu His Thr Asn Asn Asn Ser Asp Pro
785                 790                 795                 800

Ile Met Asp Gly Val Glu Leu Asp Val Lys Lys Ile Ser Glu Lys Lys
                805                 810                 815

Glu Asp Gln Ile Glu Lys Asp Lys Pro Lys Asn Asp Asn Thr Lys Asn
            820                 825                 830

Asp Asn Thr Lys Glu Asp Lys Asn Gln Asn Asp Asp Asn Lys Thr Asn
        835                 840                 845

Thr Ser Ile Pro Lys Thr Pro Lys Asn Glu Val Lys Asn Val Ile Thr
    850                 855                 860

Ser Ser Leu Leu Ser Ser Phe Asn Ile Phe Ser Ala Phe Ser Asn Ser
865                 870                 875                 880

Asn Thr Pro Asn Ser Lys Lys Asn Lys Tyr Asp Glu Glu Glu Glu Lys
                885                 890                 895

Glu Glu Lys Glu Glu Glu Glu Glu Asn Asn Lys Cys Asn Asp Lys Asp
            900                 905                 910

Asp Glu Asp Lys Asn Lys Ser Pro Gln Asn Glu Asp Asn Lys Asn Ile
        915                 920                 925

Thr Asn Asp Asn Asn Asp Asn Asn Asn Asn Asn Val Asp Lys Glu Asn
    930                 935                 940

Asn Leu Lys Glu Ser Ile Asp Asn Leu Gly Asn Val Asp Thr Asp Asn
945                 950                 955                 960

Asn Ile Lys Arg Asp Val Leu Asn Tyr Asn Asn Ile Glu Glu Asn Glu
                965                 970                 975

Gln Ser Arg Glu Tyr Ile Leu Ile Glu Ile Thr Lys Ser Ile Cys Ser
            980                 985                 990

Ile Ile Asn Leu Gln Gln Leu Met  Pro Val Asn Thr Arg  Leu Ala Asn
        995                 1000                1005

Pro Asn  Leu Ile Tyr Asp Pro  Asn Tyr Glu Thr Ile  Tyr Ser Lys
    1010                1015                1020

Trp Lys  Thr Phe Leu Arg Lys  Glu Gln Ser Ser Gly  Asn Leu Ile
    1025                1030                1035

Ser Asn  Cys Phe Ser Arg Asp  Phe Leu His Thr Ile  Leu Leu Cys
    1040                1045                1050

Asn Tyr  Val Thr Ile Ile Glu  Asp Leu Arg Lys Thr  Ala Val Lys
    1055                1060                1065

Lys Lys  Leu Lys Tyr Phe Phe  Leu His Leu Cys Leu  Glu Ser Gly
    1070                1075                1080

Ile Ser  Ile Asn Val Ala Leu  Met Leu Phe Ile Asn  Ala Thr Lys
    1085                1090                1095

Gln Ser  Asp Lys Leu Gln Ser  Leu Leu Pro Ser Glu  Thr Gly Leu
    1100                1105                1110
```

```
Gly Tyr  Leu His Arg Asp Ala  Gly Gly Ala Lys Glu  Glu Asn Met
    1115                 1120                 1125

Gly Ile  Ile Thr Phe Glu Cys  Ile Thr Asn Asp Arg  Glu Pro Asp
    1130                 1135                 1140

His Leu  Ile Lys Leu Ile Thr  Leu Lys Asn Ile Phe  Ser Arg Gln
    1145                 1150                 1155

Leu Pro  Lys Met Pro Arg Glu  Tyr Ile Val Arg Leu  Val Phe Asp
    1160                 1165                 1170

Arg Asn  His Tyr Thr Phe Cys  Leu Leu Lys Lys Asn  Thr Val Ile
    1175                 1180                 1185

Gly Gly  Val Cys Phe Arg Pro  Tyr Phe Glu Gln Lys  Phe Ala Glu
    1190                 1195                 1200

Ile Ala  Phe Leu Ala Val Thr  Ser Thr Glu Gln Val  Lys Gly Tyr
    1205                 1210                 1215

Gly Thr  Arg Leu Met Asn His  Leu Lys Glu His Val  Lys Lys Phe
    1220                 1225                 1230

Gly Ile  Glu Tyr Phe Leu Thr  Tyr Ala Asp Asn Phe  Ala Ile Gly
    1235                 1240                 1245

Tyr Phe  Arg Lys Gln Gly Phe  Ser Gln Lys Ile Ser  Met Pro Lys
    1250                 1255                 1260

Glu Arg  Trp Phe Gly Tyr Ile  Lys Asp Tyr Asp Gly  Gly Thr Leu
    1265                 1270                 1275

Met Glu  Cys Tyr Ile Phe Pro  Asn Ile Asn Tyr Leu  Arg Leu Ser
    1280                 1285                 1290

Glu Met  Leu Tyr Glu Gln Lys  Lys Ala Val Lys Lys  Ala Ile His
    1295                 1300                 1305

Phe Ile  Lys Pro Gln Val Ile  Tyr Lys Gly Ile Asn  Tyr Phe Ala
    1310                 1315                 1320

Asp Asn  Lys Gly Ala Ala Leu  His Pro Ser Thr Ile  Pro Gly Leu
    1325                 1330                 1335

Leu Glu  Val Gly Trp Lys Lys  Glu Thr Arg Glu Ile  Thr Lys Lys
    1340                 1345                 1350

Val Gln  His Lys Glu Val Gln  Leu Lys Asp Gln Ile  Leu Gly Val
    1355                 1360                 1365

Leu Asp  Tyr Leu Glu Lys Gln  Gln Ser Ala Trp Pro  Phe Leu Lys
    1370                 1375                 1380

Pro Val  Ser Leu Ser Glu Ala  Pro Asp Tyr Tyr Asp  Ile Ile Lys
    1385                 1390                 1395

Glu Pro  Thr Asp Ile Leu Thr  Met Arg Arg Lys Ala  Arg His Gly
    1400                 1405                 1410

Asp Tyr  Lys Thr Lys Glu Asp  Phe Gly Ile Glu Leu  Lys Arg Met
    1415                 1420                 1425

Phe Asp  Asn Cys Arg Leu Tyr  Asn Ala Pro Thr Thr  Ile Tyr Phe
    1430                 1435                 1440

Lys Tyr  Ala Asn Glu Leu Gln  Thr Leu Ile Trp Pro  Lys Tyr Glu
    1445                 1450                 1455

Ala Ile  Thr Asp Thr Ala Lys
    1460                 1465
```

<210> SEQ ID NO 21
<211> LENGTH: 2034
<212> TYPE: DNA
<213> ORGANISM: Plasmodium falciparum

<400> SEQUENCE: 21

```
atggctagtg caaaaggttc aaaaccaaat ttaccagaat ccaatatcgc tattggaatt     60
gatttaggta ctacttattc ttgtgttggt gtatggagaa atgaaaatgt agatattatt    120
gctaatgacc aaggtaatag aacaacccca tcttatgttg ctttcaccga taccgaaaga    180
ttaattggag atgctgctaa aaccaagta gctaggaatc cagaaaatac agtatttgat    240
gctaagagat taattggtag aaaatttaca gaatcatcag tacaaagtga tatgaaacat    300
tggccattca ctgttaaatc aggtgttgat gagaaaccaa tgattgaagt tacctatcaa    360
ggagaaaaga aattattcca tccagaagaa atttcttcta tggtattaca aaaaatgaaa    420
gaaaatgctg aagcattttt aggaaaatct ataaagaatg ctgtcattac cgttccagct    480
tattttaacg attcacaaag acaagctact aaagatgctg gtacaattgc aggattaaat    540
gttatgagaa ttattaatga acctactgca gctgctattg catatggttt acacaaaaaa    600
ggaaaaggtg aaaagaacat tttaattttc gacttaggag gaggtacatt tgatgtatca    660
ttattaacta ttgaagatgg tatttttgaa gtaaaagcta ctgctggtga tactcattta    720
ggtggtgaag atttcgataa cagattagta aatttctgtg ttgaagattt caaaagaaaa    780
aacagaggta aagatttatc aaaaaatagt agagccttaa gaagattaag aacacaatgt    840
gaaagagcaa aacgtacttt atcatcatct acacaagcta caattgaaat agattcctta    900
tttgaaggta ttgattacag tgttactgta agtagagcaa gatttgaaga attatgtatc    960
gactatttcc gtgatacttt aattccagta gaaaaagttt taaaagatgc tatgatggat   1020
aaaaaaagtg tacatgaagt tgttttagtt ggtggttcta caagaattcc aaaaatccaa   1080
actttaataa aagaattctt taatggtaaa gaagcatgca gatcaattaa cccagatgaa   1140
gctgttgcat atggtgcagc tgtacaagca gccattttat ctggtgacca atcaaatgct   1200
gtccaagatt tattattatt agatgtttgc tccttatcat taggtttaga aactgctggt   1260
ggtgttatga ccaaattaat tgaaagaaac acaaccatac ctgctaaaaa gagtcaaatc   1320
tttactactt atgctgataa ccaaccaggt gtcttaattc aagtatatga aggtgaaaga   1380
gccttaacca aagataacaa tttattagga aaatttcact tagatggtat tccacctgca   1440
ccaagaaagg taccacaaat cgaagttaca ttcgatatcg atgctaacgg tatcttaaac   1500
gttacggctg tagaaaaatc cactggtaaa caaaaccata ttacaattac caacgacaaa   1560
ggaagattat ctcaagatga aattgatcgt atggttaatg atgctgaaaa atacaaagca   1620
gaagatgaag aaaacagaaa aagaatcgaa gcaagaaaca gccttgaaaa ttactgctat   1680
ggagttaaaa gctcattaga agaccaaaaa attaaagaaa aattacaacc agctgaaatt   1740
gaaacatgta tgaaaactat tacaaccata cttgaatggt tagaaaaaaa ccaacttgct   1800
ggaaaagatg aatatgaagc caaacaaaaa gaagcagaat cggtttgtgc tccaattatg   1860
tctaaaatct atcaagatgc tgctggtgca gccggtggta tgccaggagg tatgcccggt   1920
ggaatgcccg gtggaatgcc aggtggtatg aatttcccag gaggtatgcc cggagcagga   1980
atgccaggaa atgccccagc tggaagtgga ccaacagttg aagaagttga ttaa         2034
```

<210> SEQ ID NO 22
<211> LENGTH: 677
<212> TYPE: PRT
<213> ORGANISM: Plasmodium falciparum

<400> SEQUENCE: 22

Met Ala Ser Ala Lys Gly Ser Lys Pro Asn Leu Pro Glu Ser Asn Ile

```
1               5                   10                  15

Ala Ile Gly Ile Asp Leu Gly Thr Thr Tyr Ser Cys Val Gly Val Trp
            20                  25                  30

Arg Asn Glu Asn Val Asp Ile Ile Ala Asn Asp Gln Gly Asn Arg Thr
        35                  40                  45

Thr Pro Ser Tyr Val Ala Phe Thr Asp Thr Glu Arg Leu Ile Gly Asp
    50                  55                  60

Ala Ala Lys Asn Gln Val Ala Arg Asn Pro Glu Asn Thr Val Phe Asp
65                  70                  75                  80

Ala Lys Arg Leu Ile Gly Arg Lys Phe Thr Glu Ser Ser Val Gln Ser
                85                  90                  95

Asp Met Lys His Trp Pro Phe Thr Val Lys Ser Gly Val Asp Glu Lys
            100                 105                 110

Pro Met Ile Glu Val Thr Tyr Gln Gly Glu Lys Lys Leu Phe His Pro
        115                 120                 125

Glu Glu Ile Ser Ser Met Val Leu Gln Lys Met Lys Glu Asn Ala Glu
    130                 135                 140

Ala Phe Leu Gly Lys Ser Ile Lys Asn Ala Val Ile Thr Val Pro Ala
145                 150                 155                 160

Tyr Phe Asn Asp Ser Gln Arg Gln Ala Thr Lys Asp Ala Gly Thr Ile
                165                 170                 175

Ala Gly Leu Asn Val Met Arg Ile Ile Asn Glu Pro Thr Ala Ala Ala
            180                 185                 190

Ile Ala Tyr Gly Leu His Lys Lys Gly Lys Gly Glu Lys Asn Ile Leu
        195                 200                 205

Ile Phe Asp Leu Gly Gly Gly Thr Phe Asp Val Ser Leu Leu Thr Ile
    210                 215                 220

Glu Asp Gly Ile Phe Glu Val Lys Ala Thr Ala Gly Asp Thr His Leu
225                 230                 235                 240

Gly Gly Glu Asp Phe Asp Asn Arg Leu Val Asn Phe Cys Val Glu Asp
                245                 250                 255

Phe Lys Arg Lys Asn Arg Gly Lys Asp Leu Ser Lys Asn Ser Arg Ala
            260                 265                 270

Leu Arg Arg Leu Arg Thr Gln Cys Glu Arg Ala Lys Arg Thr Leu Ser
        275                 280                 285

Ser Ser Thr Gln Ala Thr Ile Glu Ile Asp Ser Leu Phe Glu Gly Ile
    290                 295                 300

Asp Tyr Ser Val Thr Val Ser Arg Ala Arg Phe Glu Glu Leu Cys Ile
305                 310                 315                 320

Asp Tyr Phe Arg Asp Thr Leu Ile Pro Val Glu Lys Val Leu Lys Asp
                325                 330                 335

Ala Met Met Asp Lys Lys Ser Val His Glu Val Val Leu Val Gly Gly
            340                 345                 350

Ser Thr Arg Ile Pro Lys Ile Gln Thr Leu Ile Lys Glu Phe Phe Asn
        355                 360                 365

Gly Lys Glu Ala Cys Arg Ser Ile Asn Pro Asp Glu Ala Val Ala Tyr
    370                 375                 380

Gly Ala Ala Val Gln Ala Ala Ile Leu Ser Gly Asp Gln Ser Asn Ala
385                 390                 395                 400

Val Gln Asp Leu Leu Leu Leu Asp Val Cys Ser Leu Ser Leu Gly Leu
                405                 410                 415

Glu Thr Ala Gly Gly Val Met Thr Lys Leu Ile Glu Arg Asn Thr Thr
            420                 425                 430
```

```
Ile Pro Ala Lys Lys Ser Gln Ile Phe Thr Thr Tyr Ala Asp Asn Gln
        435                 440                 445

Pro Gly Val Leu Ile Gln Val Tyr Glu Gly Glu Arg Ala Leu Thr Lys
    450                 455                 460

Asp Asn Asn Leu Leu Gly Lys Phe His Leu Asp Gly Ile Pro Pro Ala
465                 470                 475                 480

Pro Arg Lys Val Pro Gln Ile Glu Val Thr Phe Asp Ile Asp Ala Asn
                485                 490                 495

Gly Ile Leu Asn Val Thr Ala Val Glu Lys Ser Thr Gly Lys Gln Asn
            500                 505                 510

His Ile Thr Ile Thr Asn Asp Lys Gly Arg Leu Ser Gln Asp Glu Ile
        515                 520                 525

Asp Arg Met Val Asn Asp Ala Glu Lys Tyr Lys Ala Glu Asp Glu Glu
    530                 535                 540

Asn Arg Lys Arg Ile Glu Ala Arg Asn Ser Leu Glu Asn Tyr Cys Tyr
545                 550                 555                 560

Gly Val Lys Ser Ser Leu Glu Asp Gln Lys Ile Lys Glu Lys Leu Gln
                565                 570                 575

Pro Ala Glu Ile Glu Thr Cys Met Lys Thr Ile Thr Thr Ile Leu Glu
            580                 585                 590

Trp Leu Glu Lys Asn Gln Leu Ala Gly Lys Asp Glu Tyr Glu Ala Lys
        595                 600                 605

Gln Lys Glu Ala Glu Ser Val Cys Ala Pro Ile Met Ser Lys Ile Tyr
    610                 615                 620

Gln Asp Ala Ala Gly Ala Ala Gly Gly Met Pro Gly Gly Met Pro Gly
625                 630                 635                 640

Gly Met Pro Gly Gly Met Pro Gly Gly Met Asn Phe Pro Gly Gly Met
                645                 650                 655

Pro Gly Ala Gly Met Pro Gly Asn Ala Pro Ala Gly Ser Gly Pro Thr
            660                 665                 670

Val Glu Glu Val Asp
        675
```

<210> SEQ ID NO 23
<211> LENGTH: 999
<212> TYPE: DNA
<213> ORGANISM: Plasmodium falciparum

<400> SEQUENCE: 23

```
atgaatgcag ccgctgtaga acttattaat agattaaaga aagaagatga aagcaataac     60

aaatgttttg attgtggaat atccaacccc gattgggtgt ctgtaaatca tggtatattt    120

ttatgtatta actgttcagg tgttcacaga agcctgggtg tacatataag tatagtaaga    180

agtataaaaa tggatatatt tacagatgaa caattaaaat atatagataa gggaggtaat    240

aaaaaatgtc aaacatattt agagaattat ggaataagtg attttattcc agaaagaaaa    300

tatagaacta aggcagctga tcattatagg aaaatattaa gatcgattgt tcataatgtg    360

gatcctcctg ctcctttacc tttagatgaa ggaaagagtt taattaatta tggaagaaat    420

gaaaatgtta atgaaaataa taaaaatcaa tattcaaatg aagaaccgga ttttatttca    480

tcattaaata catcagaaat tatagaaaat gtaagtgcca cattttccaa tttaataaat    540

aaagcatcaa gtatgacaac taatacaata aataatttaa atactaatga tttaatagaa    600

tcaactaaag gtacaataat caatagtgga agctggttta ctgagaaaac taaaaaaatt    660
```

```
gcagaaaatg ttagtgataa tccatggtgg gctaaaggac aaagtaaaat aaaagatgtt    720

acacaaaatg ctagtggatg gatatctacc atttcttcaa cagtttcaag aacaaatagt    780

aatttctttt tttcaaataa tgatactaat ataaataatg gaaacaatga agatatcaat    840

aataataata ctaacgttaa tagtaatggt aatactacta ataataataa tgaacaagca    900

caaaataata ataatgttaa ttttaattat aatagttcaa atgcaaataa tgaatattta    960

aattacggaa tgaatgaaaa taattcaact tttaattga                            999
```

```
<210> SEQ ID NO 24
<211> LENGTH: 332
<212> TYPE: PRT
<213> ORGANISM: Plasmodium falciparum

<400> SEQUENCE: 24

Met Asn Ala Ala Ala Val Glu Leu Ile Asn Arg Leu Lys Lys Glu Asp
1               5                   10                  15

Glu Ser Asn Asn Lys Cys Phe Asp Cys Gly Ile Ser Asn Pro Asp Trp
            20                  25                  30

Val Ser Val Asn His Gly Ile Phe Leu Cys Ile Asn Cys Ser Gly Val
        35                  40                  45

His Arg Ser Leu Gly Val His Ile Ser Ile Val Arg Ser Ile Lys Met
    50                  55                  60

Asp Ile Phe Thr Asp Glu Gln Leu Lys Tyr Ile Asp Lys Gly Gly Asn
65                  70                  75                  80

Lys Lys Cys Gln Thr Tyr Leu Glu Asn Tyr Gly Ile Ser Asp Phe Ile
                85                  90                  95

Pro Glu Arg Lys Tyr Arg Thr Lys Ala Ala Asp His Tyr Arg Lys Ile
            100                 105                 110

Leu Arg Ser Ile Val His Asn Val Asp Pro Pro Ala Pro Leu Pro Leu
        115                 120                 125

Asp Glu Gly Lys Ser Leu Ile Asn Tyr Gly Arg Asn Glu Asn Val Asn
    130                 135                 140

Glu Asn Asn Lys Asn Gln Tyr Ser Asn Glu Glu Pro Asp Phe Ile Ser
145                 150                 155                 160

Ser Leu Asn Thr Ser Glu Ile Ile Glu Asn Val Ser Ala Thr Phe Ser
                165                 170                 175

Asn Leu Ile Asn Lys Ala Ser Ser Met Thr Thr Asn Thr Ile Asn Asn
            180                 185                 190

Leu Asn Thr Asn Asp Leu Ile Glu Ser Thr Lys Gly Thr Ile Ile Asn
        195                 200                 205

Ser Gly Ser Trp Phe Thr Glu Lys Thr Lys Lys Ile Ala Glu Asn Val
    210                 215                 220

Ser Asp Asn Pro Trp Trp Ala Lys Gly Gln Ser Lys Ile Lys Asp Val
225                 230                 235                 240

Thr Gln Asn Ala Ser Gly Trp Ile Ser Thr Ile Ser Ser Thr Val Ser
                245                 250                 255

Arg Thr Asn Ser Asn Phe Phe Phe Ser Asn Asn Asp Thr Asn Ile Asn
            260                 265                 270

Asn Gly Asn Asn Glu Asp Ile Asn Asn Asn Asn Thr Asn Val Asn Ser
        275                 280                 285

Asn Gly Asn Thr Thr Asn Asn Asn Asn Glu Gln Ala Gln Asn Asn Asn
    290                 295                 300

Asn Val Asn Phe Asn Tyr Asn Ser Ser Asn Ala Asn Asn Glu Tyr Leu
305                 310                 315                 320
```

Asn Tyr Gly Met Asn Glu Asn Asn Ser Thr Phe Asn
325 330

<210> SEQ ID NO 25
<211> LENGTH: 1194
<212> TYPE: DNA
<213> ORGANISM: Plasmodium falciparum

<400> SEQUENCE: 25

```
atgatgagaa aattagctat tttatctgtt tcttcctttt tatttgttga ggccttattc     60
caggaatacc agtgctatgg aagttcgtca aacacaaggg ttctaaatga attaaattat    120
gataatgcag gcactaattt atataatgaa ttagaaatga attattatgg gaaacaggaa    180
aattggtata gtcttaaaaa aaatagtaga tcacttggag aaaatgatga tggaaataac    240
gaagacaacg agaaattaag gaaaccaaaa cataaaaaat taaagcaacc agcggatggt    300
aatcctgatc caaatgcaaa cccaaatgta gatcccaatg ccaacccaaa tgtagatcca    360
aatgcaaacc caaatgtaga tccaaatgca aacccaaatg caaacccaaa tgcaaaccca    420
aatgcaaacc caaatgcaaa cccaaatgca aacccaaatg caaacccaaa tgcaaaccca    480
aatgcaaacc caaatgcaaa cccaaatgca aacccaaatg caaacccaaa tgcaaaccca    540
aatgcaaacc ccaatgcaaa tcctaatgca aacccaaatg caaacccaaa cgtagatcct    600
aatgcaaatc caaatgcaaa cccaaacgca aaccccaatg caaatcctaa tgcaaacccc    660
aatgcaaatc ctaatgcaaa tcctaatgcc aatccaaatg caaatccaaa tgcaaaccca    720
aacgcaaacc ccaatgcaaa tcctaatgcc aatccaaatg caaatccaaa tgcaaaccca    780
aatgcaaacc caaatgcaaa ccccaatgca aatcctaata aaaacaatca aggtaatgga    840
caaggtcaca atatgccaaa tgacccaaac cgaaatgtag atgaaaatgc taatgccaac    900
agtgctgtaa aaaataataa taacgaagaa ccaagtgata agcacataaa agaatattta    960
aacaaaatac aaaattctct ttcaactgaa tggtccccat gtagtgtaac ttgtggaaat   1020
ggtattcaag ttagaataaa gcctggctct gctaataaac ctaaagacga attagattat   1080
gcaaatgata ttgaaaaaaa aatttgtaaa atggaaaaat gttccagtgt gtttaatgtc   1140
gtaaatagtt caataggatt aataatggta ttatccttct tgttccttaa ttag         1194
```

<210> SEQ ID NO 26
<211> LENGTH: 397
<212> TYPE: PRT
<213> ORGANISM: Plasmodium falciparum

<400> SEQUENCE: 26

```
Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
```

```
            100                 105                 110

Asn Ala Asn Pro Asn Val Asp Pro Asn Ala Asn Pro Asn Val Asp Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Val Asp Pro Asn Ala Asn Pro Asn Ala Asn Pro
        195                 200                 205

Asn Ala Asn Pro Asn Ala Asn Pro Asn Ala Asn Pro Asn Ala Asn Pro
    210                 215                 220

Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Ala Asn Pro
                245                 250                 255

Asn Ala Asn Pro Asn Ala Asn Pro Asn Ala Asn Pro Asn Ala Asn Pro
            260                 265                 270

Asn Lys Asn Asn Gln Gly Asn Gly Gln Gly His Asn Met Pro Asn Asp
        275                 280                 285

Pro Asn Arg Asn Val Asp Glu Asn Ala Asn Ala Asn Ser Ala Val Lys
    290                 295                 300

Asn Asn Asn Asn Glu Glu Pro Ser Asp Lys His Ile Lys Glu Tyr Leu
305                 310                 315                 320

Asn Lys Ile Gln Asn Ser Leu Ser Thr Glu Trp Ser Pro Cys Ser Val
                325                 330                 335

Thr Cys Gly Asn Gly Ile Gln Val Arg Ile Lys Pro Gly Ser Ala Asn
            340                 345                 350

Lys Pro Lys Asp Glu Leu Asp Tyr Ala Asn Asp Ile Glu Lys Lys Ile
        355                 360                 365

Cys Lys Met Glu Lys Cys Ser Ser Val Phe Asn Val Val Asn Ser Ser
    370                 375                 380

Ile Gly Leu Ile Met Val Leu Ser Phe Leu Phe Leu Asn
385                 390                 395
```

<210> SEQ ID NO 27
<211> LENGTH: 2526
<212> TYPE: DNA
<213> ORGANISM: Plasmodium falciparum

<400> SEQUENCE: 27

```
atgtcggctt ttgaagagtt ggggttacat agcgatttgt gcgcagtttt agaaaaaaat     60

ggcattgatt taccaacggc tattcaacaa gagtccattc ctctgacatt agggggagga    120

gatttatgtg cttgtgctga aactggtaca ggaaagacgt taagtttcat attttcttct    180

ttacaaatag ttcatgaatt ggttcgaaat ataggtaact atgaagatgt gagtattaga    240

aaaaataaca ataacatgga aataataat gatagtaata tttctaacat tatagatgat    300

aatgataaga ataagaagtc aagttacata aaaactatta ataagaactc aaaagtaata    360

attaaagaca atgaatgtat atgtaataat aataataata ataatagtaa taatttcctt    420

ttcgaagaag taaaagttga ctgtgaaata acgaatggat tatatgcata cgaaattgaa    480
```

```
atattatcta aaagttatgt gaatgttggt ttttgtccat ccattaaaga aacattaaaa    540
tataattata cctactgtag taatggtaat aaatataata ataatagaca agaacattat    600
ggtgaatatt tttcaaataa tgatattata acatgtttaa ttaataaaaa taataatact    660
atatctttta aaaaaaatgg gaaattttta ggtaacgctt ttaaaatttt ttataaatat    720
aatgatgttg catttttttcc atatatatgg ggaaaatatt tccatataaa acttcatttc    780
gaaaatttaa aatatggtga tcgttcatta cattttaatg aactatgtat tttattaact    840
tcaaattgta atgataatga tactttaagt gataggaaaa tattttttttc gtctgaaaat    900
ataagggacg aaaaaaattt taaattagag aaagcaaata tgcaaacaca taattatcaa    960
aataataata gtataataaa cgaatataca cataattata atcaacaaaa tttcaataat   1020
aaaaaaaaac tatactgtat tgttttatgt cctactagag atttagcaca acaaacttat   1080
aataattatt taacgtactc tgaatgtttt aataaccctt ctattaatat tggaatatta   1140
gtaggaggag aacaaagaaa taaaggtcat catatgaatg acgacggatc ttataatatt   1200
gttgtgggta catgctttaa attaattgaa tgtataagaa aaaattctat aaaagttaat   1260
gatataagat tattaatatt agatgaagca gatgaattaa taaataatga tgaaaaaaca   1320
gttttagaaa ttaaagattc ttgtatgaaa tatggacatc gtgtgcaaac tttatttttt   1380
tctgctactt tgcaagacaa aaatgttaaa gattgtatta ataaaataac caataaacca   1440
atatttgttg atttgaaata tggaaaaaat agtataccat cacacatata tgtgtgtcta   1500
tattatgtca atgatgaaaa ttcgaattta tcgtatatta taaaagaaaa tgataataat   1560
aatcataaca aagaaatata taatatcctt tataatgaga aattatatca tatgaataca   1620
agggaattat atgaatatac agataaagta catatcttaa ataattcaaa tagtaattta   1680
aaaaaaaatg ataaggaaca aatttcttta aatataaaaa tgaataaact aaaaaaatta   1740
gttcaaataa ttaatgtttt taatatgcaa aatggtatta tattttgtcg aaccaattta   1800
gattgtgaca atgtatataa ttttttaaat gctgtaggtg atggtaaagc ttataaaggt   1860
accgttgaat cacttaaaga aaataaatat tcctgtgtta tattaaaagg aaaaatgtca   1920
aatgacgaaa gaaaaaacaa tcttcaagct ttcaaaaaag gtgaagtacg ttttttaata   1980
tgtacagatg tcgctgcaag aggtattgat atacagaatt taagatatct tattattatg   2040
accttgtctg ataatattaa tacatttttt cataaaattg gtagagtagg aagagatgga   2100
aaaaacagtt tatgtattgt cttaagtgca gataatgagc aagaagaaaa ggtatggttt   2160
catacatgtc ctagtagagg aattaattgt tacaatagaa atttgaaaga aaataaagga   2220
tgtactgtat atattaaaga aagtgattat attaaaacta ttaatgatat gttagaagta   2280
cctatacatg tgttagattc caaatattat tatgctgaaa atgttgttga tcctttaaat   2340
tattttaaaa aacatccagt ttctaataaa agcagaagaa ataaaaatca aaatgctaac   2400
tccatttttc aagaatcatc ccatatagat gtgttatctt cctttgcttc aaacattaat   2460
agtataaaaa aattacagtc tgctattagt tataagcatt atgaattgtt gaactttcaa   2520
atatga                                                               2526
```

```
<210> SEQ ID NO 28
<211> LENGTH: 841
<212> TYPE: PRT
<213> ORGANISM: Plasmodium falciparum

<400> SEQUENCE: 28
```

-continued

```
Met Ser Ala Phe Glu Glu Leu Gly Leu His Ser Asp Leu Cys Ala Val
1               5                   10                  15

Leu Glu Lys Asn Gly Ile Asp Leu Pro Thr Ala Ile Gln Gln Glu Ser
            20                  25                  30

Ile Pro Leu Thr Leu Gly Gly Gly Asp Leu Cys Ala Cys Ala Glu Thr
        35                  40                  45

Gly Thr Gly Lys Thr Leu Ser Phe Ile Phe Ser Ser Leu Gln Ile Val
    50                  55                  60

His Glu Leu Val Arg Asn Ile Gly Asn Tyr Glu Asp Val Ser Ile Arg
65                  70                  75                  80

Lys Asn Asn Asn Asn Met Glu Asn Asn Asn Asp Ser Asn Ile Ser Asn
                85                  90                  95

Ile Ile Asp Asp Asn Asp Lys Asn Lys Lys Ser Ser Tyr Ile Lys Thr
            100                 105                 110

Ile Asn Lys Asn Ser Lys Val Ile Ile Lys Asp Asn Glu Cys Ile Cys
        115                 120                 125

Asn Asn Asn Asn Asn Asn Asn Ser Asn Asn Phe Leu Phe Glu Glu Val
    130                 135                 140

Lys Val Asp Cys Glu Ile Thr Asn Gly Leu Tyr Ala Tyr Glu Ile Glu
145                 150                 155                 160

Ile Leu Ser Lys Ser Tyr Val Asn Val Gly Phe Cys Pro Ser Ile Lys
                165                 170                 175

Glu Thr Leu Lys Tyr Asn Tyr Thr Tyr Cys Ser Asn Gly Asn Lys Tyr
            180                 185                 190

Asn Asn Asn Arg Gln Glu His Tyr Gly Glu Tyr Phe Ser Asn Asn Asp
        195                 200                 205

Ile Ile Thr Cys Leu Ile Asn Lys Asn Asn Asn Thr Ile Ser Phe Lys
    210                 215                 220

Lys Asn Gly Lys Phe Leu Gly Asn Ala Phe Lys Ile Phe Tyr Lys Tyr
225                 230                 235                 240

Asn Asp Val Ala Phe Phe Pro Tyr Ile Trp Gly Lys Tyr Phe His Ile
                245                 250                 255

Lys Leu His Phe Glu Asn Leu Lys Tyr Gly Asp Arg Ser Leu His Phe
            260                 265                 270

Asn Glu Leu Cys Ile Leu Leu Thr Ser Asn Cys Asn Asp Asn Asp Thr
        275                 280                 285

Leu Ser Asp Arg Lys Ile Phe Phe Ser Ser Glu Asn Ile Arg Asp Glu
    290                 295                 300

Lys Asn Phe Lys Leu Glu Lys Ala Asn Met Gln Thr His Asn Tyr Gln
305                 310                 315                 320

Asn Asn Asn Ser Ile Ile Asn Glu Tyr Thr His Asn Tyr Asn Gln Gln
                325                 330                 335

Asn Phe Asn Asn Lys Lys Lys Leu Tyr Cys Ile Val Leu Cys Pro Thr
            340                 345                 350

Arg Asp Leu Ala Gln Gln Thr Tyr Asn Asn Tyr Leu Thr Tyr Ser Glu
        355                 360                 365

Cys Phe Asn Asn Pro Ser Ile Asn Ile Gly Ile Leu Val Gly Gly Glu
    370                 375                 380

Gln Arg Asn Lys Gly His His Met Asn Asp Asp Gly Ser Tyr Asn Ile
385                 390                 395                 400

Val Val Gly Thr Cys Phe Lys Leu Ile Glu Cys Ile Arg Lys Asn Ser
                405                 410                 415

Ile Lys Val Asn Asp Ile Arg Leu Leu Ile Leu Asp Glu Ala Asp Glu
```

```
            420                 425                 430

Leu Ile Asn Asn Asp Glu Lys Thr Val Leu Glu Ile Lys Asp Ser Cys
        435                 440                 445

Met Lys Tyr Gly His Arg Val Gln Thr Leu Phe Phe Ser Ala Thr Leu
    450                 455                 460

Gln Asp Lys Asn Val Lys Asp Cys Ile Asn Lys Ile Thr Asn Lys Pro
465                 470                 475                 480

Ile Phe Val Asp Leu Lys Tyr Gly Lys Asn Ser Ile Pro Ser His Ile
                485                 490                 495

Tyr Val Cys Leu Tyr Tyr Val Asn Asp Glu Asn Ser Asn Leu Ser Tyr
            500                 505                 510

Ile Ile Lys Glu Asn Asp Asn Asn Asn His Asn Lys Glu Ile Tyr Asn
        515                 520                 525

Ile Leu Tyr Asn Glu Lys Leu Tyr His Met Asn Thr Arg Glu Leu Tyr
    530                 535                 540

Glu Tyr Thr Asp Lys Val His Ile Leu Asn Asn Ser Asn Ser Asn Leu
545                 550                 555                 560

Lys Lys Asn Asp Lys Glu Gln Ile Ser Leu Asn Ile Lys Met Asn Lys
                565                 570                 575

Leu Lys Lys Leu Val Gln Ile Ile Asn Val Phe Asn Met Gln Asn Gly
            580                 585                 590

Ile Ile Phe Cys Arg Thr Asn Leu Asp Cys Asp Asn Val Tyr Asn Phe
        595                 600                 605

Leu Asn Ala Val Gly Asp Gly Lys Ala Tyr Lys Gly Thr Val Glu Ser
    610                 615                 620

Leu Lys Glu Asn Lys Tyr Ser Cys Val Ile Leu Lys Gly Lys Met Ser
625                 630                 635                 640

Asn Asp Glu Arg Lys Asn Asn Leu Gln Ala Phe Lys Lys Gly Glu Val
                645                 650                 655

Arg Phe Leu Ile Cys Thr Asp Val Ala Ala Arg Gly Ile Asp Ile Gln
            660                 665                 670

Asn Leu Arg Tyr Leu Ile Ile Met Thr Leu Ser Asp Asn Ile Asn Thr
        675                 680                 685

Phe Phe His Lys Ile Gly Arg Val Gly Arg Asp Gly Lys Asn Ser Leu
    690                 695                 700

Cys Ile Val Leu Ser Ala Asp Asn Glu Gln Glu Glu Lys Val Trp Phe
705                 710                 715                 720

His Thr Cys Pro Ser Arg Gly Ile Asn Cys Tyr Asn Arg Asn Leu Lys
                725                 730                 735

Glu Asn Lys Gly Cys Thr Val Tyr Ile Lys Glu Ser Asp Tyr Ile Lys
            740                 745                 750

Thr Ile Asn Asp Met Leu Glu Val Pro Ile His Val Leu Asp Ser Lys
        755                 760                 765

Tyr Tyr Tyr Ala Glu Asn Val Val Asp Pro Leu Asn Tyr Phe Lys Lys
    770                 775                 780

His Pro Val Ser Asn Lys Ser Arg Arg Asn Lys Asn Gln Asn Ala Asn
785                 790                 795                 800

Ser Ile Phe Gln Glu Ser Ser His Ile Asp Val Leu Ser Ser Phe Ala
                805                 810                 815

Ser Asn Ile Asn Ser Ile Lys Lys Leu Gln Ser Ala Ile Ser Tyr Lys
            820                 825                 830

His Tyr Glu Leu Leu Asn Phe Gln Ile
        835                 840
```

<210> SEQ ID NO 29
<211> LENGTH: 7962
<212> TYPE: DNA
<213> ORGANISM: Plasmodium falciparum

<400> SEQUENCE: 29

```
atgatgagtg atgcaaacaa aagacagcta agaacgagaa gaaaaaaaac tatgaattca     60
ttatattata atagtgatta tagtaatgat ataaatatag aagattctaa aagtagatta    120
agtggtggca agaaaagtga gggtagttct agtaaatcaa aagatgttat atcatcttat    180
actaagaaat atagccttaa taataaaaat cataaacata gtaaaaatat tatgaatcat    240
aaaaatatga tttatagtga tgggtatatg aataatatga atgaagacaa tgtagacaat    300
gaagaaattt gtgagaatca tttgtatgag gaaaataatg ataataatat gaatgatgat    360
atgaatgaaa ataatataat agatgaagat gaaaatgaaa atacaaatct tgtaaatata    420
gacgatgaaa atattaatga tgataataat aatgaaaata atgataatat tgaagacatg    480
actaatgaca tgaataataa tgtaagtcat aataatatta ttagcaatga taattcatat    540
aataatcaaa tagatagtac atttcttaat atgaataata aaagaaaaga tgaggaacat    600
ataaataatg atgatgaata tatacataaa agtaaagata agaaaaaaag tggatcatta    660
gtacatataa aaaatgaaaa tacaaataaa ttagataata gtaataataa taataataat    720
aataaaaata aaaaagatag tgtaagtgca aatggatcta ataagaataa ttgtaataca    780
tctagtagta ataatcgtag tagacatgta cctaataata acgaaataaa ttatgcaaaa    840
atggctgaaa aattacctca tgttgttggg gttagatttg ataagtcaca aaatagatgg    900
ctatctggta tatgtattaa tggacgatgt attaacagat atttcccagt atataaattt    960
ggatttgaag aagctcgtcg gttagccatt caacatagga aaaattttga gacagctaat   1020
gtaggtcatt taaaaaaaca acagggtgag gctaaaacgt ctcacttgaa tttgttgaac   1080
cttaactcgc aaatacccaa tgactttaaa gatatccaag gaaaaaataa acttattttc   1140
aaataccttt cttatgactc cattcaaaaa gagtgggttg taacatacga ttatgacaac   1200
aaagttctcg ttaataaatt tcctgtagat atatatggat acaataatgc ctacgaaatg   1260
gctgtccatt gtatcaataa gcttaatata tgtaatcagg aaaagttgtg taaaaatatt   1320
aataaacaag agcattcaag aggattacaa ggtgatttgt taaataattt taatgataat   1380
aatattaata ataataataa tatgaatgat aacaataata ataatatact tgataataat   1440
aataatttga ttgataataa taataataat aatatttcga ttgataatca caatttgaat   1500
atatataata attccagtga acataataat atgtgtgaag atttgagttc ttttaaaata   1560
ccccaaaaca aaataactaa gttaattaat tcagggcaat caaatttttt aatgaataat   1620
caaaaatcag aaatggcttt gaacgatatt cttaataatg agaatatgat gaataattta   1680
attcatgaaa agcaaaaact gaatataaac cataataata ttaataaaaa attagaagaa   1740
ttagaaaata tgagaaaaga agatacaatg tttttaaatg acagttcttc ttatttaagt   1800
accaacgata taaaagtatt gaatggtatt aaaagattaa aaacagataa ttctcctttt   1860
aataaacagg atgaggaatt tttattaaat tctaaaaatt tgaataaata ttctactatg   1920
caaaacaata aatcttatga tattttaaat gattcaaatt ttaatatatt agaaaatgaa   1980
ggaatgtttt ctttaaatga taaaaaaggt ataaataata acgatatgtc aaaaaaataga   2040
aatattacaa attctaatta ttttaaacca ttccatgatg aagcagaaaa taatatatat   2100
```

```
cagttattaa atggaaaata tttaaccaat gaggataaaa gtgtacatat caatcttttg   2160
aatagtgtaa tgaagcaaag tactatgaac aaattatcaa atgaagaaga tctttttgaa   2220
aaaaaagaaa aaaaaagaaa attaaagaat aatatgcttg aacaaaaagg agatgatcaa   2280
tttataaata tgaacaaaag gatcgatacg aacttagtga gtaataataa taatataaat   2340
gcatttaaca acaacaataa taataatatt gtcaataata atattgtcaa taataatatt   2400
gtcagtaata atattgtcag taataatatt gtcagtaata atattagcaa taataatatt   2460
atcaataata ataataatgt aatccctttt ggtgatgaac attttgatgc cttgtcattc   2520
gatgagtatc gaaaacgtat taatagtaaa aagagtaatt attcaaatat aggagaaaat   2580
gaaaaataca agaaattagc taacgggttg ttagataatg gtgaaacact atctaaaaat   2640
ttaaatgaat taaaaatgta tcatttggca ggaaaaaaag aaaaagataa taatatgaac   2700
aatatgaata ataacatttt atataataat aataatatga aatattatac acataacgaa   2760
catcataaga atgaagaatt aaaaaggagt caacttaatg aaaatgtgaa tcatgagaat   2820
atgctaaatt tgaatcaaat gataagaaat atacttaata ataatagtgt agataataat   2880
gaaaaaataa taaaaggtat aaatatctta aaaaatatga ctatgaatga taaatttaat   2940
ttgattaatt ttaataatca atgcatgaat tattcgtata acaatatgat gaaaaaggaa   3000
aattatgtta aaaatatata taaaattatt aataagggtt cagaggattc tattaattat   3060
gatgaatatt taactgtcaa gttagaagtt gaagatggtg aagaaaaaga tcaaaatggt   3120
gaaaaaaaaa aaatcaacac atcagaggca tatcatgaag gaaaaatgaa taaaaaacat   3180
aaaaagaaaa aaaaaatgaa gcaaaataaa ttagatgaag atattactgt aaataatgga   3240
atgataaatg aaggagacaa tgacaaaatt gaagatacta ataaaaatga cgatatatca   3300
aataattcag aagttacaaa taaagatatt ataaatggtg aaagaaattc aaatgattct   3360
gaagaaaagg agaaggaaga aaaagaagat tataatgaaa atacatataa taatatgaat   3420
acagataata atacatcaaa cagtaatgat gataatgaac aaataattaa taacgaaaat   3480
gattatatat taaacaaaac aaataatgaa attaataaag aaataaatac atctataaat   3540
gaatttaatg atattgcttt ccaattgtgt ccttggaaaa aaggtattca atggaatttg   3600
ttaaaaaaaa tgtggacctg taaattatgg gataataaag gtaatgaaat tacaaaaaat   3660
attcatataa aaaaaaaaga aggtattgat attggatata aatattgtat aaaaattcga   3720
acaaattctt ttatatttta tctatcaaaa gaattaaata aatttccaca tattcctgaa   3780
atatcttacg acttacaaaa tcttcatttt gttgtatctt ataaagataa tgaaaagaaa   3840
atatattcct ttgaagatgg aatttataaa tcatttatag actgtatgga atatctaaac   3900
aaacaaaaaa gagaatataa tgaaaatatt tatgatatat ccaattttat aaaagaaaaa   3960
aataatttgg aattagatga tatatataaa gaattaaatt atttcgaata taatagaaat   4020
gtattaagta atatttgtga agaaacaaaa attgcatata gtataaaacc atggttaaga   4080
ggtattatat gggaagataa attgaaaaaa tggatagtct tttttaaaga taaaaatgaa   4140
aacttgagaa ttagcttttt tagtacatca gattataacg atgatgttat tatgtcttat   4200
aataaagctt gtgaatattt ttcacaagtt aaagaatcaa ataattttga ttccaattca   4260
gaggaatttg ctcagtccat taaaaatgtt attaaaaatg ttcaatttga taaaataata   4320
gaacaacaaa atgacgcaaa taataatgat cacaagaaag gtaatttgca agaggaccat   4380
gatatacaaa caaattatta taataaggtg acacaaggaa atgaagggga aacaaataat   4440
aataataata ataatcaagg agaaaatatg accgactctc aaattgtctt aaatacaaat   4500
```

```
gaaatccatg tccataatgt acatacatta aaacgtcctg aaggattata taatattgca   4560

gaaacacaat caacccattt tttaaaagat aataatattt cgaatgagca caaaagtatg   4620

gaaacatttt ataatgaaaa ctcttattat aatgatgata ttgcttttct aaattatgct   4680

gatagtaatg atagtcttat ttcaaaagga atgtctcaat atttatcatt accatcaaaa   4740

aaaaagaaga aaaaaagaac tactgaagat atatataaaa gcgaaattga tgttttatct   4800

tatcaaaata atgaattata tagcaatgta aaaaatgaaa actatgatga aaatatttca   4860

gagaataata aaaaatatgg aaaaaggaaa atggaattga attttttaag tcacagtgaa   4920

aataatataa ataatataaa taataatact tataataata atgattatac aaatgatgat   4980

aatcatagta gtaaggtgta ttcttctgat tgtgaaaaga atactaatca taacaaaaag   5040

acggaagata aatatgatca agagaacaat aaatattttt ataataaaga taaattatta   5100

tttgaccacg aaaatggtac aattccaaga aatataaaga aggaatcaaa caatttaaac   5160

agcgaatata atttggatta tttaaattct gaagatatta aaaataataa ccatcaccat   5220

cacaataata ataataatat tattattaat ggaccatcaa gtgatggaga aacaataatt   5280

ttatcacagt atcacaaaaa tgatgatgat gaagatgatg gaaataatac agataattca   5340

aaaatattaa gaagttttga taagtgctca aatgaaaata gtgtatgtat aaataaaagt   5400

aatgagaaac ttgaaaacat tttagacgga ggagtaaata tgagattacc aaaaagtgaa   5460

attttaaatc aagcttctag attacccaaa ttacaaggta tgttttttga taagagaaga   5520

aattattgga ctgttagtgt ttgtggtttc agaaaatcat ttggtgttag gacaagaggt   5580

gtatatcaag catacaaatt agcagctgaa tttcgtaatc gtatattaga aaacaataaa   5640

ggtaaatatt atcctcaaag aagtacaagt atgtctagta attataaata taatacaaag   5700

ggtggatcca taattattaa agatgaaaaa ttgaattata gtaatatatc tgaaatgaca   5760

tctgtagatg aagaatatga tccaaaaaaa aaaaaaagtt cgttttcttc taataatatt   5820

aataatattg ataaggaatt atattcatta aatgacaaag aaagtaatag tagtggatta   5880

tattattctt ttaatgtaaa agggaaaacc agttcaaata tatatgatta ttttttagat   5940

aaaaaagaac atgactattt cgcaacaaat aatagtagta ataatataaa taataataat   6000

aataataata ataatgatat aaataataat agtactaatg atataaataa taatggtact   6060

aatgatacaa ataataagaa agatccaaaa ggtataccta ataattcatg ttatgatgat   6120

caatataata atattgaaaa tgaagaggaa gaagaagaaa gggaagggga agaagctgaa   6180

aggtggaata tatcagataa agtgaataat aaaaataatg ataataaaat tcaaattggt   6240

aataatactt ttggacaatt aaaatatgat agtgctttag aatcaaacct tatcaatttt   6300

ataaacgagg taggttcatc tgattttttg aaagatgcca aaattaataa taataataat   6360

aacaataata ataataataa tattggtgga aataaaaaga atcaacatat aaataataat   6420

attagcaata gtaatacttt aaataatagc ttaaatgttc aaaatatttc ttctagtaat   6480

agtgctataa gtaataatgg agttataaat aattattcac ctacacatat atatgaagta   6540

gacaatctca ataatagtca agattactat ttaaaaaatg acgaaatgaa aaatgaatta   6600

aataaagtgg aagatcaaaa aaataaaaag gatatttcaa gcacaaatag tctactaaaa   6660

cattttatga atgatgatat attaataaat aataaagtaa aacaacaacc ctttttttgat   6720

agtcacaaca attataataa gttaggacac aaacaagtca aaacatctgc ttatacggaa   6780

agtgcaattg gattaggctt tagaaaaaat ggatatatta atgattgtga cttagttaat   6840
```

```
aataataata ataataataa taataacatg catataaaga acaatggtgt tatattaaat   6900

aaattgatat cttctaacca cgatagtaaa gataacagta ataacaatat taaggataaa   6960

gatagggaag ataataataa aaatatttat aataataata atgatagatc tattggtagt   7020

tatgtaaaca atcttggtgt aatagaaaac caatgtgaga atagtaaagg agcagatgaa   7080

aacacgaaaa attttaataa taataaaaca ttaaataatt atgaaccaga aaataagtct   7140

tataattaca gtccagtgtt agatgaaact ctagaagaaa gagatgtgag aataaataga   7200

gaggtaagca aatgtaaatt tgtagatgga ttaatatacg atgaagctaa taaatgtttt   7260

cgaataaaaa ttaatggtta tagaaaagca tattctgtta ttagaagagg agtaaaagaa   7320

gcttataaat taagtattga atctatagaa caaattaaaa gacaaacaca aacaaataat   7380

tttaataata atgaacagtc acaagttaat acaaataata tgacacagat atataattca   7440

agttctgaaa attcaagaca tggatcatgt tataattatc aacataatca taaaagtaaa   7500

ctagagaatt cgaatgataa tcctgaagaa aaatatgacc acatcaataa tatgaccaat   7560

gtaggacatg aaaataaaca gagcgctgaa gaaagtttgt ttccaatgtt aaatgtagat   7620

gataaatatt atgaacttct taaaacatcc attattatat gtctgaatga tatacttatg   7680

aattgtatac ctcaagtatt tcacctatac aaaaatatca atacatcaaa tgacataaaa   7740

ttagaagata tattatatac tgaaaggaaa agaaaagaac agtccttaaa atatcatatt   7800

gaatatacac aaaattctgt aggtgtgtca tcccttatac cttacttgaa attatttagt   7860

accgaaattt taaataacgt tttaccatca gcacaatcct tggaaataca aagattaata   7920

attcattcgt tggatataca aacatataat acattatatt aa                      7962
```

<210> SEQ ID NO 30
<211> LENGTH: 2653
<212> TYPE: PRT
<213> ORGANISM: Plasmodium falciparum

<400> SEQUENCE: 30

```
Met Met Ser Asp Ala Asn Lys Arg Gln Leu Arg Thr Arg Arg Lys Lys
1               5                   10                  15

Thr Met Asn Ser Leu Tyr Tyr Asn Ser Asp Tyr Ser Asn Asp Ile Asn
            20                  25                  30

Ile Glu Asp Ser Lys Ser Arg Leu Ser Gly Gly Lys Lys Ser Glu Gly
        35                  40                  45

Ser Ser Ser Lys Ser Lys Asp Val Ile Ser Ser Tyr Thr Lys Lys Tyr
    50                  55                  60

Ser Leu Asn Asn Lys Asn His Lys His Ser Lys Asn Ile Met Asn His
65                  70                  75                  80

Lys Asn Met Ile Tyr Ser Asp Gly Tyr Met Asn Asn Met Asn Glu Asp
                85                  90                  95

Asn Val Asp Asn Glu Glu Ile Cys Glu Asn His Leu Tyr Glu Glu Asn
            100                 105                 110

Asn Asp Asn Asn Met Asn Asp Asp Met Asn Glu Asn Asn Ile Ile Asp
        115                 120                 125

Glu Asp Glu Asn Glu Asn Thr Asn Leu Val Asn Ile Asp Asp Glu Asn
    130                 135                 140

Ile Asn Asp Asp Asn Asn Asn Glu Asn Asn Asp Asn Ile Glu Asp Met
145                 150                 155                 160

Thr Asn Asp Met Asn Asn Asn Val Ser His Asn Asn Ile Ile Ser Asn
                165                 170                 175
```

```
Asp Asn Ser Tyr Asn Asn Gln Ile Asp Ser Thr Phe Leu Asn Met Asn
            180                 185                 190

Asn Lys Arg Lys Asp Glu Glu His Ile Asn Asn Asp Asp Glu Tyr Ile
        195                 200                 205

His Lys Ser Lys Asp Lys Lys Lys Ser Gly Ser Leu Val His Ile Lys
    210                 215                 220

Asn Glu Asn Thr Asn Lys Leu Asp Asn Ser Asn Asn Asn Asn Asn Asn
225                 230                 235                 240

Asn Lys Asn Lys Lys Asp Ser Val Ser Ala Asn Gly Ser Asn Lys Asn
                245                 250                 255

Asn Cys Asn Thr Ser Ser Ser Asn Asn Arg Ser Arg His Val Pro Asn
            260                 265                 270

Asn Asn Glu Ile Asn Tyr Ala Lys Met Ala Glu Lys Leu Pro His Val
        275                 280                 285

Val Gly Val Arg Phe Asp Lys Ser Gln Asn Arg Trp Leu Ser Gly Ile
    290                 295                 300

Cys Ile Asn Gly Arg Cys Ile Asn Arg Tyr Phe Pro Val Tyr Lys Phe
305                 310                 315                 320

Gly Phe Glu Glu Ala Arg Arg Leu Ala Ile Gln His Arg Lys Asn Phe
                325                 330                 335

Glu Thr Ala Asn Val Gly His Leu Lys Lys Gln Gln Gly Glu Ala Lys
            340                 345                 350

Thr Ser His Leu Asn Leu Leu Asn Leu Asn Ser Gln Ile Pro Asn Asp
        355                 360                 365

Phe Lys Asp Ile Gln Gly Lys Asn Lys Leu Ile Phe Lys Tyr Leu Ser
    370                 375                 380

Tyr Asp Ser Ile Gln Lys Glu Trp Val Val Thr Tyr Asp Tyr Asp Asn
385                 390                 395                 400

Lys Val Leu Val Asn Lys Phe Pro Val Asp Ile Tyr Gly Tyr Asn Asn
                405                 410                 415

Ala Tyr Glu Met Ala Val His Cys Ile Asn Lys Leu Asn Ile Cys Asn
            420                 425                 430

Gln Glu Lys Leu Cys Lys Asn Ile Asn Lys Gln Glu His Ser Arg Gly
        435                 440                 445

Leu Gln Gly Asp Leu Leu Asn Asn Phe Asn Asp Asn Asn Ile Asn Asn
    450                 455                 460

Asn Asn Asn Met Asn Asp Asn Asn Asn Asn Asn Ile Leu Asp Asn Asn
465                 470                 475                 480

Asn Asn Leu Ile Asp Asn Asn Asn Asn Asn Asn Ile Ser Ile Asp Asn
                485                 490                 495

His Asn Leu Asn Ile Tyr Asn Asn Ser Ser Glu His Asn Asn Met Cys
            500                 505                 510

Glu Asp Leu Ser Ser Phe Lys Ile Pro Gln Asn Lys Ile Thr Lys Leu
        515                 520                 525

Ile Asn Ser Gly Gln Ser Asn Phe Leu Met Asn Asn Gln Lys Ser Glu
    530                 535                 540

Met Ala Leu Asn Asp Ile Leu Asn Asn Glu Asn Met Met Asn Asn Leu
545                 550                 555                 560

Ile His Glu Lys Gln Lys Leu Asn Ile Asn His Asn Asn Ile Asn Lys
                565                 570                 575

Lys Leu Glu Glu Leu Glu Asn Met Arg Lys Glu Asp Thr Met Phe Leu
            580                 585                 590

Asn Asp Ser Ser Ser Tyr Leu Ser Thr Asn Asp Ile Lys Val Leu Asn
```

```
        595                 600                 605

Gly Ile Lys Arg Leu Lys Thr Asp Asn Ser Pro Phe Asn Lys Gln Asp
    610                 615                 620

Glu Glu Phe Leu Leu Asn Ser Lys Asn Leu Asn Lys Tyr Ser Thr Met
625                 630                 635                 640

Gln Asn Asn Lys Ser Tyr Asp Ile Leu Asn Asp Ser Asn Phe Asn Ile
                645                 650                 655

Leu Glu Asn Glu Gly Met Phe Ser Leu Asn Asp Lys Lys Gly Ile Asn
            660                 665                 670

Asn Asn Asp Met Ser Lys Asn Arg Asn Ile Thr Asn Ser Asn Tyr Phe
        675                 680                 685

Lys Pro Phe His Asp Glu Ala Glu Asn Asn Ile Tyr Gln Leu Leu Asn
    690                 695                 700

Gly Lys Tyr Leu Thr Asn Glu Asp Lys Ser Val His Ile Asn Leu Leu
705                 710                 715                 720

Asn Ser Val Met Lys Gln Ser Thr Met Asn Lys Leu Ser Asn Glu Glu
                725                 730                 735

Asp Leu Phe Glu Lys Lys Glu Lys Lys Arg Lys Leu Lys Asn Asn Met
            740                 745                 750

Leu Glu Gln Lys Gly Asp Asp Gln Phe Ile Asn Met Asn Lys Arg Ile
        755                 760                 765

Asp Thr Asn Leu Val Ser Asn Asn Asn Asn Ile Asn Ala Phe Asn Asn
    770                 775                 780

Asn Asn Asn Asn Asn Ile Val Asn Asn Asn Ile Val Asn Asn Asn Ile
785                 790                 795                 800

Val Ser Asn Asn Ile Val Ser Asn Asn Ile Val Ser Asn Asn Ile Ser
                805                 810                 815

Asn Asn Asn Ile Ile Asn Asn Asn Asn Asn Val Ile Pro Phe Gly Asp
            820                 825                 830

Glu His Phe Asp Ala Leu Ser Phe Asp Glu Tyr Arg Lys Arg Ile Asn
        835                 840                 845

Ser Lys Lys Ser Asn Tyr Ser Asn Ile Gly Glu Asn Glu Lys Tyr Lys
    850                 855                 860

Lys Leu Ala Asn Gly Leu Leu Asp Asn Gly Glu Thr Leu Ser Lys Asn
865                 870                 875                 880

Leu Asn Glu Leu Lys Met Tyr His Leu Ala Gly Lys Lys Glu Lys Asp
                885                 890                 895

Asn Asn Met Asn Asn Met Asn Asn Asn Ile Leu Tyr Asn Asn Asn Asn
            900                 905                 910

Met Lys Tyr Tyr Thr His Asn Glu His His Lys Asn Glu Glu Leu Lys
        915                 920                 925

Arg Ser Gln Leu Asn Glu Asn Val Asn His Glu Asn Met Leu Asn Leu
    930                 935                 940

Asn Gln Met Ile Arg Asn Ile Leu Asn Asn Asn Ser Val Asp Asn Asn
945                 950                 955                 960

Glu Lys Ile Ile Lys Gly Ile Asn Ile Leu Lys Asn Met Thr Met Asn
                965                 970                 975

Asp Lys Phe Asn Leu Ile Asn Phe Asn Asn Gln Cys Met Asn Tyr Ser
            980                 985                 990

Tyr Asn Asn Met Met Lys Lys Glu  Asn Tyr Val Lys Asn  Ile Tyr Lys
        995                 1000                1005

Ile Ile  Asn Lys Gly Ser Glu  Asp Ser Ile Asn Tyr  Asp Glu Tyr
    1010                 1015                 1020
```

```
Leu Thr  Val Lys Leu Glu Val  Glu Asp Gly Glu Glu  Lys Asp Gln
    1025                 1030                 1035

Asn Gly  Glu Lys Lys Lys Ile  Asn Thr Ser Glu Ala  Tyr His Glu
    1040                 1045                 1050

Gly Lys  Met Asn Lys Lys His  Lys Lys Lys Lys Lys  Met Lys Gln
    1055                 1060                 1065

Asn Lys  Leu Asp Glu Asp Ile  Thr Val Asn Asn Gly  Met Ile Asn
    1070                 1075                 1080

Glu Gly  Asp Asn Asp Lys Ile  Glu Asp Thr Asn Lys  Asn Asp Asp
    1085                 1090                 1095

Ile Ser  Asn Asn Ser Glu Val  Thr Asn Lys Asp Ile  Ile Asn Gly
    1100                 1105                 1110

Glu Arg  Asn Ser Asn Asp Ser  Glu Glu Lys Glu Lys  Glu Glu Lys
    1115                 1120                 1125

Glu Asp  Tyr Asn Glu Asn Thr  Tyr Asn Asn Met Asn  Thr Asp Asn
    1130                 1135                 1140

Asn Thr  Ser Asn Ser Asn Asp  Asp Asn Glu Gln Ile  Ile Asn Asn
    1145                 1150                 1155

Glu Asn  Asp Tyr Ile Leu Asn  Lys Thr Asn Asn Glu  Ile Asn Lys
    1160                 1165                 1170

Glu Ile  Asn Thr Ser Ile Asn  Glu Phe Asn Asp Ile  Ala Phe Gln
    1175                 1180                 1185

Leu Cys  Pro Trp Lys Lys Gly  Ile Gln Trp Asn Leu  Leu Lys Lys
    1190                 1195                 1200

Met Trp  Thr Cys Lys Leu Trp  Asp Asn Lys Gly Asn  Glu Ile Thr
    1205                 1210                 1215

Lys Asn  Ile His Ile Lys Lys  Lys Glu Gly Ile Asp  Ile Gly Tyr
    1220                 1225                 1230

Lys Tyr  Cys Ile Lys Ile Arg  Thr Asn Ser Phe Ile  Phe Tyr Leu
    1235                 1240                 1245

Ser Lys  Glu Leu Asn Lys Phe  Pro His Ile Pro Glu  Ile Ser Tyr
    1250                 1255                 1260

Asp Leu  Gln Asn Leu His Phe  Val Val Ser Tyr Lys  Asp Asn Glu
    1265                 1270                 1275

Lys Lys  Ile Tyr Ser Phe Glu  Asp Gly Ile Tyr Lys  Ser Phe Ile
    1280                 1285                 1290

Asp Cys  Met Glu Tyr Leu Asn  Lys Gln Lys Arg Glu  Tyr Asn Glu
    1295                 1300                 1305

Asn Ile  Tyr Asp Ile Ser Asn  Phe Ile Lys Glu Lys  Asn Asn Leu
    1310                 1315                 1320

Glu Leu  Asp Asp Ile Tyr Lys  Glu Leu Asn Tyr Phe  Glu Tyr Asn
    1325                 1330                 1335

Arg Asn  Val Leu Ser Asn Ile  Cys Glu Glu Thr Lys  Ile Ala Tyr
    1340                 1345                 1350

Ser Ile  Lys Pro Trp Leu Arg  Gly Ile Ile Trp Glu  Asp Lys Leu
    1355                 1360                 1365

Lys Lys  Trp Ile Val Phe Phe  Lys Asp Lys Asn Glu  Asn Leu Arg
    1370                 1375                 1380

Ile Ser  Phe Phe Ser Thr Ser  Asp Tyr Asn Asp Asp  Val Ile Met
    1385                 1390                 1395

Ser Tyr  Asn Lys Ala Cys Glu  Tyr Phe Ser Gln Val  Lys Glu Ser
    1400                 1405                 1410
```

```
Asn Asn  Phe Asp Ser Asn Ser  Glu Glu Phe Ala Gln  Ser Ile Lys
    1415                 1420                 1425

Asn Val  Ile Lys Asn Val Gln  Phe Asp Lys Ile Ile  Glu Gln Gln
    1430                 1435                 1440

Asn Asp  Ala Asn Asn Asn Asp  His Lys Lys Gly Asn  Leu Gln Glu
    1445                 1450                 1455

Asp His  Asp Ile Gln Thr Asn  Tyr Tyr Asn Lys Val  Thr Gln Gly
    1460                 1465                 1470

Asn Glu  Gly Glu Thr Asn Asn  Asn Asn Asn Asn Asn  Gln Gly Glu
    1475                 1480                 1485

Asn Met  Thr Asp Ser Gln Ile  Val Leu Asn Thr Asn  Glu Ile His
    1490                 1495                 1500

Val His  Asn Val His Thr Leu  Lys Arg Pro Glu Gly  Leu Tyr Asn
    1505                 1510                 1515

Ile Ala  Glu Thr Gln Ser Thr  His Phe Leu Lys Asp  Asn Asn Ile
    1520                 1525                 1530

Ser Asn  Glu His Lys Ser Met  Glu Thr Phe Tyr Asn  Glu Asn Ser
    1535                 1540                 1545

Tyr Tyr  Asn Asp Asp Ile Ala  Phe Leu Asn Tyr Ala  Asp Ser Asn
    1550                 1555                 1560

Asp Ser  Leu Ile Ser Lys Gly  Met Ser Gln Tyr Leu  Ser Leu Pro
    1565                 1570                 1575

Ser Lys  Lys Lys Lys Lys Lys  Arg Thr Thr Glu Asp  Ile Tyr Lys
    1580                 1585                 1590

Ser Glu  Ile Asp Val Leu Ser  Tyr Gln Asn Asn Glu  Leu Tyr Ser
    1595                 1600                 1605

Asn Val  Lys Asn Glu Asn Tyr  Asp Glu Asn Ile Ser  Glu Asn Asn
    1610                 1615                 1620

Lys Lys  Tyr Gly Lys Arg Lys  Met Glu Leu Asn Phe  Leu Ser His
    1625                 1630                 1635

Ser Glu  Asn Asn Ile Asn Asn  Ile Asn Asn Asn Thr  Tyr Asn Asn
    1640                 1645                 1650

Asn Asp  Tyr Thr Asn Asp Asp  Asn His Ser Ser Lys  Val Tyr Ser
    1655                 1660                 1665

Ser Asp  Cys Glu Lys Asn Thr  Asn His Asn Lys Lys  Thr Glu Asp
    1670                 1675                 1680

Lys Tyr  Asp Gln Glu Asn Asn  Lys Tyr Phe Tyr Asn  Lys Asp Lys
    1685                 1690                 1695

Leu Leu  Phe Asp His Glu Asn  Gly Thr Ile Pro Arg  Asn Ile Lys
    1700                 1705                 1710

Lys Glu  Ser Asn Asn Leu Asn  Ser Glu Tyr Asn Leu  Asp Tyr Leu
    1715                 1720                 1725

Asn Ser  Glu Asp Ile Lys Asn  Asn Asn His His His  His Asn Asn
    1730                 1735                 1740

Asn Asn  Asn Ile Ile Ile Asn  Gly Pro Ser Ser Asp  Gly Glu Thr
    1745                 1750                 1755

Ile Ile  Leu Ser Gln Tyr His  Lys Asn Asp Asp Asp  Glu Asp Asp
    1760                 1765                 1770

Gly Asn  Asn Thr Asp Asn Ser  Lys Ile Leu Arg Ser  Phe Asp Lys
    1775                 1780                 1785

Cys Ser  Asn Glu Asn Ser Val  Cys Ile Asn Lys Ser  Asn Glu Lys
    1790                 1795                 1800

Leu Glu  Asn Ile Leu Asp Gly  Gly Val Asn Met Arg  Leu Pro Lys
```

```
    1805                1810                1815

Ser Glu  Ile Leu Asn Gln Ala  Ser Arg Leu Pro Lys  Leu Gln Gly
    1820                1825                1830

Met Phe  Phe Asp Lys Arg Arg  Asn Tyr Trp Thr Val  Ser Val Cys
    1835                1840                1845

Gly Phe  Arg Lys Ser Phe Gly  Val Arg Thr Arg Gly  Val Tyr Gln
    1850                1855                1860

Ala Tyr  Lys Leu Ala Ala Glu  Phe Arg Asn Arg Ile  Leu Glu Asn
    1865                1870                1875

Asn Lys  Gly Lys Tyr Tyr Pro  Gln Arg Ser Thr Ser  Met Ser Ser
    1880                1885                1890

Asn Tyr  Lys Tyr Asn Thr Lys  Gly Gly Ser Ile Ile  Ile Lys Asp
    1895                1900                1905

Glu Lys  Leu Asn Tyr Ser Asn  Ile Ser Glu Met Thr  Ser Val Asp
    1910                1915                1920

Glu Glu  Tyr Asp Pro Lys Lys  Lys Lys Ser Ser Phe  Ser Ser Asn
    1925                1930                1935

Asn Ile  Asn Asn Ile Asp Lys  Glu Leu Tyr Ser Leu  Asn Asp Lys
    1940                1945                1950

Glu Ser  Asn Ser Ser Gly Leu  Tyr Tyr Ser Phe Asn  Val Lys Gly
    1955                1960                1965

Lys Thr  Ser Ser Asn Ile Tyr  Asp Tyr Phe Leu Asp  Lys Lys Glu
    1970                1975                1980

His Asp  Tyr Phe Ala Thr Asn  Asn Ser Ser Asn Asn  Ile Asn Asn
    1985                1990                1995

Asn Asn  Asn Asn Asn Asn Asn  Asp Ile Asn Asn Asn  Ser Thr Asn
    2000                2005                2010

Asp Ile  Asn Asn Asn Gly Thr  Asn Asp Thr Asn Asn  Lys Lys Asp
    2015                2020                2025

Pro Lys  Gly Ile Pro Asn Asn  Ser Cys Tyr Asp Asp  Gln Tyr Asn
    2030                2035                2040

Asn Ile  Glu Asn Glu Glu Glu  Glu Glu Glu Arg Glu  Gly Glu Glu
    2045                2050                2055

Ala Glu  Arg Trp Asn Ile Ser  Asp Lys Val Asn Asn  Lys Asn Asn
    2060                2065                2070

Asp Asn  Lys Ile Gln Ile Gly  Asn Asn Thr Phe Gly  Gln Leu Lys
    2075                2080                2085

Tyr Asp  Ser Ala Leu Glu Ser  Asn Leu Ile Asn Phe  Ile Asn Glu
    2090                2095                2100

Val Gly  Ser Ser Asp Phe Leu  Lys Asp Ala Lys Ile  Asn Asn Asn
    2105                2110                2115

Asn Asn  Asn Asn Asn Asn Asn  Asn Asn Ile Gly Gly  Asn Lys Lys
    2120                2125                2130

Asn Gln  His Ile Asn Asn Asn  Ile Ser Asn Ser Asn  Thr Leu Asn
    2135                2140                2145

Asn Ser  Leu Asn Val Gln Asn  Ile Ser Ser Ser Asn  Ser Ala Ile
    2150                2155                2160

Ser Asn  Asn Gly Val Ile Asn  Asn Tyr Ser Pro Thr  His Ile Tyr
    2165                2170                2175

Glu Val  Asp Asn Leu Asn Asn  Ser Gln Asp Tyr Tyr  Leu Lys Asn
    2180                2185                2190

Asp Glu  Met Lys Asn Glu Leu  Asn Lys Val Glu Asp  Gln Lys Asn
    2195                2200                2205
```

```
Lys Lys  Asp Ile Ser Ser Thr  Asn Ser Leu Leu Lys  His Phe Met
    2210                 2215                 2220

Asn Asp  Asp Ile Leu Ile Asn  Asn Lys Val Lys Gln  Gln Pro Phe
    2225                 2230                 2235

Phe Asp  Ser His Asn Asn Tyr  Asn Lys Leu Gly His  Lys Gln Val
    2240                 2245                 2250

Lys Thr  Ser Ala Tyr Thr Glu  Ser Ala Ile Gly Leu  Gly Phe Arg
    2255                 2260                 2265

Lys Asn  Gly Tyr Ile Asn Asp  Cys Asp Leu Val Asn  Asn Asn Asn
    2270                 2275                 2280

Asn Asn  Asn Asn Asn Asn Met  His Ile Lys Asn Asn  Gly Val Ile
    2285                 2290                 2295

Leu Asn  Lys Leu Ile Ser Ser  Asn His Asp Ser Lys  Asp Asn Ser
    2300                 2305                 2310

Asn Asn  Asn Ile Lys Asp Lys  Asp Arg Glu Asp Asn  Asn Lys Asn
    2315                 2320                 2325

Ile Tyr  Asn Asn Asn Asn Asp  Arg Ser Ile Gly Ser  Tyr Val Asn
    2330                 2335                 2340

Asn Leu  Gly Val Ile Glu Asn  Gln Cys Glu Asn Ser  Lys Gly Ala
    2345                 2350                 2355

Asp Glu  Asn Thr Lys Asn Phe  Asn Asn Asn Lys Thr  Leu Asn Asn
    2360                 2365                 2370

Tyr Glu  Pro Glu Asn Lys Ser  Tyr Asn Tyr Ser Pro  Val Leu Asp
    2375                 2380                 2385

Glu Thr  Leu Glu Glu Arg Asp  Val Arg Ile Asn Arg  Glu Val Ser
    2390                 2395                 2400

Lys Cys  Lys Phe Val Asp Gly  Leu Ile Tyr Asp Glu  Ala Asn Lys
    2405                 2410                 2415

Cys Phe  Arg Ile Lys Ile Asn  Gly Tyr Arg Lys Ala  Tyr Ser Val
    2420                 2425                 2430

Ile Arg  Arg Gly Val Lys Glu  Ala Tyr Lys Leu Ser  Ile Glu Ser
    2435                 2440                 2445

Ile Glu  Gln Ile Lys Arg Gln  Thr Gln Thr Asn Asn  Phe Asn Asn
    2450                 2455                 2460

Asn Glu  Gln Ser Gln Val Asn  Thr Asn Asn Met Thr  Gln Ile Tyr
    2465                 2470                 2475

Asn Ser  Ser Ser Glu Asn Ser  Arg His Gly Ser Cys  Tyr Asn Tyr
    2480                 2485                 2490

Gln His  Asn His Lys Ser Lys  Leu Glu Asn Ser Asn  Asp Asn Pro
    2495                 2500                 2505

Glu Glu  Lys Tyr Asp His Ile  Asn Asn Met Thr Asn  Val Gly His
    2510                 2515                 2520

Glu Asn  Lys Gln Ser Ala Glu  Glu Ser Leu Phe Pro  Met Leu Asn
    2525                 2530                 2535

Val Asp  Asp Lys Tyr Tyr Glu  Leu Leu Lys Thr Ser  Ile Ile Ile
    2540                 2545                 2550

Cys Leu  Asn Asp Ile Leu Met  Asn Cys Ile Pro Gln  Val Phe His
    2555                 2560                 2565

Leu Tyr  Lys Asn Ile Asn Thr  Ser Asn Asp Ile Lys  Leu Glu Asp
    2570                 2575                 2580

Ile Leu  Tyr Thr Glu Arg Lys  Arg Lys Glu Gln Ser  Leu Lys Tyr
    2585                 2590                 2595
```

```
His Ile  Glu Tyr Thr Gln Asn  Ser Val Gly Val Ser  Ser Leu Ile
    2600                 2605                 2610

Pro Tyr  Leu Lys Leu Phe Ser  Thr Glu Ile Leu Asn  Asn Val Leu
    2615                 2620                 2625

Pro Ser  Ala Gln Ser Leu Glu  Ile Gln Arg Leu Ile  Ile His Ser
    2630                 2635                 2640

Leu Asp  Ile Gln Thr Tyr Asn  Thr Leu Tyr
    2645                 2650


<210> SEQ ID NO 31
<211> LENGTH: 1725
<212> TYPE: DNA
<213> ORGANISM: Plasmodium falciparum

<400> SEQUENCE: 31

atgaatcatc ttgggaatgt taaatattta gtcattgtgt ttttgatttt ctttgatttg     60

tttctagtta atggtagaga tgtgcaaaac aatatagtgg atgaaataaa atatcgtgaa    120

gaagtatgta atgatgaggt agatctttac cttctaatgg attgttctgg aagtatacgt    180

cgtcataatt gggtgaacca tgcagtacct ctagctatga aattgataca acaattaaat    240

cttaatgata atgcaattca cttatatgct agtgtttttt caaacaatgc aagagaaatt    300

attagattac atagtgatgc atctaaaaac aaagagaagg ctttaattat tataaagtca    360

ctcttaagta caaatcttcc atatggtaaa acaaacttaa ctgatgcact gttacaagta    420

agaaaacatt taaatgaccg aatcaataga gagaatgcta atcaattagt tgttatatta    480

acagatggaa ttccagatag tattcaagat tcattaaaag aatcaagaaa attaagtgat    540

cgtggtgtta aaatagctgt tttggtattt ggacaaggta ttaatgtagc tttcaacaga    600

tttcttgtag gttgtcatcc atcagatggt aaatgtaact tgtatgctga ttctgcatgg    660

gaaaatgtaa aaaatgttat cggacccttt atgaaggctg tttgtgttga agtagaaaaa    720

acagcaagtt gtggtgtttg ggacgaatgg tctccatgta gtgtaacttg tggtaaaggt    780

accaggtcaa gaaaaagaga aatcttacac gaaggatgta caagtgaatt acaagaacaa    840

tgtgaagaag aaagatgtct tccaaaacgg gaaccattag atgttccaga tgaacccgaa    900

gatgatcaac ctagaccaag aggagataat tttgctgtcg aaaaaccaaa cgaaaatata    960

atagataata atccacaaga accttcacca aatccagaag aaggaaaggg tgaaaatcca   1020

aacggatttg atttagatga aaatccagaa aatccaccaa atccaccaaa tccaccaaat   1080

ccaccaaatc caccaaatcc accaaatcca gatattcctg aacaagaacc aaatatacct   1140

gaagattcag aaaaagaagt accttctgat gttccaaaaa atccagaaga cgatcgagaa   1200

gaaaactttg atattccaaa gaaacccgaa aataagcacg ataatcaaaa taatttacca   1260

aatgataaaa gtgatagata tattccatat tcaccattat ctccaaaagt tttggataat   1320

gaaaggaaac aaagtgaccc ccaaagtcaa gataataatg gaaataggca cgtacctaat   1380

agtgaagata gagaaacacg tccacatggt agaaataatg aaaatagatc atacaataga   1440

aaacataaca atactccaaa acatcctgaa agggaagaac atgaaaagcc agataataat   1500

aaaaaaaaag caggatcaga taataaatat aaaattgcag gtggaatagc tggaggatta   1560

gctttactcg catgtgctgg acttgcttat aaattcgtag taccaggagc agcaacaccc   1620

tatgccggag aacctgcacc ttttgatgaa acattaggtg aagaagataa agatttggac   1680

gaacctgaac aattcagatt acctgaagaa aacgagtgga attaa                   1725
```

<210> SEQ ID NO 32
<211> LENGTH: 574
<212> TYPE: PRT
<213> ORGANISM: Plasmodium falciparum

<400> SEQUENCE: 32

```
Met Asn His Leu Gly Asn Val Lys Tyr Leu Val Ile Val Phe Leu Ile
1               5                   10                  15

Phe Phe Asp Leu Phe Leu Val Asn Gly Arg Asp Val Gln Asn Asn Ile
            20                  25                  30

Val Asp Glu Ile Lys Tyr Arg Glu Glu Val Cys Asn Asp Glu Val Asp
        35                  40                  45

Leu Tyr Leu Leu Met Asp Cys Ser Gly Ser Ile Arg Arg His Asn Trp
    50                  55                  60

Val Asn His Ala Val Pro Leu Ala Met Lys Leu Ile Gln Gln Leu Asn
65                  70                  75                  80

Leu Asn Asp Asn Ala Ile His Leu Tyr Ala Ser Val Phe Ser Asn Asn
                85                  90                  95

Ala Arg Glu Ile Ile Arg Leu His Ser Asp Ala Ser Lys Asn Lys Glu
            100                 105                 110

Lys Ala Leu Ile Ile Ile Lys Ser Leu Leu Ser Thr Asn Leu Pro Tyr
        115                 120                 125

Gly Lys Thr Asn Leu Thr Asp Ala Leu Leu Gln Val Arg Lys His Leu
    130                 135                 140

Asn Asp Arg Ile Asn Arg Glu Asn Ala Asn Gln Leu Val Val Ile Leu
145                 150                 155                 160

Thr Asp Gly Ile Pro Asp Ser Ile Gln Asp Ser Leu Lys Glu Ser Arg
                165                 170                 175

Lys Leu Ser Asp Arg Gly Val Lys Ile Ala Val Phe Gly Ile Gly Gln
            180                 185                 190

Gly Ile Asn Val Ala Phe Asn Arg Phe Leu Val Gly Cys His Pro Ser
        195                 200                 205

Asp Gly Lys Cys Asn Leu Tyr Ala Asp Ser Ala Trp Glu Asn Val Lys
    210                 215                 220

Asn Val Ile Gly Pro Phe Met Lys Ala Val Cys Val Glu Val Glu Lys
225                 230                 235                 240

Thr Ala Ser Cys Gly Val Trp Asp Glu Trp Ser Pro Cys Ser Val Thr
                245                 250                 255

Cys Gly Lys Gly Thr Arg Ser Arg Lys Arg Glu Ile Leu His Glu Gly
            260                 265                 270

Cys Thr Ser Glu Leu Gln Glu Gln Cys Glu Glu Glu Arg Cys Leu Pro
        275                 280                 285

Lys Arg Glu Pro Leu Asp Val Pro Asp Glu Pro Glu Asp Asp Gln Pro
    290                 295                 300

Arg Pro Arg Gly Asp Asn Phe Ala Val Glu Lys Pro Asn Glu Asn Ile
305                 310                 315                 320

Ile Asp Asn Asn Pro Gln Glu Pro Ser Pro Asn Pro Glu Glu Gly Lys
                325                 330                 335

Gly Glu Asn Pro Asn Gly Phe Asp Leu Asp Glu Asn Pro Glu Asn Pro
            340                 345                 350

Pro Asn Pro Pro Asn Pro Pro Asn Pro Pro Asn Pro Pro Asn Pro Pro
        355                 360                 365

Asn Pro Asp Ile Pro Glu Gln Glu Pro Asn Ile Pro Glu Asp Ser Glu
    370                 375                 380
```

```
Lys Glu Val Pro Ser Asp Val Pro Lys Asn Pro Glu Asp Asp Arg Glu
385                 390                 395                 400

Glu Asn Phe Asp Ile Pro Lys Lys Pro Glu Asn Lys His Asp Asn Gln
                405                 410                 415

Asn Asn Leu Pro Asn Asp Lys Ser Asp Arg Tyr Ile Pro Tyr Ser Pro
            420                 425                 430

Leu Ser Pro Lys Val Leu Asp Asn Glu Arg Lys Gln Ser Asp Pro Gln
        435                 440                 445

Ser Gln Asp Asn Asn Gly Asn Arg His Val Pro Asn Ser Glu Asp Arg
    450                 455                 460

Glu Thr Arg Pro His Gly Arg Asn Asn Glu Asn Arg Ser Tyr Asn Arg
465                 470                 475                 480

Lys His Asn Asn Thr Pro Lys His Pro Glu Arg Glu Glu His Glu Lys
                485                 490                 495

Pro Asp Asn Asn Lys Lys Lys Ala Gly Ser Asp Asn Lys Tyr Lys Ile
            500                 505                 510

Ala Gly Gly Ile Ala Gly Gly Leu Ala Leu Leu Ala Cys Ala Gly Leu
        515                 520                 525

Ala Tyr Lys Phe Val Val Pro Gly Ala Ala Thr Pro Tyr Ala Gly Glu
    530                 535                 540

Pro Ala Pro Phe Asp Glu Thr Leu Gly Glu Glu Asp Lys Asp Leu Asp
545                 550                 555                 560

Glu Pro Glu Gln Phe Arg Leu Pro Glu Glu Asn Glu Trp Asn
                565                 570


<210> SEQ ID NO 33
<211> LENGTH: 6648
<212> TYPE: DNA
<213> ORGANISM: Plasmodium falciparum

<400> SEQUENCE: 33

atgaataaat attggttgta tattgcttat gtttatctat tattaaacat actatcaaaa      60

tgtaataaaa tagaaaataa taataataag gtcaagaatt tgaccgttta caataatgat     120

ataggacaat attttaaaaa aaaggacata caatgcaaac accatataga aataaatcaa     180

gactctaatc ataatgaata ttccttttta tcattaaagg caagttcaat atttaaccag     240

tactatgttg ccaaattaat taatacccctt ttatatagag gatttcattt gaatgtctat     300

ttccataaaa atgtggctat gtatgaatcc ttttccagaa cgaacttttt cttttattta     360

accatattaa acaaaaaaaa tgtcaaaaaa attgttaaga taatatccaa agcagaacgt     420

tcaagtaata aaagaaagtt taatgtattc aagaagtatt taatttctga gtttgattat     480

cccaatttttg aaatcgacga caccgtaaaa aatgaaatga accaagcaat tttagtatat     540

aaaaaagcaa aatctgattc atactggagt gttatggatg cattaaagaa ggatggttta     600

ttattagcta gaaccttttt atctgtttct tttgttcaaa gtcttagagg tattatcggt     660

cttattaacc acaaattaat agatttatgt tttactaatg cctatgtatt taaccacgta     720

gcatcttttg ataaacttat tatgaataat atttttggtg ttataatgtc atatgtattt     780

aaatcacttt tactcttttt ctacccatta attatacctt tccgtggtgc atttgccttt     840

gctatatctg ctttttgtat cacacagttg ggaaaaatag tatttgcaat atacaaaaat     900

ctcagacaat tatatagaat atcatacaga aaaatataca gtattgtatt aaaagttaaa     960

ttaagaaatg aaccagaact taaaaaatat gccatgaaat tattatacgg tgatgcttta    1020

attatgatta caaaaatatg gaagttgtca tatgtaaatg tcagtgagca cttgaatgga    1080
```

aaaaatgttt atccaatttt aaataactta tttgaaaaaa atttgggaac aggtttcttt 1140
gattttagta actccttatt caaatatgtt atgaattact tagaggaaat aaatttatta 1200
aatgccaaaa gtgttgatgt agaaaaagaa ctcattttga acagacataa tttcaaacta 1260
ttacttaaaa ttttaaagat tactaaaaag tccttattat atgaagagtc ttatatgaag 1320
atatctgttg ctaatttatt aacaaaattt tacaccttga ttttagtaaa tatagaacat 1380
ataagtaaat taaatccaaa ggaacatttc tataatgatt tagataatga atttaaacat 1440
atatatcaag atcaaatgtt tgaattattt atacaaaaga tatcttcaga tattgttaga 1500
aaaccattta tcaaaagaaa tatcggaaga atagataaag gtagtataga attaacatta 1560
gcattaataa aagtaaaatt attacattac aaaccaacat tgaataatcc atattccagt 1620
ttatattttg atgagaattt aaaaaaacaa ttaaattatg catttaaatt aattattatt 1680
ggttctacta gtataattgc tagtcttgca aactacggag aaagatatgg tgttttaaaa 1740
caatgtccat tagatattgt taagaattta aatcaacaat gtgaatatgt ttcttttgaa 1800
attaagaaat taatattccc aataaatatt tttgtgaact tattaattcc attattttta 1860
ccatatgatg atgtattagt agataaaaat ataattgatg aagtcaaaaa attctttaac 1920
gttattatcg ataccgatga ttcttactta caaaaatata tgaaaacaac aattaacact 1980
ataagaaaat caaaagatct agatataaat aatgtaaatt atgaagaaga aatggaaaaa 2040
attgtagttc aagaagcaca taaagttatt gaagaaatta acaaagaaag acgagcatct 2100
ttcaaatttc aagattttgt agtcaaagaa gattcagtag tattgtataa taaaagtgga 2160
atccaatatt catttaaatt tgatcattta aatagaaaag aagattttat gcgtattata 2220
ggtagttatc aatttaaaaa tcccataggt tatcaaacat cacaacttgt ttttgaacct 2280
caaaataatc atattggttc tttaatggtt ggatcaaata aaaatacatt cgatggaaaa 2340
ttaagtgtat gtcatatgtg ttataaagaa gatgatgatt ctttggttgt tgatgcaata 2400
tttagtatcc tctggtcttc tggaattgat agatttagtg cctttatatt cgcttccttc 2460
atcggtgctg tgaaacaaac ttatcaccaa ggtacctcct ggaaacgtgc tctcagtaat 2520
atggccccaa ccgaatttta cgaaatgcac aaaattttta tggataagag tgtttacgga 2580
aaagaaaaaa gtcaaaatta cttcttgaaa aacataagaa aatacagatt tcaatttagt 2640
agaggctcat tctctagaat gtttagaacg ttcttagaaa attctttaaa taaaattaat 2700
ttctttaact cagaagaagc catcattatt ttagttatgt caaccttata tgctctttac 2760
aaaaatattg aaaaattcga tattccatta aaagaaacct ataaattata tcaacagaaa 2820
ttaattgaat cttattacca tgtagacaaa tattcacacc attatgaaac atatactcta 2880
aatattagaa gaaaaaaata caatgcactt gtcaagagtg aacatgaaaa ggcacaagaa 2940
gctagccaag gagaaggtaa agacgaagca gaaaatgctg aattaaaaaa aagagttgaa 3000
aagagaatta actttaatga tatacaatta actatggaag atgaagttgt aaggaataca 3060
aaatatttac aattagaatt acaagcaaaa ccacaagaaa gagaaaaaat catacaatat 3120
ttaacatata aatataagga aataccaaat catgaaatgt tcccacattt accacaccaa 3180
tgttatttct tattatatta taattatgaa cccttttag aaaaaaacct tcatggtcta 3240
gaaggtgttg ttagtaaaat tacacgaaaa tcagtcttaa gtagatactt aaaaaatatt 3300
aatttaatac aaccagagaa aacgagattt gcatctataa aattaaaaga tttaatcaat 3360
atactttgtg gtacacacat gtttttgaaa aaagaacata tcacatttga tgaaatatat 3420

```
aaatatgaaa attcaaatga tgctttgaaa catcttctta tcattgttgc attattaaga   3480
attgaaaaga gaactaaccg atattcttgg acaacatatt taactttaca aaaacaatta   3540
gatgaaagaa aaagatatta tgatacacca tttaaatatt tatttttaaa aataagcaaa   3600
gtaagaagat tttatggaag cgcaaaaaaa aaaatgttat taggatttgg taaaaaattt   3660
aaaggagtta gatttttaaa tatattaaga tataccagat tctttgaaat tatggaatat   3720
gctgaatcaa ttaatgaatt ttatccatat tgttatatta aatttgaaga tgtattaaca   3780
ttctcaaatg tattttataa atttaaatat tctcttttaa gatatacaac aagtaaacaa   3840
tctgttagaa atgttgtgaa caatttcaat ttgtctccac aaacaacagg aaacaatgaa   3900
aacttattat taagaatata tagatttatt gaattaatta ttaaaaagaa gtataatgtt   3960
gatatacagc atgttagaaa agatgataaa gattttaata gacatgcata taataagaat   4020
gaatatatat taaatgatat aaagtttaat cctaatattg aacaatattt aagacaatta   4080
actggtttca ttaaactttt aacagatatg aaatttacta atttcttatt cttaagaaac   4140
ttatattact ttgttaaatt ttatgcagta acgggtgatt taacttattc aataaataat   4200
tcttctatat atttatgtag tagaaattat ttagaattta tattaaattc cattattgaa   4260
tttgaaaatt ttaaaaaatt tatggttaag attaaagaaa aatttgatat tgaaaaatat   4320
ccaattgatc catataattt ccaaacagaa tgttattcta tagatagtgt caaaacatat   4380
agattctttt taagtgattt agataaatta aaatcatatc aagatataga aaacttacag   4440
aatgtctcat cattttataa agattactta tatatgggat tattttatga aaacttagat   4500
gtcagaaatt taaatgtata ttataatttc aataaaaaaa aaaatcaaga tcataaagca   4560
catggatcaa atgtattcct tgatgggggt ctttcattaa gtaaaaatat gtcatttagt   4620
gatataaatg atttaagtga atctattcaa aattatttat atttagaaaa atttttagct   4680
gatagtaata taccttctat tccatatcaa ggattttcgg ttagacgtgt aaatgatggt   4740
atgcatgtaa catataataa tagatcaact acaccaccac tttataaaga taatgtttta   4800
gatcaattcg aattagtagg aaaatcatta attagtgaat atttccaaaa agtcaaatgt   4860
tcatttattc aatatccatt caatttatat tattggctag tccttaatcc aggaaaacca   4920
aatataagct taagtagtaa aaccggtcta attaaagaag atgatttaat acctaaaacc   4980
gttgaagaaa aattaaagga agaagaagaa catgatatta aaattgttga aaatatatta   5040
tctgaagata tctttgattt taaagataaa tcagatgatg atcaaagtac aaccgctgat   5100
gtactttcta cagacacaga tgattcagaa actgacgctg aaaaaacatc aaacaattca   5160
aataccctac acaaaaaaga aacaccagca atgaaatata atatgaatat agcacaagat   5220
gaaattaata gacaaaatga tgtatctaaa aatacaacat atgcagaaaa taatgaatac   5280
acatctgaaa atataactaa accatcagat caaaatacag aaaactatgg aacaaaaatg   5340
ccctctccat cattcataca aatagataaa gttaaccaac aagatcaaca aaatgatgct   5400
catatagaaa gttctaaaaa tactcaagaa aatcttaact atgatgataa cactaatatg   5460
tatgaagaaa ataaaaatga taagaaaaac aaaaaattaa ataataatac aaaagaaata   5520
agtttccttg aaagaagaga aactaatcct ataccattta gttcaaatat gattaatgaa   5580
aaaaataaag aagctcataa agaacactat ggaaatttca atagaccata taatatatat   5640
gtacctaaaa aagatatctt cagaaatttc catctagttg taaaagtagt acatgcatta   5700
atatccttaa ataaattctc catggttagt ccagatacaa tattaaaaaa aggtatagaa   5760
tccatgaaaa aaaaacactc actcaaaatg attaaaaata taaatccatt tatacataaa   5820
```

```
atgatacttg acatgaatga aaccatacaa aaattaaaat ccgatagtga aaaagcatat   5880

ggtggaccaa aagcagatat tatatcttta tataaaattg tggaattcca attatttaat   5940

caatatatta tatatccacc attaaaaaga ttaaccaaaa aagaacttaa atatatactt   6000

gatgttgtta accaaggata ttatttctac ctaaaaaatg ttatcacaaa attaaaaaga   6060

gaaaatctac aaaaatcgaa agttgtcaaa atatttaata atttccaaga attctctaat   6120

ttattagatg atgatggtgt agataaatta tataatatat ttactgaaac atttaaatgt   6180

aaaaatatta aatgttttga tcttttattc caaggattct taaccgaaca atataataac   6240

attgtctatc gttatacaca tgatcatgat gctatgaact catataatga taacatattt   6300

aataataaag aattattaaa caaaatattt agaagagcat atgacaacta ttttattaca   6360

cctgttaaaa acaatcaacc aaaaaaactc atatctttag aaaaaccatc attagaacaa   6420

ccagtattga cgttagaaga atttgcatat ggattccatg aatttggaaa taaaattgaa   6480

aaatggagat caatgcttac cctattcaat ataagacata tatatattaa tatatgccac   6540

atgctattaa gtgttaaaca tagtatacaa cgatcacaca gagtttttat gcacaaattt   6600

ggtttcttcg gtatcttcag aagaaagagg gaaatttaca taccataa                6648
```

```
<210> SEQ ID NO 34
<211> LENGTH: 2215
<212> TYPE: PRT
<213> ORGANISM: Plasmodium falciparum

<400> SEQUENCE: 34

Met Asn Lys Tyr Trp Leu Tyr Ile Ala Tyr Val Tyr Leu Leu Leu Asn
1               5                   10                  15

Ile Leu Ser Lys Cys Asn Lys Ile Glu Asn Asn Asn Asn Lys Val Lys
            20                  25                  30

Asn Leu Thr Val Tyr Asn Asn Asp Ile Gly Gln Tyr Phe Lys Lys Lys
        35                  40                  45

Asp Ile Gln Cys Lys His His Ile Glu Ile Asn Gln Asp Ser Asn His
    50                  55                  60

Asn Glu Tyr Ser Phe Leu Ser Leu Lys Ala Ser Ser Ile Phe Asn Gln
65                  70                  75                  80

Tyr Tyr Val Ala Lys Leu Ile Asn Thr Leu Leu Tyr Arg Gly Phe His
                85                  90                  95

Leu Asn Val Tyr Phe His Lys Asn Val Ala Met Tyr Glu Ser Phe Ser
            100                 105                 110

Arg Thr Asn Phe Phe Phe Tyr Leu Thr Ile Leu Asn Lys Lys Asn Val
        115                 120                 125

Lys Lys Ile Val Lys Ile Ile Ser Lys Ala Glu Arg Ser Ser Asn Lys
    130                 135                 140

Arg Lys Phe Asn Val Phe Lys Lys Tyr Leu Ile Ser Glu Phe Asp Tyr
145                 150                 155                 160

Pro Asn Phe Glu Ile Asp Asp Thr Val Lys Asn Glu Met Asn Gln Ala
                165                 170                 175

Ile Leu Val Tyr Lys Lys Ala Lys Ser Asp Ser Tyr Trp Ser Val Met
            180                 185                 190

Asp Ala Leu Lys Lys Asp Gly Leu Leu Leu Ala Arg Thr Phe Leu Ser
        195                 200                 205

Val Ser Phe Val Gln Ser Leu Arg Gly Ile Ile Gly Leu Ile Asn His
    210                 215                 220
```

```
Lys Leu Ile Asp Leu Cys Phe Thr Asn Ala Tyr Val Phe Asn His Val
225                 230                 235                 240

Ala Ser Phe Asp Lys Leu Ile Met Asn Asn Ile Phe Gly Val Ile Met
                245                 250                 255

Ser Tyr Val Phe Lys Ser Leu Leu Leu Phe Phe Tyr Pro Leu Ile Ile
            260                 265                 270

Pro Phe Arg Gly Ala Phe Ala Phe Ala Ile Ser Ala Phe Cys Ile Thr
        275                 280                 285

Gln Leu Gly Lys Ile Val Phe Ala Ile Tyr Lys Asn Leu Arg Gln Leu
    290                 295                 300

Tyr Arg Ile Ser Tyr Arg Lys Ile Tyr Ser Ile Val Leu Lys Val Lys
305                 310                 315                 320

Leu Arg Asn Glu Pro Glu Leu Lys Lys Tyr Ala Met Lys Leu Leu Tyr
                325                 330                 335

Gly Asp Ala Leu Ile Met Ile Thr Lys Ile Trp Lys Leu Ser Tyr Val
            340                 345                 350

Asn Val Ser Glu His Leu Asn Gly Lys Asn Val Tyr Pro Ile Leu Asn
        355                 360                 365

Asn Leu Phe Glu Lys Asn Leu Gly Thr Gly Phe Phe Asp Phe Ser Asn
    370                 375                 380

Ser Leu Phe Lys Tyr Val Met Asn Tyr Leu Glu Glu Ile Asn Leu Leu
385                 390                 395                 400

Asn Ala Lys Ser Val Asp Val Glu Lys Glu Leu Ile Leu Asn Arg His
                405                 410                 415

Asn Phe Lys Leu Leu Leu Lys Ile Leu Lys Ile Thr Lys Lys Ser Leu
            420                 425                 430

Leu Tyr Glu Glu Ser Tyr Met Lys Ile Ser Val Ala Asn Leu Leu Thr
        435                 440                 445

Lys Phe Tyr Thr Leu Ile Leu Val Asn Ile Glu His Ile Ser Lys Leu
    450                 455                 460

Asn Pro Lys Glu His Phe Tyr Asn Asp Leu Asp Asn Glu Phe Lys His
465                 470                 475                 480

Ile Tyr Gln Asp Gln Met Phe Glu Leu Phe Ile Gln Lys Ile Ser Ser
                485                 490                 495

Asp Ile Val Arg Lys Pro Phe Ile Lys Arg Asn Ile Gly Arg Ile Asp
            500                 505                 510

Lys Gly Ser Ile Glu Leu Thr Leu Ala Leu Ile Lys Val Lys Leu Leu
        515                 520                 525

His Tyr Lys Pro Thr Leu Asn Asn Pro Tyr Ser Ser Leu Tyr Phe Asp
    530                 535                 540

Glu Asn Leu Lys Lys Gln Leu Asn Tyr Ala Phe Lys Leu Ile Ile Ile
545                 550                 555                 560

Gly Ser Thr Ser Ile Ile Ala Ser Leu Ala Asn Tyr Gly Glu Arg Tyr
                565                 570                 575

Gly Val Leu Lys Gln Cys Pro Leu Asp Ile Val Lys Asn Leu Asn Gln
            580                 585                 590

Gln Cys Glu Tyr Val Ser Phe Glu Ile Lys Lys Leu Ile Phe Pro Ile
        595                 600                 605

Asn Ile Phe Val Asn Leu Leu Ile Pro Leu Phe Leu Pro Tyr Asp Asp
    610                 615                 620

Val Leu Val Asp Lys Asn Ile Ile Asp Glu Val Lys Lys Phe Phe Asn
625                 630                 635                 640

Val Ile Ile Asp Thr Asp Asp Ser Tyr Leu Gln Lys Tyr Met Lys Thr
```

```
            645                 650                 655

Thr Ile Asn Thr Ile Arg Lys Ser Lys Asp Leu Asp Ile Asn Asn Val
        660                 665                 670

Asn Tyr Glu Glu Glu Met Glu Lys Ile Val Val Gln Glu Ala His Lys
    675                 680                 685

Val Ile Glu Glu Ile Asn Lys Glu Arg Arg Ala Ser Phe Lys Phe Gln
    690                 695                 700

Asp Phe Val Val Lys Glu Asp Ser Val Val Leu Tyr Asn Lys Ser Gly
705                 710                 715                 720

Ile Gln Tyr Ser Phe Lys Phe Asp His Leu Asn Arg Lys Glu Asp Phe
            725                 730                 735

Met Arg Ile Ile Gly Ser Tyr Gln Phe Lys Asn Pro Ile Gly Tyr Gln
        740                 745                 750

Thr Ser Gln Leu Val Phe Glu Pro Gln Asn Asn His Ile Gly Ser Leu
    755                 760                 765

Met Val Gly Ser Asn Lys Asn Thr Phe Asp Gly Lys Leu Ser Val Cys
    770                 775                 780

His Met Cys Tyr Lys Glu Asp Asp Asp Ser Leu Val Val Asp Ala Ile
785                 790                 795                 800

Phe Ser Ile Leu Trp Ser Ser Gly Ile Asp Arg Phe Ser Ala Phe Ile
            805                 810                 815

Phe Ala Ser Phe Ile Gly Ala Val Lys Gln Thr Tyr His Gln Gly Thr
        820                 825                 830

Ser Trp Lys Arg Ala Leu Ser Asn Met Ala Pro Thr Glu Phe Tyr Glu
    835                 840                 845

Met His Lys Ile Phe Met Asp Lys Ser Val Tyr Gly Lys Glu Lys Ser
    850                 855                 860

Gln Asn Tyr Phe Leu Lys Asn Ile Arg Lys Tyr Arg Phe Gln Phe Ser
865                 870                 875                 880

Arg Gly Ser Phe Ser Arg Met Phe Arg Thr Phe Leu Glu Asn Ser Leu
            885                 890                 895

Asn Lys Ile Asn Phe Phe Asn Ser Glu Glu Ala Ile Ile Ile Leu Val
        900                 905                 910

Met Ser Thr Leu Tyr Ala Leu Tyr Lys Asn Ile Glu Lys Phe Asp Ile
    915                 920                 925

Pro Leu Lys Glu Thr Tyr Lys Leu Tyr Gln Gln Lys Leu Ile Glu Ser
    930                 935                 940

Tyr Tyr His Val Asp Lys Tyr Ser His His Tyr Glu Thr Tyr Thr Leu
945                 950                 955                 960

Asn Ile Arg Arg Lys Lys Tyr Asn Ala Leu Val Lys Ser Glu His Glu
            965                 970                 975

Lys Ala Gln Glu Ala Ser Gln Gly Glu Gly Lys Asp Glu Ala Glu Asn
        980                 985                 990

Ala Glu Leu Lys Lys Arg Val Glu  Lys Arg Ile Asn Phe  Asn Asp Ile
    995                 1000                1005

Gln Leu  Thr Met Glu Asp Glu  Val Val Arg Asn Thr  Lys Tyr Leu
    1010                1015                1020

Gln Leu  Glu Leu Gln Ala Lys  Pro Gln Glu Arg Glu  Lys Ile Ile
    1025                1030                1035

Gln Tyr  Leu Thr Tyr Lys Tyr  Lys Glu Ile Pro Asn  His Glu Met
    1040                1045                1050

Phe Pro  His Leu Pro His Gln  Cys Tyr Phe Leu Leu  Tyr Tyr Asn
    1055                1060                1065
```

```
Tyr Glu  Pro Phe Leu Glu Lys  Asn Leu His Gly Leu  Glu Gly Val
    1070                 1075                 1080

Val Ser  Lys Ile Thr Arg Lys  Ser Val Leu Ser Arg  Tyr Leu Lys
    1085                 1090                 1095

Asn Ile  Asn Leu Ile Gln Pro  Glu Lys Thr Arg Phe  Ala Ser Ile
    1100                 1105                 1110

Lys Leu  Lys Asp Leu Ile Asn  Ile Leu Cys Gly Thr  His Met Phe
    1115                 1120                 1125

Leu Lys  Lys Glu His Ile Thr  Phe Asp Glu Ile Tyr  Lys Tyr Glu
    1130                 1135                 1140

Asn Ser  Asn Asp Ala Leu Lys  His Leu Leu Ile Ile  Val Ala Leu
    1145                 1150                 1155

Leu Arg  Ile Glu Lys Arg Thr  Asn Arg Tyr Ser Trp  Thr Thr Tyr
    1160                 1165                 1170

Leu Thr  Leu Gln Lys Gln Leu  Asp Glu Arg Lys Arg  Tyr Tyr Asp
    1175                 1180                 1185

Thr Pro  Phe Lys Tyr Leu Phe  Leu Lys Ile Ser Lys  Val Arg Arg
    1190                 1195                 1200

Phe Tyr  Gly Ser Ala Lys Lys  Lys Met Leu Leu Gly  Phe Gly Lys
    1205                 1210                 1215

Lys Phe  Lys Gly Val Arg Phe  Leu Asn Ile Leu Arg  Tyr Thr Arg
    1220                 1225                 1230

Phe Phe  Glu Ile Met Glu Tyr  Ala Glu Ser Ile Asn  Glu Phe Tyr
    1235                 1240                 1245

Pro Tyr  Cys Tyr Ile Lys Phe  Glu Asp Val Leu Thr  Phe Ser Asn
    1250                 1255                 1260

Val Phe  Tyr Lys Phe Lys Tyr  Ser Leu Leu Arg Tyr  Thr Thr Ser
    1265                 1270                 1275

Lys Gln  Ser Val Arg Asn Val  Val Asn Asn Phe Asn  Leu Ser Pro
    1280                 1285                 1290

Gln Thr  Thr Gly Asn Asn Glu  Asn Leu Leu Leu Arg  Ile Tyr Arg
    1295                 1300                 1305

Phe Ile  Glu Leu Ile Ile Lys  Lys Lys Tyr Asn Val  Asp Ile Gln
    1310                 1315                 1320

His Val  Arg Lys Asp Asp Lys  Asp Phe Asn Arg His  Ala Tyr Asn
    1325                 1330                 1335

Lys Asn  Glu Tyr Ile Leu Asn  Asp Ile Lys Phe Asn  Pro Asn Ile
    1340                 1345                 1350

Glu Gln  Tyr Leu Arg Gln Leu  Thr Gly Phe Ile Lys  Leu Leu Thr
    1355                 1360                 1365

Asp Met  Lys Phe Thr Asn Phe  Leu Phe Leu Arg Asn  Leu Tyr Tyr
    1370                 1375                 1380

Phe Val  Lys Phe Tyr Ala Val  Thr Gly Asp Leu Thr  Tyr Ser Ile
    1385                 1390                 1395

Asn Asn  Ser Ser Ile Tyr Leu  Cys Ser Arg Asn Tyr  Leu Glu Phe
    1400                 1405                 1410

Ile Leu  Asn Ser Ile Ile Glu  Phe Glu Asn Phe Lys  Lys Phe Met
    1415                 1420                 1425

Val Lys  Ile Lys Glu Lys Phe  Asp Ile Glu Lys Tyr  Pro Ile Asp
    1430                 1435                 1440

Pro Tyr  Asn Phe Gln Thr Glu  Cys Tyr Ser Ile Asp  Ser Val Lys
    1445                 1450                 1455
```

```
Thr Tyr  Arg Phe Phe Leu Ser  Asp Leu Asp Lys Leu  Lys Ser Tyr
    1460                 1465                 1470

Gln Asp  Ile Glu Asn Leu Gln  Asn Val Ser Ser Phe  Tyr Lys Asp
    1475                 1480                 1485

Tyr Leu  Tyr Met Gly Leu Phe  Tyr Glu Asn Leu Asp  Val Arg Asn
    1490                 1495                 1500

Leu Asn  Val Tyr Tyr Asn Phe  Asn Lys Lys Lys Asn  Gln Asp His
    1505                 1510                 1515

Lys Ala  His Gly Ser Asn Val  Phe Leu Asp Gly Gly  Leu Ser Leu
    1520                 1525                 1530

Ser Lys  Asn Met Ser Phe Ser  Asp Ile Asn Asp Leu  Ser Glu Ser
    1535                 1540                 1545

Ile Gln  Asn Tyr Leu Tyr Leu  Glu Lys Phe Leu Ala  Asp Ser Asn
    1550                 1555                 1560

Ile Pro  Ser Ile Pro Tyr Gln  Gly Phe Ser Val Arg  Arg Val Asn
    1565                 1570                 1575

Asp Gly  Met His Val Thr Tyr  Asn Asn Arg Ser Thr  Thr Pro Pro
    1580                 1585                 1590

Leu Tyr  Lys Asp Asn Val Leu  Asp Gln Phe Glu Leu  Val Gly Lys
    1595                 1600                 1605

Ser Leu  Ile Ser Glu Tyr Phe  Gln Lys Val Lys Cys  Ser Phe Ile
    1610                 1615                 1620

Gln Tyr  Pro Phe Asn Leu Tyr  Tyr Trp Leu Val Leu  Asn Pro Gly
    1625                 1630                 1635

Lys Pro  Asn Ile Ser Leu Ser  Ser Lys Thr Gly Leu  Ile Lys Glu
    1640                 1645                 1650

Asp Asp  Leu Ile Pro Lys Thr  Val Glu Glu Lys Leu  Lys Glu Glu
    1655                 1660                 1665

Glu Glu  His Asp Ile Lys Ile  Val Glu Asn Ile Leu  Ser Glu Asp
    1670                 1675                 1680

Ile Phe  Asp Phe Lys Asp Lys  Ser Asp Asp Asp Gln  Ser Thr Thr
    1685                 1690                 1695

Ala Asp  Val Leu Ser Thr Asp  Thr Asp Asp Ser Glu  Thr Asp Ala
    1700                 1705                 1710

Glu Lys  Thr Ser Asn Asn Ser  Asn Thr Leu His Lys  Lys Glu Thr
    1715                 1720                 1725

Pro Ala  Met Lys Tyr Asn Met  Asn Ile Ala Gln Asp  Glu Ile Asn
    1730                 1735                 1740

Arg Gln  Asn Asp Val Ser Lys  Asn Thr Thr Tyr Ala  Glu Asn Asn
    1745                 1750                 1755

Glu Tyr  Thr Ser Glu Asn Ile  Thr Lys Pro Ser Asp  Gln Asn Thr
    1760                 1765                 1770

Glu Asn  Tyr Gly Thr Lys Met  Pro Ser Pro Ser Phe  Ile Gln Ile
    1775                 1780                 1785

Asp Lys  Val Asn Gln Gln Asp  Gln Gln Asn Asp Ala  His Ile Glu
    1790                 1795                 1800

Ser Ser  Lys Asn Thr Gln Glu  Asn Leu Asn Tyr Asp  Asp Asn Thr
    1805                 1810                 1815

Asn Met  Tyr Glu Glu Asn Lys  Asn Asp Lys Lys Asn  Lys Lys Leu
    1820                 1825                 1830

Asn Asn  Asn Thr Lys Glu Ile  Ser Phe Leu Glu Arg  Arg Glu Thr
    1835                 1840                 1845

Asn Pro  Ile Pro Phe Ser Ser  Asn Met Ile Asn Glu  Lys Asn Lys
```

```
    1850                 1855                 1860

Glu Ala  His Lys Glu His Tyr  Gly Asn Phe Asn Arg  Pro Tyr Asn
    1865                 1870                 1875

Ile Tyr  Val Pro Lys Lys Asp  Ile Phe Arg Asn Phe  His Leu Val
    1880                 1885                 1890

Val Lys  Val Val His Ala Leu  Ile Ser Leu Asn Lys  Phe Ser Met
    1895                 1900                 1905

Val Ser  Pro Asp Thr Ile Leu  Lys Lys Gly Ile Glu  Ser Met Lys
    1910                 1915                 1920

Lys Lys  His Ser Leu Lys Met  Ile Lys Asn Ile Asn  Pro Phe Ile
    1925                 1930                 1935

His Lys  Met Ile Leu Asp Met  Asn Glu Thr Ile Gln  Lys Leu Lys
    1940                 1945                 1950

Ser Asp  Ser Glu Lys Ala Tyr  Gly Gly Pro Lys Ala  Asp Ile Ile
    1955                 1960                 1965

Ser Leu  Tyr Lys Ile Val Glu  Phe Gln Leu Phe Asn  Gln Tyr Ile
    1970                 1975                 1980

Ile Tyr  Pro Pro Leu Lys Arg  Leu Thr Lys Lys Glu  Leu Lys Tyr
    1985                 1990                 1995

Ile Leu  Asp Val Val Asn Gln  Gly Tyr Tyr Phe Tyr  Leu Lys Asn
    2000                 2005                 2010

Val Ile  Thr Lys Leu Lys Arg  Glu Asn Leu Gln Lys  Ser Lys Val
    2015                 2020                 2025

Val Lys  Ile Phe Asn Asn Phe  Gln Glu Phe Ser Asn  Leu Leu Asp
    2030                 2035                 2040

Asp Asp  Gly Val Asp Lys Leu  Tyr Asn Ile Phe Thr  Glu Thr Phe
    2045                 2050                 2055

Lys Cys  Lys Asn Ile Lys Cys  Phe Asp Leu Leu Phe  Gln Gly Phe
    2060                 2065                 2070

Leu Thr  Glu Gln Tyr Asn Asn  Ile Val Tyr Arg Tyr  Thr His Asp
    2075                 2080                 2085

His Asp  Ala Met Asn Ser Tyr  Asn Asp Asn Ile Phe  Asn Asn Lys
    2090                 2095                 2100

Glu Leu  Leu Asn Lys Ile Phe  Arg Arg Ala Tyr Asp  Asn Tyr Phe
    2105                 2110                 2115

Ile Thr  Pro Val Lys Asn Asn  Gln Pro Lys Lys Leu  Ile Ser Leu
    2120                 2125                 2130

Glu Lys  Pro Ser Leu Glu Gln  Pro Val Leu Thr Leu  Glu Glu Phe
    2135                 2140                 2145

Ala Tyr  Gly Phe His Glu Phe  Gly Asn Lys Ile Glu  Lys Trp Arg
    2150                 2155                 2160

Ser Met  Leu Thr Leu Phe Asn  Ile Arg His Ile Tyr  Ile Asn Ile
    2165                 2170                 2175

Cys His  Met Leu Leu Ser Val  Lys His Ser Ile Gln  Arg Ser His
    2180                 2185                 2190

Arg Val  Phe Met His Lys Phe  Gly Phe Phe Gly Ile  Phe Arg Arg
    2195                 2200                 2205

Lys Arg  Glu Ile Tyr Ile Pro
    2210                 2215
```

```
<210> SEQ ID NO 35
<211> LENGTH: 1728
<212> TYPE: DNA
<213> ORGANISM: Plasmodium falciparum
```

<400> SEQUENCE: 35

```
atgtttattg ctgttgtggg ttgtactcac ggagaattag atttaatata ctcgactctc     60
gaaaagatag aagaagaaaa taaaataaag gttgaccttt taatttgttg tggtgatttt    120
caaagtgtac gatataatgt tgataatgag tgtttgaatg ttcctgcgaa atataaaaaa    180
gaacaaaatg atttcgtaga ttattttaca ggaaaaaaga aggcgaagat cttaactata    240
tttgtaggag gaaaccatga ggccatgaat gttttgaaac agttgtatta tggtgggtgg    300
gttgctccta atatatatta tttaggatac tctagtgttc ataatattaa taatttcaga    360
atatgtagtt taagcggtat atataaaaaa tatagttttt ttaagaaata ttatgaatcc    420
tatccttata cagatattac aaaggttagc gcatatcata taagaaaata tgaaatagaa    480
aaattaaaat tattaaaaaa taacgttgat attgttgtaa cacatgattg gccaaataat    540
attgaaaaac atggagatgt acatgactta ttaagaagaa aatatcattt tcaatctgac    600
gtatataata atacattagg taatcctcat accgaaatat tattaaataa attaaaacct    660
tatttctggt ttgcatcaca tttacatgta aaatattcgg cattgtatat ccacaatgat    720
cagaaacagt atactagatt tctttctcta gataaggctc aagaatataa acattttata    780
caaattttaa atattgtaaa gaaaaaggat tcttctatac atttaaattt tgatcatgtt    840
cctaaggtgt tgttaccaga accaggtagc aaaatggaca ttcaaaatga tgcacagcct    900
aatcatgatt tggagaattg tcctaataca aaaacaaata catgcaacaa taatgatcat    960
cataatgatg attctattaa tttagattat gatcatgaaa aggcattata cgaactagac   1020
agaaatatgc aactggatca ggaaaaaaat gacgaaaaaa atgttgacaa aagtgcagat   1080
aaaaatgtgt gcaataaaga catatcctta gaagataaaa atcaacataa taataacaat   1140
aataataatg atgatgatga tgatggtgta gatatacaag ctgatacatc aacaaatgtt   1200
gctgatcaaa ataataactc tgttccaaca aatttaaaag aaaatgagga agaatcttta   1260
aatgatcaaa atgaaaataa agatgaagaa actagccaag atgaaaatat aacagatgaa   1320
aaaaaaaaaa aaaaatttta tttatgttat gatatagaat ggctagctat agtaaaagca   1380
aatcatcatc tcatttctgc ctcatgtgat aaggattata atttagaaac actaacatat   1440
ccaacaaaag aagatttcga ttttgtagag aataaactta aagagttgga taataaaata   1500
acaataaaag gtaaagatta ttattgtgta aatggttata atacgccaaa ttataaaaac   1560
ctccaagaac aaagacagtt atttttaaaa cgtttcgaat tagaggagtt aagtatatac   1620
acagagtcag agttgaattt ttttgctgaa gaaatgaaaa cattggaaaa aatgaatact   1680
gatattcata atgaggagga taagaatgaa tgtactatag aagcatag                1728
```

<210> SEQ ID NO 36
<211> LENGTH: 575
<212> TYPE: PRT
<213> ORGANISM: Plasmodium falciparum

<400> SEQUENCE: 36

```
Met Phe Ile Ala Val Val Gly Cys Thr His Gly Glu Leu Asp Leu Ile
1               5                   10                  15

Tyr Ser Thr Leu Glu Lys Ile Glu Glu Glu Asn Lys Ile Lys Val Asp
            20                  25                  30

Leu Leu Ile Cys Cys Gly Asp Phe Gln Ser Val Arg Tyr Asn Val Asp
        35                  40                  45

Asn Glu Cys Leu Asn Val Pro Ala Lys Tyr Lys Lys Glu Gln Asn Asp
```

```
    50                  55                  60

Phe Val Asp Tyr Phe Thr Gly Lys Lys Lys Ala Lys Ile Leu Thr Ile
65                  70                  75                  80

Phe Val Gly Gly Asn His Glu Ala Met Asn Val Leu Lys Gln Leu Tyr
                85                  90                  95

Tyr Gly Gly Trp Val Ala Pro Asn Ile Tyr Tyr Leu Gly Tyr Ser Ser
            100                 105                 110

Val His Asn Ile Asn Asn Phe Arg Ile Cys Ser Leu Ser Gly Ile Tyr
        115                 120                 125

Lys Lys Tyr Ser Phe Phe Lys Lys Tyr Tyr Glu Ser Tyr Pro Tyr Thr
    130                 135                 140

Asp Ile Thr Lys Val Ser Ala Tyr His Ile Arg Lys Tyr Glu Ile Glu
145                 150                 155                 160

Lys Leu Lys Leu Leu Lys Asn Asn Val Asp Ile Val Val Thr His Asp
                165                 170                 175

Trp Pro Asn Asn Ile Glu Lys His Gly Asp Val His Asp Leu Leu Arg
            180                 185                 190

Arg Lys Tyr His Phe Gln Ser Asp Val Tyr Asn Asn Thr Leu Gly Asn
        195                 200                 205

Pro His Thr Glu Ile Leu Leu Asn Lys Leu Lys Pro Tyr Phe Trp Phe
    210                 215                 220

Ala Ser His Leu His Val Lys Tyr Ser Ala Leu Tyr Ile His Asn Asp
225                 230                 235                 240

Gln Lys Gln Tyr Thr Arg Phe Leu Ser Leu Asp Lys Ala Gln Glu Tyr
                245                 250                 255

Lys His Phe Ile Gln Ile Leu Asn Ile Val Lys Lys Lys Asp Ser Ser
            260                 265                 270

Ile His Leu Asn Phe Asp His Val Pro Lys Val Leu Leu Pro Glu Pro
        275                 280                 285

Gly Ser Lys Met Asp Ile Gln Asn Asp Ala Gln Pro Asn His Asp Leu
    290                 295                 300

Glu Asn Cys Pro Asn Thr Lys Thr Asn Thr Cys Asn Asn Asn Asp His
305                 310                 315                 320

His Asn Asp Asp Ser Ile Asn Leu Asp Tyr Asp His Glu Lys Ala Leu
                325                 330                 335

Tyr Glu Leu Asp Arg Asn Met Gln Leu Asp Gln Glu Lys Asn Asp Glu
            340                 345                 350

Lys Asn Val Asp Lys Ser Ala Asp Lys Asn Val Cys Asn Lys Asp Ile
        355                 360                 365

Ser Leu Glu Asp Lys Asn Gln His Asn Asn Asn Asn Asn Asn Asn Asp
    370                 375                 380

Asp Asp Asp Asp Gly Val Asp Ile Gln Ala Asp Thr Ser Thr Asn Val
385                 390                 395                 400

Ala Asp Gln Asn Asn Asn Ser Val Pro Thr Asn Leu Lys Glu Asn Glu
                405                 410                 415

Glu Glu Ser Leu Asn Asp Gln Asn Glu Asn Lys Asp Glu Glu Thr Ser
            420                 425                 430

Gln Asp Glu Asn Ile Thr Asp Glu Lys Lys Lys Lys Lys Phe Tyr Leu
        435                 440                 445

Cys Tyr Asp Ile Glu Trp Leu Ala Ile Val Lys Ala Asn His His Leu
    450                 455                 460

Ile Ser Ala Ser Cys Asp Lys Asp Tyr Asn Leu Glu Thr Leu Thr Tyr
465                 470                 475                 480
```

```
Pro Thr Lys Glu Asp Phe Asp Phe Val Glu Asn Lys Leu Lys Glu Leu
                485                 490                 495

Asp Asn Lys Ile Thr Ile Lys Gly Lys Asp Tyr Tyr Cys Val Asn Gly
            500                 505                 510

Tyr Asn Thr Pro Asn Tyr Lys Asn Leu Gln Glu Gln Arg Gln Leu Phe
        515                 520                 525

Leu Lys Arg Phe Glu Leu Glu Glu Leu Ser Ile Tyr Thr Glu Ser Glu
    530                 535                 540

Leu Asn Phe Phe Ala Glu Glu Met Lys Thr Leu Glu Lys Met Asn Thr
545                 550                 555                 560

Asp Ile His Asn Glu Glu Asp Lys Asn Glu Cys Thr Ile Glu Ala
                565                 570                 575


<210> SEQ ID NO 37
<211> LENGTH: 2739
<212> TYPE: DNA
<213> ORGANISM: Plasmodium falciparum

<400> SEQUENCE: 37

atgaatttcc taatattagt tgtattaatt aagatggttg tatgtaaaat tattaattat     60

gttagaagtg attataattt tatgctgtca tttttaagga cgagaaaaat atttagtcat    120

aaaaagattt atttcaattt taaagtttct aagaatatta caaagaattc atcatctaat    180

agttatagtg atatattaaa atgtttctct tttccaagaa aaggaactaa cgataagacg    240

aaggaaaatg aaacatttga aaaaggagaa gtaaaagaag aagaagaaga aaaagataaa    300

aacgtcaaaa ggaaaattat taatgaaagt agtaaaaata aaagagctaa agttaagaat    360

gaaaatgatg ttataaaaaa agggtcgtta tttaattgtg ttgtaagaga agatgaaaaa    420

gtgaatgatt tgagctcacc taaatttaat cctgtacatt ttaatataaa tgatttatat    480

ttatctgaaa aagataaaga aaaacataaa tttaaagact ccttattatt taccttttta    540

acaaatgcat ttaatcaaat agaagaatta aaaggtagtg gtacaggaag taaaaaaaat    600

gtatctatta tattatcgaa tatatttagg gttttaatat attatagccc taatgactta    660

ataccagctg tatatataac cttaaataaa gtagctcccg attatttaaa tgtcgaagct    720

ggtgtaggtg aagccttgat attaaaaacg atgtctgaag catatagtag aacggaaagt    780

agtataaaga aggatttaca acaaattgaa gatttaggaa taatagcgga gaattgttct    840

tgtaaaatga gaacaatatt tccgttacct cgcttaacta tacaatctgt tttcatgag     900

ctaaaaagta tacctaacct tataggatca aattcacaac agaagaaaag ggaagtcata    960

aagaaattgt tagtaagtgc taaaacatct gaagctaaat atattgtaag atttttacaa   1020

cagcgtttaa ggataggtgt aaattctgca acggtcgtac aagctttgtc atatgccttt   1080

atattaacaa gacctagtat acctgatgat attataaaaa gagggaaaga aattaatgag   1140

aatttgatta atggtaaatt ggatggtact aataatttaa ttaataaatc taataacaag   1200

acggaagagt ggctaaccca atcaggtgat aggaattgta taaaggaaga aaatttaaat   1260

gatgaattat tatcaaagga tgatataaat aaatgtgaaa acatggattc attaattaat   1320

gagatacgta ttcgaaatga aaaaataaac aaaccgaata ttttttataa ccttattgaa   1380

aaggtgggtg acacacgatt attaccatta ttttttaaag aattaaaaaa tatatattgt   1440

gaagaaaata atgatattga tatatttgaa tgtatggaaa aatcagttaa gagtgcttta   1500

tgtgaattac ccaatatcga aataataata caaaatttat taaatggtga tgatatgaat   1560
```

```
accttaagta aaaaatgtac tgttaaaaca ggtattcccg ttcaacctat gttagcaaaa   1620

ccaactaagg gtgttcaaga agtgttggat agatttaata atgttacatt tacttgtgaa   1680

tataaatatg atggtgaacg agcacaaata cattatatag ataaagataa tataaaaata   1740

ttcagtcgaa atttagaaac gatgactgaa aaatatccag atgttataca aataataaag   1800

gatcaaatag gagagaatgt aaaggaatgt attatagata gtgaagttgt tgcttatgat   1860

atagttaata ataaaatatt accattccaa gtcttaacta ctagaaaaag aaaagatgta   1920

gatatagaaa atattaaagt gaaagtatgt ctttttccat ttgatttaat atgttgtaat   1980

ggtataccag taattaaaga acctttagct gttagaagga aattattata ttctttatta   2040

aagtcaaaag atggggtgtt atcatatgct acccattctg aaatgaataa tattgaagat   2100

attgatatgt tcttacaaga tgctatcgaa aataattgtg aaggtttaat ggttaagact   2160

ttagtagaaa atgcatccta tgaaccttct aggagatcat taaattggtt aaaggtcaag   2220

aaagattatg ttgaaggtct ttcagattcg gttgatttag ttccgatagc tggttattat   2280

gggaaaggaa aaagaagtgg agtatatgga gcttttgttt tagcagctta taattctgaa   2340

acggaaaatt ttcaaaccgt ttgtaaggca ggtacaggtt ttagtgatga gatattaagt   2400

acattatatg aaacattaag tgaaaaaatt ataccaaata aaaaatcgta ttacgaagta   2460

tctgacaaat taaatcctga tgtgtggttt gatgctcact atgtatggga ggttaaggca   2520

gcagatttat ctttgtcacc tgtacataca gcagctattg gtatatatgc agatgataaa   2580

ggtattggtt taaggtttcc tcgattttta cgtttaagag aagataaaaa tgcagaacaa   2640

gcaaccacta cacaacaaat tgtagatttt tatgaggcac aatttagtag taataaaaat   2700

aaaaatattg attataatga tgatactgaa agtgaataa                          2739
```

<210> SEQ ID NO 38
<211> LENGTH: 912
<212> TYPE: PRT
<213> ORGANISM: Plasmodium falciparum

<400> SEQUENCE: 38

```
Met Asn Phe Leu Ile Leu Val Val Leu Ile Lys Met Val Val Cys Lys
1               5                   10                  15

Ile Ile Asn Tyr Val Arg Ser Asp Tyr Asn Phe Met Leu Ser Phe Leu
            20                  25                  30

Arg Thr Arg Lys Ile Phe Ser His Lys Lys Ile Tyr Phe Asn Phe Lys
        35                  40                  45

Val Ser Lys Asn Ile Thr Lys Asn Ser Ser Ser Asn Ser Tyr Ser Asp
    50                  55                  60

Ile Leu Lys Cys Phe Ser Phe Pro Arg Lys Gly Thr Asn Asp Lys Thr
65                  70                  75                  80

Lys Glu Asn Glu Thr Phe Glu Lys Gly Glu Val Lys Glu Glu Glu Glu
                85                  90                  95

Glu Lys Asp Lys Asn Val Lys Arg Lys Ile Ile Asn Glu Ser Ser Lys
            100                 105                 110

Asn Lys Arg Ala Lys Val Lys Asn Glu Asn Asp Val Ile Lys Lys Gly
        115                 120                 125

Ser Leu Phe Asn Cys Val Val Arg Glu Asp Glu Lys Val Asn Asp Leu
    130                 135                 140

Ser Ser Pro Lys Phe Asn Pro Val His Phe Asn Ile Asn Asp Leu Tyr
145                 150                 155                 160

Leu Ser Glu Lys Asp Lys Glu Lys His Lys Phe Lys Asp Ser Leu Leu
```

```
                165                 170                 175

Phe Thr Phe Leu Thr Asn Ala Phe Asn Gln Ile Glu Glu Leu Lys Gly
            180                 185                 190

Ser Gly Thr Gly Ser Lys Lys Asn Val Ser Ile Ile Leu Ser Asn Ile
        195                 200                 205

Phe Arg Val Leu Ile Tyr Tyr Ser Pro Asn Asp Leu Ile Pro Ala Val
    210                 215                 220

Tyr Ile Thr Leu Asn Lys Val Ala Pro Asp Tyr Leu Asn Val Glu Ala
225                 230                 235                 240

Gly Val Gly Glu Ala Leu Ile Leu Lys Thr Met Ser Glu Ala Tyr Ser
                245                 250                 255

Arg Thr Glu Ser Ser Ile Lys Lys Asp Leu Gln Gln Ile Glu Asp Leu
            260                 265                 270

Gly Ile Ile Ala Glu Asn Cys Ser Cys Lys Met Arg Thr Ile Phe Pro
        275                 280                 285

Leu Pro Arg Leu Thr Ile Gln Ser Val Phe His Glu Leu Lys Ser Ile
    290                 295                 300

Pro Asn Leu Ile Gly Ser Asn Ser Gln Gln Lys Lys Arg Glu Val Ile
305                 310                 315                 320

Lys Lys Leu Leu Val Ser Ala Lys Thr Ser Glu Ala Lys Tyr Ile Val
                325                 330                 335

Arg Phe Leu Gln Gln Arg Leu Arg Ile Gly Val Asn Ser Ala Thr Val
            340                 345                 350

Val Gln Ala Leu Ser Tyr Ala Phe Ile Leu Thr Arg Pro Ser Ile Pro
        355                 360                 365

Asp Asp Ile Ile Lys Arg Gly Lys Glu Ile Asn Glu Asn Leu Ile Asn
    370                 375                 380

Gly Lys Leu Asp Gly Thr Asn Asn Leu Ile Asn Lys Ser Asn Asn Lys
385                 390                 395                 400

Thr Glu Glu Trp Leu Thr Gln Ser Gly Asp Arg Asn Cys Ile Lys Glu
                405                 410                 415

Glu Asn Leu Asn Asp Glu Leu Leu Ser Lys Asp Asp Ile Asn Lys Cys
            420                 425                 430

Glu Asn Met Asp Ser Leu Ile Asn Glu Ile Arg Ile Arg Asn Glu Lys
        435                 440                 445

Ile Asn Lys Pro Asn Ile Phe Tyr Asn Leu Ile Glu Lys Val Gly Asp
    450                 455                 460

Thr Arg Leu Leu Pro Leu Phe Phe Lys Glu Leu Lys Asn Ile Tyr Cys
465                 470                 475                 480

Glu Glu Asn Asn Asp Ile Asp Ile Phe Glu Cys Met Glu Lys Ser Val
                485                 490                 495

Lys Ser Ala Leu Cys Glu Leu Pro Asn Ile Glu Ile Ile Ile Gln Asn
            500                 505                 510

Leu Leu Asn Gly Asp Asp Met Asn Thr Leu Ser Lys Lys Cys Thr Val
        515                 520                 525

Lys Thr Gly Ile Pro Val Gln Pro Met Leu Ala Lys Pro Thr Lys Gly
    530                 535                 540

Val Gln Glu Val Leu Asp Arg Phe Asn Asn Val Thr Phe Thr Cys Glu
545                 550                 555                 560

Tyr Lys Tyr Asp Gly Glu Arg Ala Gln Ile His Tyr Ile Asp Lys Asp
                565                 570                 575

Asn Ile Lys Ile Phe Ser Arg Asn Leu Glu Thr Met Thr Glu Lys Tyr
            580                 585                 590
```

-continued

```
Pro Asp Val Ile Gln Ile Ile Lys Asp Gln Ile Gly Glu Asn Val Lys
        595                 600                 605

Glu Cys Ile Ile Asp Ser Glu Val Val Ala Tyr Asp Ile Val Asn Asn
    610                 615                 620

Lys Ile Leu Pro Phe Gln Val Leu Thr Thr Arg Lys Arg Lys Asp Val
625                 630                 635                 640

Asp Ile Glu Asn Ile Lys Val Lys Val Cys Leu Phe Pro Phe Asp Leu
                645                 650                 655

Ile Cys Cys Asn Gly Ile Pro Val Ile Lys Glu Pro Leu Ala Val Arg
            660                 665                 670

Arg Lys Leu Leu Tyr Ser Leu Leu Lys Ser Lys Asp Gly Val Leu Ser
        675                 680                 685

Tyr Ala Thr His Ser Glu Met Asn Asn Ile Glu Asp Ile Asp Met Phe
    690                 695                 700

Leu Gln Asp Ala Ile Glu Asn Asn Cys Glu Gly Leu Met Val Lys Thr
705                 710                 715                 720

Leu Val Glu Asn Ala Ser Tyr Glu Pro Ser Arg Arg Ser Leu Asn Trp
                725                 730                 735

Leu Lys Val Lys Lys Asp Tyr Val Glu Gly Leu Ser Asp Ser Val Asp
            740                 745                 750

Leu Val Pro Ile Ala Gly Tyr Tyr Gly Lys Gly Lys Arg Ser Gly Val
        755                 760                 765

Tyr Gly Ala Phe Val Leu Ala Ala Tyr Asn Ser Glu Thr Glu Asn Phe
    770                 775                 780

Gln Thr Val Cys Lys Ala Gly Thr Gly Phe Ser Asp Glu Ile Leu Ser
785                 790                 795                 800

Thr Leu Tyr Glu Thr Leu Ser Glu Lys Ile Ile Pro Asn Lys Lys Ser
                805                 810                 815

Tyr Tyr Glu Val Ser Asp Lys Leu Asn Pro Asp Val Trp Phe Asp Ala
            820                 825                 830

His Tyr Val Trp Glu Val Lys Ala Ala Asp Leu Ser Leu Ser Pro Val
        835                 840                 845

His Thr Ala Ala Ile Gly Ile Tyr Ala Asp Asp Lys Gly Ile Gly Leu
    850                 855                 860

Arg Phe Pro Arg Phe Leu Arg Leu Arg Glu Asp Lys Asn Ala Glu Gln
865                 870                 875                 880

Ala Thr Thr Thr Gln Gln Ile Val Asp Phe Tyr Glu Ala Gln Phe Ser
                885                 890                 895

Ser Asn Lys Asn Lys Asn Ile Asp Tyr Asn Asp Asp Thr Glu Ser Glu
            900                 905                 910
```